US006716861B2

United States Patent
Datta et al.

(10) Patent No.: US 6,716,861 B2
(45) Date of Patent: Apr. 6, 2004

(54) 3-OX(ADI)AZOLYLPROPANOHYDROXAMIC ACIDS USEFUL AS PROCOLLAGEN C-PROTEINASE INHIBITORS

(75) Inventors: Usa Datta, Sandwich (GB); Paul Vincent Fish, Sandwich (GB); Kim James, Sandwich (GB); Gavin Alistair Whitlock, Sandwich (GB)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/021,721

(22) Filed: Dec. 12, 2001

(65) Prior Publication Data

US 2002/0151535 A1 Oct. 17, 2002

Related U.S. Application Data

(60) Provisional application No. 60/262,355, filed on Jan. 17, 2001.

(30) Foreign Application Priority Data

Dec. 21, 2000 (GB) .............................................. 0031321

(51) Int. Cl.[7] .................. A61K 31/4245; C07D 263/32
(52) U.S. Cl. ........................ 514/364; 514/376; 548/131; 548/236
(58) Field of Search ................. 548/131, 236; 514/364, 376

(56) References Cited

U.S. PATENT DOCUMENTS 5,304,604 A * 4/1994 Davidson et al. ......... 514/238.2
6,448,278 B2 9/2002 Bailey et al. ............... 514/364

FOREIGN PATENT DOCUMENTS

| WO | 9523790 | 9/1995 |
|----|---------|--------|
| WO | 0147901 | 7/2001 |

OTHER PUBLICATIONS

Dankwardt et al., "Solid–Phase Synthesis of Di– and Tripeptidic Hydroxamic Acids as Inhibitors of Procollagen C–proteinase", *Bioorganic & Medicinal Chemistry Letters*, vol. 10, pp. 2513–2516, 2000.

Fray and Ellis, "Application of Epimerisation–Free Amide Copuling Conditions to the Synthesis of Matrix Metalloprotease Inhibitor Intermediates", *Tetrahedron*, vol. 54, pp. 13825–13832, 1998.

Fray et al., "Selectivity of Inhibition of Matrix Metalloproteases MMP–3 and MMP–2 by Succinyl Hydroxamates and their Carboxylic Acid Analogues is Dependent on P3' Group Chirality", *Bioorganic & Medicinal Chemistry Letters*, vol. 11, pp. 567–570, 2001.

Yamamoto et al., "Inhibition of Membrane–Type 1 Matrix Metalloproteinase by Hydroxamate Inhibitors: An Examination of the Subsite Pocket", *J. Med. Chem.*, vol. 41, No. 8, pp. 1209–1217, 1998.

Floyd C., et al, "Rapid Synthesis of Matrix Metalloproteinase Inhibitors via Ugi Four–Component Condensation", SYNLETT, Jun. 1988, p. 637.

\* cited by examiner

Primary Examiner—Joseph K. McKane
Assistant Examiner—Kamal Saeed
(74) Attorney, Agent, or Firm—J. Michael Dixon

(57) ABSTRACT

Compounds of formula (I):

wherein the substituents are as defined herein, and their salt, solvates, and prodrugs are procollagen C-proteinase (PCP) inhibitors useful in treating conditions mediated by PCP.

17 Claims, No Drawings

3-OX(ADI)AZOLYLPROPANOHYDROXAMIC ACIDS USEFUL AS PROCOLLAGEN C-PROTEINASE INHIBITORS

This application claims priority from Great Britain Application No. GB 0031321.3, filed Dec. 21, 2000, and U.S. Provisional Application Ser. No. 60/262,355, filed Jan. 17, 2001.

This invention relates to a certain class of compounds, and the pharmaceutically acceptable salts, solvates and prodrugs thereof, which inhibit Procollagen C-proteinase ("PCP"). They are therefore useful in the treatment of mammals having conditions alleviable by inhibition of PCP. Especially of interest is an antiscarring treatment for wounds.

Fibrotic tissues, including dermal scars, are characterised by excessive accumulation of extracellular matrix, mainly collagen type I. It is thought that inhibition of collagen deposition will reduce formation of scar tissue. Collagen is secreted as the precursor, procollagen, which is transformed into the insoluble collagen by cleavage of the C-terminal propeptide by PCP. PCP is a zinc-dependent metalloprotease which is secreted from TGF-β-activated fibroblasts belonging to the subfamily of astacin-like proteases and able to cleave the C-terminal peptide of types I, II and III procollagens. Furthermore, data suggest that PCP activates lysyl oxidase, an enzyme essential for the formation of covalent cross-links which stabilise the fibrous form of collagen. Therefore, inhibition of PCP may not only reduce collagen deposition but may also make collagen more accessible for degradation.

Collagen is integral to, among other things, the proper formation of connective tissue. Thus, the over- or under-production of collagen or the production of abnormal collagen (including incorrectly processed collagen) has been linked with numerous connective tissue diseases and disorders. Mounting evidence suggests that PCP is an essential key enzyme for the proper maturation of collagen (see for example International Patent Application publication number WO 97/05865).

The present invention relates to substances capable of inhibiting PCP activity in order to regulate, modulate and/or reduce collagen formation and deposition. More specifically, the invention relates to the use of compounds and pharmaceutical compositions thereof for the treatment of various conditions relating to production of collagen.

At present more than nineteen types of collagens have been identified. These collagens, including fibrillar collagen types I, II, III are synthesized as procollagen precursor molecules which contain amino- and carboxy-terminal peptide extensions. These peptide extensions, referred to as "pro-regions," are designated as N- and C-propeptides, respectively. The pro-regions are typically cleaved upon secretion of the procollagen triple helical precursor molecule from the cell to yield a mature triple helical collagen molecule. Upon cleavage, the "mature" collagen molecule is capable of association, for example, into highly structured collagen fibers. See e.g., Fessler and Fessler, 1978, Annu. Rev. Biochem. 47:129–162; Bornstein and Traub, 1979, in: The Proteins (eds. Neurath, H. and Hill, R. H.), Academic Press, New York, pp. 412–632; Kivirikko et al., 1984, in: Extracellur Matrix Biochemistry (eds. Piez, K. A. and Reddi. A. H.), Elsevier Science Publishing Co., Inc., New York, pp. 83–118; Prockop and Kivirikko, 1984, N. Engl, J. Med. 311:376–383; Kuhn, 1987, in: Structure and Function of Collagen Types (eds. Mayne, R. and Burgeson, R. E.), Academic Press, Inc., Orlando, Fla., pp. 1–42.

An array of conditions has been associated with the inappropriate or unregulated production of collagen, including pathological fibrosis or scarring, including endocardial sclerosis, idiopanthic interstitial fibrosis, interstitial pulmonary fibrosis, perimuscular fibrosis, Symmers' fibrosis, pericentral fibrosis, hepatitis, dermatofibroma, cirrhosis such as binary cirrhosis and alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture and Pyronie's disease. Further fibrotic disorders may be induced or initiated by surgery, including scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis. Other conditions where collagen plays a key role include burns, and chronic dermal ulcers which sometimes have a build-up of periulcer fibrosed material around them. Fibrosis of lung tissue is also observed in patients suffering from chronic obstructive airways disease (COAD) and asthma. One strategy for the treatment of these diseases and conditions is to inhibit the overproduction and/or deposition and/or unregulation of collagen. Thus, identification and isolation of molecules which control, inhibit and/or modulate the production and deposition of collagen are of major medical interest.

Recent evidence suggests that PCP is the essential key enzyme that catalyzes the cleavage of the Procollagen C-propeptide. This has been demonstrated in fibrillar collagens, including type I, type II, and type III collagen.

PCP was first observed in the culture media of human and mouse fibroblasts (Goldberg et al., 1975, Cell 4:45–50; Kessler and Goldberg, 1978, Anal. Biochem. 86:463–469), and chick tendon fibroblasts (Duskin et al., 1978, Arch. Biochem. Biophys. 185:326–332; Leung et al., 1979, J. Biol, Chem. 254:224–232). An acidic proteinase which removes the C-terminal propeptides from type I procollagen has also been identified (Davidson et al., 1979, Eur. J. Biochem. 100:551).

A partially purified protein having PCP activity was obtained from chick calvaria in 1982. Njieha et al., 1982, Biochemistry 23:757–764. In 1985, chicken PCP was isolated, purified and characterized from conditioned media of chick embryo tendons. Hojima et al., 1985, J. Biol. Chem. 260:15996–16003. Murine PCP has been subsequently purified from media of cultured mouse fibroblasts. Kessler et al., 1986, Collagen Relat. Res. 6:249–266; Kessler and Adar, 1989, Eur. J. Biochem. 186:115–121. Finally, the cDNA encoding human PCP has been identified, as set forth in the above-referenced articles and references disclosed therein.

Experiments conducted with these purified forms of chick and mouse PCP have indicated that the enzyme is instrumental in the formation of functional collagen fibers. Fertala et al., 1994, J. Biol. Chem. 269:11584.

As a consequence of the enzyme's apparent importance to collagen production, scientists have identified a number of PCP inhibitors. See e.g., Hojima et al., supra. For example, several metal chelators have demonstrated activity as PCP inhibitors. Likewise, chymostatin and pepstatin A were found to be relatively strong inhibitors of PCP. Additionally, $\alpha_2$-Macroglobuline, ovostatin, and fetal bovine serum appear to at least partially inhibit PCP activity.

Dithiothreitol, SDS, concanavalin A, $Zn^{2+}$, $Cu^{2+}$, and $Cd^{2+}$ are similarly reported to be inhibitory at low concentrations. Likewise, some reducing agents, several amino acids, phosphate, and ammonium sulfate were inhibitory at concentrations of 1–10 mM. Further, the enzyme was shown to be inhibited by the basic amino acids lysine and arginine (Leung et al., supra; Ryhänen et al., 1982, Arch. Biochem. Biophys. 215:230–235). Finally, high concentrations of NaCl or Tris-HCl buffer were found to inhibit PCP's activity. For example, it is reported that, with 0.2, 0.3, and 0.5M NaCl, the activity of PCP was reduced 66, 38, and 25%, respectively, of that observed with the standard assay concentration of 0.15M. Tris-HCl buffer in a concentration of 0.2–0.5M markedly inhibited activity (Hojima et al., supra). PCP activity and its inhibition have been determined using a wide array of assays. See e.g., Kessler and Goldberg, 1978, Anal. Biochem. 86:463; Njieha et al., 1982, Biochemistry 21:757–764. As articulated in numerous publications, the enzyme is difficult to isolate by conventional biochemical means and the identity of the cDNA sequence encoding such enzyme was not known until reported in the above references and related patent applications.

In view of its essential role in the formation and maturation of collagen PCP appears to be an ideal target for the treatment of disorders associated with the inappropriate or unregulated production and maturation of collagen. The identification of effective compounds which specifically inhibit the activity of PCP to regulate and modulate abnormal or inappropriate collagen production is therefore desirable and the object of this invention.

Matrix metalloproteases (MMPs) constitute a family of structurally similar zinc-containing metalloproteases, which are involved in the remodelling, repair and degradation of extracellular matrix proteins, both as part of normal physiological processes and in pathological conditions.

Another important function of certain MMPs is to activate other enzymes, including other MMPs, by cleaving the pro-domain from their protease domain. Thus, certain MMPs act to regulate the activities of other MMPs, so that over-production in one MMP may lead to excessive proteolysis of extracellular matrix by another, e.g. MMP-14 activates pro-MMP-2

During the healing of normal and chronic wounds, MMP-1 is expressed by migrating keratinocytes at the wound edges (U. K. Saarialho-Kere, S. O. Kovacs, A. P. Pentland, J. Clin. Invest. 1993, 92, 2858–66). There is evidence which suggests MMP-1 is required for keratinocyte migration on a collagen type I matrix in vitro, and is completely inhibited by the presence of the non-selective MMP inhibitor SC44463 ((N4-hydroxy)-N1-[(1S)-2-(4-methoxyphenyl)methyl-1-((1R)-methylamino)carbonyl)]-(2R)-2-(2-methylpropyl)butanediamide) (B. K. Pilcher, J. A. Dumin, B. D. Sudbeck, S. M. Krane, H. G. Welgus, W. C. Parks, J. Cell Biol., 1997, 137, 1–13). Keratinocyte migration in vivo is essential for effective wound healing to occur.

MMP-2 and MMP-9 appear to play important roles in wound healing during the extended remodelling phase and the onset of re-epithelialisation, respectively (M. S. Agren, Brit. J. Dermatology, 1994, 131, 634–40; T. Salo, M. Mäkänen, M. Kylmäniemi, Lab. Invest., 1994, 70, 176–82). The potent, non-selective MMP inhibitor BB94 ((2S,3R)-5-methyl-3-{[(1S)-1-(methylcarbamoyl)-2-phenylethyl]carbamoyl}-2-[(2-thienylthio)methyl]hexanohydroxamic acid, batimastat), inhibits endothelial cell invasion of basement membrane, thereby inhibiting angiogenesis (G. Tarboletti, A. Garofalo, D. Belotti, T. Drudis, P. Borsotti, E. Scanziani, P. D. Brown, R. Giavazzi, J. Natl. Cancer Inst., 1995, 87, 293–8). There is evidence that this process requires active MMP-2 and/or 9.

Thus PCP inhibitors which significantly inhibit MMPs 1 and/or 2 and/or 9 would be expected to impair wound healing. MMP-14 is responsible for the activation of MMP-2, and thus inhibition of MMP-14 might also result in impaired wound healing.

For recent reviews of MMPs, see Zask et al, Current Pharmaceutical Design, 1996, 2, 624–661; Beckett, Exp. Opin. Ther. Patents, 1996, 6, 1305–1315; and Beckett et al, Drug Discovery Today, vol 1 (no.1), 1996, 16–26.

Alternative names for various MMPs and substrates acted on by these are shown in the table below (Zask et al, supra).

| Enzyme | Other names | Preferred substrates |
| --- | --- | --- |
| MMP-1 | Collagenase-1, interstitial collagenase | Collagens I, II, III, VII, X, gelatins |
| MMP-2 | Gelatinase A, 72kDa gelatinase | Gelatins, collagens IV, V, VII, X, elastin, fibronectin; activates pro-MMP-13 |
| MMP-3 | Stromelysin-1 | Proteoglycans, laminin, fibronectin, gelatins. |
| MMP-7 | Pump, Matrilysin | Proteoglycans, laminin, fibronectin, gelatins, collagen IV, elastin, activates pro-MMP-1 and -2. |
| MMP-8 | Collagenase-2, neutrophil collagenase | Collagens I, II, III |
| MMP-9 | Gelatinase B, 92 kDa gelatinase | Gelatins, collagens IV, V, elastin |
| MMP-12 | Macrophage metalloelastase | Elastin, collagen IV, fibronectin, activates pro-MMP-2 & 3. |
| MMP-13 | Collagenase-3 | Collagens I, II, III, gelatins |
| MMP-14 | MT-MMP-1 | Activates pro-MMP-2 & 13, gelatins |
| MMP-15 | MT-MMP-2 | unknown |
| MMP-16 | MT-MMP-3 | Activates pro-MMP-2 |
| MMP-17 | MT-MMP-4 | unknown |

International Patent Application publication number WO 01/47901 discloses a number of 3-heterocyclylpropanohydroxamic acid PCP inhibitors.

International Patent Application publication number WO 95/23790 discloses a number of imidazole-substituted hydroxamic acid derivatives as MMP inhibitors, including collagenase inhibitors.

Yamamoto et al, in J.Med.Chem. (1998) 41, 1209 discloses a series of hydroxamic acid derivatives as MMP-1 inhibitors.

Dankhardt et al, in Bioorg.Med.Chem Letters (2000) 10, 2513 discloses various peptidic hydroxamic acid inhibitors of PCP.

According to one aspect of the present invention, there are provided compounds of formula (I):

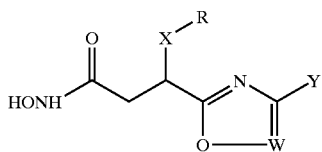

(I)

wherein:
X is $C_{1-6}$ alkylene or $C_{2-6}$ alkenylene, each of which is optionally substituted by one or more fluorine atoms;
R is aryl or $C_{3-8}$ cycloalkyl optionally substituted by one or more fluorine atoms;
W is N or CZ;
Y is
(a) $NR^1R^3$,
(b) $C_{1-4}$ alkyl substituted by $NR^1R^2$ or by a 4- to 7-membered N-heterocycle attached via the N-atom, which heterocycle optionally contains 1 or 2 further ring hetero-atoms independently selected from N, O and S, and which heterocycle is optionally substituted by one or more substituents independently selected from $R^2$, =O, OH, $SO_2(C_{1-4}$ alkyl) and/or $C(O)_p(C_{1-4}$ alkyl) groups,
or (c) a 4- to 7-membered saturated or partially or fully unsaturated N-heterocycle, which heterocycle optionally contains 1 or 2 further ring hetero-atoms independently selected from N, O and S, and which heterocycle is optionally substituted by one or more substituents independently selected from $R^2$, =O, OH, $SO_2(C_{1-4}$ alkyl) and/or $C(O)_p(C_{1-4}$ alkyl) groups,
Z is H or $C_{1-4}$ alkyl,
or when W is CZ, Y can be H or $C_{1-4}$ alkyl, and Z can be
(a) $NR^1R^3$,
(b) $C_{1-4}$ alkyl substituted by $NR^1R^2$ or by a 4- to 7-membered N-heterocycle attached via the N-atom, which heterocycle optionally contains 1 or 2 further ring hetero-atoms independently selected from N, O and S, and which heterocycle is optionally substituted by one or more substituents independently selected from $R^2$, =O, OH, $SO_2(C_{1-4}$ alkyl) and/or $C(O)_p(C_{1-4}$ alkyl) groups,
or (c) a 4- to 7-membered saturated or partially or fully unsaturated N-heterocycle attached via the N-atom, which heterocycle optionally contains 1 or 2 further ring hetero-atoms independently selected from N, O and S, and which heterocycle is optionally substituted by one or more substituents independently selected from $R^2$, =O, OH, $SO_2(C_{1-4}$ alkyl) and/or $C(O)_p(C_{1-4}$ alkyl) groups,
$R^2$ is
H,
$C_{1-6}$ alkyl (optionally substituted by one or more substituents independently selected from OH,
$C_{1-4}$ alkoxy, $C(O)_p(C_{1-4}$ alkyl, aryl, heteroaryl, or $NR^1R^3)$, $CONR^1R^3$ or $NR^1R^3)$,
$SO_2(C_{1-4}$ alkyl, aryl, heteroaryl or $NR^1R^3)$,
$C(O)_p(C_{1-4}$ alkyl optionally substituted by $C_{1-4}$ alkoxy or $NR^1R^3)$,
$C(O)_p(C_{3-7}$ cycloalkyl),
$C(O)_p(aryl)$,
$C(O)_p(heteroaryl)$,
$CONR^1R^3$,
$C_{3-7}$ cycloalkyl optionally substituted by one or more substituents independently selected from OH and $C_{1-4}$ alkoxy, a 4- to 7-membered saturated or partially or fully unsaturated heterocycle, which heterocycle ring contains up to 3 ring hetero-atoms independently selected from N, O and S, and which heterocycle is optionally substituted by one or more substituents independently selected from $R^3$, =O, OH, $SO_2(C_{1-4}$ alkyl) and/or $C(O)_p(C_{1-4}$ alkyl) groups,
or aryl,
$R^1$ and $R^3$ are each independently selected from H and $C_{1-4}$ alkyl optionally substituted by OH, $NR^4R^5$ or by $C_{1-4}$ alkoxy,
$R^4$ and $R^5$ are each independently selected from H and $C_{1-4}$ alkyl,
p is 1 or 2,
"aryl" is phenyl optionally substituted by one or more substituents independently selected from $R^3$, OH, $SO_2(C_{1-4}$ alkyl) and/or $C(O)_p(C_{1-4}$ alkyl) groups,
"heteroaryl" is a 5- to 7-membered aromatic heterocycle with 1, 2 or 3 ring hetero-atoms independently selected from N, O and S, and which ring is optionally substituted by one or more substituents independently selected from $R^3$, =O, OH, $SO_2(C_{1-4}$ alkyl) and/or $C(O)_p(C_{1-4}$ alkyl) groups,
and the pharmaceutically acceptable salts, solvates (including hydrates) and prodrugs thereof.
"Alkyl", "alkylene", "alkoxy", "alkanoyl", and "alkenylene" groups, including in groups incorporating said moieties, may be straight chain or branched where the number of carbon atoms allows.

Halogen is taken to mean fluorine, chlorine, bromine or iodine.

Pharmaceutically-acceptable salts are well known to those skilled in the art, and for example include those mentioned in the art cited above, and by Berge et al, in J.Pharm.Sci., 66, 1–19 (1977). Suitable acid addition salts are formed from acids which form non-toxic salts and include the hydrochloride, hydrobromide, hydroiodide, nitrate, sulphate, bisulphate, phosphate, hydrogen phosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate, pamoate, camsylate, and p-toluenesulphonate salts.

Pharmaceutically acceptable base addition salts are well known to those skilled in the art, and for example include those mentioned in the art cited above, and can be formed from bases which form non-toxic salts and include the aluminium, calcium, lithium, magnesium, potassium, sodium and zinc salts, and salts of non-toxic amines such as diethanolamine.

Certain of the compounds of formula (I) may exist in one or more zwitterionic forms. Certain of the compounds of formula (I) may exist in one or more tautomeric forms. Certain of the compounds of formula (I), their salts, solvates, prodrugs, etc. may exist in one or more polymorphic forms. It is to be understood that the compounds of formula (I) include all such zwitterions, tautomers and polymorphs.

The compounds of formula (I), their salts, hydrates, prodrugs etc. can exhibit isotopic variation, e.g. forms with enriched $^2H$, $^3H$, $^{13}C$, $^{14}C$, $^{15}N$, $^{18}O$, etc. may be prepared, for example by suitable variation of the synthetic methods described herein using methods and reagents known in the art or routine modification thereof. All such isotopic variants are included in the scope of the invention.

Prodrug moieties are well-known to those skilled in the art (see for example the article by H Feres, in Drugs of Today, vol 19, no.9 (1983) pp.499–538, especially section A1), and for example include those specifically mentioned in A. A. Sinkula's article in Annual Reports in Medicinal Chemistry, vol 10, chapter 31, pp.306–326, herein incorporated by reference, and the references therein. Specific prodrug moieties which may be specifically mentioned are aliphatic-aromatic, carbonate, phosphate and carboxylic esters, carbamates, peptides, glycoside, acetals and ketals, tetrahydropyranyl and silyl ethers. Such prodrug moieties can be cleaved in situ, e.g. are hydrolysable in physiological conditions, to give compounds of formula (I).

Certain of the compounds of the formula (I) may exist as geometric isomers. The compounds of the formula (I) may possess one or more asymmetric centres, apart from the specified centres in formula (I), and so exist in two or more stereoisomeric forms. The present invention includes all the individual stereoisomers and geometric isomers of the compounds of formula (I) and mixtures thereof.

Preferably the compounds of formula (I) have the following stereochemistry (IA):

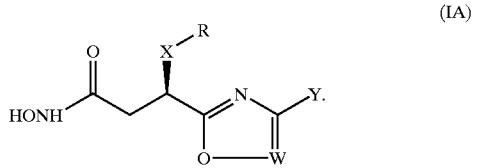

(IA)

Preferably W is N.

Preferably X is a linear $C_{2-6}$ alkylene moiety optionally substituted by one or more fluorine atoms. More preferably X is propylene.

Preferably R is $C_{3-8}$ cycloalkyl optionally substituted by one or more fluorine atoms. More preferably R is cyclobutyl, cyclopentyl or cyclohexyl optionally substituted by one or more fluorine atoms. Most preferably R is cyclohexyl.

Preferably Y is $C_{1-4}$ alkyl substituted by $NR^1R^2$, or Y is a 4- to 7-membered saturated or partially or fully unsaturated N-heterocycle, which heterocycle optionally contains 1 or 2 further ring hetero-atoms independently selected from N, O and S, and which heterocycle is optionally substituted by one or more substituents independently selected from $R^2$, =O, OH, $SO_2(C_{1-4}$ alkyl) and/or $C(O)_p(C_{1-4}$ alkyl) groups. More preferably Y is $CH_2$ substituted by $NR^1R^2$, or Y is a 6-membered saturated or partially or fully unsaturated N-heterocycle, and which heterocycle is optionally substituted by one or more substituents independently selected from $R^2$, =O, OH, $SO_2(C_{1-4}$ alkyl) and/or $C(O)_p(C_{1-4}$ alkyl) groups. Yet more preferably Y is $CH_2N(H$ or $CH_3)(SO_2(C_{1-4}$ alkyl, aryl, heteroaryl or $NR^1R^3))$, or Y is a 6-membered saturated or partially or fully unsaturated N-heterocycle, and which heterocycle is optionally substituted by $SO_2(C_{1-4}$ alkyl) and/or $C(O)_p(C_{1-4}$ alkyl) groups. Further more preferably Y is $CH_2NHSO_2(C_{1-4}$ alkyl), or Y is a 6-membered saturated N-heterocycle, and which heterocycle is optionally substituted by $SO_2(C_{1-4}$ alkyl) or $C(O)_p(C_{1-4}$ alkyl). Most preferably Y is $CH_2NHSO_2CH_3$ or methylsulphonylpiperidinyl.

Preferably Z is H or $CH_3$

A preferred group of compound of formula (I) are those wherein each substituent is as specified in the Examples below.

Another preferred group are the compounds of the Examples below and the salts, solvates and prodrugs thereof.

A further aspect of the invention is a PCP inhibitor of formula (I) which is selective against MMP-1 and/or MMP-2 and/or MMP-9 and/or MMP-14. A further aspect of the invention is the use of a PCP inhibitor of formula (I) which is selective against MMP-1 and/or MMP-2 and/or MMP-9 and/or MMP-14 in medicine. Further related to this aspect of the invention is the use of a PCP inhibitor of formula (I) which is selective against MMP-1 and/or MMP-2 and/or MMP-9 and/or MMP-14 in the manufacture of an antiscarring medicament. Further related to this aspect of the invention is a method of treating a condition mediated by PCP and in which MMP-1 and/or MMP-2 and/or MMP-9 and/or MMP-14 have a beneficial effect, with an effective amount of PCP inhibitor of formula (I) which is selective against MMP-1 and/or MMP-2 and/or MMP-9 and/or MMP-14, an example of such a condition being a wound.

Preferably the PCP inhibitor of formula (I) mentioned in this aspect of the invention is selective against at least MMP-1, MMP-2 and MMP-9. Most preferably the said PCP inhibitor of formula (I) is selective against MMP-1, MMP-2, MMP-9, and MMP-14. Preferably the said selective PCP inhibitor of formula (I) has an $IC_{50}$ vs. PCP of 0.5 $\mu$M or lower, and selectivities vs. MMP-2 and MMP-9 of at least 30-fold, in the tests described herein. Preferably the selective PCP inhibitor of formula (I) has an $IC_{50}$ vs. PCP of 0.1 $\mu$M or lower, and selectivities vs. MMP-1, MMP-2, MMP-9 and MMP-14 of at least 300-fold, in the tests described herein.

Another aspect of the invention is a substance of formula (I) described herein, including the salts, solvates and prodrugs thereof, for use in medicine.

Another aspect of the invention is the use of the substances of formula (I) described herein, including the salts, solvates and prodrugs thereof, in the manufacture of a medicament for treatment of a PCP-mediated condition (e.g. an antiscarring medicament).

Another aspect of the invention is a pharmaceutical composition comprising a compound of formula (I), salts thereof, solvates thereof and/or prodrugs thereof, and a pharmaceutically acceptable diluent, carrier or adjuvant.

Another aspect of the invention is the combination of a compound of formula (I), or a salt, solvate or prodrug thereof, with one or more other active agent useful in treating wounds, such as:

(i) a growth factor such as TGF-β-3 (Renovo), IGF-1 (Genentech), IGF-1 complex (Celtrix), KGF-2 or FGF-10 (Sumitomo), DWP-401/EGF (Daewoong) or SNK-863 (Sanwa Kagaku Kenkyusho);

(ii) a growth factor agonist such as Noggin (Regeneron);

(iii) a growth factor antibody/antisense material, such as those to: TGF-β-1 or 2 (Renovo, CaT), PDGF (II Yang) or CTGF (Fibrogen);

(iv) a hormone such as DHEAS (Pharmadigm), ConXn/Relaxin (Connetics);

(v) an antibody to adhesion compounds such as ICAM-1 (Boehringer);

(vi) a MMP beneficial to healing of wounds, such as Collagenase ABC (BioSpecifics);

(vii) a barrier such as ADCON (Gliatech);

(viii) skin products such as artificial skin systems such as those based on DermaGraft (Advanced Tissue Sciences Inc.), INTEGRA Artificial Skin (Integra Life Sciences Holding Corp.), cell cultures such as Apligraf/Graftskin (Novartis), those developed by Cell Genesys Inc., AlloDerm (LifeCell) or matrix formulation products such as Argidene gel (Telios Pharmaceuticals Inc.);

(ix) a uPA inhibitor such as those disclosed in patent applications WO 99/20608, WO 00/05214 and EP 1 044 967; and/or (x) a MMP-3 inhibitor such as those disclosed in patent applications WO99/35124, WO 99/29667, EP 0 931 788 and WO 00/74681.

Yet another aspect of the invention is a method of treatment of a condition mediated by PCP comprising administration of a therapeutically-effective amount of a substance according to the above definitions.

It is to be appreciated that reference to treatment includes prophylaxis as well as the alleviation of established symptoms of PCP-mediated conditions and diseases.

The invention further provides Methods for the production of compounds of the invention, which are described below and in the Examples and Preparations. The skilled man will appreciate that the compounds of the invention could be made by methods other than those specifically described herein, by adaptation of the methods herein described in the sections below and/or adaptation thereof, for example by methods known in the art. Suitable guides to synthesis, functional group transformations, use of protecting groups, etc. are, for example, "Comprehensive Organic Transformations" by R C Larock, VCH Publishers Inc. (1989), "Advanced Organic Chemistry" by J March, Wiley Interscience (1985), "Designing Organic Synthesis" by S Warren, Wiley Interscience (1978), "Organic Synthesis—The Disconnection Approach" by S Warren, Wiley Interscience (1982), "Guidebook to Organic Synthesis" by R K Mackie and D M Smith, Longman (1982), "Protective Groups in Organic Synthesis" by T W Greene and P G M Wuts, John Wiley and Sons Inc. (1999), and P J Kocienski, in "Protecting Groups", Georg Thieme Verlag (1994), and any updated versions of said standard works.

In the Methods below, unless otherwise specified, the substituents are as defined above with reference to the compounds of formula (I) above.

The compounds of formula (I) where W is N can be prepared according to the chemistry outlined in the schemes below.

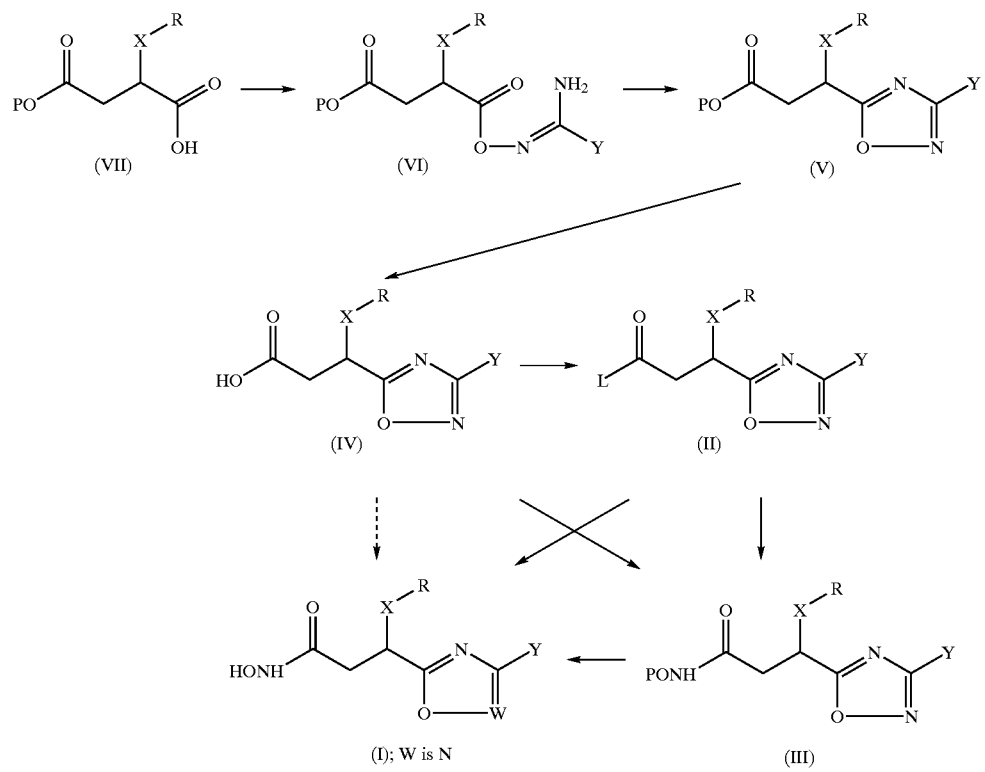

The hydroxamic acid compounds of formula (I) where W is N can be made by reaction of the corresponding activated acid derivative of formula (II), where L⁻ is a suitable leaving group, with hydroxylamine.

Suitable leaving groups are generally those which would leave in a more efficient manner than the hydroxide of the parent acid (IV), in a nucleophilic substitution reaction, such as a halide, $C_{1-4}$ alkoxide optionally substituted by halogen, an alkylsulphonate such as methylsulphonate or mesylsulphonate, an arylsulphonate such as p-tosylsulphonate. Other suitable leaving groups are familiar to those working in the field of amino acid coupling.

Such compounds of formula (II) may be made via standard chemistry from the corresponding acid (IV). Compounds of formula (II) where L is a leaving group such as Cl, Br, I, OCO($C_{1-4}$ alkyl optionally substituted by one or more halogen), mesylate, tosylate, and the like, can be made from the corresponding compound of formula (II) where L is OH by conventional methods, using an acid-activating agent including methods typified in e.g. Examples 1–6, etc.

A coupling agent such as a diimide coupling agent, e.g. carbonyldiimidazole or N,N'-dicyclohexylcarbodiimide, may be used to convert compounds of formula (IV) to compounds of formula (I) (see e.g. Examples 7, 19), under standard conditions with the agents mentioned previously, e.g. via intermediates of formulae (II) and/or (III).

The hydroxylamine used in this reaction can be suitably generated in situ by treatment of a hydroxylamine salt such as the hydrochloride salt with a suitable base such as triethylamine. Suitably the reaction is carried out in a polar solvent such as DMF. This reaction, leaving groups, solvents, reagents, etc. are exemplified below in the relevant Examples below.

Alternatively the compounds of formula (I) may be made from a NHO-protected compound of formula (III), where P is a suitable O-protecting group, by suitable deprotection. Suitable O-protecting groups can be found in the text by Greene and Wuts, supra, and include trialkylsilyl (such as trimethylsilyl), benzyl, etc. Compounds of formula (III) can be made in an analogous manner to the compounds of formula (I) from the compounds of formula (II), using a protected hydroxylamine $PONH_2$ or a suitable salt thereof in place of hydroxylamine itself or the hydroxylamine salt. The deprotection method is determined by the protective group used, as is well known in the art (see e.g. Greene and Wuts, supra). E.g. benzyl groups may be hydrogenated, suitably using a catalytic transfer hydrogenation method. The reagents and conditions for reaction (III)→(I) are typified in certain of the Examples below, such as where a protected hydroxylamine reagent (e.g. O-trimethylsilylhydroxylamine) can be used (e.g. Examples 1–6, etc.), where conveniently the deprotection is carried out in the same vessel as the previous step.

Other methods of making hydroxamic acids (I) are known and may be used, e.g. those mentioned in the text by J. March, supra, chapters 0–54, 0–57 and 6–4, and relevant references therein.

Acids of formula (IV) may be made by deprotection of the O-protected species of formula (V). Suitable O-protecting groups can be found in the chapter on O-protection in the book by Greene and Wuts, supra, and include $C_{1-4}$ alkoxy such as t-butoxy (as typified in Preparations 4, 7, 9, 11, 13, 15, etc.), benzyloxy, trialkylsilyloxy such as trimethylsilyloxy, etc. The deprotection method is determined by the protective group used, as is well known in the art (see Greene and Wuts, supra). E.g. benzyl groups may be removed by hydrogenation, suitably using a catalytic transfer hydrogenation method, t-butyl groups may be removed by treatment with an acid in a suitable solvent, such as trifluoroacetic acid in dioxan, hydrochloric acid in toluene, etc.

Compounds of formula (V), e.g. where P is a t-butoxy can be made for example by condensation reaction of a corresponding compound of formula (VI), for example by heating to elevated temperature in an inert solvent such as in xylene at about 130° C., this reaction being typified by Preparation 3, 32, etc. below.

Compounds of formula (VI) can be made for example by coupling an acid of formula (VII) with a reagent of formula $C(NH_2)(Y)=NOH$, which is available via literature methods or adaptation thereof in a conventional manner (see e.g. Preparation 1), such as typified in methods described herein (e.g. see Preparation 2, etc.). Typically the condensation is carried out by adding a solution of the acid (VII) in a suitable inert solvent such as 1,4-dioxane or dichloromethane or the like, to a suitable agent such as 1-hydroxybenzotriazole hydrate, followed by addition of a suitable coupling agent such as a carbodiimide coupling agent, e.g. N,N'-dicyclohexylcarbodiimide, then treatment with the reagent $C(NH_2)(Y)=NOH$. Suitably the coupling is carried out at ambient temperature.

Compounds of formula (VII), and salts thereof which can generate the acid in situ on acidification, can be made by hydrogenation of the corresponding itaconate derivative, which in turn can be made by conventional methods such as the Stobbe condensation (see e.g. Preparation 168). Compounds of formula (VII) where R is cyclohexyl can be made by catalytic hydrogenation of the corresponding compound of formula (I) where R is phenyl, using suitable catalysts and conditions, such as those mentioned in Preparation 168 (in part).

The compounds of formula (I), where W is CZ, can be prepared according to the chemistry outlined in the scheme below:

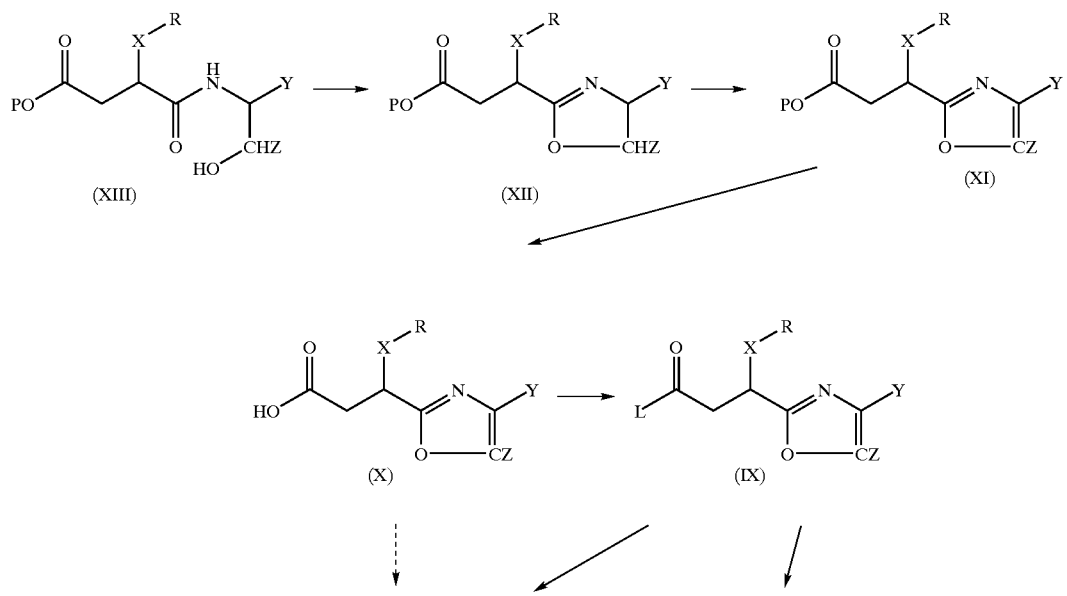

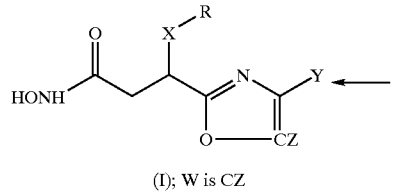

(I); W is CZ

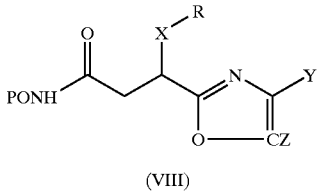

(VIII)

The hydroxamic acid compounds of formula (I) where W is CZ can be made by reaction of the corresponding activated acid derivative of formula (IX), where L⁻ is a suitable leaving group, with hydroxylamine. The leaving groups, reagents, etc. are the same as those mentioned above in relation to the corresponding compounds of formula (I) where W is N.

Such compounds of formula (IX) may be made via standard chemistry from the corresponding acid (X) using the same or similar chemistry to that outlined above in relation to the corresponding compounds of formula (II) where W is N (supra).

Alternatively the compounds of formula (I) may be made from a NHO-protected compound of formula (VIII), where P is a suitable O-protecting group, by suitable deprotection. Suitable O-protecting groups can be found in the text by Greene and Wuts, supra, and include trialkylsilyl (such as trimethylsilyl), benzyl, etc.

Compounds of formula (VIII) can be made in an analogous manner to the compounds of formula (II) from the compounds of formula (II), using a protected hydroxylamine PONH$_2$ or a suitable salt thereof in place of hydroxylamine itself or the hydroxylamine salt. The deprotection method is determined by the protective group used, as is well known in the art. E.g. benzyl groups may be hydrogenated, suitably using a catalytic transfer hydrogenation method. The reagents and conditions for reaction (VIII)→(I) are typified in Examples 68–72 below.

Other methods of making hydroxamic acids (I) are known and may be used, e.g. those mentioned in the text by J. March, supra, chapters 0–54, 0–57 and 6–4, and relevant references therein.

Acids of formula (X) may be made by deprotection of the O-protected species of formula (XI). Suitable O-protecting groups can be found in the chapter on O-protection in the book by Greene and Wuts, supra, and include Can alkoxy such as t-butoxy (as typified by the conditions mentioned in Preparation 4, etc.), benzyloxy, trialkylsilyloxy such as trimethylsilyloxy, etc. The deprotection method is determined by the protective group used, as is well known in the art (see Greene and Wuts, supra). E.g. benzyl groups may be removed by hydrogenation, suitably using a catalytic transfer hydrogenation method, t-butyl groups may be removed by treatment with an acid such as trifluoroacetic acid, etc.

Compounds of formula (XI), e.g. where P is a t-butoxy group can be made for example by oxidation of a compound of formula (XII). Suitably the oxidation is carried out using copper (II) bromide with hexamethylenetetramine and a base such as DBU.

Compounds of formula (XII) may be made by condensation of compounds of formula (XIII), for example by treatment of the compound of formula (XIII) with s suitable agent such as Burgess Reagent, in an anhydrous solvent such as THF.

Compounds of formula (XIII) may be made by condensation of the acid of formula (II) above with an agent of formula NH$_2$CH(Y)CH(Z)OH. Compounds of formula NH$_2$CH(Y)CH(Z)OH are available commercially, from the literature or by routine modification thereof.

Alternatively, compounds of formula (XI) may be made by condensation of compounds of formula (XIV) (see for example, Preparation 173):

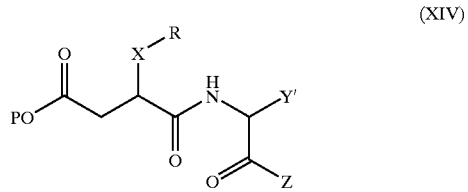

(XIV)

where Y' is a precursor moiety which can undergo functional group transformation to give Y as defined earlier to give compounds of formula (XI).

Certain other of the intermediates mentioned earlier (en route to compounds of formula (I) where W is N or CZ) can incorporate a Y' moiety instead of the Y moiety, which Y' moiety can undergo suitable functional group transformations at a suitable juncture at some point in the synthetic sequence to give intermediates or final compounds of formula (I) where the Y group is present as defined above.

Some specific routes to compounds of formula (I) (where X is propylene and R is cyclohexyl) are outlined in the following schemes, and with reference to certain Examples mentioned below, as further illustrations of the methods of preparation. As the skilled reader will recognise immediately, in these schemes the "Y" substituent in formula (I) above is designated in a different manner. The chemistry mentioned below can readily be extrapolated to give certain other compounds of formula (I) as defined above.

In the scheme below, W is N, and the Y substituent is represented as R:

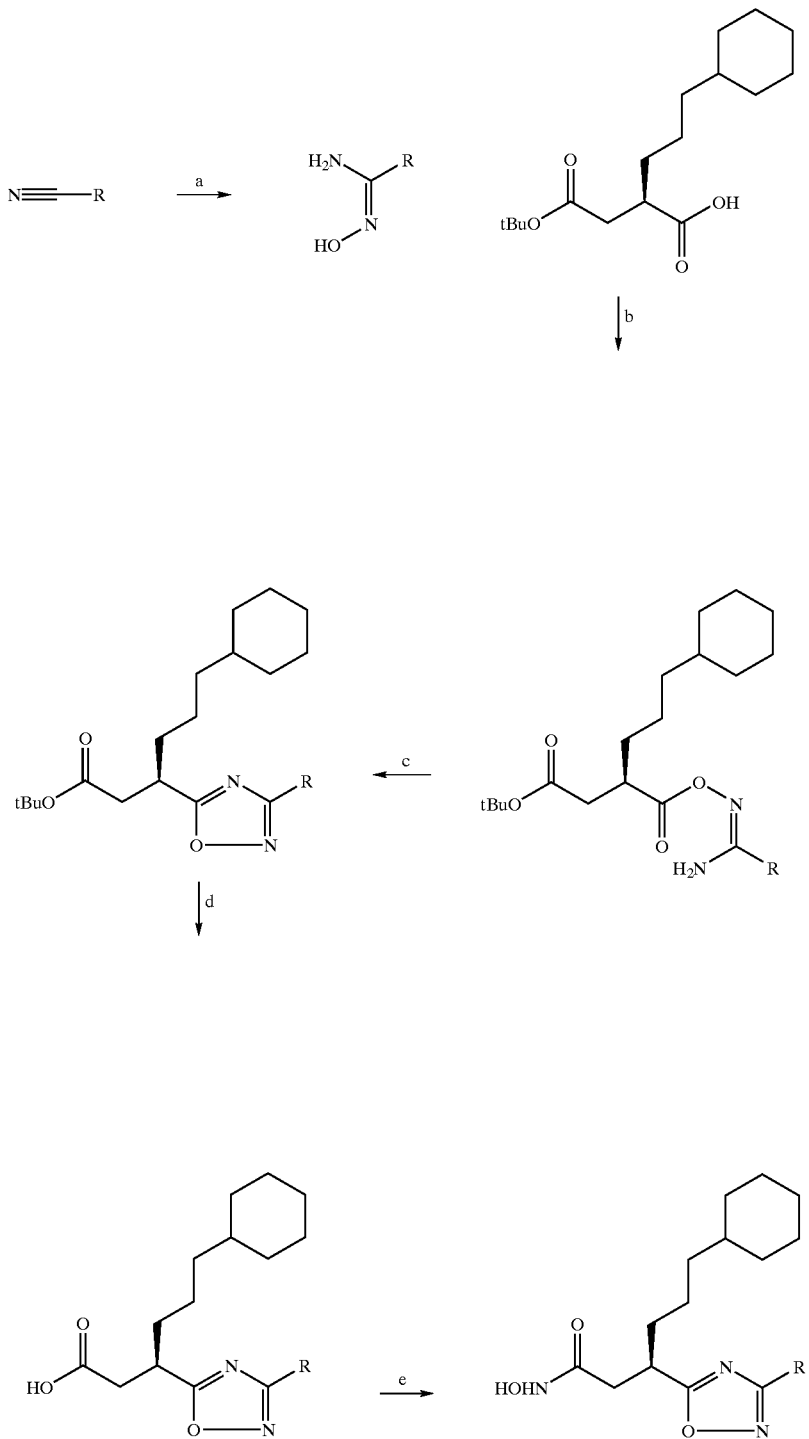
Examples 1, 12–14, 29, 53–55, 67
(a), HONH$_2$;
(b), CDI or WSCDI/HOBt;
(c), Xylene 130° C.;
(d), TFA;
(e), iBuOCOCl or CDI, then TMSONH$_2$, then MeOH.

(a), HONH$_2$; (b), CDI or WSCDI/HOBt; (c), Xylene 130° C.; (d), TFA; (e), iBuOCOCl or CDI, then TMSONH$_2$, then MeOH.
The scheme below illustrates synthesis of certain compounds where W is N and Y is an amine moiety (NB The functional group interconversions could equally be applied to the corresponding oxazoles (i.e. where W is CZ)):
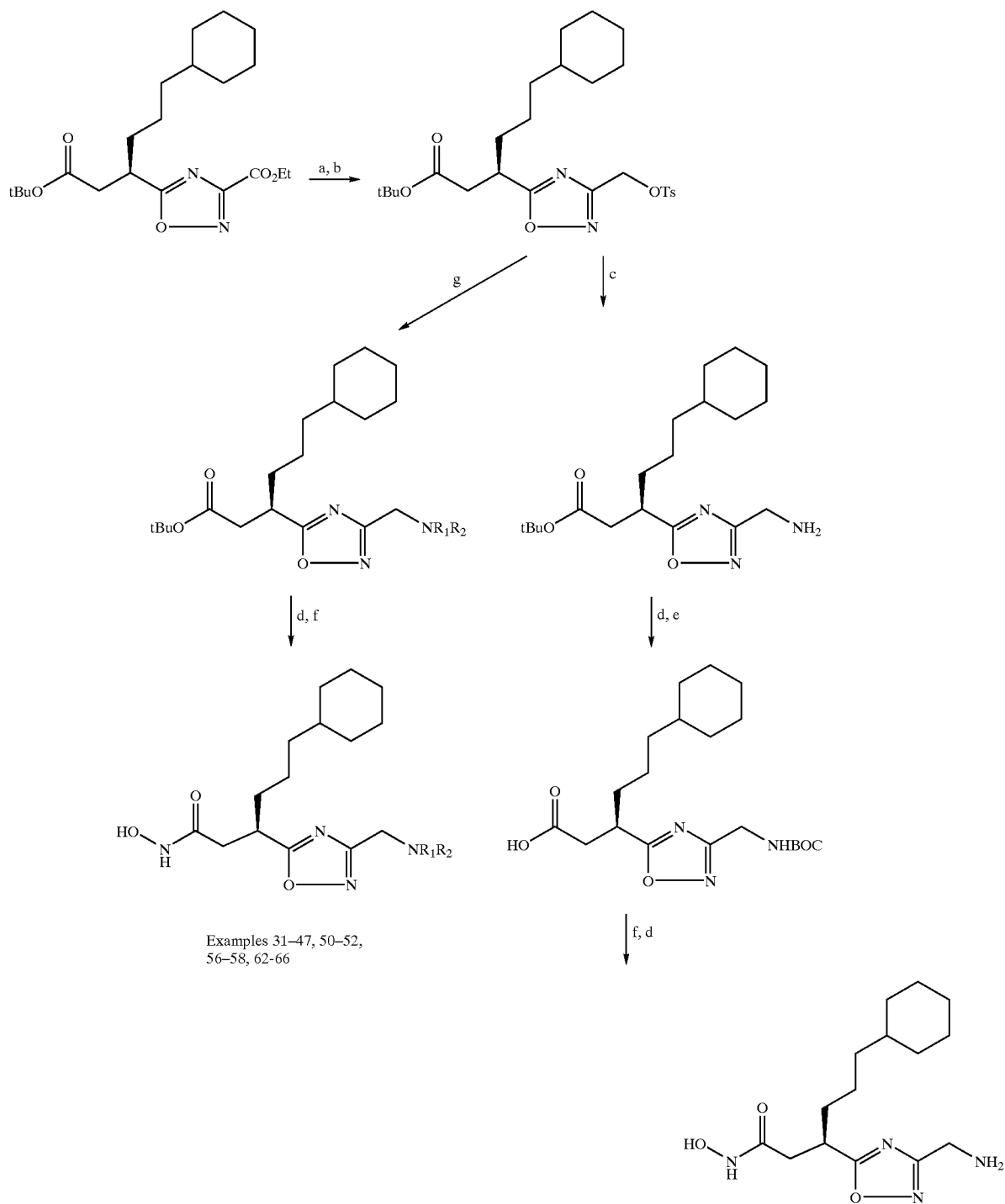
Examples 31–47, 50–52, 56–58, 62–66
Example 30

(a), $NaBH_4$; (b), TsCl; (c), $NH_3$; (d), TFA; (e), BOC-on; (f), iBuOCOCl or CDI, then $TMSONH_2$, then MeOH; (g), $NHR_1R_2$.

The scheme below represents a general route to compounds where W is N and Y incorporates a certain sulfonamide, amide, or urea moiety (NB again this chemistry will be equally applicable to the corresponding oxazole compounds, i.e. where W is CZ):

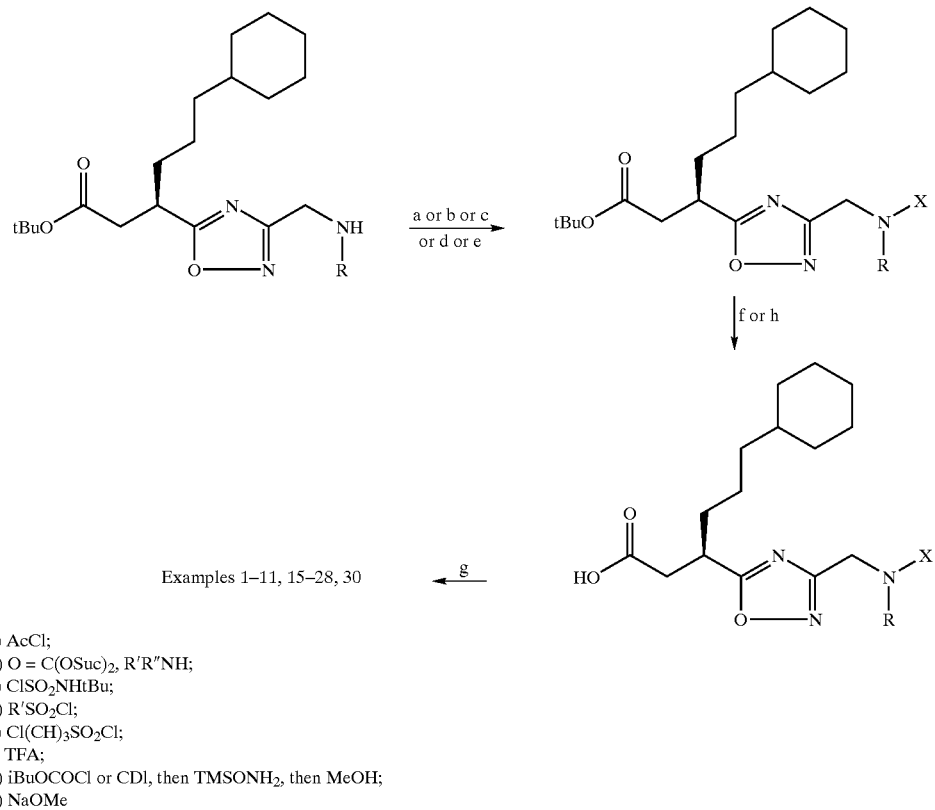

(a) AcCl;
(b) O = $C(OSuc)_2$, R'R"NH;
(c) $ClSO_2NHtBu$;
(d) $R'SO_2Cl$;
(e) $Cl(CH)_3SO_2Cl$;
(f) TFA;
(g) iBuOCOCl or CDI, then $TMSONH_2$, then MeOH;
(h) NaOMe (a) AcCl; (b) O=$C(OSuc)_2$, R'R"NH; (c) $ClSO_2NHtBu$; (d) $R'SO_2Cl$; (e) $Cl(CH)_3SO_2Cl$; (f) TFA; (g) iBuOCOCl or CDI, then $TMSONH_2$, then MeOH; (h) NaOMe The scheme below represents a general route to compounds where W is N and Y incorporates certain amide moieties (NB again this chemistry will be equally applicable to the corresponding oxazole compounds, i.e. where W is CZ):

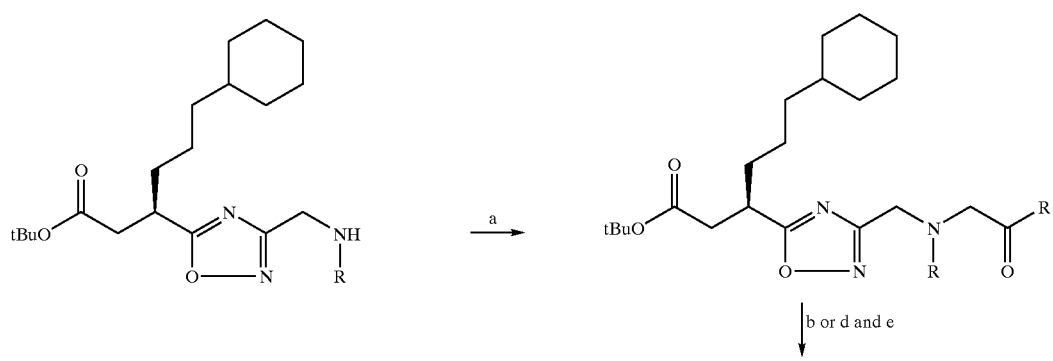

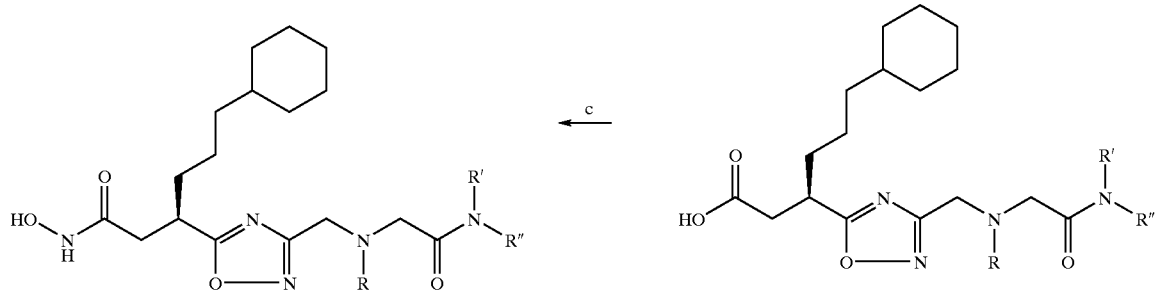

Examples 48, 49, 59–61
(a) BrCH$_2$CO$_2$Me or BrCH$_2$CONH$_2$;
(b) TFA;
(c) iBuOCOCl or CDI, then TMSONH$_2$, then MeOH.
(d) LiOH
(e) R'R"NH, WSCDI, HOBT.

(a), BrCH$_2$CO$_2$Me or BrCH$_2$CONH$_2$; (b) TFA; (c) iBuO-COCl or CDI, then TMSONH$_2$, then MeOH. (d) LiOH, (e) R'R"NH, WSCDI, HOBT.

The scheme below represents a general route to compounds where W is CZ and Y incorporates an amine moiety (NB the latter stages of this chemistry will be equally applicable to the corresponding oxadiazole compounds, i.e. where W is N):

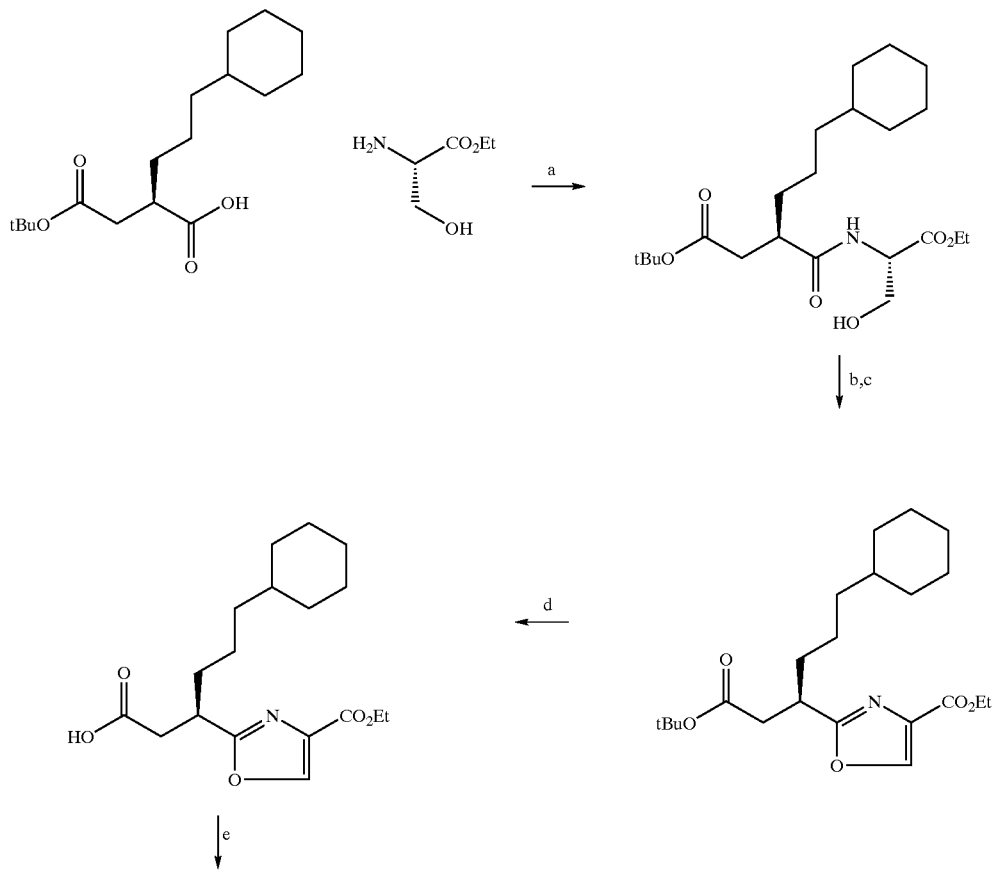

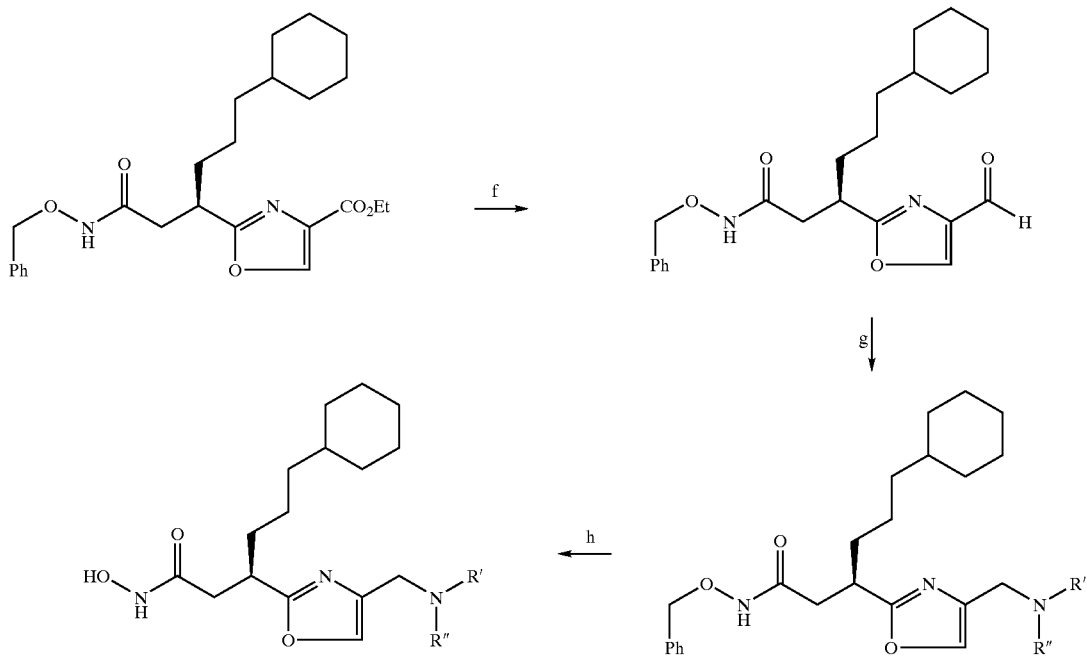

Examples 68–70
(a) HOBT, WSCDI;
(b) Burgess reagent;
(c) CuBr$_2$, DBU;
(d) TFA;
(e) BnONH$_2$, HOBT, WSCDI;
(f) DIBAL;
(g) R'R"NH, NaHB(OAc)$_3$,
(h) H$_2$, Pd(OH)$_2$/C (a) HOBT, WSCDI; (b) Burgess reagent; (c) CuBr$_2$, DBU; (d) TFA; (e) BnONH$_2$, HOBT, WSCDI; (f) DIBAL; (g) R'R"NH, NaHB(OAc)$_3$, (h) H$_2$, Pd(OH)$_2$/C Similar types of chemistry were used used in the preparation of the compounds of Examples 71 and 72.

It will be apparent to those skilled in the art that other protection and subsequent deprotection regimes during synthesis of a compound of the invention may be achieved by conventional techniques, for example as described in the volumes by Greene and Wuts, and Kocienski, supra.

Where desired or necessary the compound of formula (I) is converted into a pharmaceutically acceptable salt thereof. A pharmaceutically acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent.

Certain compounds of the invention may be interconverted into certain other compounds of the invention by methods mentioned in the Examples and Preparations, and well-known methods from the literature.

Compounds of the invention are available by either the methods described herein in the Methods, Examples and Preparations or suitable adaptation thereof using methods known in the art. It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

The compounds, salts, solvates and prodrugs of the invention may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base. In certain cases preferential crystallisation of one of the enantiomers can occur from a solution of a mixture of enantiomers, thus enriching the remaining solution in the other enantiomer.

For human use, the compounds of formula (I) or their salts can be administered alone, but will generally be administered in admixture with a pharmaceutically acceptable diluent or carrier selected with regard to the intended route of administration and standard pharmaceutical practice.

For example, they can be administered orally, including bucally and sublingually. The compounds or salts can be injected parenterally, for example, intravenously, intradermally intramuscularly or subcutaneously. They can be administered topically and/or transdermally. The compound or salt could also be administered intraocularly for ophthalmic use. For certain uses, vaginal, rectal and nasal (e.g. by inhalation of a dry powder or aerosol) administration would be suitable.

Formulations may be of immediate-, delayed-, modified-, sustained-, pulsed- or controlled-release type, and may be sterile or preserved or self-preserving.

Suitable formulations for oral administration would include tablets containing such excipients as starch or lactose, capsules or ovules either alone or in admixture with excipients, or in the form of elixirs, solutions or suspensions containing flavouring or colouring agents. The compound or salt could be incorporated into capsules or tablets for targetting the colon or duodenum via delayed dissolution of said capsules or tablets for a particular time following oral administration. Dissolution could be controlled by susceptibility of the formulation to bacteria found in the duodenum or colon, so that no substantial dissolution takes places before reaching the target area of the gastrointestinal tract.

The compounds or salts can be administered parenterally, by injection for example, intravenously, intradermally intramuscularly or subcutaneously. For parenteral administration, they are best used in the form of a sterile, preserved or self-preserving aqueous solution or suspension which may contain other substances, for example, enough salt or glucose to make the solution isotonic with blood. The compounds or salts may be used in combination with cyclodextrins. By injection we include standard injection techniques, and also needlefree injector or implant injection techniques.

The compounds or salts can be administered topically, and/or transdermally, in the form of sterile or preserved or self-preserving creams, gels, suspensions, lotions, solutions, sponges, fibres, microemulsions, films, ointments, dusting powders, sprays, foams, mousses, drug-incorporated dressings, skin patches, ointments such as petrolatum or white soft paraffin based ointments or via a skin patch or other device. They could be administered directly onto a wound. The compounds or salts may be delivered using iontophoresis, electroporation, phonophoresis and sonophoresis. They could be incorporated into a coated suture. For example they can be incorporated into a lotion or cream consisting of an aqueous or oily emulsion of mineral oils; sorbitan monostearate; polysorbate 60; cetyl esters wax; cetearyl alcohol; 2-octyldodecanol; benzyl alcohol; water; polyethylene glycols and/or liquid paraffin, or they can be incorporated into a suitable ointment consisting of one or more of the following - mineral oil; liquid petrolatum; white petrolatum; propylene glycol; polyoxyethylene polyoxypropylene compound; emulsifying wax and water, or as a gel such as a hydrogel with cellulose or polyacrylate derivatives or other viscosity modifiers, or as a dry powder or liquid spray or aerosol with butane/propane, HFA, CFC, $CO_2$ or other suitable propellant, optionally also including a lubricant such as sorbitan trioleate, or as a drug-incorporated dressing either as a tulle dressing, with white soft paraffin or polyethylene glycols impregnated gauze dressings or with a gel such as a hydrogel, hydrocolloid, alginate or film dressings. The compound can be dissolved or suspended in, for example, water, appropriate buffers, alcohols (e.g. ethanol, isopropyl alcohol, benzyl alcohol), glycols (e.g. propylene glycol, glycerol, polyethylene glycols), diethylene glycol ethers, poloxamers (polyoxyethylene polyoxypropylene compounds), isopropylmyristate, isopropylpalmitate, fixed oils (e.g. castor oil), mineral oil, silicone oils (e.g. dimeticone), other synthetic mono-/di-/triglycerides, fatty acids, liquid petrolatum, white petrolatum, liquid paraffin, emulsifying wax, sorbitan monostearate, polysorbates, cetostearyl alcohol, cetyl alcohol, 2-octyldodecanol or combinations thereof. Suitable viscosity modifiers, for example cellulose or polyacrylate derivatives can also be incorporated. Penetration enhancers may also be used.

The compound or salt could also be administered intraocularly for ophthalmic use e.g. in a lens implant, ointment, micronised suspension, absorbable gel sponges, implants, particulate or vesicular systems such as niosomes or liposomes, or as an eye drop with appropriate buffers, viscosity modifiers (e.g. cellulose or polyacrylate derivatives), preservatives (e.g. benzalkonium chloride (BZK)) and agents to adjust tonicity (e.g. sodium chloride). The compound may be used in combination with cyclodextrins. In addition, compounds may be delivered by iontophoresis. Such formulation techniques are well-known in the art.

For certain uses, vaginal, rectal and nasal (e.g. by inhalation of a dry powder or aerosol) administration would be suitable.

All such formulations may also contain auxiliaries such as appropriate stabilisers, preservatives such as antioxidants and chelating agents, flavours, colourings, cyclodextrins, etc. Such auxiliaries are well-known in the formulation art and the skilled person will be able to choose from such auxiliaries based on the properties of the compound or salt to be administered, the administration route, etc.

For oral and parenteral administration to human patients, the daily dosage level of the compounds of formula (I) or their salts or prodrugs will be from 0.001 to 20, preferably from 0.01 to 20, more preferably from 0.1 to 10, and most preferably from 0.5 to 5 mg/kg with respect to the active compound (in single or divided doses). Thus tablets or capsules of the compounds will contain from 0.1 to 500, preferably from 50 to 200, mg of active compound for administration singly or two or more at a time as appropriate.

For topical administration to human patients with acute/surgical wounds or scars, the daily dosage level of the compounds, in suspension or other formulation, could be from 0.01 to 50 mg/ml, preferably from 0.3 to 30 mg/ml.

For treatment of a wound, the dosage will vary with the size of the wound, whether or not the wound is open or closed or partially closed, and whether or not the skin is intact.

The physician in any event will determine the actual dosage which will be most suitable for a an individual patient and it will vary with the condition to be treated, the age, weight and response of the particular patient, as well as the efficacy of the drug compound. The above dosages are exemplary of the average case; there can of course be individual instances where higher or lower dosage ranges are merited, and such are within the scope of this invention.

Biological Test Methods
PCP Inhibition

In order to determine potency of PCP inhibitors a fluorogenic PCP cleavage assay was used. This assay is based on the template of Beekman et al. (FEBS Letters (1996), 390: 221–225) using a fluorogenic substrate. The substrate (Dabcyl-Arg-Tyr-Tyr-Arg-Ala-Asp-Asp-Ala-Asn-Val-Glu (EDANS)-$NH_2$) contains the cleavage site of human PCP (Hojima et al., J Biol Chem (1985), 260: 15996–16003). Human PCP has been purified from supernatant of stable transfected CHO cells using hydrophobic interaction column followed by Superdex 200 gel filtration. 4 $\mu$g total protein of this enzyme preparation was incubated with various concentrations of the substance to be tested and $3\times10^{-6}$ M substrate in assay buffer (50 mM Tris-Base, pH 7.6 containing 150 mM NaCl, 5 mM $CaCl_2$, 1 $\mu$M $ZnCl_2$ and 0.01% Brij 35). The assay was performed in 96-well black fluorimeter plates and fluorescence was read continuously in a fluorimeter over 2.5 hours ($\lambda_{ex}$=340 nm, $\lambda_{em}$=485 nm) at a constant 37° C. with shaking. Release of the fluorogenic signal was in linear correlation to PCP activity. Reading of the mean velocity from 30 min after start of experiment until 2.5 hours was calculated by the Biolise software. $IC_{50}$ values were calculated by plotting % inhibition values against compound concentration using Tessela add in for Excel spreadsheet. Example compounds were tested and were found to have $IC_{50}$ values vs. PCP of 1 µM or less.

MMP Inhibition

The ability of compounds to inhibit the cleavage of fluorogenic peptides by MMPs 1, 2, 9, and 14 is described below. The assays for MMPs 2, 9, and 14 are based upon the original protocol described by Knight et al. (Fed.Euro.Biochem.Soc., 296 (3), 263–266; 1992) with the slight modifications given below.

Inhibition of MMP-1

(i) Enzyme Preparation

Catalytic domain MMP-1 was prepared at Pfizer Central Research. A stock solution of MMP-1 (1 µM) was activated by the addition of aminophenylmercuric acetate (APMA), at a final concentration of 1 mM, for 20 minutes at 37° C. MMP-1 was then diluted in Tris-HCl assay buffer (50 mM Tris, 200 mM NaCl, 5 mM $CaCl_2$, 20 µM $ZnSO_4$, 0.05% Brij 35) pH 7.5 to a concentration of 10 nM. The final concentration of enzyme used in the assay was 1 nM.

(ii) Substrate

The fluorogenic substrate used in this assay was Dnp-Pro-cyclohexyl-Ala-Gly-Cys(Me)-His-Ala-Lys(N-Me-Ala)-$NH_2$ as originally described by Bickett et al (Anal. Biochem, 212, 58–64, 1993). The final substrate concentration used in the assay was 10 µM.

(iii) Determination of Enzyme Inhibition

Test compounds were dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence (substrate cleavage) using a fluorimeter (Fluostar; BMG LabTechnologies, Aylesbury, UK) at an excitation wavelength of 355 nm and emission wavelength of 440 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-2 and MMP-9

(i) Enzyme Preparation

Catalytic domain MMP-2 and MMP-9 were prepared at Pfizer Central Research. A stock solution of MMP-2/MMP-9 (1 M) was activated by the addition of aminophenylmercuric acetate (APMA). For MMP-2 and MMP-9, a final concentration of 1 mM APMA was added, followed by incubation for 1 hour at 37° C. The enzymes were then diluted in Tris-HCl assay buffer (100 mM Tris, 100 mM NaCl, 10 mM $CaCl_2$ and 0.16% Brij 35, pH 7.5), to a concentration of 10 nM. The final concentration of enzyme used in the assays was 1 nM.

(ii) Substrate

The fluorogenic substrate used in this screen was Mca-Arg-Pro-Lys-Pro-Tyr-Ala-Nva-Trp-Met-Lys(Dnp)-$NH_2$ (Bachem Ltd, Essex, UK) as originally described by Nagase et al (J.Biol.Chem., 269(33), 20952–20957, 1994). This substrate was selected because it has a balanced hydrolysis rate against MMPs 2 and 9 ($k_{cat}/k_m$ of 54,000, 59,400 and 55,300 $s^{-1}$ $M^{-1}$ respectively). The final substrate concentration used in the assay was 5 µM.

(iii) Determination of Enzyme Inhibition

Test compounds were dissolved in dimethyl sulphoxide and diluted with test buffer solution (as above) so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence using a fluorimeter (Fluostar; BMG LabTechnologies, Aylesbury, UK) at an excitation wavelength of 328 nm and emission wavelength of 393 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-14

(i) Enzyme Preparation

Catalytic domain MMP-14 was purchased from Prof. Tschesche, Department of Biochemistry, Faculty of Chemistry, University of Bielefeld, Germany. A 10 M enzyme stock solution was activated for 20 minutes at 25° C. following the addition of 5 g/ml of trypsin (Sigma, Dorset, UK). The trypsin activity was then neutralised by the addition of 50 g/ml of soyabean trypsin inhibitor (Sigma, Dorset, UK), prior to dilution of this enzyme stock solution in Tris-HCl assay buffer (100 mM Tris, 100 mM NaCl, 10 mM $CaCl_2$ and 0.16% Brij 35, pH 7.5) to a concentration of 10 nM. The final concentration of enzyme used in the assay was 1 nM.

(ii) Substrate

The fluorogenic substrate used in this screen was Mca-Pro-Leu-Gly-Leu-Dpa-Ala-Arg-$NH_2$ (Bachem Ltd, Essex, UK) as described by Will et al (J.Biol.Chem., 271(29), 17119–17123, 1996). The final substrate concentration used in the assay was 10 µM.

Determination of enzyme inhibition by test compounds was performed in the same manner as described for MMPs-2 and -9 above.

All the compounds of the Examples had $IC_{50}$ values vs PCP of 0.5 µM or less. The compounds of Examples 6, 17, and 72 had $IC_{50}$ values vs PCP of 107 nM, 98 nM and 37 nM respectively.

All references mentioned herein in this specification are incorporated by reference in their entirety.

The compounds of the invention are illustrated by the Examples below.

EXAMPLES AND PREPARATIONS

Melting points were determined using open glass capillary tubes and a Gallenkamp melting point apparatus and are uncorrected. Nuclear magnetic resonance (NMR) data were obtained using Varian Unity Inova-400, Varian Unity Inova-300 or Bruker AC300 spectrometers and are quoted in parts per million from tetramethylsilane. Mass spectral (MS) data were obtained on a Finnigan Mat. TSQ 7000 or a Fisons Instruments Trio 1000. The calculated and observed ions quoted refer to the isotopic composition of lowest mass. Infra red (IR) spectra were measured using a Nicolet Magna 550 Fourier transform infra-red spectrometer. Flash chromatography refers to column chromatography on silica gel (Kieselgel 60, 230–400 mesh, from E. Merck, Darmstadt. Kieselgel 60 $F_{254}$ plates from E. Merck were used for TLC, and compounds were visualised using UV light, 5% aqueous potassium permanagate or Dragendorff's reagent (oversprayed with aqueous sodium nitrite). Thermal analyses by Differential Scanning Calorimetry (DSC) and ThermoGravimetric Analysis (TGA) were obtained using Perkin Elmer DSC7 and TGA7.

Moisture sorption characteristics were recorded using Surface Measurement Systems Ltd. Automated Water Sorption Analyser DVS 1. Water content was determined on a Mitsubishi CA100 (Coulometric Karl Fisher Titrator). Powder X-ray diffraction (PXRD) pattern was determined using a Siemens D5000 powder X-ray diffractometer fitted with an automatic sample changer, a theta—theta goniometer, automatic beam divergence slits, a secondary monochromator and a scintillation counter. Other measurements were taken using standard equipment. Hexane refers to a mixture of hexanes (hplc grade) b.p. 65–70° C. "Ether" and "Et$_2$O" refers to diethyl ether. Acetic acid refers to glacial acetic acid. 1-Hydroxy-7-aza-1H-1,2,3-benzotriazole (HOAt). "HOBt" is 1-hydroxy-1H-1,2,3-benzotriazole. N-[(dimethylamino)-1H-1,2,3-triazolo[4,5-b]pyridin-1-ylmethylene]-N-methylmethaninium hexafluorophosphate N-oxide (HATU) and 7-azabenzotriazol-1-yloxytris (pyrrolidino)phosphonium hexafluorophosphate (PyAOP) were purchased from PerSeptive Biosystems U.K. Ltd. "DIPE" refers to diisopropyl ether. Reverse-phase silica gel for flash chromatography was obtained from Fluka (Fluka 100, C$_{18}$, 40–63 μ). "DCM" is dichloromethane. "THF" is tetrahydrofuran. "WSCDI" is 1-(3-dimethylaminopropyl)-3-ethylcarbodiimide hydrochloride. "CDI" is carbonyldiimidazole. "EtOAc" is ethyl acetate. "MeOH" is methanol. "DMSO" is dimethylsulphoxide. "ACE-Cl" is 1-chloroethyl chloroformate. "NMM" is N-methylmorpholine. "Pentane" refers to High Performance Liquid Chromatography (HPLC) grade n-pentane (b.pt.35–37° C.). Nomenclature has been allocated using the commercially available ACD program. Standard abbreviations are used throughout, e.g. "Me" is methyl, "Et" is ethyl, "Pr" is propyl, "Ph" is phenyl, etc.

[a]HPLC autopurification performed using 2 columns—Phenomonex LUNA C8 150×21.2 mm, 10 μm and Phenomonex MAGELLEN C18 150×21.2 mm, 5 μm, eluting with a gradient system of organic solvent [ammonium acetate (aq) 100 mM:acetonitrile (1:9)]:aqueous solvent [ammonium acetate (aq) 100 mM:acetonitrile (9:1)]

[b]HPLC autopurification performed using 2 columns—Phenomonex LUNA C8 150×21.2 mm, 10 μm and Phenomonex MAGELLEN C18 150×21.2 mm, 5 μm, eluting with a gradient system of organic solvent (acetonitrile):aqueous solvent (0.1% aqueous trifluoroacetic acid)

Example 1

(3R)-6-cyclohexyl-N-hydroxy-3-(3-{[(methylsulfonyl)amino]methyl}-1,2,4-oxadiazol-5-yl)hexanamide

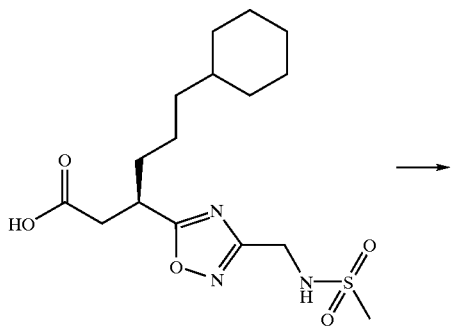

→

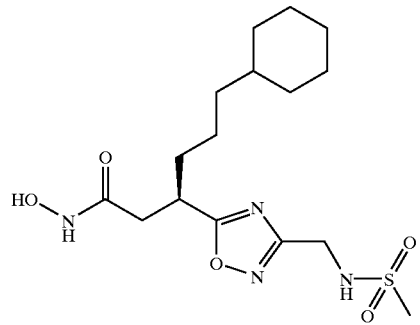

METHOD A. A solution of (3R)-6-cyclohexyl-3-(3-{[(methylsulfonyl)amino]methyl}-1,2,4-oxadiazol-5-yl) hexanoic acid (preparation 4) (6.80 g, 18.2 mmol) and 2,6-lutidine (2.3 ml, 20.0 mmol) in THF (100 ml) at 0° C., under a nitrogen atmosphere was treated with i-butyl chloroformate (2.6 ml, 20.0 mmol) and stirred at 0° C. for 1.5 hours. o-(trimethylsilyl)hydroxylamine (4.9 ml, 40.0 mmol) was added and the reaction mixture was stirred for 18 hours warming to room temperature over this time. MeOH was added and the reaction mixture stirred for a further 2 hours. The solvent was removed under reduced pressure. The yellow solid was dissolved in EtOAc (400 ml), washed with dilute HCl (150 ml 2M HCl+200 ml H$_2$O) and brine, dried over MgSO$_4$ and filtered. The solvent was remove under reduced pressure. The solid was recrystallised from hot EtOAc to afford the title compound as a white solid (4.74 g, 67%).

METHOD B. CDI (7.6 g, 47 mmol) was added portionwise over 2 min to a solution of (3R)-6-cyclohexyl-3-(3-{[(methylsulfonyl)amino]methyl}-1,2,4-oxadiazol-5-yl) hexanoic acid (preparation 4) (14.0 g, 42 mmol) in THF (160 ml), at ambient temperature, under a nitrogen. The mixture was stirred at ambient temperature for 30 min and then cooled to 0° C. Aqueous hydroxylamine (50%, 13.1 ml, 0.21 mol) was added between 0 and 5° C. and the reaction mixture was stirred for 18 hours warming to room temperature over this time. Aqueous citric acid solution (10%, 160 ml) was added and the mixture was extracted with ethyl acetate (2×160 ml). The combined organic fractions were washed with demineralised water (160 ml) and then concentrated in vacuo to a colourless solid. Ethyl acetate (64 ml) was added and the mixture was stirred at ambient temeprature for 1 hour and then filtered. The residue was dried in vacuo at 45° C. to afford the title compound as an off-white solid (14.2 g, 85%).

Mpt: 115–116° C.

$^1$H nmr: (d$_6$DMSO) 0.80 (2H, m), 1.00–1.15 (8H, m), 1.50–1.70 (8H, m), 2.50–2.55 (2H, obs), 2.89 (3H, s), 3.41 (1H, m), 4.24 (2H, d), 7.63 (1H, brs), 8.62 (1H, brs), 10.38 (1H, brs)

MS: 411 (MNa$^+$)

CHN: Found: C49.42%; H7.40%; N14.48%; C$_{16}$H$_{28}$N$_4$O$_5$S requires C49.47%; H7.26%; N14.42%

METHOD C (Alternative Synthesis):

Ethyl chloroformate (0.11 ml, 1.2 mmol) was added to a stirred solution of (3R)-6-cyclohexyl-3-(3-{[(methylsulfonyl)amino]methyl}-1,2,4-oxadiazol-5-yl) hexanoic acid (preparation 4) (0.40 g, 1.1 mmol) in THF (10 ml) and ether (10 ml) at 0° C. under a nitrogen atmosphere. The reaction was stirred at 0° C. for 40 minutes then aqueous hydroxylamine (80 μl of 50% solution by weight, 1.2 mmol)

Example 2

(3R)-6-cyclohexyl-N-hydroxy-3-(3-{[methyl(methylsulfonyl)amino]methyl}-5,2,4-oxadiazol-5-yl)hexanamide

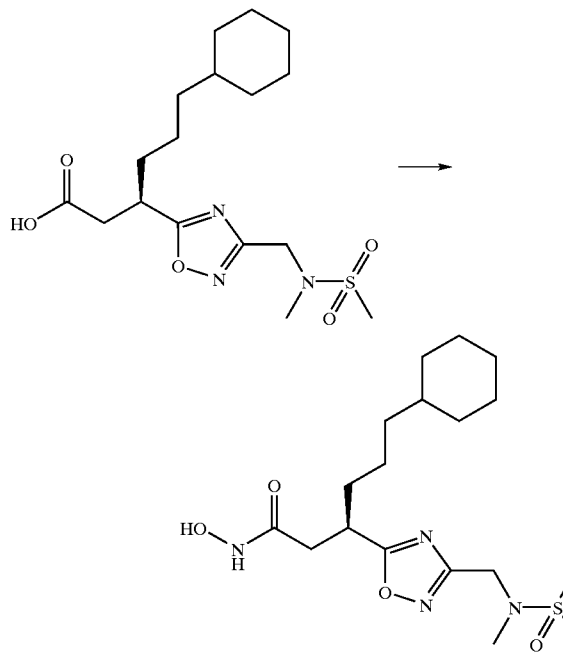

Method is the same as for Example 1 using (3R)-6-cyclohexyl-3-(3-{[methyl(methylsulfonyl)amino]methyl}-1,2,4-oxadiazol-5-yl)hexanoic acid (preparaton 7) (225 mg, 0.58 mmol) as starting material.

Purification: The crude material was purified on a silica column eluting with a solvent gradient of DCM: MeOH (100:0) gradually changing to (97:3) to yield the title compound as sticky colourless gum (180 mg, 77%)

$^1$H nmr: (d$_6$DMSO) 0.80 (2H, m), 1.05–1.30 (8H, m), 1.50–1.70 (7H, m), 2.52 (2H, obs), 2.80 (3H, s), 2.93 (3H, s), 3.42 (1H, m), 4.44 (1H, m), 8.62 (1H, brs), 10.38 (1H, brs).

MS: 425 (MNa$^+$)

CHN: Found: C50.87%; H7.69%; N13.47%; C$_{17}$H$_{30}$N$_4$O$_5$S. 0.1H$_2$O requires C50.50%; N13.86%

Example 3

(3R)-6-cyclohexyl-3-(3-{[(ethylsulfonyl)amino]methyl}-1,2,4-oxadiazol-5-yl)-N-hydroxyhexanamide

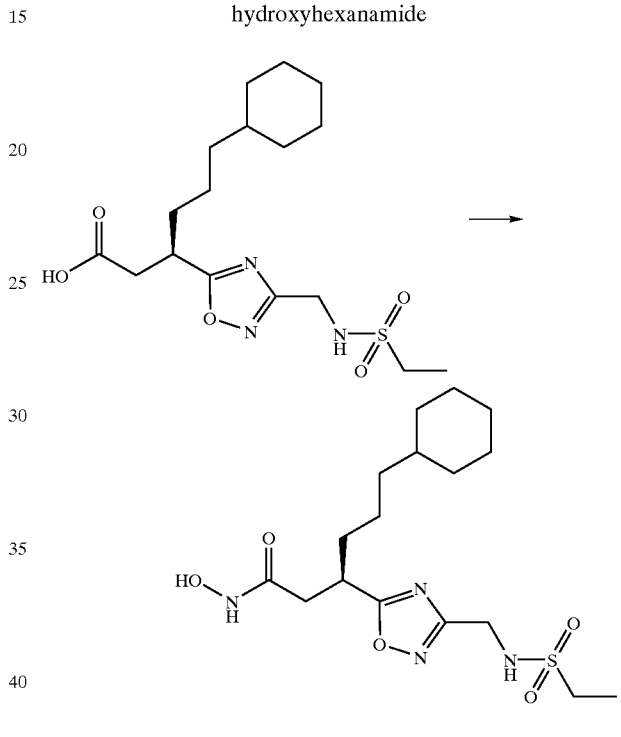

Method same is for Example 1 using (3R)-6-cyclohexyl-3-(3-{[(ethylsulfonyl)amino]methyl}-1,2,4-oxadiazol-5-yl)hexanoic acid (preparation 9) (143 mg, 0.37 mmol) as starting material.

Purification: Crude material was purified on a silica column eluting with a solvent gradient of DCM:MeOH (100:0) gradually changing to (95:5) to afford the title compound as a sticky yellow gum (103 mg, 69%).

$^1$H nmr: (d$_6$DMSO) 0.80 (2H, m), 1.00–1.25 (11H, m), 1.55–1.70 (7H, m), 2.52 (2H, obs), 300 (2H, q), 3.41 (1H, m), 4.24 (2H, d), 7.67 (1H, brs), 10.38 (1H, brs).

MS: 403 (MH$^+$)

Accurate mass: Found 425.1828 (MNa$^+$), Calculated C$_{17}$H$_{30}$N$_4$O$_5$S 425.1829 (MNa$^+$)

Example 4

(3R)-6-cyclohexyl-N-hydroxy-3-(3-{[(isopropylsulfonyl)amino]methyl}-1,2,4-oxadiazol-5-yl)hexanamide

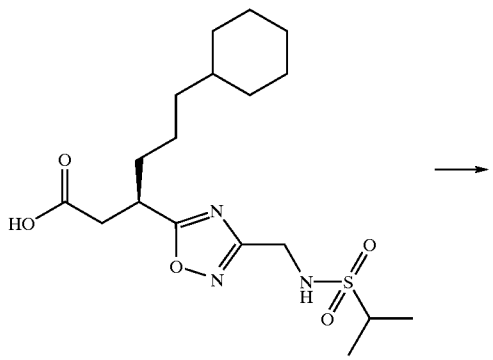

Method same as for example 1 using (3R)-6-cyclohexyl-3-(3-{[(isopropylsulfonyl)amino]methyl}-1,2,4-oxadiazol-5-yl)hexanoic acid (prepapration 11) (88 mg, 0.22 mmol) as starting material.

Purification: The crude material was purified on a silica column eluting with a solvent gradient of DCM:MeOH (100:0) gradually changing to (95:5) to afford the title compound as an orange gum (76 mg, 83%).

$^1$H nmr: (CD$_3$OD) 0.80–0.90 (2H, m), 1.10–1.30 (14H, m+d), 1.60–180 (7H, m), 2.50 (1H, dd), 2.60 (1H, dd), 3.20 (1H, m), 3.50 (1H, m), 4.35 (2H, s).

MS: 439 (MNa$^+$)

CHN: Found: C50.61%; H7.72%; N12.83%; C$_{18}$H$_{32}$N$_4$O$_5$S. 0.3 H$_2$O. 0.1 DCM requires C50.51%; H7.68%; N13.02%

Example 5

(3R)-6-cyclohexyl-N-hydroxy-3-(3-{[(phenylsulfonyl)amino]methyl}-1,2,4-oxadiazol-5-yl)hexanamide

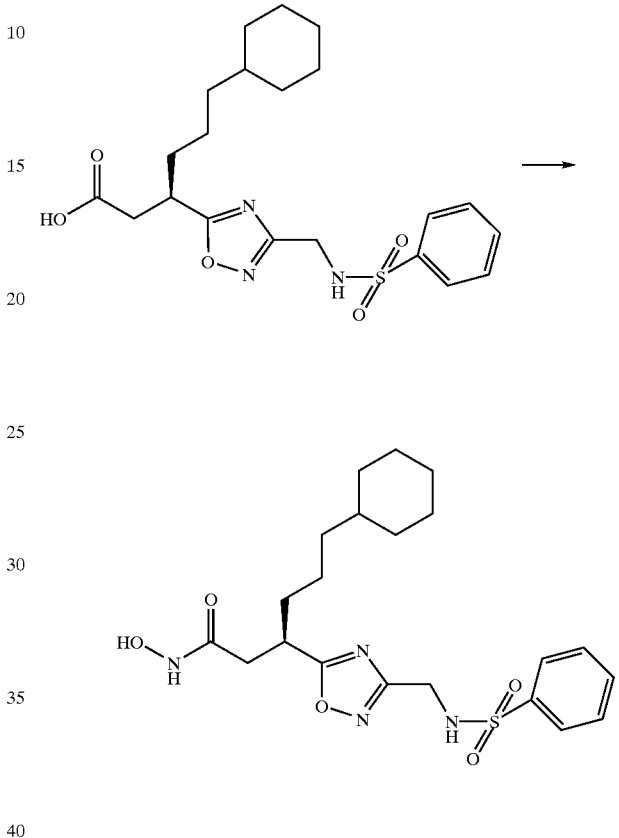

Method same as for example 1 using (3R)-6-cyclohexyl-3-(3-{[(phenylsulfonyl)amino]methyl}-1,2,4-oxadiazol-5-yl)hexanoic acid (preparation 13) (149 mg, 0.34 mmol) as starting material.

Purification: The crude material was purified on a silica column eluting with a solvent gradient of DCM:MeOH (100:0) gradually changing to (95:5) to afford the title compound as a colourless gum (116 mg, 75%).

$^1$H nmr: (d$_6$DMSO) 0.80 (2H, m), 1.00–1.20 (8H, m), 1.50–1.70 (7H, m), 2.38 (1H, dd), 2.52 (1H, obs), 3.37 (1H, m), 4.11 (2H, s), 7.48–7.62 (3H, m), 7.78 (2H, d), 8.25 (1H, brs), 10.38 (1H, brs).

MS: 473 (MNa$^+$)

Accurate mass: Found 451.2004 (MH$^+$), Calculated C$_{21}$H$_{30}$N$_4$O$_5$S 451.2010 (MH$^+$)

Example 6

(3R)-6-cyclohexyl-N-hydroxy-3-(3-{[(2-pyridinyisulfonyl)amino]methyl}-1,2,4-oxadiazol-5-yl)hexanamide

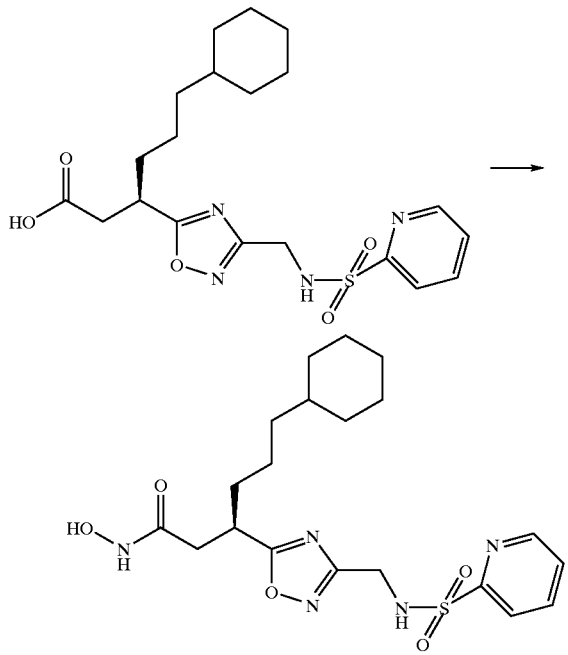

Method same as for example 1 except using NMM as the base and (3R)-6-cyclohexyl-3-(3-{[(2-pyridinylsulfonyl)amino]methyl}-1,2,4-oxadiazol-5-yl)hexanoic acid (preparation 15) (231 mg, 0.53 mmol) as the starting material.

Purification: Crude material was purified on a silica column eluting with Et$_2$O:MeOH (19:1) to afford the title compound as a white foam (36 mg).

$^1$H nmr: (d$_6$DMSO) 0.80 (2H, m), 1.05–1.25 (8H, m), 1.50–1.70 (7H, m), 2.38 (2H, m), 3.37 (1H, m), 4.28 (2H, d), 7.60 (1H, m), 7.88 (1H, d), 8.03 (1H, t), 8.44 (1H, brs), 8.62 (2H, brd), 10.38 (1H, brs).

MS: 474 (MNa$^+$)

Example 7

(3R)-6-cyclohexyl-N-hydroxy-3-(3-{[(3-pyridinylsulfonyl)amino]methyl}-1,2,4-oxadiazol-5-yl)hexanamide

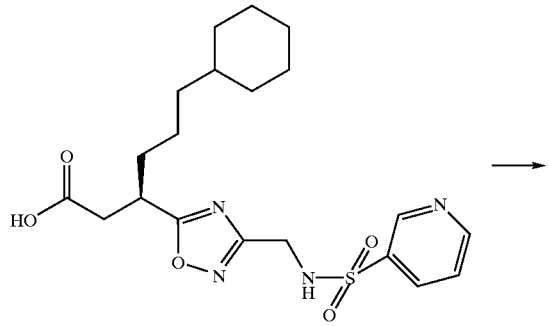

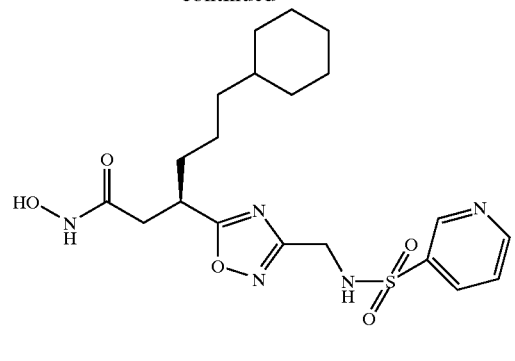

A solution of (3R)-6-cyclohexyl-3-(3-{[(3-pyridinylsulfonyl)amino]methyl}-1,2,4-oxadiazol-5yl) hexanoic acid (preparation 17) (167 mg, 0.33 mmol) DCM (6 ml) under a nitrogen atmosphere was treated with CDI (80 mg, 0.49 mmol) and stirred at room temperature for 1 hour. o-(trimethylsilyl)hydroxylamine (121 μl, 0.99 mmol) was added and the reaction mixture was stirred for 18 hours. MeOH (3 ml) was added and the reaction mixture stirred for a further 2 hours. The solvent was removed under reduced pressure. The residue was dissolved in EtOAc, washed with H$_2$O and brine, dried over MgSO$_4$ and filtered. The solvent was removed under reduced pressure. The crude material was purified on a silica column eluting with a solvent gradient of DCM:MeOH (100:0) gradually changing to (95:5) to afford the title compound as a white solid (100 mg, 67%).

$^1$H nmr: (d$_6$DMSO) 0.80 (2H, m), 1.00–1.30 (8H, m), 1.50–1.70 (7H, m), 2.38 (2H, brm), 3.35 (1H, m), 4.21 (2H, s), 7.59 (1H, m), 8.11 (1H, d), 8.63 (1H, brs), 8.77 (1H, d), 8.90 (1H, s).

MS: 450 (M–H)

Accurate mass: Found 452.1947 (MH$^+$), Calculated C$_{20}$H$_{29}$N$_5$O$_5$S 452.1962

Example 8

(3R)-6-cyclohexyl-N-hydroxy-3-[3-({[(1-methyl-1H-imidazol-4-yl)sulfonyl]amino}methyl)-1,2,4-oxadiazol-5-yl]hexanamide

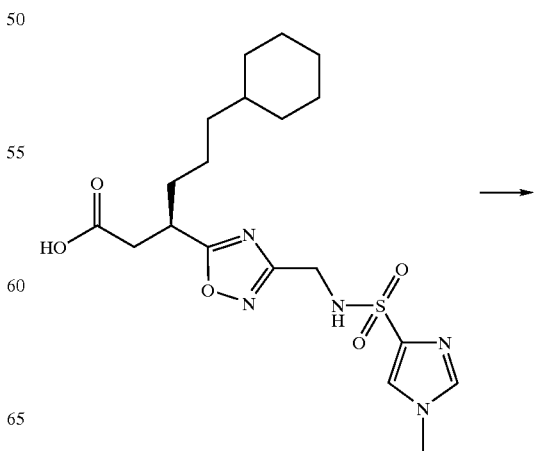

37
-continued

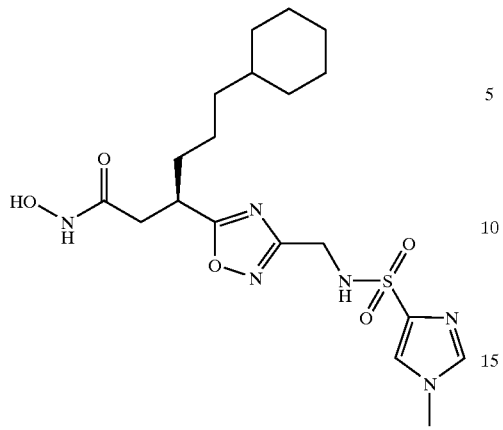

Method same as for example 7 using (3R)-6-cyclohexyl-3-[3-({[(1-methyl-1H-imidazol-4-yl)sulfonyl]amino}methyl)-1,2,4-oxadiazol-5-yl]hexanoic acid (preparation 20) (205 mg, 0.43 mmol) as starting material.

Purification: Crude material purified on a silca column eluting with a solvent gradient of DCM:MeOH:NH₃ (98:2:0) gradually changing to (90:10:1) to afford the title compound as a white solid (105 mg, 54%)

¹H nmr: (d₆DMSO) 0.80 (2H, m), 1.05–1.25 (8H, m), 1.50–1.70 (7H, m), 2.41 (2H, m), 3.40 (1H, m), 3.70 (3H, s), 4.14 (2H, d), 7.66 (1H, s), 7.71 (1H, s), 7.98 (1H, brs), 8.66 (1H, brs), 10.39 (1H, brs).

MS: 477 (MNa⁺)

CHN: Found: C49.86%; H6.67%; N18.28%; C₁₉H₃₀N₆O₅S. 0.1 H₂O requires C50.01%; H6.67%; N18.42%

Example 9

(3R)-6-cyclohexyl-N-hydroxy-3-(3-{[(1H-pyrazol-4-ylsulfonyl)amino]methyl}-1,2,4-oxadiazo-5-yl)hexanamide

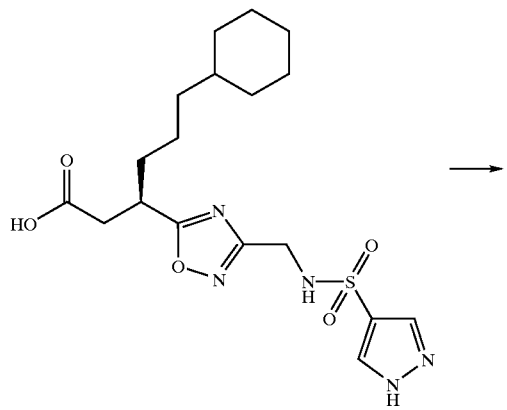

38
-continued

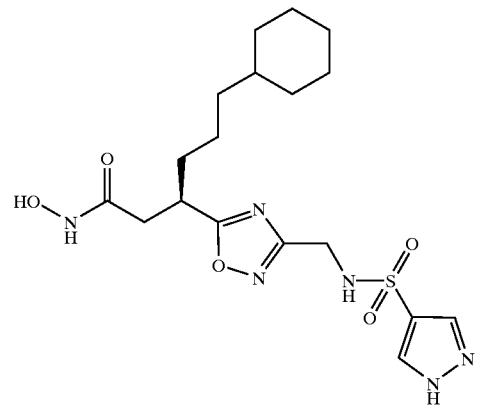

Method same as for example 7 using (3R)-6-cyclohexyl-3-(3-{[(1H-pyrazol-4-ylsulfonyl)amino]methyl}-1,2,4-oxadiazol-5-yl)hexanoic acid (preparation 23) (122 mg, 0.29 mmol) as starting material.

Purification: The cude material was purified on 2 silica columns both eluting with a solvent gradient of DCM:MeOH (95:5) gradually changing to (90:10) to afford the title compound as a white sold (64 mg, 50%).

M.pt. 124–126° C. dcc (formed a glass at 60–62° C.)

¹H nmr: (CD₃OD) 0.85 (2H, m), 1.10–1.30 (8H, m), 1.55–1.75 (7H, m), 2.40–2.60 (2H, m), 3.47 (1H, m), 4.22 (2H, s), 7.92 (2H, brs).

MS: 463 (MNa⁺)

CHN: Found: C47.87%; H6.58%; N18.53%; C₁₈H₂₈N₆O₅S. 0.6 H₂O requires C47.90%; H6.52%; N18.62%

Example 10

(3R)-6-cyclohexyl-N-hydroxy-3-(3-{[(4H-1,2,4-triazol-3-ylsulfonyl)amino]methyl}-1,2,4-oxadiazol-5-yl)hexanamide

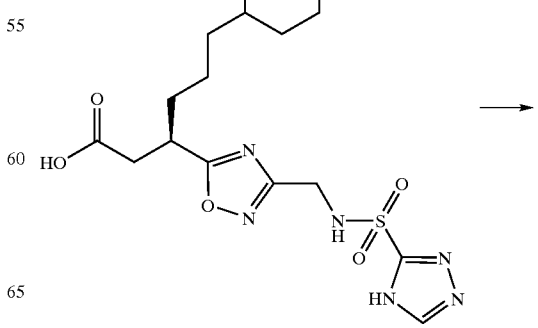

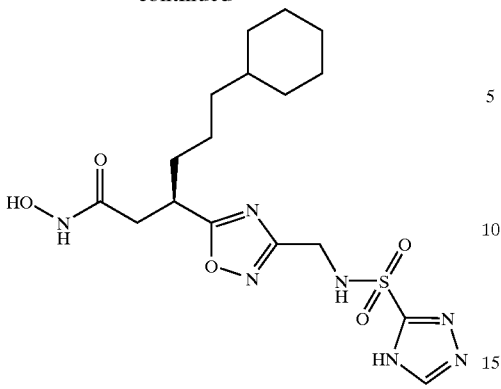

Method as for example 7 using (3R)-6-cyclohexyl-3-(3-{[(4H-1,2,4-triazol-3-ylsulfonyl)amino]methyl}-1,2,4-oxadiazol-5-yl)hexanoic acid (preparation 26) (200 mg, 0.47 mmol) as starting material.

Purification: Crude material was purified on a silica column eluting with EtOAc and changing to a solvent gradient of DCM:MeOH (95:5) gradually changing to (90:10) and finally neat MeOH was used to afford the title compound as a light brown solid (50 mg, 24%).

$^1$H nmr: (CD$_3$OD) 0.83 (2H, m), 1.05–1.30 (8H, m), 1.55–1.75 (7H, m), 2.40–2.65 (2H, m), 3.49 (1H, m), 4.39 (2H, s), 8.28 (1H, s).

MS: 440 (M–H)

Example 11

(3R)-6-cyclohexyl-3-[3-({[(3,5-dimethyl-4-isoxazolyl)sulfonyl]amino}methyl)-1,2,4-oxadiazol-5yl]-N-hydroxyhexanamide

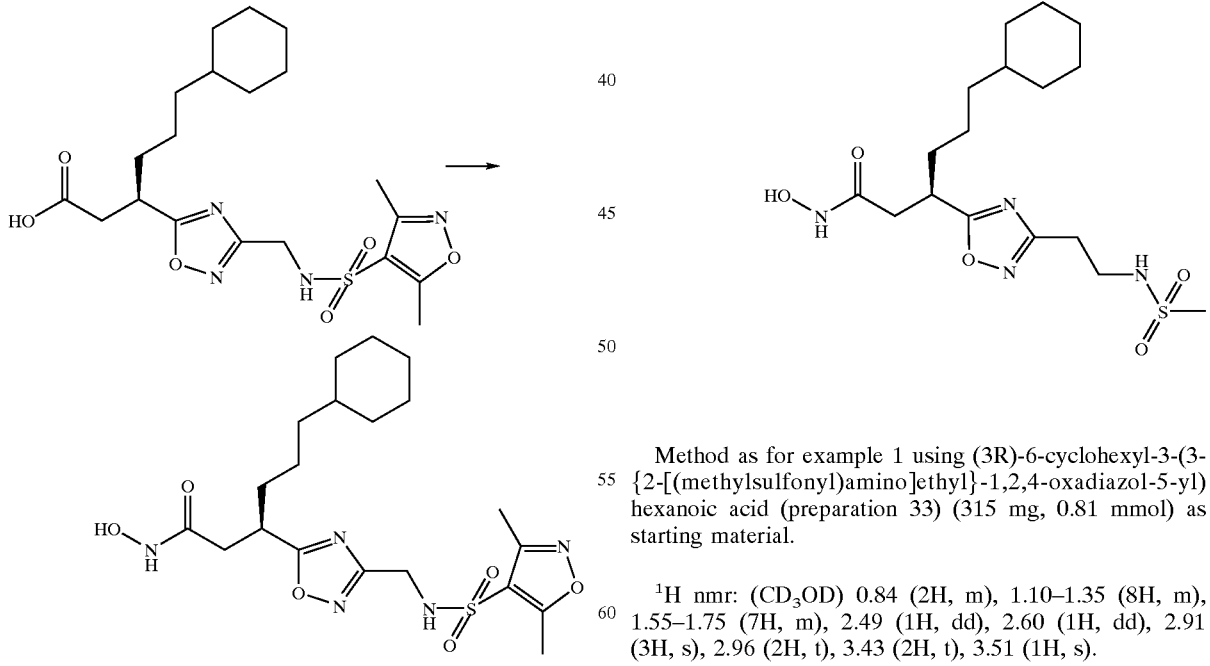

Method as for Example 1 using (3R)-6-cyclohexyl-3-[3-({[(3,5-dimethyl-4-isoxazolyl)sulfonyl]amino}methyl)-1,2,4-oxadiazol-5-yl]hexanoic acid (preparation 28) (220 mg, 0.48 mmol) as starting material.

Purification: The crude material was purified on a silica column eluting with DCM:MeOH (95:5) to afford the title compound as a white foam (92 mg, 41%).

hu 1H nmr: (d$_6$-DMSO) 0.81 (2H, m), 1.05–1.20 (8H, m), 1.50–1.70 (7H, m), 2.27 (3H, s), 2.41 (2H, dd), 2.54 (3H, s), 3.36 (1H, m), 4.21 (2H, d), 8.61 (2H, brs), 10.39 (1H, s).

MS: 492 (MNa$^+$)

CHN: Found: C51.08%; H6.77%; N14.16%; C$_{20}$H$_{31}$N$_5$O$_6$S. 0.15 H$_2$O. 0.15 EtOAc requires C51.19%; H6.84%; N14.49%

Example 12

(3R)-6-cyclohexyl-N-hydroxy-3-(3-{2-[(methylsulfonyl)amino]ethyl}-1,2,4-oxadiazol-5-yl)hexanamide Method as for example 1 using (3R)-6-cyclohexyl-3-(3-{2-[(methylsulfonyl)amino]ethyl}-1,2,4-oxadiazol-5-yl)hexanoic acid (preparation 33) (315 mg, 0.81 mmol) as starting material.

$^1$H nmr: (CD$_3$OD) 0.84 (2H, m), 1.10–1.35 (8H, m), 1.55–1.75 (7H, m), 2.49 (1H, dd), 2.60 (1H, dd), 2.91 (3H, s), 2.96 (2H, t), 3.43 (2H, t), 3.51 (1H, s).

MS: 425 (MNa$^+$)

CHN: Found: C47.35%; H7.04%; N12.47%; C$_{17}$H$_{30}$N$_4$O$_5$S requires C47.24%; H7.02%; N12.59%

Example 13

(3R)-6-cyclohexyl-N-hydroxy-3-{3-[1-(methylsulfonyl)-3-azetidinyl]-1,2,4-oxadiazol-5-yl}hexanamide

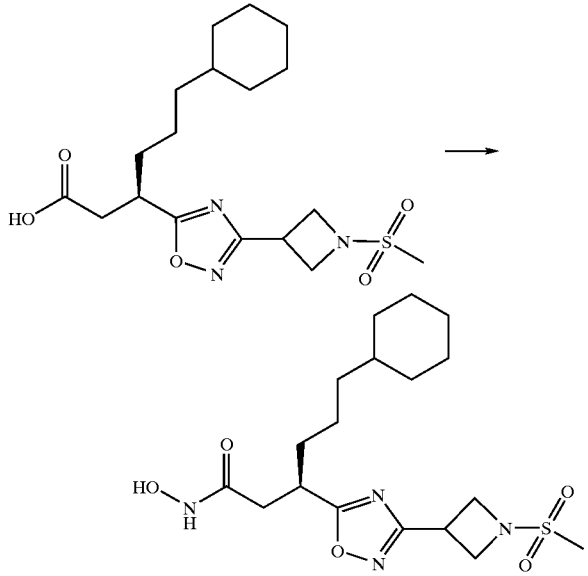

Method as for example 1 using (3R)-6-cyclohexyl-3-{3-[1-(methylsulfonyl)-3-azetidinyl]-1,2,4-oxadiazol-5-yl}hexanoic acid (preparation 39) (150 mg, 0.38 mmol) as starting material. Purification: Crude material was purified on a silica column eluting with a solvent gradient of DCM:MeOH (98:2) gradually changing to (90:10) to afford the title compound as a sticky, glassy oil (140 mg, 90%).

$^1$H nmr: (CD$_3$OD) 0.82 (2H, m), 1.05–1.35 (8H, m), 1.55–1.80 (7H, m), 2.53 (1H, dd), 2.61 (1H, dd), 2.98 (3H, s), 3.55 (1H, m), 4.00 (1H, m), 4.15 (2H, m), 4.25 (2H, m).

MS: 437 (MNa$^+$)

CHN: Found: C51.04%; H7.26%; N12.93%; C$_{18}$H$_{30}$N$_4$O$_5$S.0.25 EtOAC.0.05DCM requires C51.22%; H7.29%; N13.24%.

Example 14

(3R)-6-cyclohexyl-N-hydroxy-3-{3-[1-(methylsulfonyl)-4-piperidinyl]-1,2,4-oxadiazol-5-yl}hexanamide

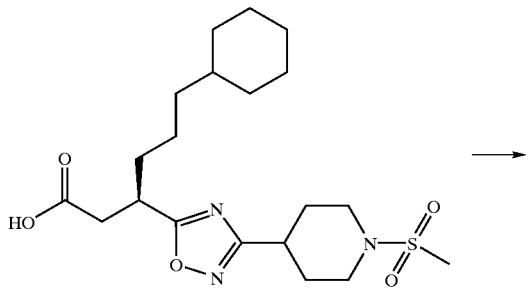

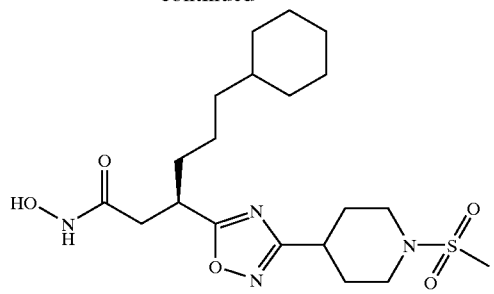

Method as for example 1 using (3R)-6-cyclohexyl-3-{3-[1-(methylsulfonyl)-4-piperidinyl]-1,2,4-oxadiazol-5-yl}hexanoic acid (preparation 44) (230 mg, 0.54 mmol) as starting material.

Purification: Crude material triturated with DIPE, filtered off and dried under reduced pressure to afford the title compound as fluffy white solid (204 mg, 85%).

$^1$H nmr: (CD$_3$OD) 0.83 (2H, m), 1.05–1.35 (8H, m), 1.55–1.75 (7H, m), 1.88 (2H, m), 2.09 (2H, m), 2.48 (1H, dd), 2.60 (1H, dd), 2.82 (3H, s), 2.98 (3H, m), 3.52 (1H, m), 3.70 (2H, m).

MS: 465 (MNa$^+$)

CHN: Found: C54.08%; H7.75%; N12.48%; C$_{20}$H$_{34}$N$_4$O$_5$S requires C54.28%; H7.74%; N12.66%.

Example 15

(3R)-6-cyclohexyl-3-[3-(1,1-dioxido-2-isothiazolidinyl)-1,2,4-oxadiazol-5-yl]-N-hydroxyhexanamide

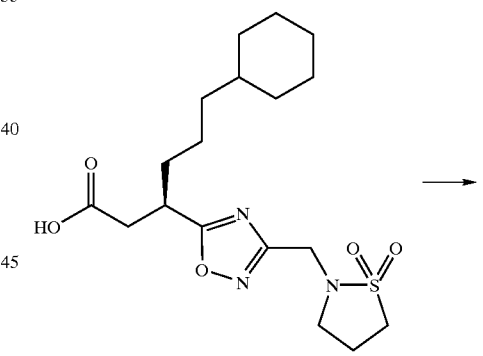

Method as for example 1 using (3R)-6-cyclohexyl-3-[3-(1,1-dioxido-2-isothiazolidinyl)-1,2,4-oxadiazol-5-yl] hexanoic acid (preparation 46) (194 mg, 0.49 mmol) as starting material and NMM as base.

Purification: The crude material was purified on a silica column eluting with Et$_2$O to removed the impurities and changing to DCM:MeOH (9:1) as eluent to afford the title compound as a colourless oil 103 mg, 51%).

$^1$H nmr: (d$_6$-DMSO) 0.80 (2H, m), 1.00–1.25 (8H, m), 1.50–1.70 (7H, m), 2.22 (2H, m), 2.52 (2H, obs), 2.74 (2H, t), 3.20 (2H, obs), 3.26 (2H, t), 3.41 (1H, m), 4.20 (2H, s), 8.62 (1H, brs), 10.39 (1 H, brs).

MS: 437 (MNa$^+$)

CHN: Found: C51.86%; H7.37%; N13.03%; C$_{18}$H$_{30}$N$_4$O$_5$S.0.2 H$_2$O requires C51.71%; H7.33%; N13.40%.

Examples 16 and 17

(3R)-3-[3-({[(tert-butylamino)sulfonyl]amino}methyl)-1,2,4-oxadiazol-5-yl]-6-cyclohexyl-N-hydroxyhexanamide(17) and (3R)-3-(3-{[(aminosulfonyl)amino]methyl}-1,2,4-oxadiazol-5-yl)-6-cyclohexyl-N-hydroxyhexanamide(16)

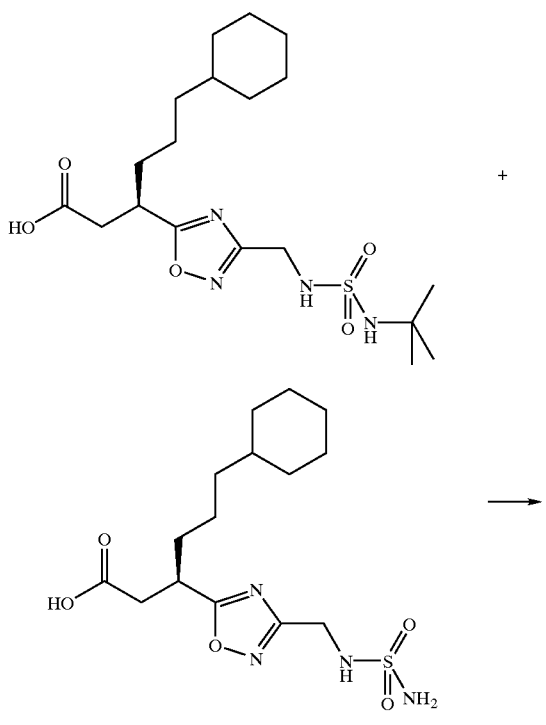

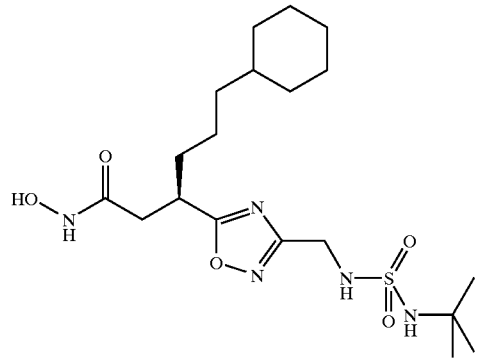

+

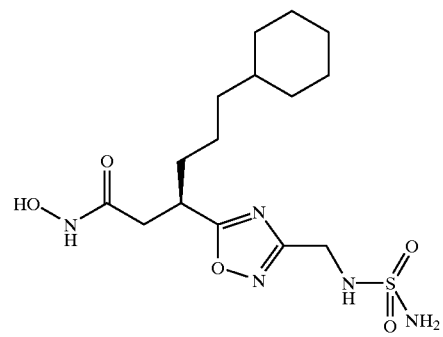

Method as for example 1 using (3R)-3-[3-({[(tert-butylamino)sulfonyl]amino}methyl)-1,2,4-oxadiazol-5-yl]-6-cyclohexylhexanoic acid and (3R)-3-(3-{[(aminosulfonyl)amino]methyl}-1,2,4-oxadiazol-5-yl)-6-cyclohexylhexanoic acid (preparations 48 and 49) as starting material.

Purification: The crude mixture of products was purified on a silica column eluting with a solvent gradient of DCM:MeOH (100:0) gradually changing to (98:2).

Top spot was (3R)-3-(3-{[(aminosulfonyl)amino]methyl}-1,2,4-oxadiazol-5-yl)-6-cyclohexyl-N-hydroxyhexanamide (example 16) isolated as a white foam (38 mg).

$^1$H nmr: (d$_6$-DMSO) 0.80 (2H, m), 1.00–1.25 (8H, m), 1.50–1.70 (7H, m), 2.41 (1H, dd), 2.65 (1H, dd), 3.41 (1H, m), 4.16 (2H, d), 6.53 (2H, brs), 7.01 (1H, brs), 8.64 (1H, brs), 10.40 (1H, brs).

MS: 390 (MH$^+$)

Accurate mass: Found 390.1794 (MH$^+$), Calculated C$_{15}$H$_{27}$N$_5$O$_5$S, 390.1806.

Second spot was (3R)-3-[3-({[(tert-butylamino)sulfonyl]amino}methyl)-1,2,4-oxadiazol-5-yl]-6-cyclohexyl-N-hydroxyhexanamide (example 17) (34 mg).

$^1$H nmr: (d$_6$-DMSO) 0.81 (2H, m), 1.00–1.20 (8H, m), 2.40 (9H, s), 1.50–1.70 (7H, m), 2.40 (1H, dd), 2.66 (1H, dd), 3.41 (1H, m), 4.08 (2H, d), 6.52 (1H, brs), 7.17 (1H, brs), 8.63 (1H, brs), 10.38 (1H, brs).

MS: 468 (MNa$^+$)

Accurate mass: Found 468.2235 (MNa$^+$), Calculated C$_{19}$H$_{35}$N$_5$O$_5$S, 468.2251.

Example 18

(3R)-3-{3-[(acetylamino)methyl]-1,2,4-oxadiazol-5-yl}-6-cyclohexyl-N-hydroxyhexanamide

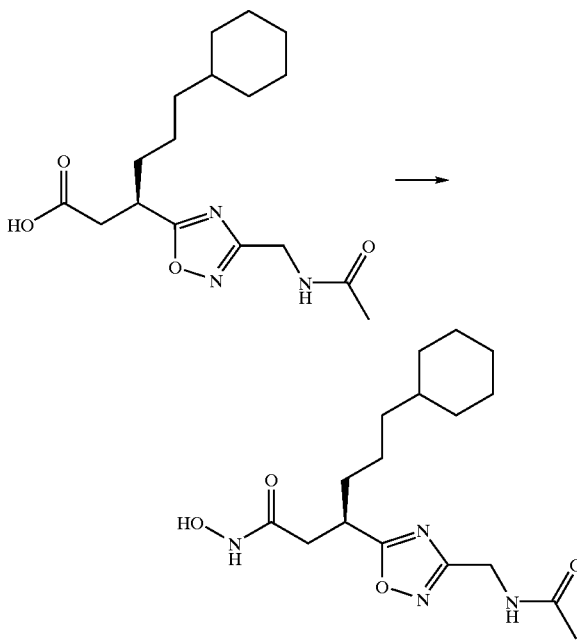

Method as for example 1 using (3R)-3-{3-[(acetylamino)methyl]-1,2,4-oxadiazol-5-yl}-6-cyclohexylhexanoic acid (preparation 51) (215 mg, 0.64 mmol) as strating material and NMM as base.

Purification: Crude material was purified on a silica column eluting with a solvent gradient of $Et_2O$:MeOH (19:1) gradually changing to (9:1) to afford the title compound as a colourless gum (39 mg, 17%)

$^1$H nmr: ($d_6$-DMSO) 0.80 (2H, m), 1.05–1.25 (8H, m), 1.55–1.70 (7H, m), 1.81 (3H, s), 2.40 (2H, m), 3.39 (1H, m), 4.32 (2H, d), 8.31 (1H, brs), 8.62 (1H, s), 10.38 (1H, brs).

MS: 375 (MNa$^+$)

CHN: Found: C56.17%; H7.93%; N14.86%; $C_{17}H_{27}N_3O_4$.0.4 $H_2O$.0.1 DCM requires C55.79%; H7.94%; N15.22%.

Example 19

(3R)-3-(3-{[acetyl(methyl)amino]methyl}-1,2,4-oxadiazol-5-yl)-6-cyclohexyl-N-hydroxyhexanamide

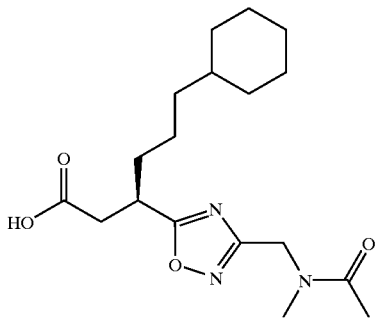

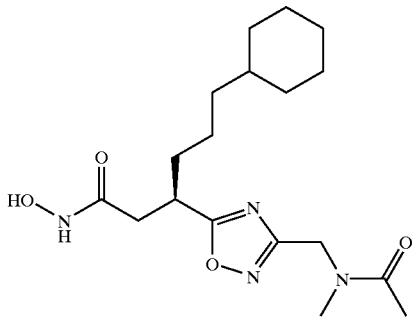

Method as for example 7 using (3R)-3-(3-{[acetyl(methyl)amino]methyl}-1,2,4-oxadiazol-5-yl)-6-cyclohexylhexanoic acid (preparation 53) (122 mg, 0.37 mmol) as starting material.

Purification: Crude material was purified on a silica column eluting with DCM:MeOH (9:1) to afford the title compound as a colourless oil (23 mg, 18%).

$^1$H nmr: (CD$_3$OD): 0.83 (2H, m), 1.10–1.35 (8H, m), 1.60–1.80 (7H, m), 2.12–2.18 (3H, s+s), 2.52 (1H, m), 2.59 (1H, m), 2.95–3.10 (3H, s+s), 3.54 (1H, m), 4.65 (2H, s) and some imidazole.

MS: 389 (MNa$^+$)

CHN: Found: C56.04%; H8.20%; N15.26%; $C_{18}H_{30}N_4O_4$.0.6 $H_2O$.0.1 DCM.0.1 imidazole requires C56.30%; H8.16%; N14.99%.

Example 20

N-[(5-{(1R)-4-cyclohexyl-1-[2-(hydroxyamino)-2-oxoethyl]butyl}-1,2,4-oxadiazol-3-yl)methyl]cyclopropanecarboxamide

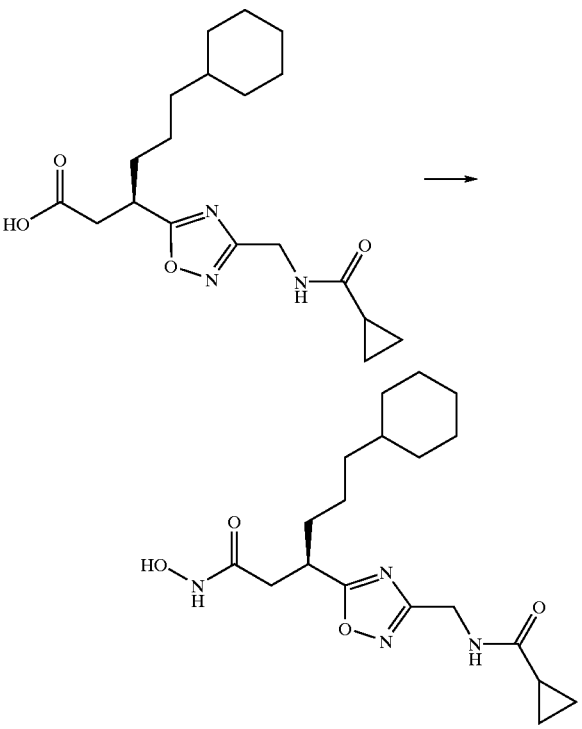

Method as for example 1 using (3R)-6-cyclohexyl-3-(3-{[(cyclopropylcarbonyl)amino]methyl)-1,2,4-oxadiazol-5-yl)hexanoic acid (preparation 55) (198 mg, 0.54 mmol) as starting material and NMM as the base.

Purification: The crude material was purified on a silica column eluting with DCM:MeOH (19:1) to afford the title compound as a white foam (141 mg, 68%).

$^1$H nmr: (d$_6$DMSO) 0.65 (4H, t), 0.80 (2H, m), 1.00–1.25 (8H, m), 1.50–1.70 (8H, m), 2.41 (2H, m), 3.40 (1H, m), 4.37 (2H, d), 8.49 (1H, brs), 8.61 (1H, brs), 10.37 (1H, brs).

MS: 401 (MNa$^+$)

CHN: Found: C59.61%; H8.05%; N14.19%; C$_{19}$H$_{30}$N$_4$O$_4$.0.3 H$_2$O requires C59.45%; H8.03%; N14.59%.

Example 21

(3R)-6-cyclohexyl-N-hydroxy-3-(3-{[(methoxyacetyl)amino]methyl}-1,2,4-oxadiazol-5-yl)hexanamide

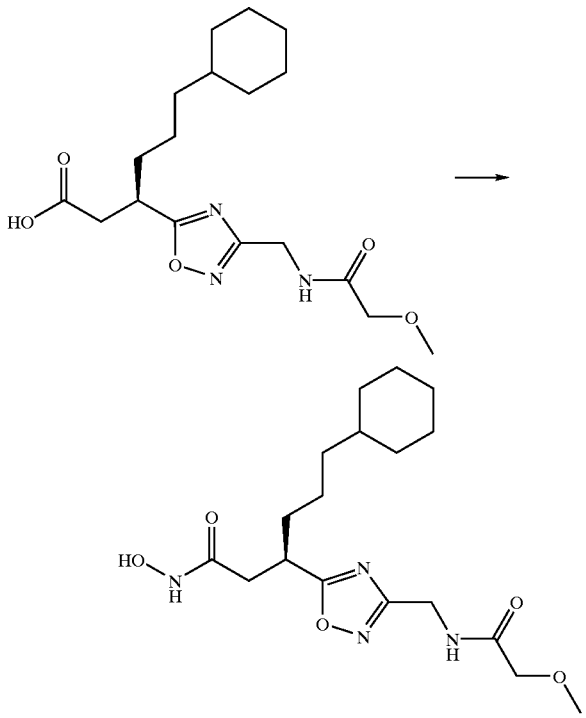

Method as for example 1 using (3R)-6-cyclohexyl-3-(3-{[(methoxyacetyl)amino]methyl}-1,2,4-oxadiazol-5-yl)hexanoic acid (preparation 57) (186 mg, 0.51 mmol) and NMM as the base.

Purification: The crude material was purified on a silica column eluting with DCM:MeOH (19:1) to afford the title compound as a colourless, sticky gum (90 mg, 46%).

$^1$H nmr: (d$_6$DMSO) 0.80 (2H, m), 1.00–1.25 (8H, m), 1.55–1.70 (7H, m), 2.41 (2H, m), 3.32 (3H, s), 3.40 (1H, m), 3.82 (2H, s), 4.39 (2H, d), 8.21 (1H, brs), 8.63 (1H, brs), 10.38 (1H, brs).

MS: 405 (MNa$^+$)

CHN: Found: C54.09%; H7.79%; N13.81%; C$_{18}$H$_{30}$N$_4$O$_5$.0.8 H$_2$O requires C54.48%; H8.03%; N14.12%.

Example 22

(3R)-6-cyclohexyl-3-[3-({[(dimethylamino)acetyl]amino}methyl)-1,2,4-oxadiazol-5-yl]-N-hydroxyhexanamide

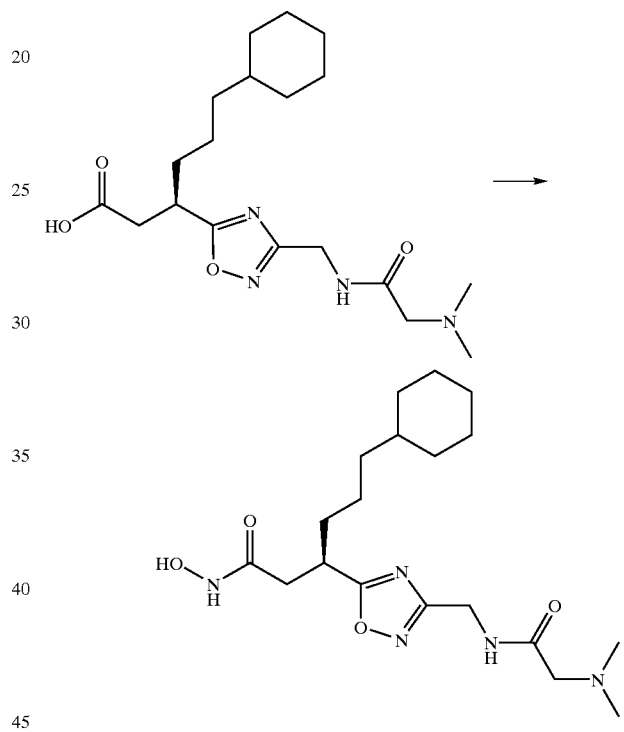

Method as for example 7 using (3R)-6-cyclohexyl-3-[3-({[(dimethylamino)acetyl]amino}methyl)-1,2,4-oxadiazol-5-yl]hexanoic acid (preparation 59) (215 mg, 0.52 mmol) as starting material.

Purification: The crude material was purified on a silica column eluting with DCM:MeOH (9:1) to afford the title compound as a colourless oil (60 mg, 29%).

$^1$H nmr: (d$_6$DMSO) 0.80 (2H, m), 1.00–1.20 (8H, m), 1.50–1.65 (8H, m), 2.21 (6H, s), 2.40 (2H, m), 2.91 (2H, s), 3.40 (1H, m), 4.38 (2H, d), 8.18 (1H, brs), 10.37 (1H, brs).

MS: 396 (MH$^+$)

CHN: Found: C55.31%; H7.76%; N22.53%; C$_{19}$H$_{32}$N$_4$O$_4$.0.5 H$_2$O.1.6 imidazole requires C55.68%; H7.93%; N22.37%.

Example 23

N-[(5-{(1R)-4-cyclohexyl-1-[2-(hydroxyamino)-2-oxoethyl]butyl}-1,2,4-oxadiazol-3-yl)methyl]benzamide

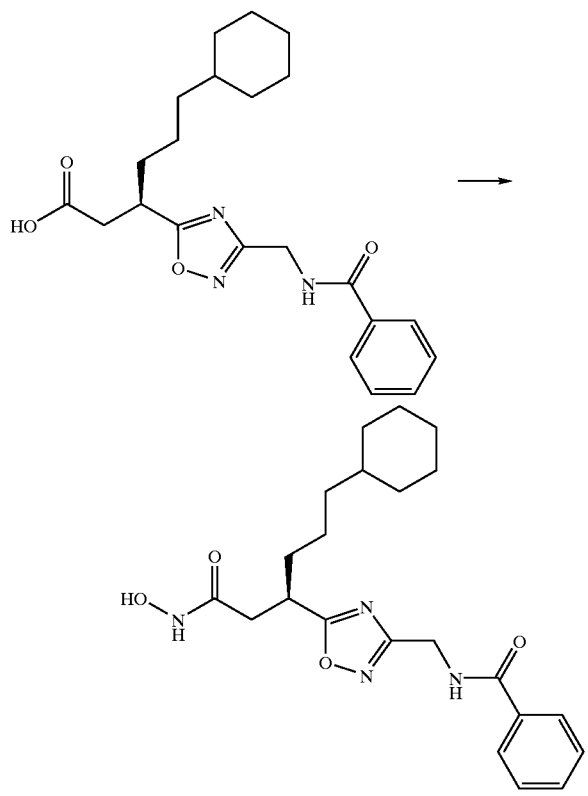

Method as for example 1 using (3R)-3-{3-[(benzoylamino)methyl]-1,2,4-oxadiazol-5-yl)-6-cyclohexylhexanoic acid (preparation 61) (202 mg, 0.51 mmol) and NMM as the base.

Purification: The crude material was purified on a silica column eluting with Et$_2$O:MeOH (19:1) to afford the title compound as a colourless oil (112 mg, 53%).

$^1$H nmr: (d$_6$DMSO) 0.79 (2H, m), 1.00–1.25 (8H, m), 1.50–1.70 (7H, m), 2.41 (2H, m), 3.41 (1H, m), 4.54 (2H, d), 7.42 (2H, t), 7.53 (1H, t), 7.83 (2H, d), 8.61 (1H, brs), 8.97 (1H, brs), 10.37 (1H, brs).

MS: 437 (MNa$^+$)

CHN: Found: C61.11%; H7.18%; N11.83%; C$_{22}$H$_{30}$N$_4$O$_4$.0.4 H$_2$O.0.2 DCM.0.2 DIPE requires C61.22%; H7.46%; N12.20%.

Example 24

N-[(5-{(1R)-4-cyclohexyl-1-[2-(hydroxyamino)-2-oxoethyl]butyl}-1,2,4-oxadiazol-3-yl)methyl]-2-pyridinecarboxamide

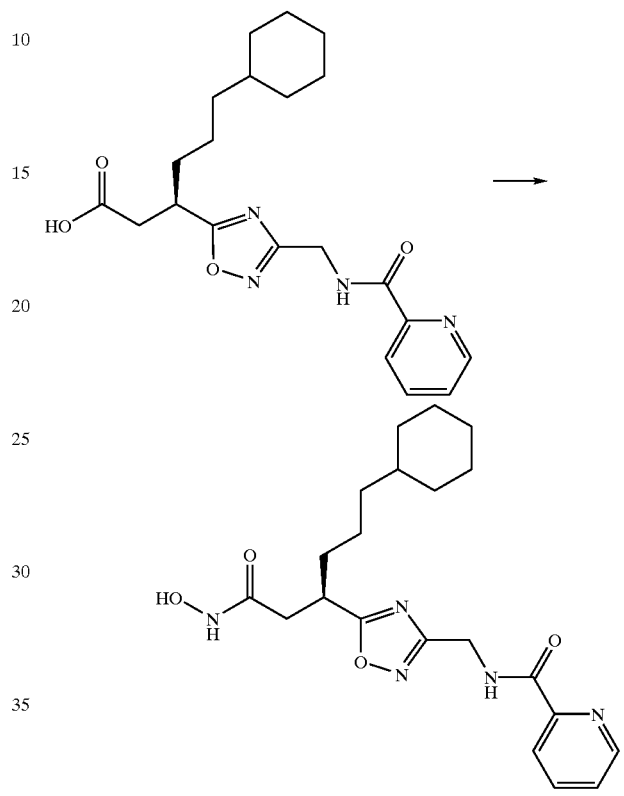

Method as for example 7 using (3R)-6-cyclohexyl-3-(3-{[(2-pyridinylcarbonyl)amino]methyl}-1,2,4-oxadiazol-5-yl)hexanoic acid (preparation 63) (188 mg, 0.43 mmol) as starting material.

Purification: The crude material was purified on a silica column eluting with DCM:MeOH (19:1) to afford the title compound as a colourless oil (41 mg, 23%).

$^1$H nmr: (d$_6$DMSO) 0.78 (2H, m), 1.00–1.25 (8H, m), 1.50–1.65 (7H, m), 2.40 (2H, m), 3.40 (1H, m), 4.58 (2H, d), 7.59 (1H, t), 7.98 (2H, m), 8.61 (2H, brs), 9.12 (1H, brs), 10.38 (1H, brs).

MS: 438 (MNa$^+$)

CHN: Found: C60.09%; H7.15%; N15.82%; C$_{21}$H$_{29}$N$_5$O$_4$.0.4 H$_2$O.0.1 DIPE requires C59.93%; H7.26%; N16.18%.

Example 25

(3R)-3-(3-{[(aminocarbonyl)amino]methyl}-1,2,4-oxadiazol-5-yl)-6-cyclohexyl-N-hydroxyhexanamide

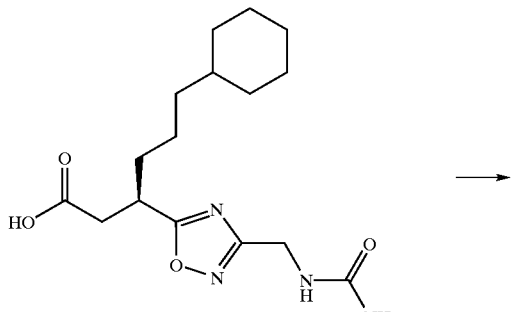

Method as for example 7 using (3R)-3-(3-{[(aminocarbonyl)amino]methyl}-1,2,4-oxadiazol-5-yl)-6-cyclohexylhexanoic acid (preparation 65) (78 mg, 0.23 mmol) as starting material.

Purification: Crude material was purified on a silica column eluting with DCM:MeOH:NH$_3$ (90:10:1) to afford the title compound as a white solid (13 mg)

$^1$H nmr: (d$_6$DMSO) 0.81 (2H, m), 1.05–1.30 (8H, m), 1.50–1.70 (7H, m), 2.42 (2H, m), 3.41 (1H, m), 4.31 (2H, d), 6.60 (2H, brs).

Example 26

(3R)-6-cyclohexyl-N-hydroxy-3-[3-({[(methylamino)carbonyl]amino}methyl)-1,2,4-oxadiazol-5-yl]hexanamide

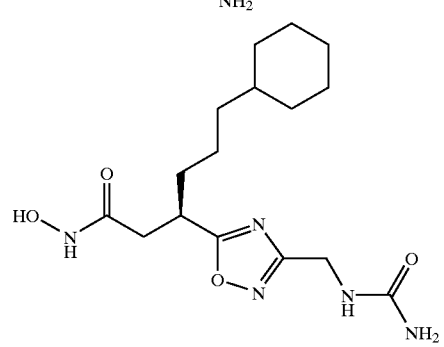

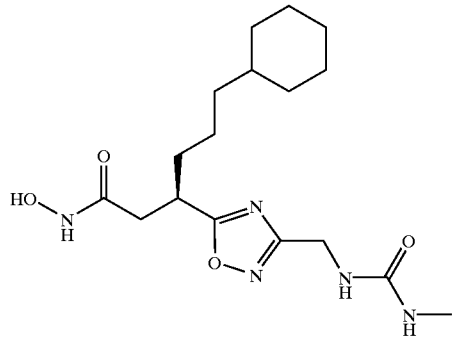

Method as for example 1 using (3R)-6-cyclohexyl-3-[3-({[(methylamino)carbonyl]amino}methyl)-1,2,4-oxadiazol-5-yl]hexanoic acid (preparation 67) (119 mg, 0.34 mmol) as starting material and Et$_3$N as base.

Purification: Two silica columns were required to purify the crude material the first eluting with DCM:MeOH:NH$_3$ (90:10:1) and the second eluting with DCM:MeOH (95:5) to afford the title compound as a colourless oil (11 mg).

$^1$H nmr: (d$_6$DMSO) 0.79 (2H, m), 1.05–1.20 (8H, m), 1.50–1.70 (7H, m), 2.41 (2H, m), 2.55 (3H, d), 3.40 (1H, m), 4.25 (2H, d), 6.42 (1H, brs), 8.80 (1H, brs), 10.50 (1H, brs).
MS: 366 (M–H)

Example 27

(3R)-6-cyclohexyl-3-[3-({[(dimethylamino)carbonyl]amino}methyl)-1,2,4-oxadiazol-5-yl]-N-hydroxyhexanamide

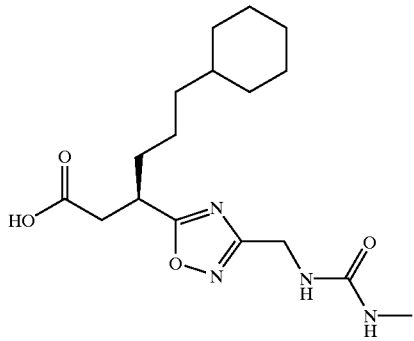

Method as for example 1 using (3R)-6-cyclohexyl-3-[3-({[(dimethylamino)carbonyl]amino}methyl)-1,2,4-oxadiazol-5-yl]hexanoic acid (preparation 69) (204 mg, 0.56 mmol) as starting material and Et$_3$N as base.

53

Purification: The crude material was purified on a silica column eluting with a solvent gradient of DCM:MeOH (98:2) gradually changing to (90:10) to afford the title compound as a crunchy, white foam (147 mg).

$^1$H nmr: (d$_6$DMSO) 0.80 (2H, m), 1.05–1.30 (8H, m), 1.50–1.70 (7H, m), 2.40 (2H, m), 2.79 (6H, m), 3.40 (1H, m), 4.25 (2H, d), 6.75 (1H, brs), 8.62 (1H, brs), 10.38 (1H, brs).

MS: 380 (M−H)

Example 28 tert-butyl (5-{(1R)-4-cyclohexyl-1-[2-(hydroxyamino)-2-oxoethyl]butyl}-1,2,4-oxadiazol-3-yl)methylcarbamate

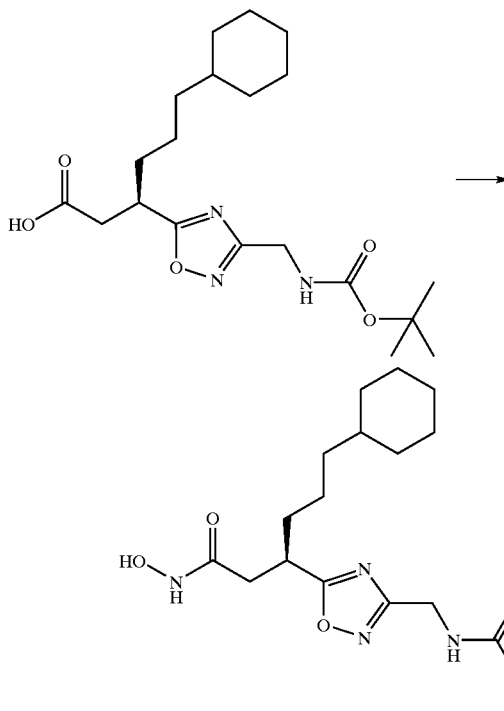

Method as for example 1 using (3R)-3-(3-{[(tert-butoxycarbonyl)amino]methyl}-1,2,4-oxadiazol-5-yl)-6-cyclohexylhexanoic acid (preparation 70) (113 mg, 0.29 mmol) as starting material and NMM as the base.

$^1$H nmr: (CDCl$_3$) 0.81 (2H, m), 1.10–1.35 (8H, m), 1.43 (9H, s), 1.60–1.80 (7H, m), 2.59 (1H, dd), 2.70 (1H, m), 3.57 (1H, m), 4.40 (2H, d), 5.01 (1H, brs).

MS: 433 (MNa$^+$)

CHN: Found: C57.95%; H8.40%; N13.16%; C$_{20}$H$_{34}$N$_4$O$_5$·0.25 H$_2$O requires C57.88%; H8.38%; N13.50%.

54

Example 29

(3R)-3-(3-amino-1,2,4-oxadiazol-5-yl)-6-cyclohexyl-N-hydroxyhexanamide

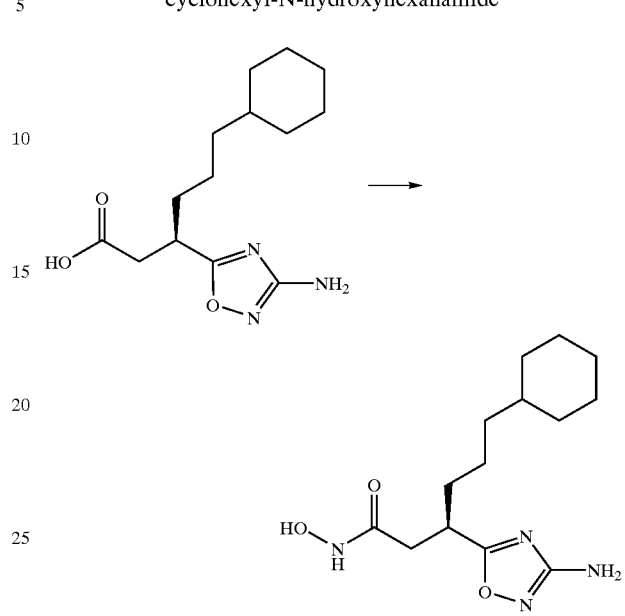

Method as for example 7 using (3R)-3-(3-amino-1,2,4-oxadiazol-5-yl)-6-cyclohexylhexanoic acid (preparation 72) (390 mg, 1.38 mmol) as starting material.

Purification: The crude material was purified on a silica column eluting with a solvent gradient of DCM:MeOH:NH$_3$ (95:5:0.5) gradually changing to (70:30:5) to afford the title compound as a white foam (170 mg, 42%).

$^1$H nmr: (d$_6$DMSO) 0.80 (2H, m), 1.00–1.20 (8H, m), 1.50–1.70 (7H, m), 2.35 (2H, m), 3.21 (1H, m), 6.10 (2H, brs).

MS: 319 (MNa$^+$)

Example 30 tert-butyl (3R)-3-[3-(aminomethyl)-1,2,4-oxadiazol-5-yl]-6-cyclohexylhexanoate

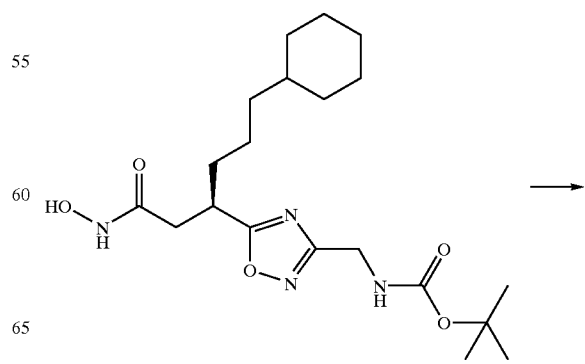

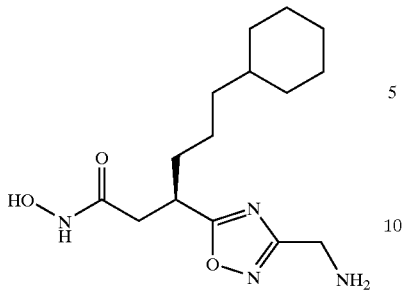

Method as for preparation 11 using tert-butyl (5-{(1R)-4-cyclohexyl-1-[2-(hydroxyamino)-2-oxoethyl]butyl}-1,2,4-oxadiazol-3-yl)methylcarbamate (example 28) (65 mg, 0.16 mmol) as starting material. The crude material was azeotroped from DCM (×4) and Et$_2$O (2×) and the residue dried under reduced pressure to afford the title compound as a pale yellow foam (61 mg, 90%).

$^1$H nmr: (d$_6$DMSO) 0.80 (2H, m), 1.05–1.25 (8H, m), 1.50–1.70 (7H, m), 2.40 (2H, m), 3.46 (1H, m), 4.22 (2H, s), 8.45 (2H, brs).

MS: 31 1(MH$^+$)

Example 31

(3R)-6-cyclohexyl-N-hydroxy-3-{3-[(methylamino)methyl]-1,2,4-oxadiazol-5-yl}hexanamide

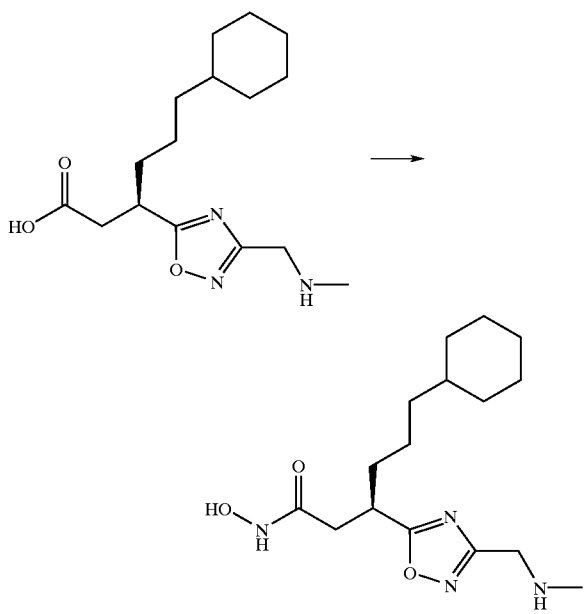

Method as for example 7 using (3R)-6-cyclohexyl-3-{3-[(methylamino)methyl]-1,2,4-oxadiazol-5-yl}hexanoic acid (preparation 73) (370 mg, 1.07 mmol) as starting material.

Purification: The crude material was purified on a silica column eluting with DCM:MeOH (9:1) to afford the title compound as a colourless oil (93 mg, 27%).

$^1$H nmr: (CD$_3$OD) 0.85 (2H, m), 1.10–1.35 (8H, m), 1.60–1.80 (7H, m), 2.40 (3H, s), 2.50 (1H, dd), 2.60 (1H, dd), 3.37 (1H, s), 3.54 (1H, m), 3.80 (2H, s).

MS: 325 (MH$^+$)

CHN: Found: C57.95%; H8.84%; N16.57%; C$_{16}$H$_{28}$N$_4$O$_3$·0.4 H$_2$O requires C57.95%; H8.75%; N16.89%.

Example 32

(3R)-6-cyclohexyl-3-{3-[(ethylamino)methyl]-1,2,4-oxadiazol-5-yl}-N-hydroxyhexanamide

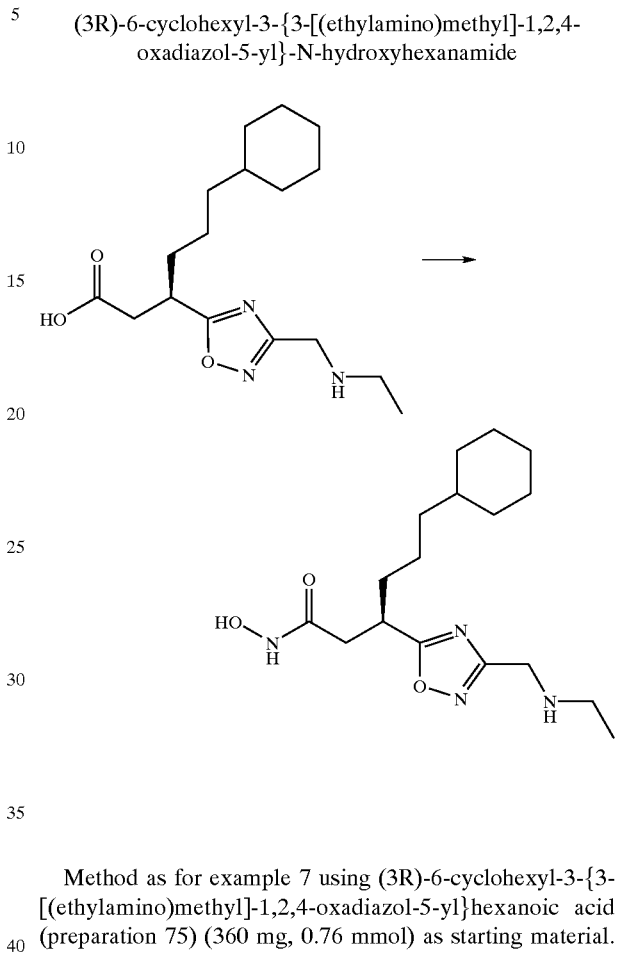

Method as for example 7 using (3R)-6-cyclohexyl-3-{3-[(ethylamino)methyl]-1,2,4-oxadiazol-5-yl}hexanoic acid (preparation 75) (360 mg, 0.76 mmol) as starting material.

Purification: The crude material was purified on a silica column eluting with a solvent gradient of DCM:MeOH:NH$_3$ (97.5:2.5:0.5) gradually changing to (90:10:1). The product was recrystallised from Et$_2$O to afford the title compound as white crystals (79 mg, 31%).

M. Pt.: 69.4–71.4° C.

$^1$H nmr: (d$_6$DMSO) 0.80 (2H, m), 0.99 (3H, t), 1.05–1.20 (8H, m), 1.50–1.70 (7H, m), 2.40 (2H, m), 2.53 (2H, q), 3.40 (1 H, m), 3.71 (2H, s).

MS: 339 (MH$^+$)

CHN: Found: C59.58%; H8.85%; N16.47%; C$_{17}$H$_{30}$N$_4$O$_3$·0.08 DCM requires C59.42%; H8.81%; N16.23%.

Example 33

(3R)-6-cyclohexyl-N-hydroxy-3-{3-[(propylamino)methyl]-1,2,4-oxadiazol-5-yl}hexanamide

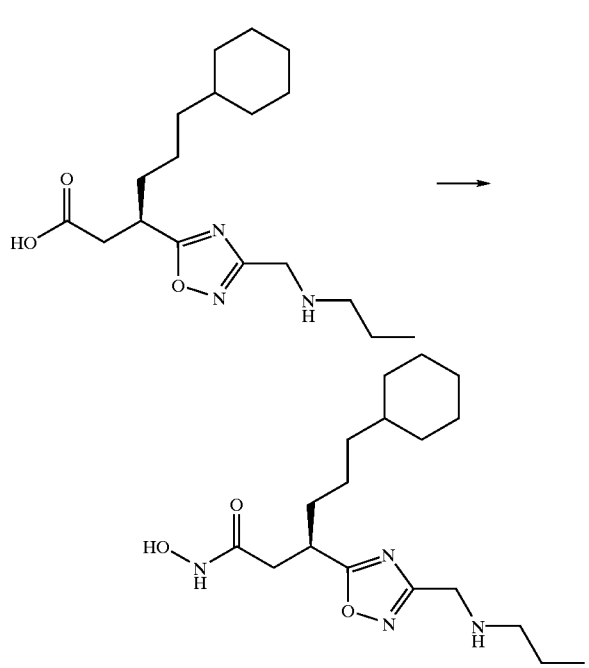

Method as for example 7 using (3R)-6-cyclohexyl-3-{3-[(propylamino)methyl]-1,2,4-oxadiazol-5-yl}hexanoic acid (preparation 77) (270 mg, 0.60 mmol) as starting material.

Purification: The crude material was purified on a silica column eluting with a solvent gradient of DCM:MeOH:NH$_3$ (97.5:2.5:0.25) gradually changing to (90:10:1). The product was recrystallised from Et$_2$O to afford the title compound as a sticky solid (46 mg).

M.Pt.: 90.4–91.8° C.

$^1$H nmr: (d$_6$DMSO) 0.79 (5H, m), 1.00–1.20 (8H, m), 1.39 (2H, m), 1.50–1.70 (7H, m), 1.99 (1H, brs), 2.30–2.45 (3H, m), 3.41 (1H, m), 3.74 (2H, s), 8.74 (1H, brs), 10.41 (1H, brs).

MS: 353 (MH$^+$)

CHN: Found: C58.03%; H8.65%; N15.00%; C$_{18}$H$_{32}$N$_4$O$_3$.0.3 DCM requires C58.16; H8.69%; N14.82%.

Example 34

(3R)-6-cyclohexyl-N-hydroxy-3-{3-[(isopropylamino)methyl]-1,2,4-oxadiazol-5-yl}hexanamide

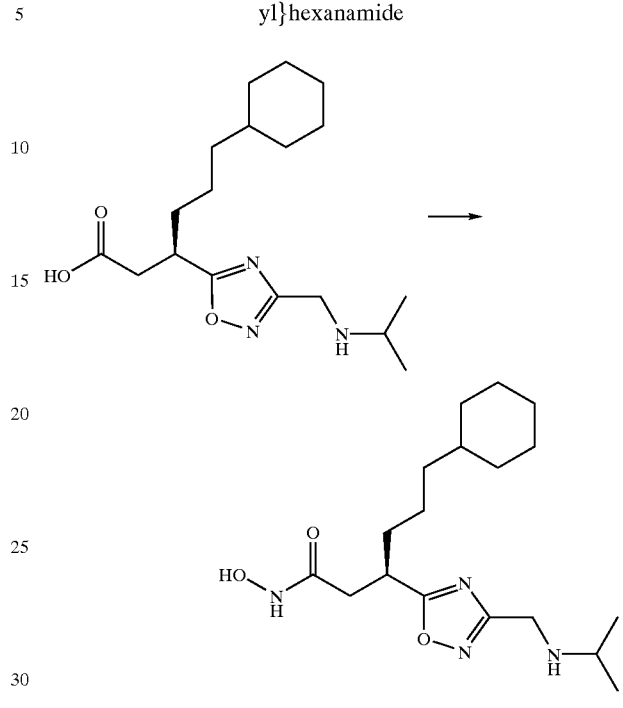

Method as for example 7 using (3R)-6-cyclohexyl-3-{3-[(isopropylamino)methyl]-1,2,4-oxadiazol-5-yl}hexanoic acid (preparation 79) (198 mg, 0.44 mmol) as starting material.

Purification: The crude material was purified on a silica column eluting with a solvent gradient of DCM:MeOH:NH$_3$ (95:5:0.5) gradually changing to (90:10:1). The oil was treated with Et$_2$O to afford the title compound as a white solid (67 mg, 44%).

$^1$H nmr: (CD$_3$OD) 0.82 (2H, m), 1.09 (6H, d), 1.10–1.30 (8H, m), 1.60–1.80 (7H, m), 2.51 (1H, dd), 2.61 (1H, dd), 2.81 (1H, m), 3.57 (1H, m), 3.86 (2H, s).

MS: 353 (MH$^+$)

Example 35

(3R)-6-cyclohexyl-N-hydroxy-3-{3-[(isobutylamino)methyl]-1,2,4-oxadiazol-5-yl}hexanamide

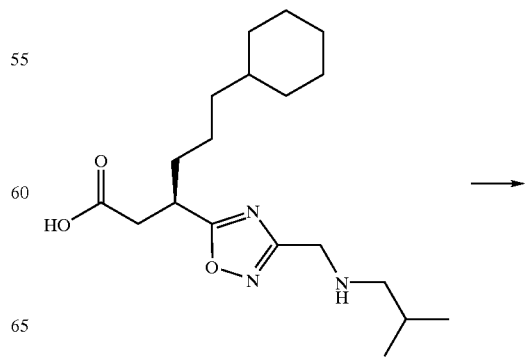

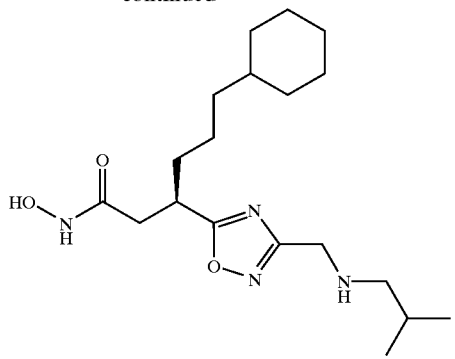

Method as for example 7 using (3R)-6-cyclohexyl-3-{3-[(isobutylamino)methyl]-1,2,4-oxadiazol-5-yl}hexanoic acid (preparation 81) (495 mg, 1.06 mmol) as starting material.

Purification: The crude material was purified on a silica column eluting with a solvent gradient of DCM:MeOH:NH$_3$ (97.5:2.5:0.25) gradually changing to (90:10:1). The glass obtained was recrystallised from Et$_2$O to afford the title compound as colourless crystals (71 mg).

M.Pt.: 97.8–99.0° C.

$^1$H nmr: (d$_6$DMSO) 0.83 (2H, m), 0.92 (6H, d), 1.10–1.35 (8H, m), 1.60–1.80 (8H, m), 2.46 (2H, d), 2.59 (1H, brs), 2.69 (1H, brs), 3.59 (1H, m), 3.88 (2H, s).

MS: 367 (MH$^+$)

CHN: Found: C62.21%; H9.48%; N15.47%; C$_{19}$H$_{34}$N$_4$O$_3$ requires C62.27; H9.35%; N15.29%.

Example 36

(3R)-3-{3-[(tert-butylamino)methyl]-1,2,4-oxadiazol-5-yl}-6-cyclohexyl-N-hydroxyhexanamide

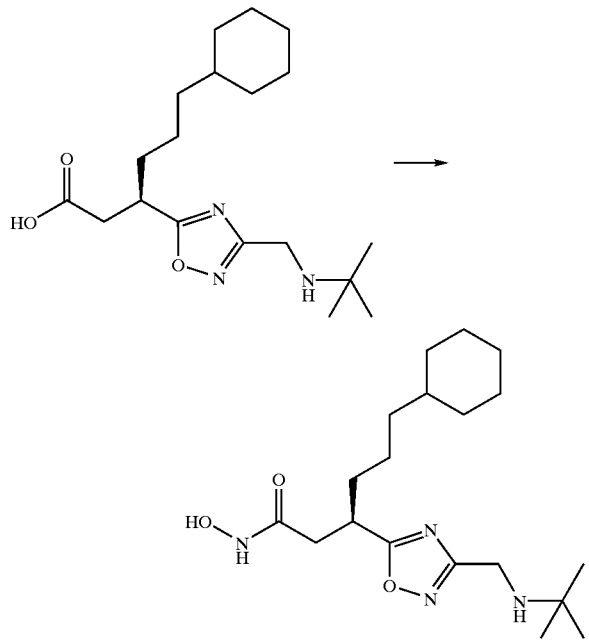

Method as for example 7 using (3R)-3-{3-[(tert-butylamino)methyl]-1,2,4-oxadiazol-5-yl}-6-cyclohexylhexanoic acid (preparation 83) (274 mg, 0.59 mmol) as starting material.

Purification: The crude material was purified on a silica column eluting with a solvent gradient of DCM:MeOH:NH$_3$ (97.5:2.5:0.25) gradually changing to (90:10:1). Second column was required eluting with DCM:MeOH:NH$_3$ (95:5:0.5). The product was partitioned between Et$_2$O and H$_2$O. The organic extracts were concentrated under reduced pressure. The residue was dissolved in DCM, dried over anhydrous Na$_2$SO$_4$, filtered and the solvent removed under reduced pressure. The residue was dired under reduced pressure to afford the title compound (52 mg).

$^1$H nmr: (CDCl$_3$) 0.83 (2H, m), 1.10–1.40 (17H, s+m), 1.60–1.80 (7H, m), 2.50–2.75 (2H, brd), 3.59 (1H, m), 3.85 (2H, s).

MS: 367 (MH$^+$)

Accurate mass: Found 367.2711 (MH$^+$), Calculated C$_{19}$H$_{35}$N$_4$O$_3$, 367.2709.

Example 37

(3R)-6-cyclohexyl-3-(3-{[(1-ethylpropyl)amino]methyl}-1,2,4-oxadiazol-5-yl)-N-hydroxyhexanamide

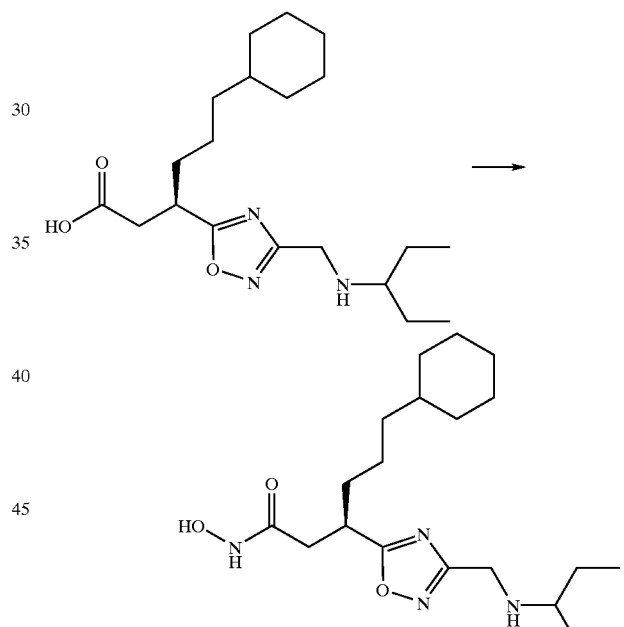

Method as for example 7 using (3R)-6-cyclohexyl-3-(3-{[(1-ethylpropyl)amino]methyl}-1,2,4-oxadiazol-5-yl)hexanoic acid (preparation 85) as starting material.

Purification: Crude material purified on a silica column eluting with DCM:MeOH:NH$_3$ (97.5:2.50.25). The solid was recrystallised from Et$_2$O to afford the title compound as fluffy crystals (212 mg).

M.Pt.: 102.7–104.3° C.

$^1$H nmr: (d$_6$DMSO) 0.79 (8H, m+t), 1.00–1.20 (8H, m), 1.33 (4H, m),1.50–1.75 (7H, m), 2.29 (1H, t), 2.40 (2H, m), 3.41 (1H, m), 3.74 (2H, s).

MS: 381 (MH$^+$)

CHN: Found: C63.12%; H9.64%; N14.85%; C$_{20}$H$_{36}$N$_4$O$_3$ requires C63.13; H9.54%; N14.72%.

Example 38

(3R)-6-cyclohexyl-3-{3-[(cyclopropylamino)methyl]-1,2,4-oxadiazol-5-yl}-N-hydroxyhexanamide

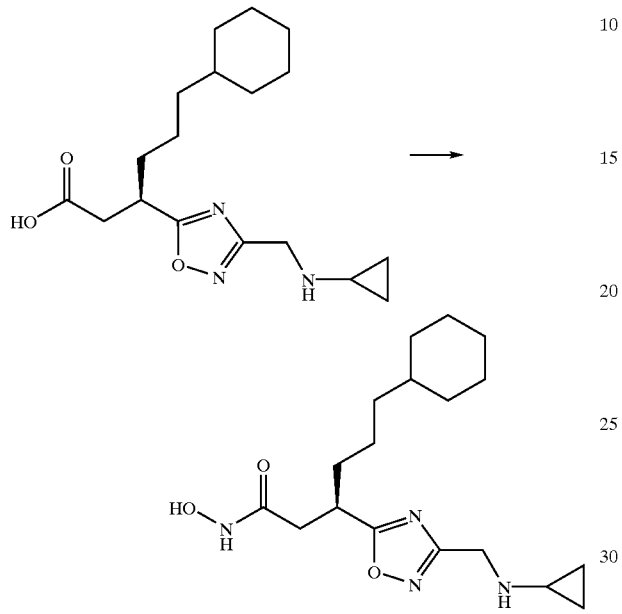

Method as for Example 7 using (3R)-6-cyclohexyl-3-{3-[(cyclopropylamino)methyl]-1,2,4-oxadiazol-5-yl}hexanoic acid (preparation 87) (300 mg, 0.67 mmol) as starting material.

Purification: Crude material purified on a silica column eluting with a solvent gradient of DCM:MeOH:NH$_3$ (97.5:2.5:0.25) gradually changing to (90:10:1). The material was dissolved in Et$_2$O and washed with H$_2$O (×5) and the organic extracts were concentrated under reduced pressure. The residue was dissolved in DCM, dried over anhydrous Na$_2$SO$_4$ and filtered. The solvent was removed under reduced pressure to afford the title compound (41 mg).

$^1$H nmr: (CDCl$_3$) 0.40 (2H, s), 0.46 (2H, m), 0.86 (2H, m), 1.10–1.40 (8H, m), 1.60–1.80 (7H, m), 2.19 (1H, m), 2.59 (1H, dd), 2.71 (1H, brs), 3.58 (1H, m), 3.92 (2H, s).

MS: 351 (MH$^+$)

CHN: Found: C61.77%; H8.78%; N15.13%; C$_{18}$H$_{30}$N$_4$O$_3$.0.25 Et$_2$O requires C61.85; H8.88%; N15.18%.

Example 39

(3R)-3-{3-[(cyclobutylamino)methyl]-1,2,4-oxadiazol-5-yl}-6-cyclohexyl-N-hydroxyhexanamide

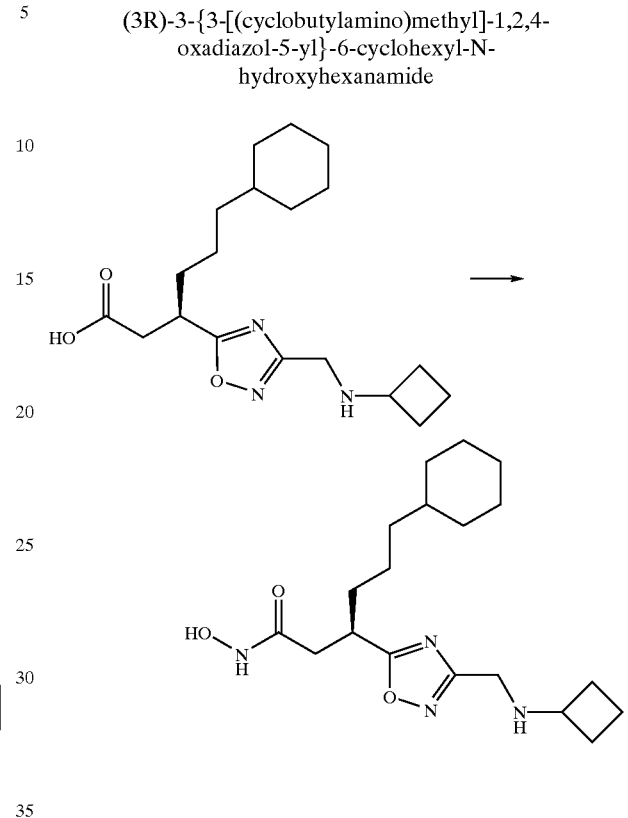

Method as for example 7 using (3R)-3-{3-[(cyclobutylamino)methyl]-1,2,4-oxadiazol-5-yl}-6-cyclohexylhexanoic acid (preparation 89) (300 mg, 0.67 mmol) as starting material.

Purification: Crude material purified on a silica column eluting with a solvent gradient of DCM MeOH:NH$_3$ (97.5:2.5:0.25) gradually changing to (90:10:1). The material was triturated with DIPE to afford the title compound as a white solid (27 mg).

M.Pt.: 82.0–83.9° C.

$^1$H nmr: (d$_6$DMSO) 0.79 (2H, m), 1.00–1.20 (8H, m), 1.40–1.70 (1H, m), 2.39 (1H, dd), 2.42 (1H, dd), 3.15 (1H, m), 3.40 (1H, m), 3.64 (2H, s), 8.74 (1H, brs), 10.41 (1H, brs).

MS: 365 (MH$^+$)

CHN: Found: C62.38%; H8.86%; N15.29%; C$_{19}$H$_{32}$N$_4$O$_3$ requires C62.61; H8.85%; N15.37%.

Example 40

(3R)-6-cyclohexyl-3-{3-[(cyclopentylamino)methyl]-1,2,4-oxadiazol-5-yl}-N-hydroxyhexanamide

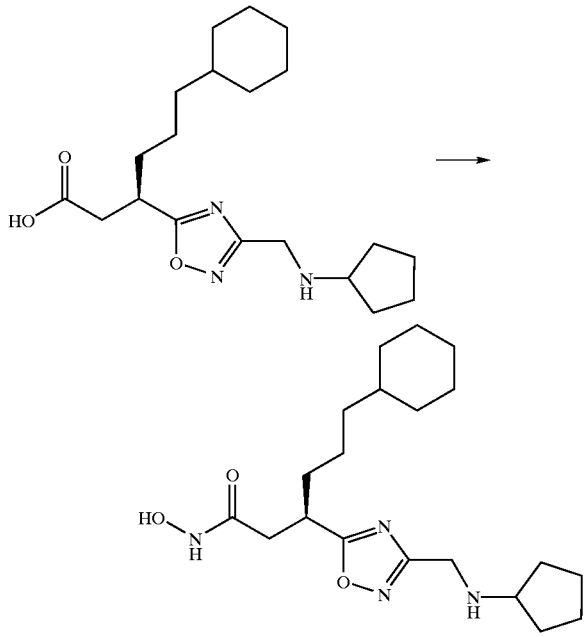

Method as for example 7 using (3R)-6-cyclohexyl-3-{3-[(cyclopentylamino)methyl]-1,2,4-oxadiazol-5-yl}hexanoic acid (preparation 91) (240 mg, 0.50 mmol) as starting material.

Purification: The crude material was purified on a silica column eluting with DCM:MeOH:NH₃ (90:10:1) and the white solid was recrystallised from EtOAc to afford the title compound as a white solid (60 mg).

¹H nmr: (d₆DMSO) 0.79 (2H, m), 0.95–1.10 (12H, m), 1.45–1.70 (9H, m), 1.78 (2H, m), 1.95 (1H, brs), 2.25–2.45 (3H, m), 3.41 (1H, m), 3.75 (2H, s), 8.80 (1H, brs), 10.48 (1H, brs).

MS: 379 (MH⁺)

CHN: Found: C63.53%; H9.16%; N14.66%; C₂₀H₃₄N₄O₃ requires C63.46; H9.05%; N14.80%.

Example 41

(3R)-6-cyclohexyl-3-{3-[(cyclohexylamino)methyl]-1,2,4-oxadiazol-5-yl}-N-hydroxyhexanamide

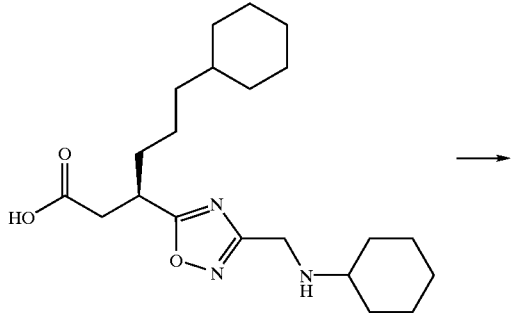

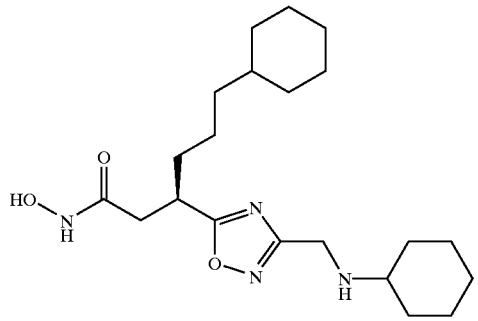

Method as for example 7 using (3R)-6-cyclohexyl-3-{3-[(cyclohexylamino)methyl]-1,2,4-oxadiazol-5-yl}hexanoic acid (preparation 93) (262 mg, 0.53 mmol) as starting material.

Purification: The crude material was purified on a silica column eluting with DCM:MeOH:NH₃ (90:10:1) to afford the title compound as a white solid (130 mg).

M. Pt.: 127° C.

¹H nmr: (d₆DMSO) 0.79 (2H, m), 0.95–1.20 (10H, m), 1.27 (2H, m), 1.41 (2H, m), 1.50–1.70 (11H, m), 2.40 (2H, m), 2.97 (1H, m), 3.40 (1H, m), 3.71 (2H, s), 8.79 (1H, brs), 10.45 (1H, brs).

MS: 393 (MH⁺)

CHN: Found: C63.79%; H9.24%; N14.32%; C₂₁H₃₆N₄O₃ requires C64.20; H9.24%; N14.27%.

Example 42

(3R)-6-cyclohexyl-N-hydroxy-3-(3-{[(2-hydroxyethyl)amino]methyl}-1,2,4-oxadiazol-5-yl)hexanamide

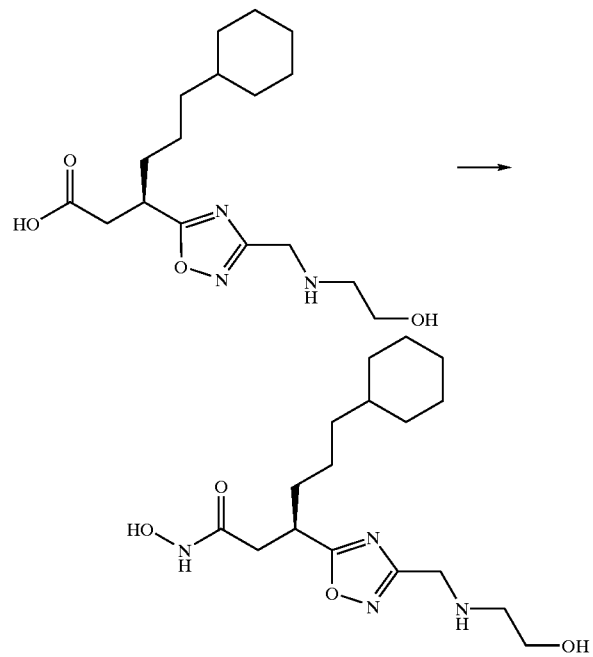

A solution of (3R)-6-cyclohexyl-3-(3-{[(2-hydroxyethyl)amino]methyl}-1,2,4-oxadiazol-5-yl)hexanoic acid (preparation 95) (398 mg, 0.82 mmol) in DCM (8 ml) was treated with imidazole (56 mg, 0.82 mmol) and stirred at room temperature until all imidazole had dissolved. TMSCI (100 μl, 0.82 mmol) was added and the reaction mixture was stirred at room temperature for 1 hour. Method as for example 7 was then followed.

Purification: The crude material was purified on 2 silica columns. The first eluting with DCM:MeOH:NH$_3$ (90:10:1) and the second eluting with DCM:MeOH:NH$_3$ (80:20:2) to afford the title compound as a oil (90 mg).

$^1$H nmr: (CD$_3$OD) 0.82 (2H, m), 1.10–1.35 (8H, m), 1.60–1.80 (7H, m), 2.50–2.70 (2H, m), 2.86 (2H, t), 3.55 (1 H, m), 3.70 (2H, t), 4.04 (2H, s)+some impurities.

MS: 355 (MH$^+$)

Example 43

(3R)-6-cyclohexyl-N-hydroxy-3-(3-{[(2-hydroxy-1,1-dimethylethyl)amino]methyl}-1,2,4-oxadiazol-5-yl)hexanamide

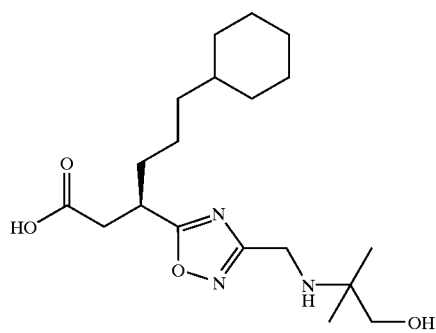

Method as for example 42 using (3R)-6-cyclohexyl-3-(3-{[(2-hydroxy-1,1-dimethylethyl)amino]methyl}-1,2,4-oxadiazol-5-yl)hexanoic acid (preparation 97) (2.59 g, 4.95 mmol) as starting material.

Purification: The crude material was purifed on a silica column eluting with DCM:MeOH:NH$_3$ (98:2:0.2) gradually changing to (90:10:1). The material was azeotroped from DCM followed by Et$_2$O to afford the title compound as a white foam (980 mg, 52%).

M.Pt.: 49–51° C.

$^1$H nmr: (d$_6$DMSO) 0.80 (2H, m), 0.98 (6H, s), 1.05–1.25 (8H, m), 1.50–1.70 (7H, m), 2.40 (2H, m), 3.20 (2H, m), 3.40 (1H, m), 3.73 (2H, s), 4.43 (1H, brs), 8.62 (1H, brs), 10.38 (1H, brs).

MS: 383 (MH$^+$)

CHN: Found: C59.27%; H9.06%; N14.22%; C$_{19}$H$_{34}$N$_4$O$_4$.0.05 H$_2$O requires C59.52%; H8.96%; N14.61%.

Example 44

(3R)-6-cyclohexyl-N-hydroxy-3-(3-{[(2-methoxyethyl)amino]methyl}-1,2,4-oxadiazol-5-yl)hexanamide

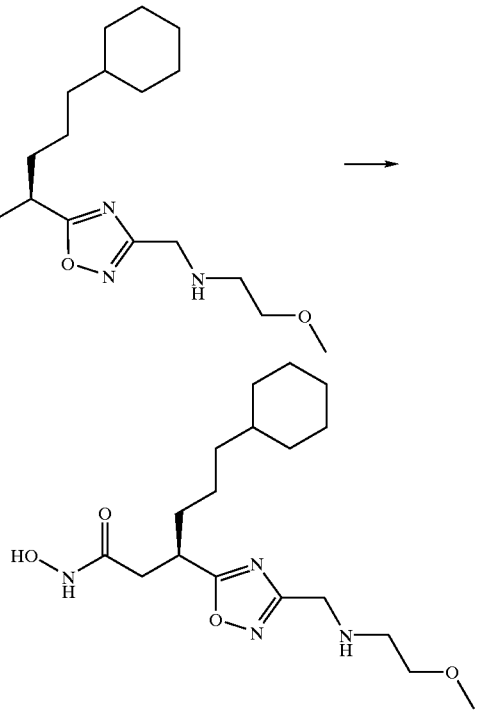

Method as for example 7 using (3R)-6-cyclohexyl-3-(3-{[(2-methoxyethyl)amino]methyl}-1,2,4-oxadiazol-5-yl)hexanoic acid (preparation 99) (429 mg, 0.93 mmol) as starting material.

Purification: The oil solidified on standing to afford the title compound (44 mg).

$^1$H nmr: (d$_6$DMSO) 0.79 (2H, m), 1.05–1.20 (8H, m), 1.55–1.65 (7H, m), 2.42 (2H, m), 2.69 (2H, t), 3.20 (3H, s), 3.39 (2H, t), 3.41 (1H, m), 3.80 (2H, s), 8.78 (1H, brs), 10.46 (1H, brs).

Example 45

(3R)-6-cyclohexyl-N-hydroxy-3-(3-{[(3-methoxypropyl)amino]methyl}-1,2,4-oxadiazol-5-yl)hexanamide

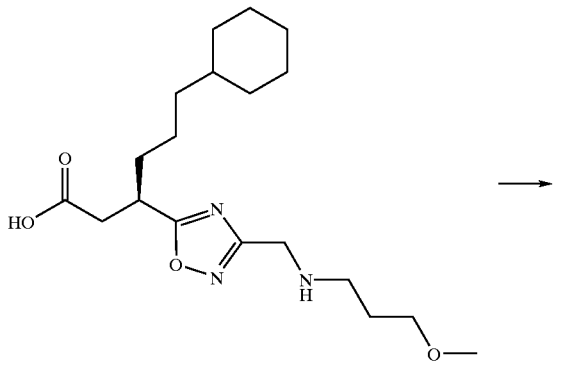

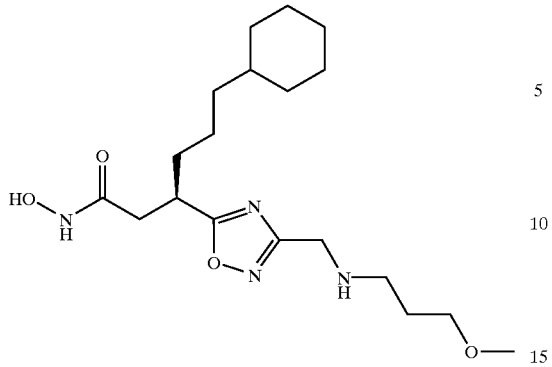

Method as for example 7 using (3R)-6-cyclohexyl-3-(3-{[(3-methoxypropyl)amino]methyl}-1,2,4-oxadiazol-5-yl)hexanoic acid (preparation 101) (226 mg, 0.62 mmol) as starting material.

Purification: The crude material was purified on a silica column eluting with DCM:MeOH:NH$_3$ (92.5:7.5:0.5) to afford the title compound as a white solid (52 mg, 25%).

M.Pt.: 60° C.

$^1$H nmr: (CD$_3$OD) 0.83 (2H, m), 1.10–1.30 (8H, m), 1.60–1.80 (9H, m), 2.52 (1H, dd), 2.61 (1H, dd), 2.68 (2H, t), 3.33 (3H, obs), 3.42 (2H, t), 3.58 (1 H, m), 3.83 (2H, s).

MS: 383 (MH$^+$)

Example 46

(3R)-6-cyclohexyl-N-hydroxy-3-(3-{[(4-hydroxycyclohexyl)amino]methyl}-1,2,4-oxadiazol-5-yl)hexanamide

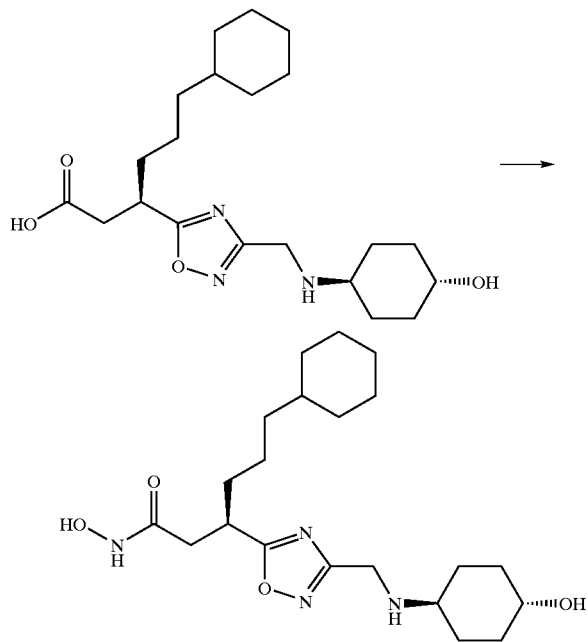

Method as for example 7 using (3R)-6-cyclohexyl-3-(3-{[(4-hydroxycyclohexyl)amino]methyl}-1,2,4-oxadiazol-5-yl)hexanoic acid (preparation 103) (179 mg, 0.35 mmol) as starting material.

Purification: The crude material was purified on a silica column eluting with a solvent gradient of DCM:MeOH:NH$_3$ (90:10:1) gradually changing to (80:20:1) to afford the title compound as a colourless oil (70 mg).

$^1$H nmr: (CD$_3$OD) 0.82 (2H, m), 1.10–1.35 (12H, m), 1.60–1.80.(7H, m), 1.99 (4H, brd), 2.52 (1H, dd), 2.60 (1 H, dd), 2.63 (1 H, m), 3.54 (2H, m), 4.01 (2H, s).

MS: 409 (MH$^+$)

Example 47

(3R)-6-cyclohexyl-N-hydroxy-3-(3-{[(4-methoxycyclohexyl)amino]methyl}-1,2,4-oxadiazol-5-yl)hexanamide

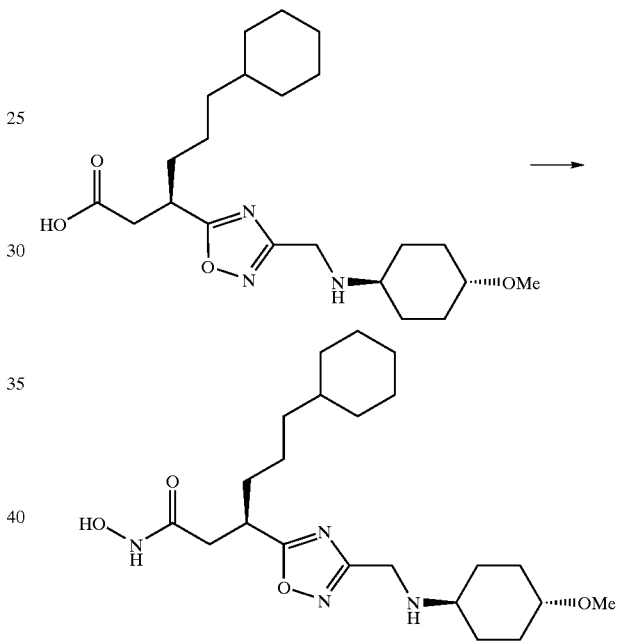

Method as for example 7 using (3R)-6-cyclohexyl-3-(3-{[(4-methoxycyclohexyl)amino]methyl}-1,2,4-oxadiazol-5-yl)hexanoic acid (preparation 105) (175 mg, 0.34 mmol) as starting material.

Purification: The crude material was purified on a silica column eluting with a solvent gradient of DCM:MeOH:NH$_3$ (97.5:2.5:0.25) gradually changing to (90:10:1) to afford the title compound as a gum (68 mg).

$^1$H nmr: (CDCl$_3$) 0.82 (2H, m), 1.10–1.35 (10H, m), 1.40–1.90 (13H, m), 2.60 (3H, m), 3.26 (4H, s+m), 3.59 (1H, m), 3.91 (2H, s). Evidence of the presence of the cis-isomer of the cyclohexanamine.

MS: 424 (MH$^+$)

Example 48 methyl {[(5-{(1R)-4-cyclohexyl-1-[2-(hydroxyamino)-2-oxoethyl]butyl}-1,2,4-oxadiazol-3-yl)methyl]amino}acetate

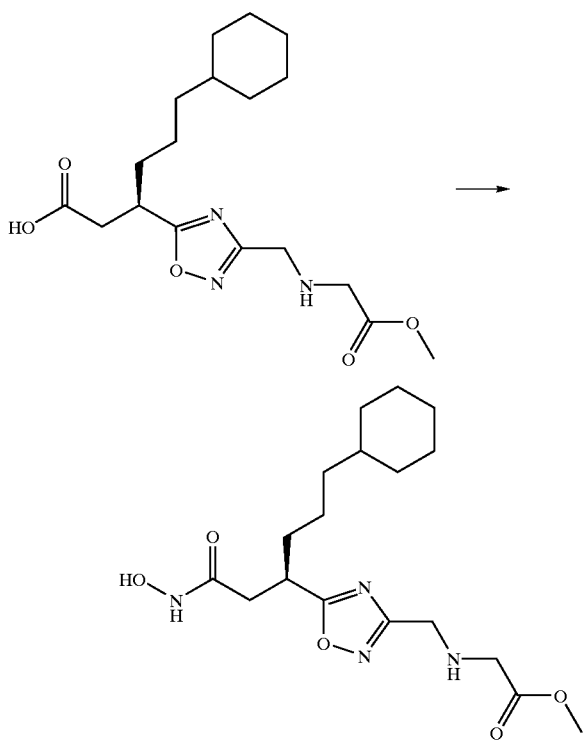

Method as for example 7 using (3R)-6-cyclohexyl-3-(3-{[(2-methoxy-2-oxoethyl)amino]methyl}-1,2,4-oxadiazol-5-yl)hexanoic acid (preparation 107) (135 mg, 0.37 mmol) as starting material.

Purification: The crude material was purified on a silica column eluting with a solvent gradient of DCM:MeOH (100:0) gradually changing to (90:10) to afford the title compound as a colourless oil (30 mg, 21%).

$^1$H nmr: (CDCl$_3$) 0.82 (2H, m), 1.10–1.40 (8H, m), 1.60–1.85 (7H, m), 2.55–2.79 (2H, m), 3.49 (2H, s), 3.59 (1H, m), 3.77 (3H, s), 3.93 (2H, s).

MS: 383 (MH$^+$)

Accurate mass: Found 383.2300 (MH$^+$), Calculated C$_{18}$H$_{30}$N$_4$O$_5$, 383.2289.

Example 49

(3R)-3-(3-{[[(2-amino-2-oxoethyl)amino]methyl}-1,2,4-oxadiazol-5-yl)-6-cyclohexyl-N-hydroxyhexanamide

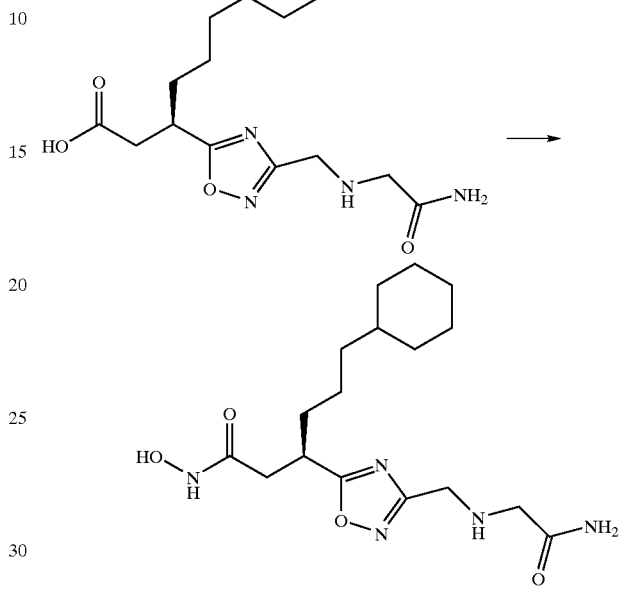

Method as for example 7 using (3R)-3-(3-{[[(2-amino-2-oxoethyl)amino]methyl}-1,2,4-oxadiazol-5-yl)-6-cyclohexylhexanoic acid (preparation 109) (137 mg, 0.35 mmol) as starting material.

Purification: The crude material was purified on a silica column eluting with a solvent gradient of DCM:MeOH (9:1) gradually changing to (1:1) To afford the title compound as a white solid (15 mg).

M.Pt.: 60–70° C.

$^1$H nmr: (d$_6$DMSO) 0.80 (2H, m), 1.00–1.25 (8H, m), 1.50–1.70 (7H, m), 2.41 (2H, m), 3.08 (2H, s), 3.40 (1H, m), 3.79 (2H, s), 6.82 (1H, brs), 7.18 (1H, brs), 8.62 (1H, brs), 10.38 (1H, brs).

MS: 390 (MNa$^+$)

Example 50

(3R)-6-cyclohexyl-N-hydroxy-3-{3-[(tetrahydro-2H-pyran-4-ylamino)methyl]-1,2,4-oxadiazol-5-yl}hexanamide

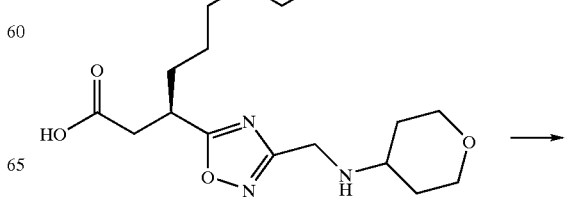

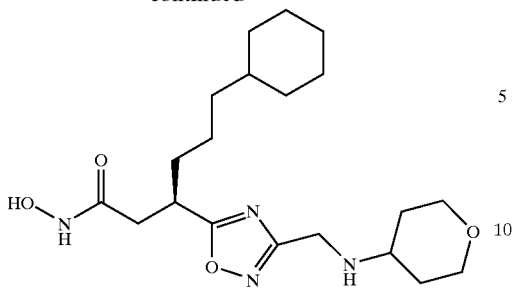

Method as for example 7 using (3R)-6-cyclohexyl-3-{3-[(tetrahydro-2H-pyran-4-ylamino)methyl]-1,2,4-oxadiazol-5-yl}hexanoic acid (preparation 111) (223 mg, 0.45 mmol) as starting material.

Purification: The crude material was purified on a silica column eluting with a solvent gradient of DCM:MeOH:NH₃ (97.5:2.5:0.25) gradually changing to (90:10:1). The material was azeotroped from Et₂O and then triturated with Et₂O to afford the title compound as a white solid, which was dried under reduced pressure (35.3 mg).

M. Pt.: 108.9–110.3° C.

¹H nmr: (CDCl₃) 0.81 (2H, m), 1.10–1.35 (8H, m), 1.43 (2H, m), 1.60–1.80 (7H, m), 1.82 (2H, brd), 2.55 (1H, m), 2.62 (1H, m), 2.78 (1H, m), 3.39 (2H, t), 3.59 (1H, m), 3.93 (2H, s), 3.98 (2H, d).

MS: 395 (MH⁺)

CHN: Found: C60.53%; H8.73%; N14.04%; $C_{20}H_{34}N_4O_4$ requires C60.89; H8.69%; N14.2%.

Example 51

(3R)-6-cyclohexyl-N-hydroxy-3-{3-[(1H-pyrazol-3-ylamino)methyl]-1,2,4-oxadiazol-5-yl}hexanamide

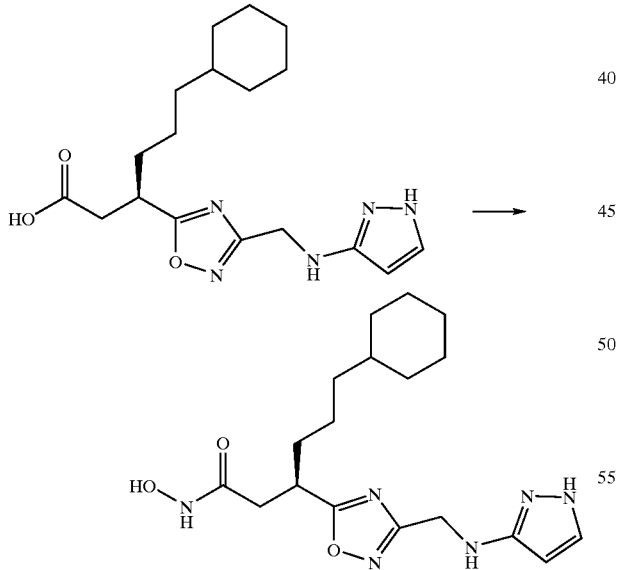

Method as for example 7 using (3R)-6-cyclohexyl-3-{3-[(1H-pyrazol-3-ylamino)methyl]-1,2,4-oxadiazol-5-yl}hexanoic acid (preparation 113) (132 mg, 0.27 mmol) as starting material.

Purification: The crude material was purified on a silica column eluting with DCM:MeOH:NH₃ (90:10:1) to afford the title compound as a colourless oil (4.1 mg)

¹H nmr: (d₆DMSO) 0.79 (2H, m), 1.00–1.20 (8H, m), 1.50–1.65 (7H, m), 2.40 (2H, m), 3.40 (1H, m), 5.19 (2H, s), 5.24 (3H, s), 7.02 (1H, s).

Example 52

(3R)-6-cyclohexyl-3-(3-{[(1-ethyl-1H-pyrazol-5-yl)amino]methyl}-1,2,4-oxadiazol-5-yl)-N-hydroxyhexanamide

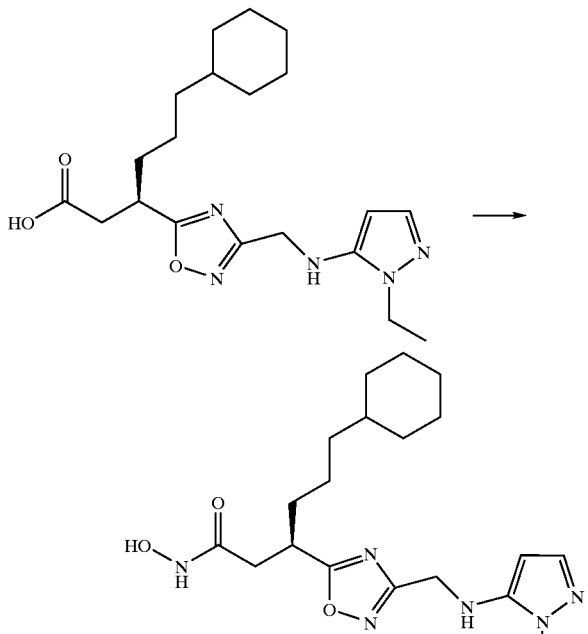

Method as for example 1 using (3R)-6-cyclohexyl-3-(3-{[(1-ethyl-1H-pyrazol-5-yl)amino]methyl}-1,2,4-oxadiazol-5-yl)hexanoic acid (preparation 115) (40 mg, 0.10 mmol) as starting material and NMM as the base.

Purification: The crude material was purified on a silica column eluting with DCM:MeOH:NH₃ (97:3:0.3) gradually changing to (90:10:1) to afford the title compound as a white foam (31 mg).

¹H nmr: (CDCl₃) 0.79 (2H, m), 1.05–1.40 (11H, m), 1.55–1.80 (7H, m), 2.52 (2H, brs), 3.59 (1H, m), 3.92 (2H, brs), 4.33 (2H, brs), 5.51 (1H, brs), 7.26 (1H, obs).

MS: 405 (MH⁺)

CHN: Found: C57.94%; H7.92%; N20.08%; $C_{20}H_{32}N_6O_3 \cdot 0.5\,H_2O$ requires C58.09; H8.04%; N20.32%.

Example 53 tert-butyl (2S)-2-(5-{(1R)-4-cyclohexyl-1-[2-(hydroxyamino)-2-oxoethyl]butyl}-1,2,4-oxadiazol-3-yl)-1-pyrrolidinecarboxylate

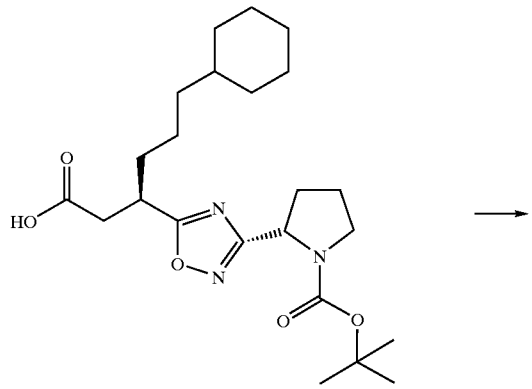

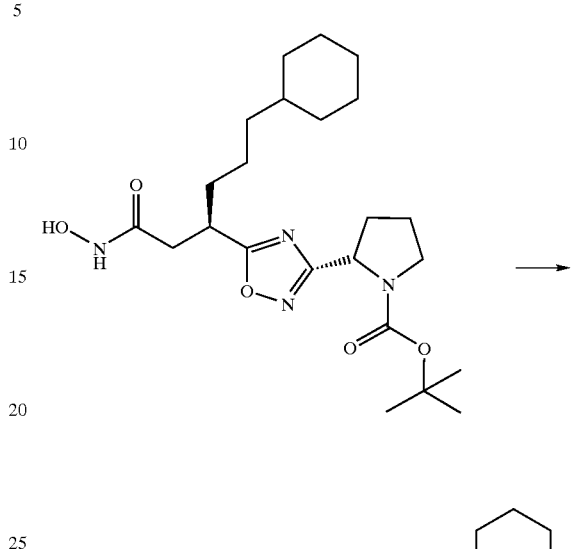

Method as for example 7 using (3R)-3-{3-[(2S)-1-(tert-butoxycarbonyl)pyrrolidinyl]-1,2,4-oxadiazol-5-yl}-6-cyclohexylhexanoic acid (preparation 120) (220 mg, 0.50 mmol) as starting material.

Purification: The crude material was purified on a silica column eluting with DCM:MeOH (95:5) to afford the title compound as a colourless oil (95 mg).

¹H nmr: (d₆DMSO) 0.79 (2H, m), 1.10–1.40 (17H, m+s+m), 1.50–1.65 (7H, m), 1.70–1.95 (3H, m), 2.22 (1H, m), 2.40 (2H, m), 3.39 (3H, m), 4.81 (1H, brs), 8.78 (1H, brs), 10.42 (1H, brs).

MS: 473 (MNa⁺)

Example 54

(3R)-6-cyclohexyl-N-hydroxy-3-{3-[(2S)-pyrrolidinyl]-1,2,4-oxadiazol-5-yl}hexanamide

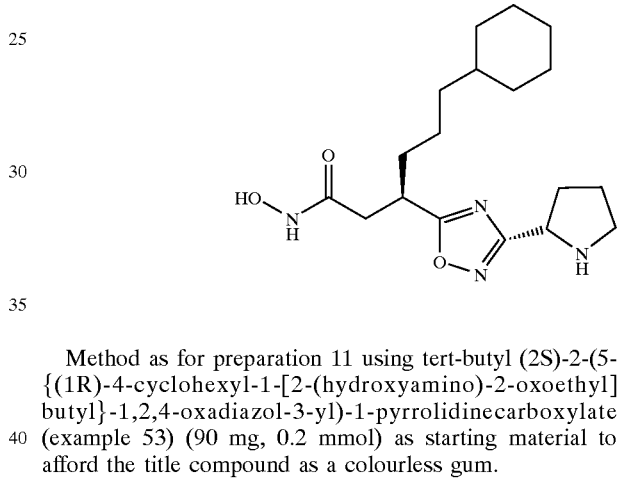

Method as for preparation 11 using tert-butyl (2S)-2-(5-{(1R)-4-cyclohexyl-1-[2-(hydroxyamino)-2-oxoethyl]butyl}-1,2,4-oxadiazol-3-yl)-1-pyrrolidinecarboxylate (example 53) (90 mg, 0.2 mmol) as starting material to afford the title compound as a colourless gum.

¹H nmr: (d₆DMSO) 0.80 (2H, m), 1.00–1.25 (8H, m), 1.50–1.70 (7H, m), 2.02 (4H, m), 2.40 (2H, m), 3.31 (2H, m), 4.48 (1H, m), 4.83 (1H, brs), 9.28 (1H, brs), 9.80 (1H, brs).

MS: 351 (MH⁺)

Example 55

(3R)-6-cyclohexyl-N-hydroxy-3-(3-[(2S)-piperidinyl]-1,2,4-oxadiazol-5-yl}hexanamide

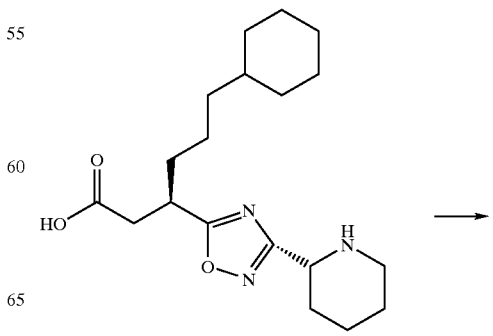

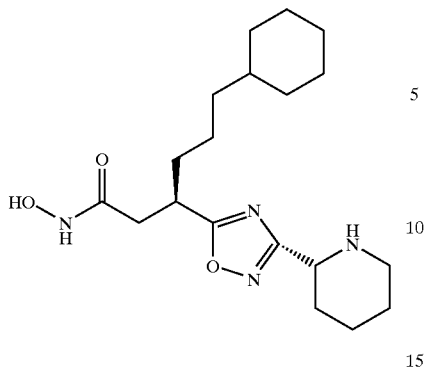

Method as for example 7 using (3R)-6-cyclohexyl-3-{3-[(2S)-piperidinyl]-1,2,4-oxadiazol-5-yl}hexanoic acid (preparation 123) (319 mg, 0.83 mmol) as starting material.

Purification: The crude material was purified on a silica column eluting with a solvent gradient of DCM:MeOH (100:0) gradually changing to (95:5) to afford the title compound contaminated with imidazole. The material was dissolved in EtOAc and washed with $H_2O$ (×2) followed by brine. The organic extract was dried over anhydrous $MgSO_4$ and filtered. The solvent was removed under reduced pressure to afford the title compound as a white foam.

$^1$H nmr: ($d_6$DMSO) 0.80 (2H, m), 1.00–1.30 (8H, m), 1.30–1.65 (11H, m), 1.74 (1H, m), 1.82 (1H, d), 2.45 (2H, obs), 2.60 (1H, t), 2.97 (1H, d), 3.40 (1H, m), 3.79 (1H, d), 8.61 (1H, brs), 10.38 (1H, brs).

MS: 365 (MH$^+$)

CHN: Found: C60.88%; H8.82%; N15.06%; $C_{19}H_{32}N_4O_3 \cdot 0.5H_2O$ requires C61.10; H8.91%; N15.00%.

Example 56

(3R)-6-cyclohexyl-3-(3-[(dimethylamino)methyl]-1,2,4-oxadiazol-5-yl}-N-hydroxyhexanamide

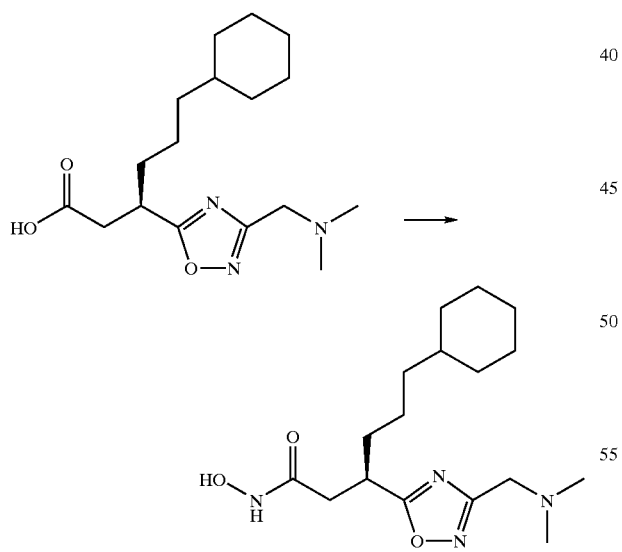

Method as for example 7 using (3R)-6-cyclohexyl-3-{3-[(dimethylamino)methyl]-1,2,4-oxadiazol-5-yl}hexanoic acid (Preparation 125) (495 mg, 1.14 mmol) as starting material.

Purification: The residue was purified on a silica column eluting with DCM:MeOH:NH$_3$ (90:10:1) to afford the title compound (90 mg).

$^1$Hnmr (CD$_3$OD):0.85 (2H, m), 1.10–1.30 (8H, m), 1.60–1.80 (7H, m), 2.38 (6H, s), 2.51 (1H, dd), 2.61 (1H, dd), 3.54 (1H, m), 3.65 (2H, s).

MS: 339 (MH$^+$)

Example 57

(3R)-6-cyclohexyl-N-hydroxy-3-(3-{[(2-methoxyethyl)(methyl)amino]methyl}-1,2,4-oxadiazol-5-yl)hexanamide

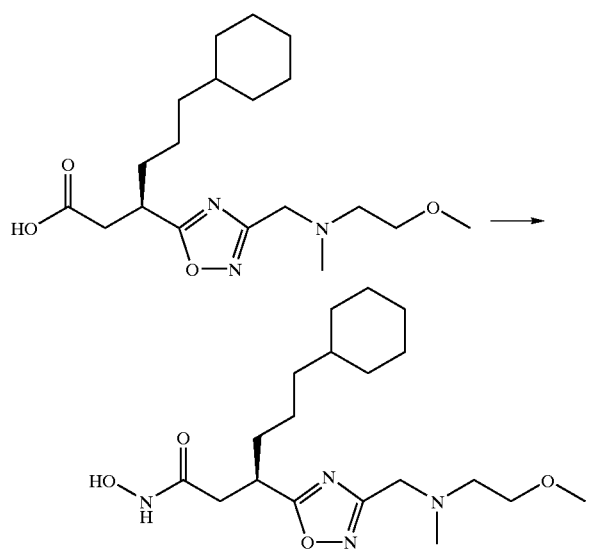

Method as for example 7 using (3R)-6-cyclohexyl-3-(3-{[(2-methoxyethyl)(methyl)amino]methyl}-1,2,4-oxadiazol-5-yl)hexanoic acid (preparation 127) (209 mg, 0.57 mmol) as starting material.

Purification: The crude material was purified on a silica column eltuing with DCM:MeOH:NH$_3$ (90:10:1) to afford the title compound as a colourless gum (145 mg, 66%).

$^1$Hnmr (CD$_3$OD):0.83 (2H, m), 1.10–1.30 (8H, m), 1.60–1.80 (7H, m), 2.37 (3H, s), 2.53 (1H, dd), 2.61 (1H, dd), 2.71 (2H, t), 3.36 (3H, s), 3.55 (3H, t+m), 3.78 (2H, s).

MS: 383 (MH$^+$)

Example 58

(3R)-6-cyclohexyl-3-(3-{[[2-(dimethylamino)ethyl](methyl)amino]methyl}-1,2,4-oxadiazol-5-yl)-N-hydroxyhexanamide

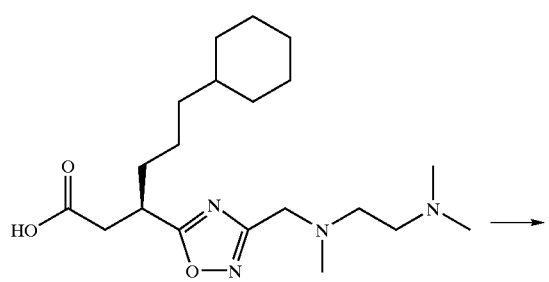

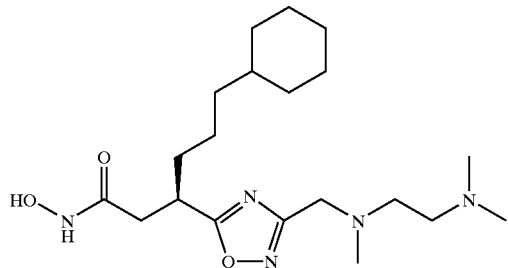

Method as for example 7 using (3R)-6-cyclohexyl-3-(3-{[[2-(dimethylamino)ethyl](methyl)amino]methyl}-1,2,4-oxadiazol-5-yl)hexanoic acid (preparation 129) (354 mg, 0.58 mmol) as starting material.

Purification: The crude material was purified on a silica column eluting with DCM:MeOH:NH₃ (90:10:1) to afford the title compound as a colourless oil (40 mg).

¹Hnmr (d₆DMSO): 0.78 (2H, m), 1.00–1.20 (8H, m), 1.50–1.70 (7H, m), 2.08 (6H, s), 2.19 (3H, s), 2.32 (2H, t), 2.42 (4H, m), 3.41 (1H, m), 3.65 (2H, s).

MS: 397 (M–H)

Example 59

(3R)-3-(3-{[(2-amino-2-oxoethyl)(methyl)amino]methyl}-1,2,4-oxadiazol-5-yl)-6-cyclohexyl-N-hydroxyhexanamide

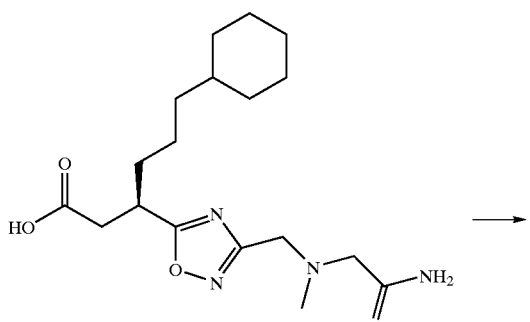

Method as for example 7 using (3R)-3-(3-{[(2-amino-2-oxoethyl)(methyl)amino]methyl}-1,2,4-oxadiazol-5-yl)-6-cyclohexylhexanoic acid (preparation 131) (223 mg, 0.57 mmol) as starting material.

Purification: The crude material was purified on a silica column eluting with DCM:MeOH (9:1) to afford the title compound as a colourless oil (74 mg).

¹H nmr: (CD₃OD) 0.83 (2H, m), 1.10–1.30 (8H, m), 1.60–1.80 (7H, m), 2.39 (3H, s), 2.52 (1H, dd), 2.61 (1H, dd), 3.18 (2H, s), 3.56 (1H, m), 3.80 (2H, s)+imidazole MS: 404 (MNa⁺)

CHN: Found: C55.09%; H8.03%; N18.63%; C₁₈H₃₁N₅O₄.0.5 H₂O.0.1 imidazole requires C55.33; H8.22%; N18.33%.

Example 60

(3R)-6-cyclohexyl-N-hydroxy-3-[3-({methyl[2-(methylamino)-2-oxoethyl]amino}methyl)-1,2,4-oxadiazol-5-yl]hexanamide

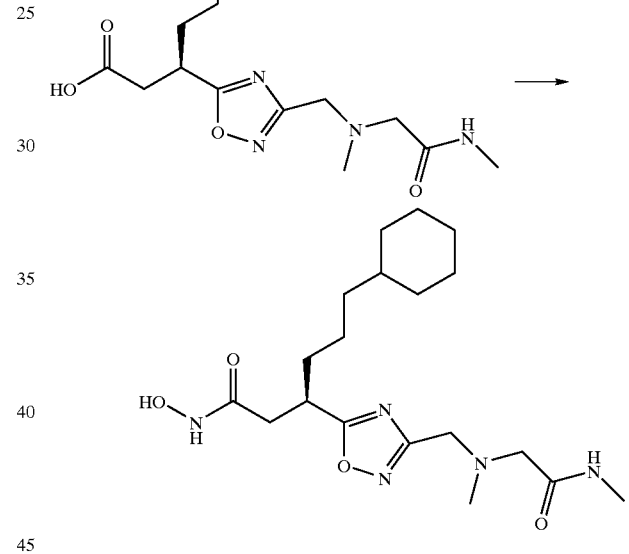

Method as for example 7 using (3R)-6-cyclohexyl-3-[3-({methyl[2-(methylamino)-2-oxoethyl]amino}methyl)-1,2,4-oxadiazol-5-yl]hexanoic acid (preparation 135) (398 mg, 0.95 mmol) as starting material.

Purification: The crude material was purified on a silica column eluting with DCM:MeOH (19:1) to afford the title compound as a colourless gum (198 mg, 52%).

¹H nmr: (d₆DMSO) 0.80 (2H, m), 1.00–1.25 (8H, m), 1.50–1.70 (7H, m), 2.23 (3H,2), 2.41 (2H, m), 2.60 (3H, d), 3.02 (2H, s), 3.41 (1H, m), 3.78 (2H, s), 7.58 (1H, brs), 8.63 (1H, brs), 10.39 (1H, brs).

MS: 418 (MNa⁺)

CHN: Found: C56.22%; H8.22%; N17.23%; C₁₉H₃₃N₅O₄.0.5 H₂O requires C56.42; H8.47%; N17.31%.

Example 61

(3R)-6-cyclohexyl-3-(3-{[[2-(dimethylamino)-2-oxoethyl](methyl)amino]methyl}-1,2,4-oxadiazol-5-yl)-N-hydroxyhexanamide

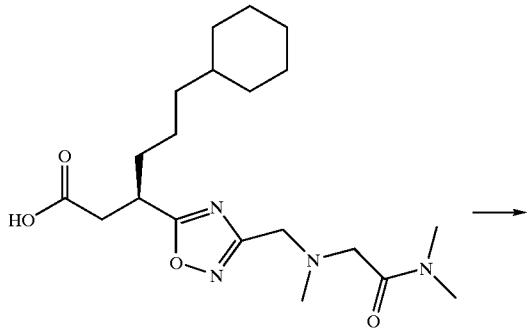

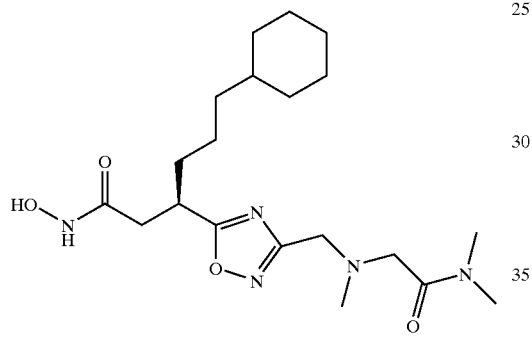

Method as for example 7 using (3R)-6-cyclohexyl-3-(3-{[[2-(dimethylamino)-2-oxoethyl](methyl)amino]methyl}-1,2,4-oxadiazol-5-yl)hexanoic acid (preparation 137) (403 mg, 0.94 mmol) as starting material.

Purification: The crude material was purified on a 2 silica columns eluting with DCM:MeOH (19:1) to afford the title compound as a colourless sticky gum (76 mg).

$^1$H nmr: (d$_6$DMSO) 0.80 (2H, m), 1.00–1.25 (8H, m), 1.50–1.70 (7H, m), 2.27 (3H, s), 2.41 (2H, m), 2.80 (3H, s), 2.93 (3H, s), 3.27 (2H, s), 3.41 (1H, m), 3.78 (2H, s), 8.64 (1H, brs), 10.39 (1H, brs).

MS: 432 (MNa$^+$)

CHN: Found: C56.58%; H8.56%; N16.46%; C$_{20}$H$_{35}$N$_5$O$_4$·0.7 H$_2$O requires C56.91; H8.69%; N16.59%.

Example 62

(3R)-3-(3-{[bis(2-methoxyethyl)amino]methyl}-1,2,4-oxadiazol-5-yl)-6-cyclohexyl-N-hydroxyhexanamide

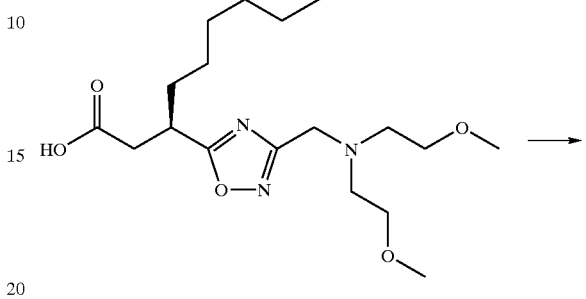

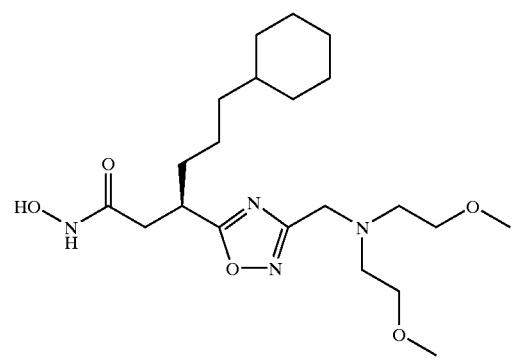

Method as for example 7 using (3R)-3-(3-{[bis(2-methoxyethyl)amino]methyl}-1,2,4-oxadiazol-5-yl)-6-cyclohexylhexanoic acid (preparation 139) (176 mg, 0.42 mmol) as starting material.

Purification: The crude material was purififed on a silica column eluting with DCM:MeOH:NH$_3$ (90:10:1) to afford the title compound as a colourless oil (76 mg).

$^1$Hnmr (d$_6$DMSO):0.79 (2H, m), 1.00–1.20 (8H, m), 1.50–1.70 (7H, m), 2.42 (2H, m), 2.69 (4H, t), 3.20 (6H, s), 3.19 (4H, t), 3.20 (1H, m), 3.80 (2H, s).

Example 63

(3R)-6-cyclohexyl-N-hydroxy-3-[3-(1-pyrrolidinylmethyl)-1,2,4-oxadiazol-5-yl]hexanamide

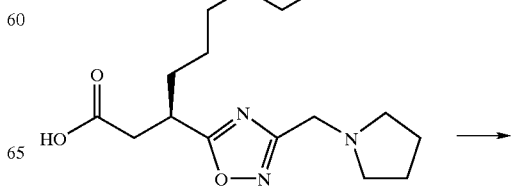

81

-continued

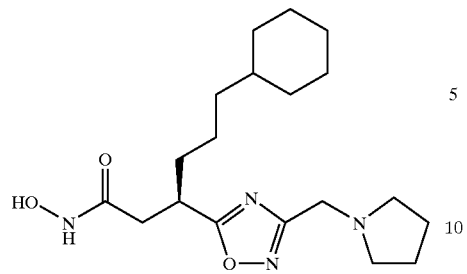

Method as for example 7 using (3R)-6-cyclohexyl-3-[3-(1-pyrrolidinylmethyl)-1,2,4-oxadiazol-5-yl]hexanoic acid (Preparation 141) (97 mg, 0.24 mmol).

Purification: The residue was purified a silica column eluting with a solvent gradient system of DCM:MeOH:NH$_3$ (95:5:0.5) gradually changing to (90:10:1) to afford the title compound (14 mg).

$^1$Hnmr (CD$_3$OD): 0.86 (2H, m), 1.05–1.35 (8H, m), 1.60–1.90 (11H, m), 2.52 (1H, dd), 2.60 (1H, dd), 2.72 (4H, m), 3.54 (1H, m), 3.83 (2H, s), MS: 365 (MH$^+$), 387 (MNa$^+$)

Example 64

(3R)-6-cyclohexyl-N-hydroxy-3-{3-[(4-hydroxy-1-piperidinyl)methyl]-1,2,4-oxadiazol-5-yl}hexanamide

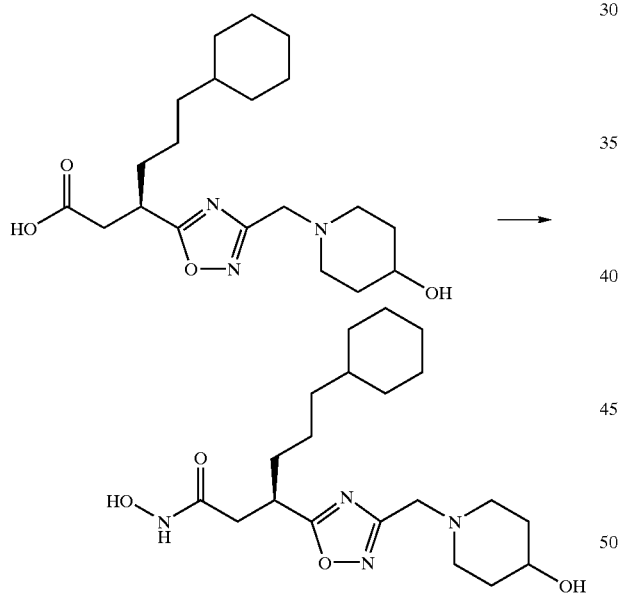

Method as for example 7 using (3R)-6-cyclohexyl-3-{3-[(4-hydroxy-1-piperidinyl)methyl]-1,2,4-oxadiazol-5-yl}hexanoic acid trifluoroacetate (Preparation 143) (414 mg, 0.84 mmol) as starting material.

Purification: The crude material was purified on a silica column eluting with DCM:MeOH:NH$_3$ (90:10:1). The residue was azeotroped from Et$_2$O to afford the title compound as a white foam (240 mg).

M.Pt.: 85° C.

$^1$Hnmr (CD$_3$OD): 0.85 (2H, m), 1.05–1.35 (8H, m), 1.55–1.80 (9H, m), 1.88 (2H, m), 2.42 (2H, m), 2.54 (1H, dd), 2.61 (1H, dd), 2.93 (2H, m), 3.55 (1H, m), 3.63 (1H, m), 3.76 (2H, s)

MS: 395 (MH$^+$), 417 (MNa$^+$)

82

Example 65

(3R)-6-cyclohexyl-N-hydroxy-3-[3-(4-morpholinylmethyl)-1,2,4-oxadiazol-5-yl]hexanamide

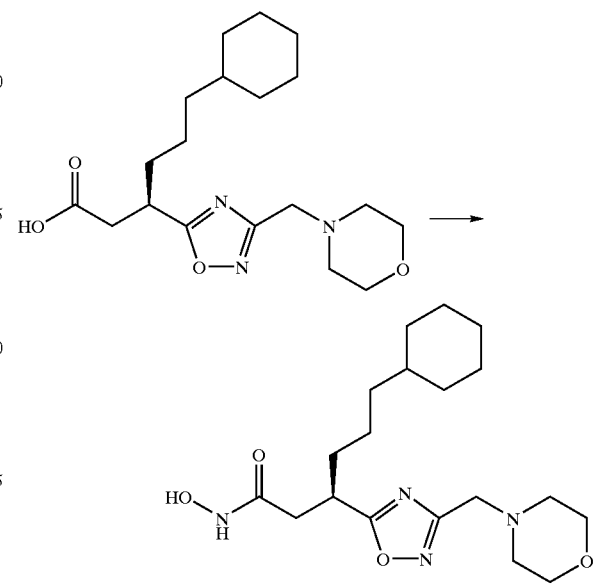

Method as for example 7 using (3R)-6-cyclohexyl-3-[3-(4-morpholinylmethyl)-1,2,4-oxadiazol-5-yl]hexanoic acid (Preparation 145) (120 mg, 0.33 mmol) as starting material.

Purification: The crude material was purified on a silica column eluting with DCM:MeOH:NH$_3$ (90:10:1). The residue was triturated with Et$_2$O to afford the title compound as a white solid (29 mg).

M.Pt.: 138–139° C.

$^1$Hnmr (d$_6$DMSO): 0.77 (2H, m), 1.00–1.25 (8H, m), 1.50–1.70 (7H, m), 2.35–2.55 (6H, m), 3.42 (1H, m), 3.53 (4H, m), 3.60 (2H, s), 8.74 (1H, s), 10.45 (1H, s)

MS: 381 (MH$^+$)

Example 66

(3R)-6-cyclohexyl-N-hydroxy-3-{3-[(4-methyl-1-piperazinyl)methyl]-1,2,4-oxadiazol-5-yl}hexanamide

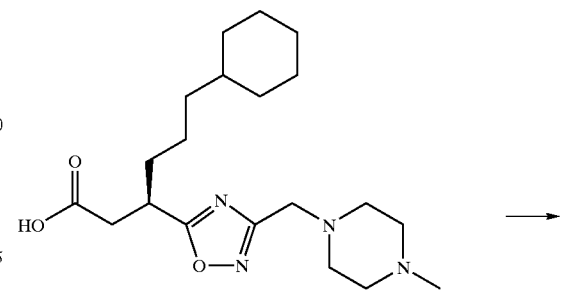

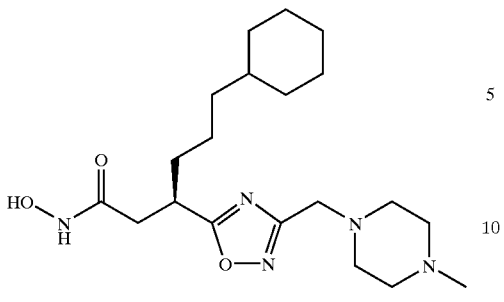

Method as for example 7 using (3R)-6-cyclohexyl-3-{3-[(4-methyl-1-piperazinyl)methyl]-1,2,4-oxadiazol-5-yl}hexanoic acid trifluoroacetate (Preparation 147) (343 mg, 0.91 mmol) as starting material.

Purification: The crude material was purified on a silica column eluting with a gradient system of DCM:MeOH:NH$_3$ (95:5:0.5) gradually changing to (80:20:1) to afford the title compound as a white gum (140 mg).

$^1$Hnmr (CD$_3$OD):0.87 (2H, m), 1.10–1.40 (8H, m), 1.60–1.80 (7H, m), 2.50–3.45 (13H, m), 3.52 (1H, m), 3.84 (2H, s)

MS: 394 (MH$^+$)

Example 67

(3R)-6-cyclohexyl-N-hydroxy-3-[3-(1H-1,2,4-triazol-1-ylmethyl)-1,2,4-oxadiazol-5-yl]hexanamide

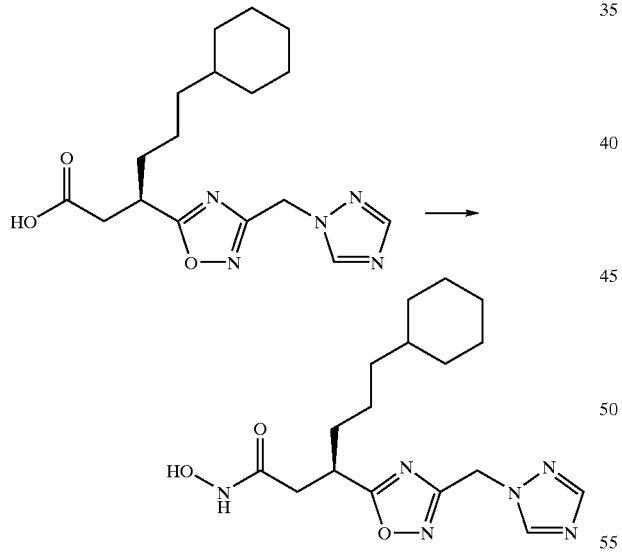

Method as for example 7 using (3R)-6-cyclohexyl-3-[3-(H-1,2,4-triazol-1-ylmethyl)-1,2,4-oxadiazol-5-yl]hexanoic acid (Preparation 150) (174 mg, 0.50 mmol) as starting material to afford the title compound as a white solid (68 mg).

M.Pt.: 118–120° C.

$^1$Hnmr (d$_6$DMSO): 0.75 (2H, m), 1.0–1.20 (8H, m), 1.45–1.65 (7H, m), 2.35–2.55 (2H, m), 3.40 (1H, m), 5.61 (2H, s), 7.98 (1H, s), 8.63 (1H, s), 8.76 (1H, s), 10.45 (1H, s)

Example 68

(3R)-6-cyclohexyl-N-hydroxy-3-{4-[(isopropylamino)methyl]-1,3-oxazol-2-yl}hexanamide

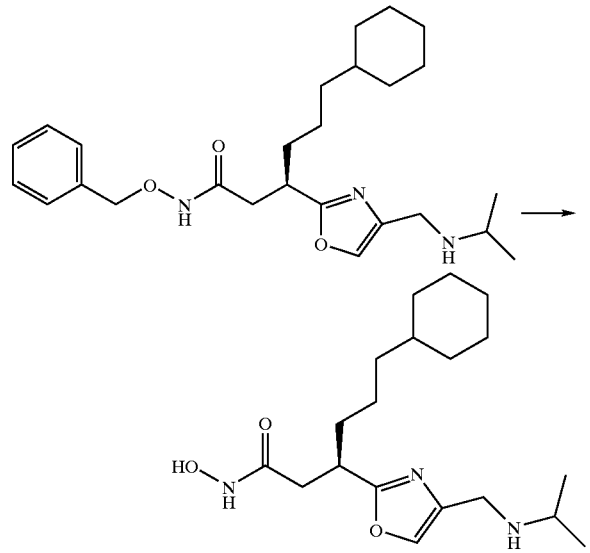

A solution of (3R)-N-(benzyloxy)-6-cyclohexyl-3-{4-[(isopropylamino)methyl]-1,3-oxazol-2-yl}hexanamide (preparation 157) (85 mg, 0.20 mmol) in EtOH (5 ml) was treated with HCO$_2$NH$_4$ (63 mg, 1.00 mmol) and Pd(OH)$_2$ (20 mg) and the reaction mixture heated at 43° C. for 18 hours. 2 further portions of HCO$_2$NH$_4$ (30 mg+30 mg) and Pd(OH)$_2$ (10 mg+30 mg) were added over a period of 4 hours. The catalyst was filtered off and washed with EtOH. The solvent was removed under reduced pressure. The crude material was purified on a silica column eluting with DCM:MeOH:NH$_3$ (90:10:1) to afford the title compound.

$^1$H nmr: (d$_6$DMSO) 0.79 (2H, m), 0.96 (6H, d), 1.00–1.20 (8H, m), 1.50–1.65 (7H, m), 2.24 (1H, m), 2.40 (1H, m), 3.70 (1H, m), 3.20 (1H, obs), 3.52 (2H, s), 7.68 (1H, s).

MS: 352 (MH$^+$)

Acc. Mass: Found 374.2415 (MNH$_4^+$); Calculated C$_{19}$H$_{33}$N$_3$O$_3$ 374.2420 (MNH$_4$+).

Example 69

(3R)-6-cyclohexyl-3-{4-[(cyclopentylamino)methyl]-1,3-oxazol-2-yl}-N-hydroxyhexanamide

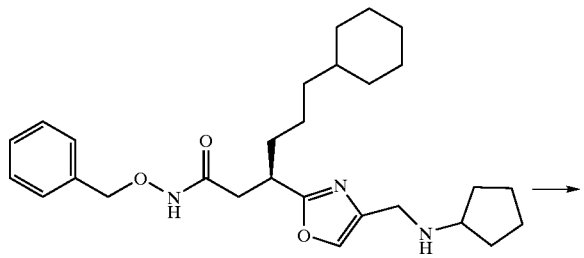

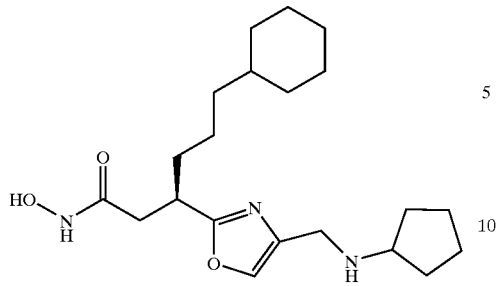

Method and purification as for example 67 using (3R)-N-(benzyloxy)-6-cyclohexyl-3-{4-[(cyclopentylamino)methyl]-1,3-oxazol-2-yl}hexanamide (preparation 158) (112 mg, 0.23 mmol) as starting material to afford the title compound as a white solid (30 mg, 35%).

M.Pt.: 124–127° C.

$^1$H nmr: (d$_6$DMSO) 0.80 (2H, m), 1.00–1.20 (8H, m+Et$_2$O), 1.28 (2H, m), 1.42 (2H, m), 1.50–1.75 (11H, m), 2.25 (1H, m), 2.39 (1H, m), 2.99 (1H, m), 3.20 (1H, m), 3.49 (2H, s), 7.64 (1H, s).

MS: 378 (MH$^+$)

CHN: Found: C66.40%; H9.48%; N11.08%; C$_{21}$H$_{35}$N$_3$O$_3$·0.1 H$_2$O requires C66.49; H9.35%; N11.08%.

Example 70

(3R)-6-cyclohexyl-N-hydroxy-3-[4-(4-morpholinylmethyl)-1,3-oxazol-2-yl]hexanamide

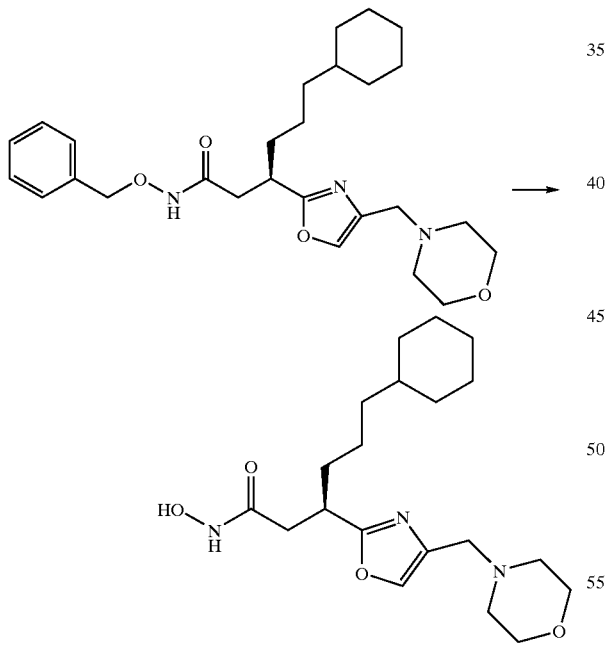

Method as for example 67 using (3R)-N-(benzyloxy)-6-cyclohexyl-3-[4-(4-morpholinylmethyl)-1,3-oxazol-2-yl]hexanamide (preparation 159) (130 mg, 0.28 mmol) as starting material.

Purification: The crude material was purified on a silica column eluting with a solvent gradient of DCM:MeOH:NH$_3$ (98:2:0.2) gradually changing to (90:10:1) to afford the title compound as a white solid (32 mg, 30%).

M.Pt.: 117–119° C.

$^1$H nmr: (d$_6$DMSO) 0.79 (2H, m), 1.00–1.20 (8H, m), 1.50–1.65 (7H, m), 2.25 (1H, m), 2.26 (1H, m), 2.38 (4H, t), 2.41 (1H, m), 3.20 (1H, m), 3.53 (4H, t), 3.90 (2H, d), 7.77 (1H, s), 8.58 (1H, brs), 10.28 (1H, brs).

MS: 402 (MNa$^+$)

CHN: Found: C63.09%; H8.80%; N11.01%; C$_{20}$H$_{33}$N$_3$O$_4$ requires C63.30; H8.76%; N11.07%.

Example 71

(3R)-6-cyclohexyl-N-hydroxy-3-{5-methyl-4-[(tetrahydro-2H-pyran-4-ylamino)methyl]-1,3-oxazol-2-yl}hexanamide

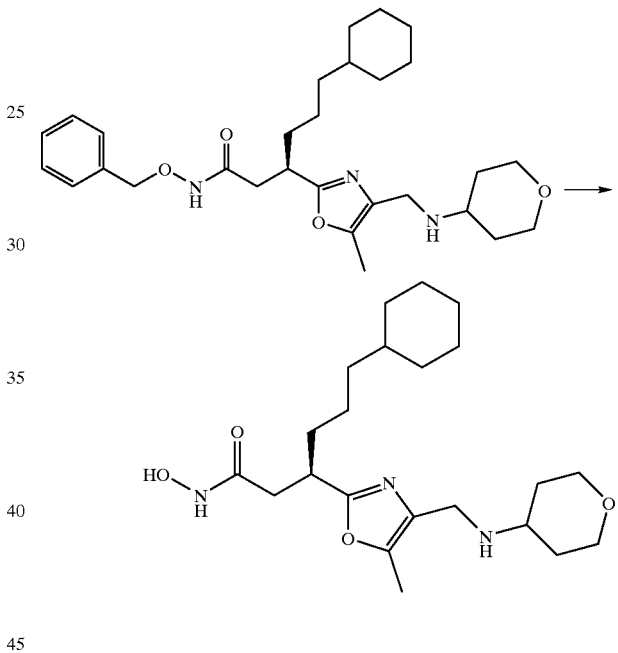

Method as for example 67 using (3R)-N-(benzyloxy)-6-cyclohexyl-3-{5-methyl-4-[(tetrahydro-2H-pyran-4-ylamino)methyl]-1,3-oxazol-2-yl}hexanamide (preparation 161) (200 mg, 0.40 mmol) as starting material.

Purification: The crude material was purified on a silica column eluting with DCM:MeOH:NH$_3$ (95:5:0.5) to afford the title compound as a white solid (28 mg, 17%).

M.Pt.: 108–110° C.

$^1$H nmr: (d$_6$DMSO) 0.79 (2H, m), 1.05–1.30 (10H, m), 1.50–1.65 (7H, m), 1.70 (2H, brd), 2.20 (3H, s), 2.37 (1H, m), 2.50 (2H, obs), 3.15 (1H, obs), 3.21 (2H, t), 3.46 (2H, s), 3.79 (2H, m), 8.58 (1H, brs), 10.27 (1H, brs).

MS: 408 (MH$^+$)

CHN: Found: C64.37%; H9.25%; N10.27%; C$_{22}$H$_{37}$N$_3$O$_4$·0.1 H$_2$O requires C64.55; H9.16%; N10.26%.

Example 72

(3R)-6-cyclohexyl-N-hydroxy-3-[5-methyl-4-(4-morpholinylmethyl)-1,3-oxazol-2-yl]hexanamide

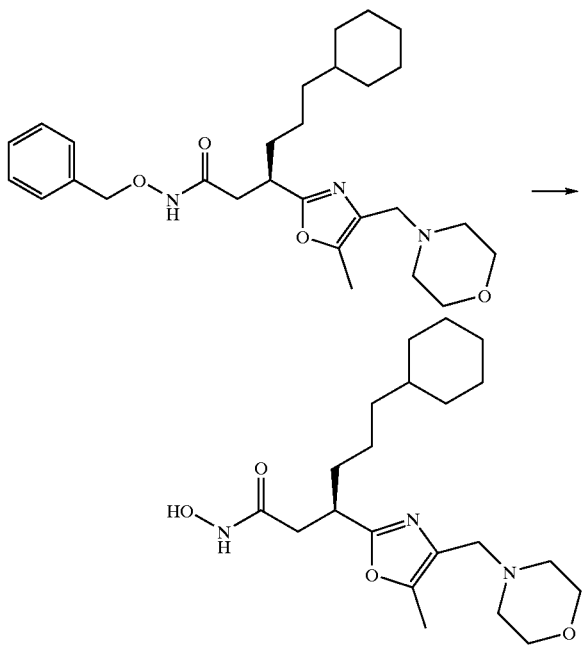

Method as for example 67 using (3R)-N-(benzyloxy)-6-cyclohexyl-3-[5-methyl-4-(4-morpholinylmethyl)-1,3-oxazol-2-yl]hexanamide (preparation 162) (154 mg, 0.32 mmol) as starting material.

Purification: 3 silica columns were required to purify the crude material. First column eluting with a solvent gradient of DCM:MeOH:NH$_3$ (100:0:0) gradually changing to (95:5:0.5). The second column eluting with toluene: EtOAc (9:1) and the final column eluting with DCM:MeOH:NH$_3$ (95:5:0.5) to afford the title compound as a white foam (50 mg, 40%).

$^1$H nmr: (d$_6$DMSO) 0.79 (2H, m), 1.00–1.20 (8H, m), 1.50–1.65 (7H, m), 2.21 (3H, s), 2.35 (5H, m), 2.50 (1H, obs), 3.14 (1H, obs)3.22 (2H, s), 3.51 (4H, m), 8.58 (1H, brs), 10.28 (1H, brs).

MS: 394 (MH$^+$)

CHN: Found: C63.15%; H9.20%; N10.57%; C$_{21}$H$_{35}$N$_3$O$_4$.0.2 H$_2$O requires C63.51; H8.98%; N10.58%.

Preparation 1:

(1Z)-N'-hydroxy-2-[(methylsulfonyl)amino]ethanimidamide

(a) N-(Cyanomethyl)methanesulfonamide (Known Compound, WO 92/02521)

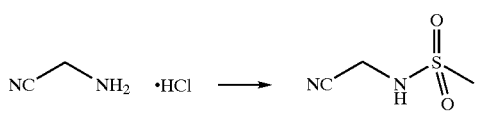

N-methyl morpholine (1.12 Kg, 11.1 mol) was added dropwise over 30 min to a stirred suspension of aminoacetonitrile.hydrochloride (500 g, 5.4 mol) in dichloromethane (2.5 liters), between 25 and 28° C. The mixture was stirred at ambient temperature for 30 min. Methanesulfonyl chloride (619 g, 5.4 mol) was added dropwise over 60 min, maintaining the temperature between 15 and 22° C. The mixture was stirred at ambient temperature for 45 min and then cooled to 12° C. The mixture was filtered and the filtrate concentrated in vacuo to a brown suspension. Acetone (2 liters) was added and the mixture was cooled to 10° C. and then filtered. Silica (1 Kg) was added to the filtrate, which was then filtered through a plug of silica (1 Kg). The residue was washed with acetone (2×2.5 liters) and the combined filtrate was concentrated in vacuo to afford the title compound as a brown oil (725 g, quantitative).

(b) (1Z)-N'-hydroxy-2-[(methylsulfonyl)amino]ethanimidamide

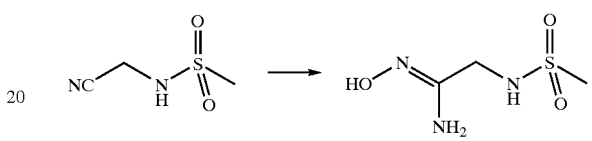

METHOD A. A solution of 50% aqueous hydroxylamine (367 g, 5.4 mol) was added over 60 min to a solution of N-(cyanomethyl)methanesulfonamide (725 g, 5.4 mol) in EtOH (3.6 liters), between 25 and 35° C. The mixture was stirred at ambient temperature for 60 min and then cooled to 5° C. The mixture was filtered and the residue washed with EtOH (3×250 ml) and then dried by suction overnight to afford the title compound as white crystals (781 g, 87%).

METHOD B. A solution of N-(cyanomethyl)methanesulfonamide (WO 92/02521) (10.85 g, 81.0 mmol) in EtOH (370 ml) was treated with hydroxylamine.HCl (5.63 g, 81.0 mmol) followed by a solution of aqueous NaOH (3.24 g, 82.0 mmol in 125 ml) and stirred at room temperature, under a nitrogen atmosphere for 20 hours. The solvent was removed under reduced pressure. The solid was dissolved in hot EtOH and the solid NaCl was filtered off. A solid began to crystallise out after 1 hour. The solid was filtered off and washed with Et$_2$O to afford the title compound as white crystals (9.77 g, 72%).

$^1$H nmr: (d$_6$DMSO) 2.87 (3H, s), 3.49 (2H, s), 5.22 (2H, brs), 7.09 (1H, brs), 9.00 (1H, s)

MS: 190 (MNa$^+$)

CHN: Found: C21.46%; H5.41%; N24.58%; C$_3$H$_9$N$_3$O$_3$S.0.1H$_2$O requires C21.32%; H5.49%; N24.87%.

Preparation 2:

tert-butyl (5Z,9R)-5-amino-9-(3-cyclohexylpropyl)-8-oxo-7-oxa-2-thia-3,6-diazaundec-5-en-11-oate 2,2-dioxide

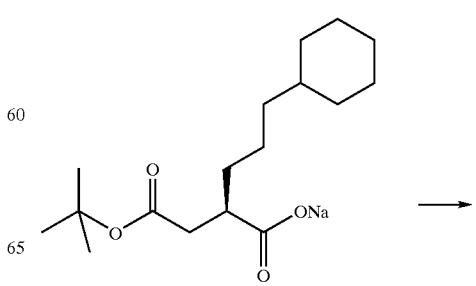

-continued

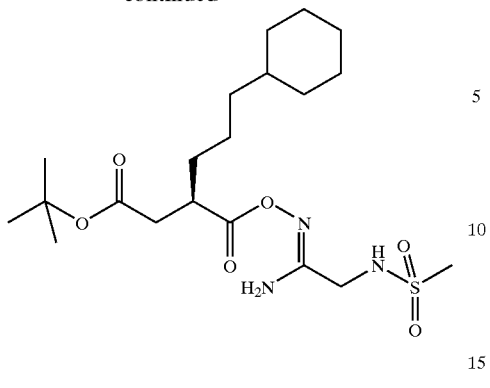

METHOD A. Sodium (2R)-2-(2-tert-butoxy-2-oxoethyl)-5-cyclohexylpentanoate (Preparation 167) (18.68 g, 58.4 mmol) was partitioned between 10% citric acid solution (190 ml) and EtOAc (190 ml). The organic layer was washed with brine, dried over anhydrous MgSO$_4$, filtered and the solvent removed under reduced pressure to afford the free acid as a colourless oil. A solution of the free acid in DCM (185 ml) was treated CDI (9.46 g, 58.4 mmol) and the reaction mixture was stirred at room temperature for 1.5 hours. (1Z)-N'-hydroxy-2-[(methylsulfonyl)amino]ethanimidamide (preparation 1) (9.75 g, 58.4 mmol) was added portionwise but required the addition of DMF (50 ml) to dissolve the solid. The reaction mixture was stirred at room temperature for 18 hours. The solvents were removed under reduced pressure. The residue was dissolved on EtOAc (500 ml) and washed with water (2×500 ml) and brine, dried over anhydrous MgSO$_4$, filtered and the solvent removed under reduced pressure to afford the title compound as a white solid (26.3 g, ~100%).

METHOD B. Sodium (2R)-2-(2-tert-butoxy-2-oxoethyl)-5-cyclohexylpentanoate (Preparation 167) (50.0 g, 0.16 mol) was partitioned between 10% citric acid solution (500 ml) and dichloromethane (500 ml). The organic layer was separated, washed with demineralised water (500 ml), and then dried by azeotropic distillation at constant volume of dichloromethane. The mixture was allowed to cool to ambient temperature and then CDI (25.3 g, 0.16 mol) was added portionwise over 2 min, under nitrogen. The mixture was stirred at ambient temperature for 30 min and then (1Z)-N'-hydroxy-2-[(methylsulfonyl)amino]ethanimidamide (preparation 1) (26.1 g, 0.16 mol) was added in one portion. The mixture was stirred at ambient temperature for 18 hours and then filtered. The filtrate was washed with water (2×500 ml), 10% aqueous citric acid solution (500 ml) and water (500 ml) and then concentrated in vacuo to afford the title compound as a white solid (58.3 g, 83%).

$^1$H nmr: (d$_6$DMSO) 0.81 (2H, m), 1.00–1.30 (9H, m), 1.37 (9H, s), 1.40–1.65 (6H, m), 2.39 (1H, dd), 2.55 (1H, dd), 2.79 (1H, m), 2.94 (3H, s), 3.62 (2H, s), 6.19 (2H, brs), 7.30 (1H, brs)

MS: 470 (MNa$^+$)

Preparation 3:

tert-butyl (3R)-6-cyclohexyl-3-(3-{[(methylsulfonyl)amino]methyl}-1,2,4-oxadiazol-5-yl)hexanoate METHOD A. tert-butyl (5Z,9R)-5-amino-9-(3-cyclohexylpropyl)-8-oxo-7-oxa-2-thia-3,6-diazaundec-5-en-11-oate 2,2-dioxide (preparation 2) (26.0 g, 58.2 mmol) was heated at 130° C. in xylene (500 ml) under a nitrogen atmosphere for 20 hours. The crude reaction mixture was purified on a silica column diluted at first by pentane and eluting the column with a solvent gradient of DCM:MeOH (100:0) gradually changing to (90:10). Mixed fractions were combined and the solvent removed under reduced pressure to give a brown residue. This was triturated with pentane and the solid filtered off to afford the title compound as a white solid (9.43 g, 38%).

METHOD B. A stirred suspension of tert-butyl (5Z,9R)-5-amino-9-(3-cyclohexylpropyl)-8-oxo-7-oxa-2-thia-3,6-diazaundec-5-en-11-oate 2,2-dioxide (preparation 2) (50.0 g, 0.11 mol) and basic aluminium oxide (150 g) in toluene was heated to reflux for 5 hours, under nitrogen. Basic aluminium oxide (50 g) was added and the mixture was held at reflux for a further 1 hour. The mixture was allowed to cool to ambient temperature and then filtered. The residue was washed with toluene (100 ml) and the combined filtrate was concentrated in vacuo to afford the title compound as a white solid (24.0 g, 50%).

$^1$H nmr: (CD$_3$OD) 0.83 (2H, m), 1.10–1.30 (9H, m), 1.38 (9H, s), 1.60–1.75 (7H, m), 2.67 (1H, dd), 2.79 (1H, dd), 2.98 (3H, s), 3.42 (1H, m), 4.39 (2H, s)

MS: 452 (MNa$^+$)

Alternative synthesis:

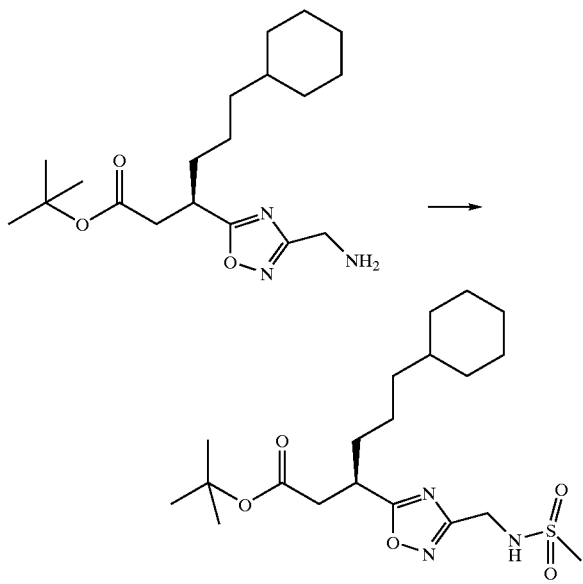

A solution of tert-butyl (3R)-3-[3-(aminomethyl)-1,2,4-oxadiazol-5-yl]-6-cyclohexylhexanoate (preparation 18) (1.0 g, 2.85 mmol) in pyridine (10 ml) at 0° C. was treated with methanesulphonylchloride (221 μl, 2.85 mmol) and stirred under a nitrogen atmosphere for 5 hours. The solvent was removed under reduced pressure. The residue was dissolved in ethyl acetate and washed with 1 M HCl followed by brine. The organic extract was dried over anhydrous MgSO$_4$, filtered and the solvent removed under reduced pressure. The residue was purified on a silica column eluting with a gradient solvent system EtOAc:pentane (0:100) gradually changing to (35:65) to afford the title compound as a pale yellow oil (1.22 g, 98%).

$^1$H nmr: (CDCl$_3$) 0.84 (2H, m), 1.10–1.35 (8H, m), 1.40 (9H, s), 1.60–1.80 (7H, m), 2.62 (1H, dd), 2.79 (1H, dd), 2.99 (3H, s), 3.42 (1H, m), 4.45 (2H, d), 4.82 (1H, s).

MS: 452 (MNa$^+$)

Preparation 4:

(3R)-6-cyclohexyl-3-(3-{[(methylsulfonyl)amino]methyl}-1,2,4-oxadiazol-5-yl)hexanoic acid

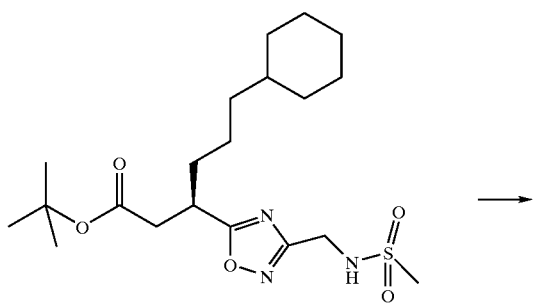

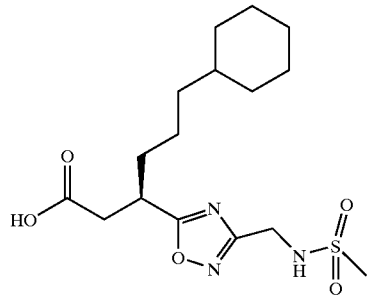

METHOD A. A solution of tert-butyl (3R)-6-cyclohexyl-3-(3-{[(methylsulfonyl)amino]methyl}-1,2,4-oxadiazol-5-yl)hexanoate (preparation 3) (9.36 g, 21.8 mmol) in toluene (100 ml) was treated with TFA (50 ml) and stirred under a nitrogen atmosphere, at room temperature for 20 hours. The solvent was removed under reduced pressure and azeotroped with EtOAc. The residue was dissolved in EtOAc (250 ml) and washed with H$_2$O followed by brine. The organic layer was dried over anhydrous MgSO$_4$, filtered and the solvent was removed under reduced pressure. The solid was triturated with Et$_2$O, filtered off and dried under reduced pressure to afford the title compound as an off-white solid (7.06 g, 87%).

METHOD B. Trifluoroacetic acid (48 ml) was added in one portion to a stirred solution of tert-butyl (3R)-6-cyclohexyl-3-(3-{[(methylsulfonyl)amino]methyl}-1,2,4-oxadiazol-5-yl)hexanoate (preparation 3) (24.0 g, 56 mmol) in toluene (120 ml), under nitrogen. The mixture was stirred at ambient temperature for 20 hours and then concentrated in vacuo to a yellow oil. Toluene (100 ml) was added and the mixture was filtered. The residue was washed with toluene (2×20 ml) and then dried in vacuo at 45° C. to afford the title compound as an off-white solid (16.4 g, 78%).

$^1$H nmr: (CD$_3$OD) 0.83 (2H, m), 1.10–1.35 (8H, m), 1.60–1.80 (7H, m), 2.75 (1H, dd), 2.85 (1H, dd), 2.97 (3H, s), 3.48 (1H, m), 4.39 (2H, s)

MS: 396 (MNa$^+$)

CHN: Found: C51.45%; H7.29%; N11.20%; C$_{16}$H$_{27}$N$_3$O$_5$S requires C51.46%; H7.29%; N11.25%.

Preparation 5:

tert-butyl (3R)-6-cyclohexyl-3-{3-[(methylamino)methyl]-1,2,4-oxadiazol-5-yl}hexanoate

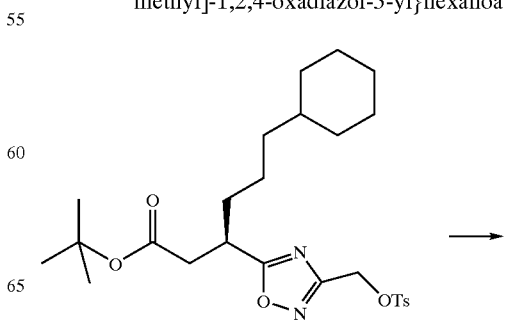

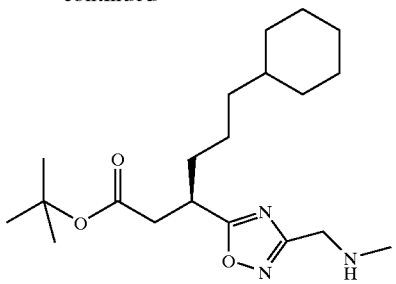

A solution of tert-butyl (3R)-6-cyclohexyl-3-[3-({[(4-methylphenyl)sulfonyl]oxy}methyl)-1,2,4-oxadiazol-5-yl]hexanoate (preparation 177) (492 mg, 0.97 mmol) in THF (1 ml) was treated with a solution of 2M methylamine in THF (7 ml, 14.4 mmol) and stirred at 40° C. in a sealed vessel for 75 minutes. The reaction mixture was allowed to cool to room temperature and dissolved in EtOAc (100 ml) which was washed with sat. NaHCO$_3$ (100 ml) solution followed by brine. The organic extract was dried over MgSO$_4$, filtered and the solvent was removed under reduced pressure to afford the title compound as a colourless oil (337 mg, 95%).

$^1$H nmr: (CDCl$_3$) 0.82 (2H, m), 1.10–1.35 (8H, m), 1.39 (9H, s), 1.55–1.80 (7H, m), 2.43 (3H, s), 2.60 (1H, dd), 2.79 (1H, dd), 3.43 (1H, m), 3.83 (2H, s).

MS: 366 (MH$^+$)

CHN: Found: C65.32%; H9.67%; N11.22%; C$_{20}$H$_{35}$N$_3$O$_3$ requires C65.72%; H9.65%; N11.50%.

Preparation 6:

tert-butyl (3R)-6-cyclohexyl-3-(3-{[methyl(methylsulfonyl)amino]methyl}-1,2,4-oxadiazol-5-yl)hexanoate

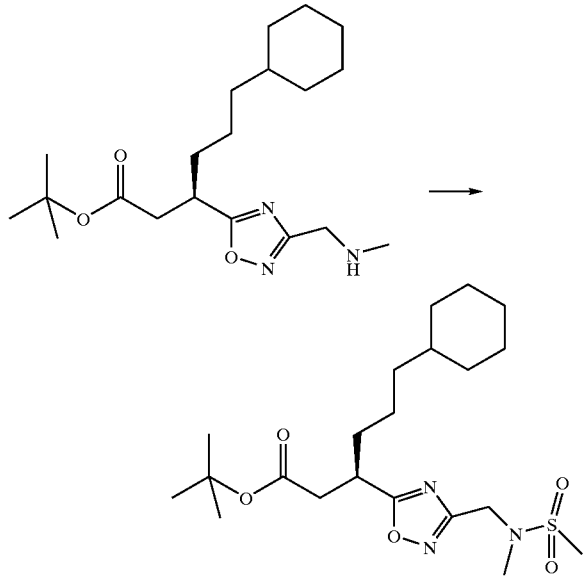

A solution of tert-butyl (3R)-6-cyclohexyl-3-{3-[(methylamino)methyl]-1,2,4-oxadiazol-5-yl}hexanoate (preparation 5) (300 mg, 0.82 mmol) in pyridine (2 ml) in a water bath was treated with methanesulphonylchloride (64 μl, 0.82 mmol) and stirred under a nitrogen atmosphere for 20 minutes. The solvent was removed under reduced pressure. The residue was dissolved in EtOAc and washed with 2M HCl followed by brine. The organic extract was dried over MgSO$_4$, filtered and the solvent removed under reduced pressure. The residue was purified on a silica column eluting with a solvent gradient of EtOAc:pentane (5:95) gradually changing to (30:70) to afford the title compound as a colourless oil (273 mg, 75%).

$^1$H nmr: (CDCl$_3$) 0.84 (2H, m), 1.10–1.35 (8H, m), 1.39 (9H, s), 1.60–1.80 (7H, m), 2.61 (1H, dd), 2.79 (1H, dd), 2.93 (3H, s), 2.97 (3H, s), 3.43 (1H, m), 3.59 (2H, s).

MS: 466 (MNa$^+$)

CHN: Found: C57.03%; H8.43%; N9.39%; C$_{21}$H$_{37}$N$_3$O$_5$S requires C56.86%; H8.41%; N9.47%.

Preparation 7:

(3R)-6-cyclohexyl-3-(3-{[methyl(methylsulfonyl)amino]methyl}-1,2,4-oxadiazol-5-yl)hexanoic acid

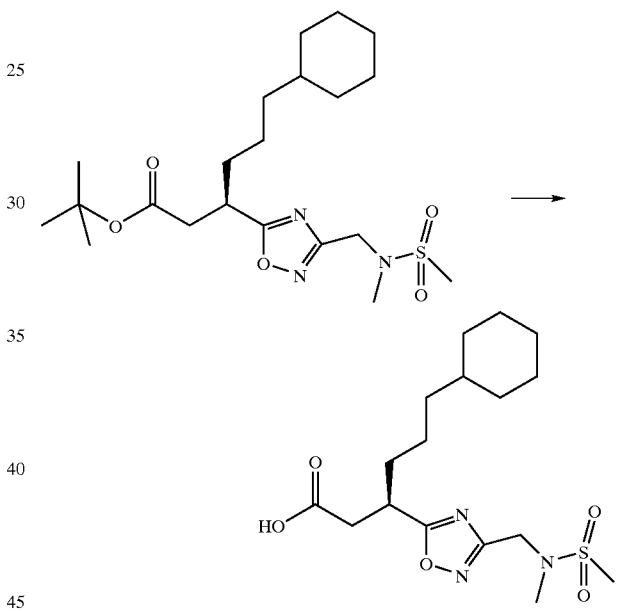

A solution of tert-butyl (3R)-6-cyclohexyl-3-(3-{[methyl(methylsulfonyl)amino]methyl}-1,2,4-oxadiazol-5-yl)hexanoate (preparation 6) (264 mg, 0.60 mmol) in 4M HCl in dioxan (2 ml) was stirred at room temperature for 20 hours. Further 4M HCl in dioxan (2 ml) was added and stirred for a further 3 hours. A few drops of concentrated HCl was added and the reaction mixture was stirred at room temperature for 18 hours. The solvent was removed under reduced pressure to afford the title compound (245 mg—contained some dioxan as impurity).

$^1$H nmr: (CDCl$_3$) 0.84 (2H, m), 1.10–1.35 (8H, m), 1.60–1.85 (7H, m), 2.61 (1H, dd), 2.79 (1H, dd), 2.88–2.99 (7H, m), 3.47 (1H, m), 4.58 (2H, s).

MS: 386 (M–H)

CHN: Found: C50.82%; H7.45%; N9.93%; C$_{17}$H$_{29}$N$_3$O$_5$S.0.75 H$_2$O.0.15 dioxan requires C51.03%; H7.71%; N10.14%.

Preparation 8:

tert-butyl (3R)-6-cyclohexyl-3-(3-{[(ethylsulfonyl)amino]methyl}-1,2,4-oxadiazol-5-yl)hexanoate

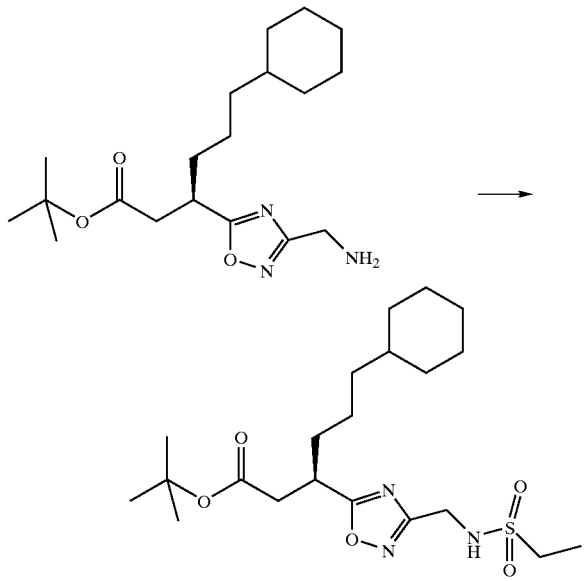

Method the same as for Preparation 6 using tert-butyl (3R)-3-[3-(aminomethyl)-1,2,4-oxadiazol-5-yl]-6-cyclohexylhexanoate (preparation 18) (200 mg, 0.57 mmol) and ethanesulphonylchloride (54 μl, 0.57 mmol) as starting materials. The reaction was carried out at 0° C.

Purification: Crude material was purified on a silica column eluting with a solvent gradient of DCM:MeOH (100:0) gradually changing to (90:10) to yield the title compound as a colourless oil (190 mg, 90%).

$^1$H nmr: (CDCl$_3$) 0.84 (2H, m), 1.05–1.35 (11H, m), 1.40 (9H, s), 1.60–1.80 (7H, m), 2.61 (1H, dd), 2.79 (1H, dd), 3.09 (2H, q), 3.42 (1H, m), 4.43 (2H, d), 4.73 (1H, brs).

MS: 466 (MNa$^+$)

CHN: Found: C57.14%; H8.48%; N9.47%; C$_{21}$H$_{37}$N$_3$O$_5$S requires C56.86%; H8.41%; N9.47%.

Preparation 9:

(3R)-6-cyclohexyl-3-(3-{[(ethylsulfonyl)amino]methyl}-1,2,4-oxadiazol-5-yl)hexanoic acid

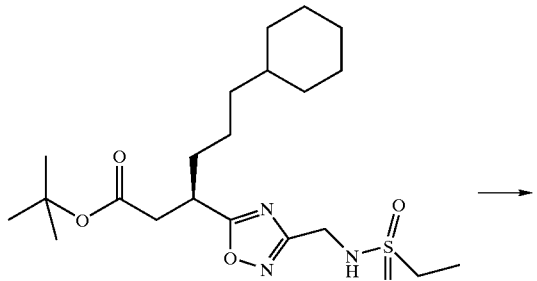

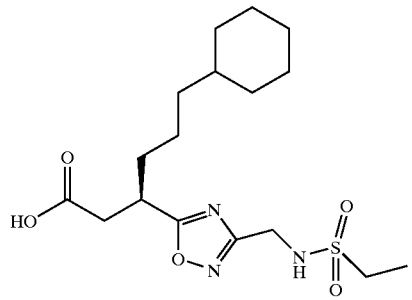

Method same as for preparation 7 using tert-butyl (3R)-6-cyclohexyl-3-(3-{[(ethylsulfonyl)amino]methyl}-1,2,4-oxadiazol-5-yl)hexanoate (preparation 8) (174 mg, 0.40 mmol) as starting material. After 24 hours the reaction had not gone to completion. The solvent was removed under reduced pressure. DCM (4 ml) and TFA (2 ml) were added and the reaction mixture was stirred at room temperature for 2 hours. The solvent was removed under reduced pressure and azeotroped with DCM (×3) and Et$_2$O. The residue was dissolved in EtOAc and washed with H$_2$O and brine. The organic extracts were dried over MgSO$_4$, filtered and the solvent removed under reduced pressure to afford the title compound as a colourless oil (148 mg, 96%).

$^1$H nmr: (CDCl$_3$) 0.81 (2H, m), 1.05–1.35 (11H, m), 1.60–1.80 (7H, m), 2.78 (1H, dd), 2.97 (1H, dd), 3.09 (2H, q), 3.48 (1H, m), 4.43 (2H, d), 5.14 (1H, brs).

MS: 386 (M–H)

CHN: Found: C52.07%; H7.38%; N10.30%; C$_{17}$H$_{29}$N$_3$O$_5$S.0.1TFA requires C51.79%; H7.35%; N10.53%.

Preparation 10:

tert-butyl (3R)-6-cyclohexyl-3-(3-{[(isopropylsulfonyl)amino]methyl}-1,2,4-oxadiazol-5-yl)hexanoate

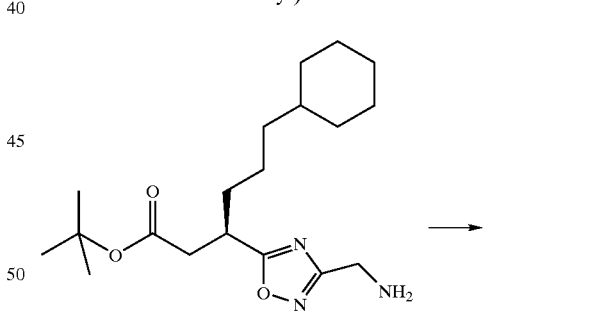

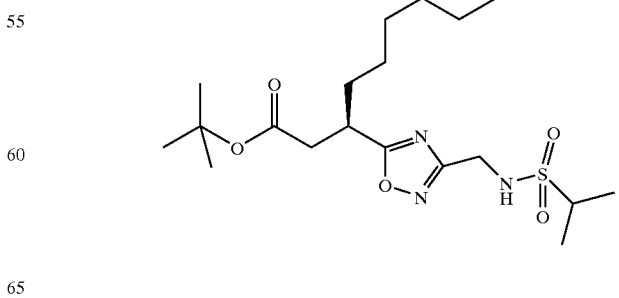

A solution of tert-butyl (3R)-3-[3-(aminomethyl)-1,2,4-oxadiazol-5-yl]-6-cyclohexylhexanoate (preparation 18)

(216 mg, 0.61 mmol) and 2,6-lutidine (180 µl, 1.50 mmol) in DCM (3 ml) was treated with isopropanesulphonylchloride (100 µl, 0.90 mmol) and stirred at room temperature for 18 hours. Reaction was complete but it was left for 12 days before purification commenced. The reaction mixture was diluted with DCM and washed with 1M HCl (2×20 ml), sat. NaHCO₃ solution and brine. The organic extract was dried over anhydrous MgSO₄, filtered and the solvent removed under reduced pressure. The residue was purified on a silica column eluting with a solvent gradient of pentane:EtOAc (90:10) gradually changing to (50:50) to afford the title compound as a colourless oil (157 mg, 56%).

¹H nmr: (CDCl₃) 0.80–0.90 (2H, m), 1.00–1.30 (8H, m), 1.30–1.40 (15H, d+s), 1.60–1.80 (7H, m), 2.60 (1H, dd), 2.80 (1H, dd), 3.20 (1H, m), 3.45 (1H, m), 4.45 (2H, d), 4.60 (1H, m).

MS:458 (MH⁺)

Preparation 11:

(3R)-6-cyclohexyl-3-(3-{[(isopropylsulfonyl)amino]methyl}-1,2,4-oxadiazol-5-yl)hexanoic acid

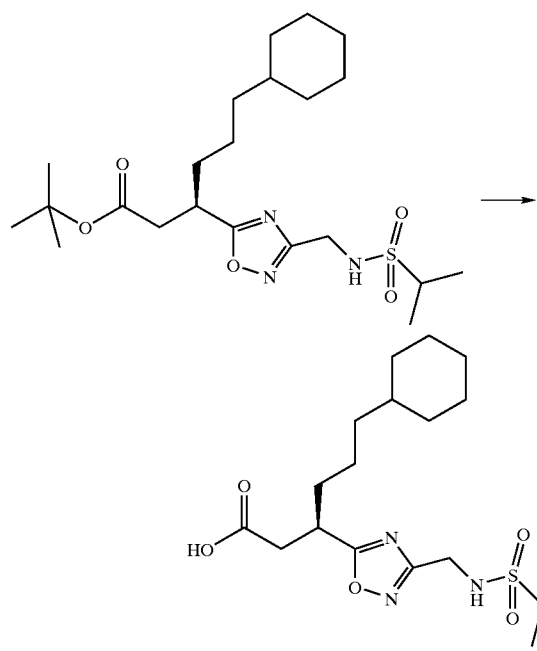

A solution of tert-butyl (3R)-3-[3-(aminomethyl)-1,2,4-oxadiazol-5-yl]-6-cyclohexylhexanoate (preparation 10) (145 mg, 0.32 mmol) in DCM (4 ml) was treated with TFA (2 ml) and stirred at room temperature for 6 hours. The solvent was removed under reduced pressure and azeotroped with toluene (×3) and DCM (×3) to afford the title compound as a yellow oil (117 mg, 92%).

¹H nmr: (CDCl₃) 0.80–0.90 (2H, m), 1.10–1.30 (8H, m), 1.35 (6H, d), 1.60–1.80 (7H, m), 2.75 (1H, dd), 2.90 (1H, dd), 3.20 (1H, m), 3.50 (1H, m), 4.40 (2H, d), 4.90 (1H, m).

MS: 400 (M−H)

Preparation 12:

tert-butyl (3R)-6-cyclohexyl-3-(3-{[(phenylsulfonyl)amino]methyl}-1,2,4-oxadiazol-5-yl)hexanoate

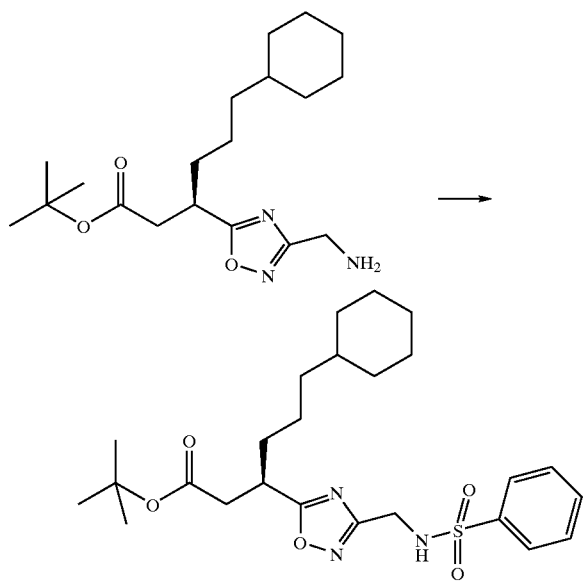

Method as for preparation 6 using tert-butyl (3R)-3-[3-(aminomethyl)-1,2,4-oxadiazol-5-yl]-6-cyclohexylhexanoate (preparation 18) (205 mg, 0.58 mmol) and benzenesulphonylchloride (75 µl, 0.58 mmol) as starting materials.

Purification: The crude material was purified on a silica column eluting with a solvent gradient of pentane:EtOAc (100:0) gradually changing to (65:35) to afford the title compound as a colourless oil (241 mg, 85%).

¹H nmr: (CDCl₃) 0.83 (2H, m), 1.10–1.30 (8H, m), 1.39 (9H, s), 1.60–1.75 (7H, m), 2.55 (1H, dd), 2.68 (1H, dd), 3.37 (1H, m), 4.31 (2H, d), 5.00 (1H, brs), 7.47 (2H, t), 7.56 (1H, d), 7.86 (2H, d)

MS: 514 (MNa⁺)

CHN: Found: C60.34%; H7.60%; N8.29%; $C_{25}H_{37}N_3O_5S \cdot 0.25\ H_2O$ requires C60.52% H7.62%; N8.47%.

Preparation 13:

(3R)-6-cyclohexyl-3-(3-{[(phenylsulfonyl)amino]methyl}-1,2,4-oxadiazol-5-yl)hexanoic acid

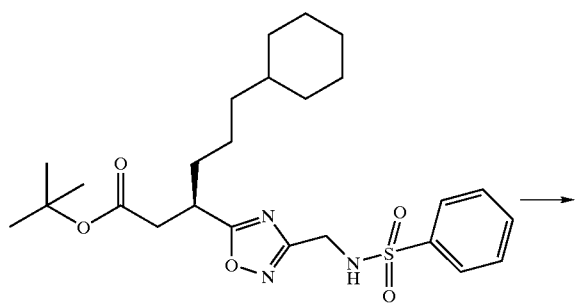

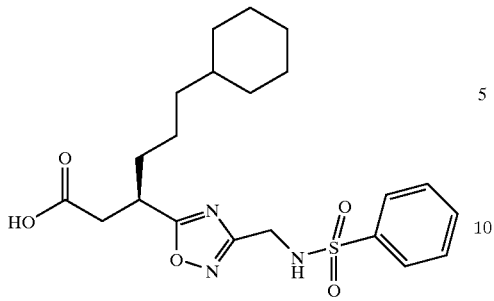

Method same as preparation 11 using tert-butyl (3R)-6-cyclohexyl-3-(3-{[(phenylsulfonyl)amino]methyl}-1,2,4-oxadiazol-5-yl)hexanoate (preparation 12) (231 mg, 0.47 mmol) as starting material.

Purification: The crude product was dissolved in EtOAc and washed with H$_2$O and brine. The organic extract was dried over anhydrous MgSO$_4$, filtered and the solvent removed under reduced pressure to afford the title compound as a white solid (168 mg, 82%).

$^1$H nmr: (CD$_3$OD) 0.85 (2H, m), 1.10–1.30 (8H, m), 1.60–1.75 (7H, m), 2.62 (1H, dd), 2.76 (1H, dd), 3.38 (1H, m), 4.21 (2H, d), 7.50 (2H, m), 7.58 (1H, m), 7.81 (2H, d)

MS: 458 (MNa$^+$)

CHN: Found: C57.73%; H6.68%; N9.51%; C$_{21}$H$_{29}$N$_3$O$_5$S requires C57.91%; H6.71%; N9.65%.

Preparation 14:

tert-butyl (3R)-6-cyclohexyl-3-(3-{[(2-pyridinylsulfonyl)amino]methyl}-1,2,4-oxadiazol-5-yl)hexanoate

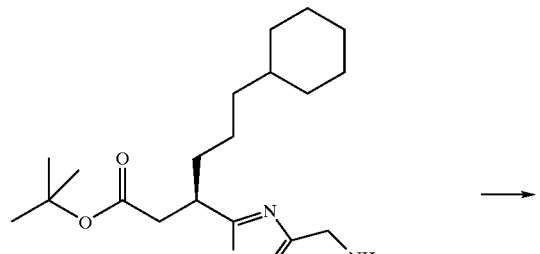

Method same as for preparation 10 using tert-butyl (3R)-3-[3-(aminomethyl)-1,2,4-oxadiazol-5-yl]-6-cyclohexylhexanoate (preparation 18) (210 mg, 057 mmol) and 2-pyridinesulphonylchloride (J. Med. Chem; 1997, 40, 1149) (170 mg, 0.96 mmol) as starting materials.

Purification: Attempted purification on a silica column eluting with DCM failed as the title compound could only be isolated with 0.5 eq 2,6-lutidine as an impurity.

Preparation 15:

(3R)-6-cyclohexyl-3-(3-{[(2-pyridinylsulfonyl)amino]methyl}-1,2,4-oxadiazol-5-yl)hexanoic acid

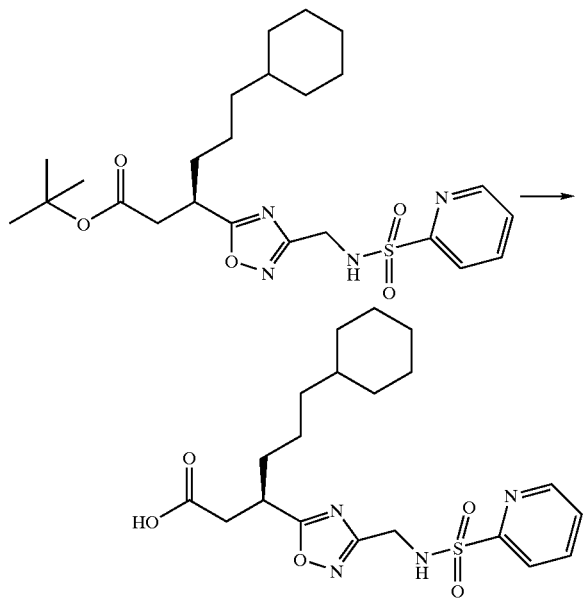

Method same as for preparation 7 using tert-butyl (3R)-6-cyclohexyl-3-(3-{[(2-pyridinylsulfonyl)amino]methyl}-1,2,4-oxadiazol-5-yl)hexanoate (preparation 14) (300 mg, 0.61 mmol) as starting material to afford the title compound as a pale yellow oil (250 mg).

$^1$H nmr: (d$_6$DMSO) 0.81 (2H, m), 1.05–1.25 (8H, m), 1.50–1.70 (7H, m), 2.68 (2H, d), 3.31 (1H, m), 4.32 (2H, d), 7.60 (1H, m), 7.88 (1H, d), 8.03 (1H, t), 8.48 (1H, brs), 8.66 (1H, d).

MS: 459 (MNa$^+$)

CHN: Found: C54.80%; H6.79%; N11.21%; C$_{20}$H$_{28}$N$_4$O$_5$S.0.2 H$_2$O.0.5 dioxan requires C54.57%; H6.74%; N11.57%.

Preparation 16:

tert-butyl (3R)-6-cyclohexyl-3-(3-{[(3-pyridinylsulfonyl)amino]methyl}-1,2,4-oxadiazol-5-yl)hexanoate

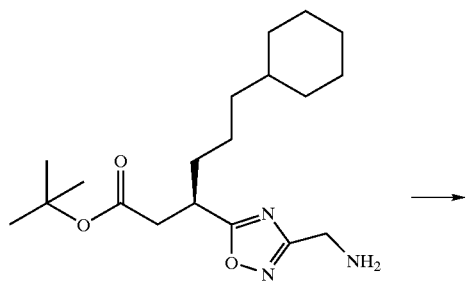

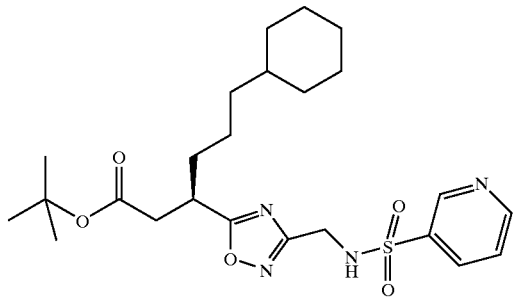

Method same as Preparation 14 using tert-butyl (3R)-3-[3-(aminomethyl)-1,2,4-oxadiazol-5-yl]-6-cyclohexylhexanoate (preparation 18) (200 mg, 057 mmol) and 3-pyridinesulphonylchloride (EP911333) (134 mg, 0.63 mmol) as starting materials.

Purification: The crude material was purified on a silica column eluting with a solvent gradient of pentane:EtOAc (100:0) gradually changing to (50:50) to afford the title compound as a colourless oil (192 mg, 68%).

$^{1}$H nmr: (CDCl$_3$) 0.84 (2H, m), 1.10–1.30 (8H, m), 1.40 (9H, s), 1.60–1.75 (7H, m), 2.58 (1H, dd), 2.67 (1H, dd), 3.38 (1H, m), 4.40 (2H, d), 5.19 (1H, brs), 7.40 (1H, m), 8.14 (1H, d), 8.78 (1H, d), 9.08 (1H, s).

MS: 515 (MNa$^+$)

CHN: Found: C57.96%; H7.48%; N10.99%; C$_{24}$H$_{36}$N$_4$O$_5$S.0.1 H$_2$O requires C58.30%, H7.38%; N11.33%.

Preparation 17:

(3R)-6-cyclohexyl-3-(3-{[(3-pyridinylsulfonyl)amino]methyl}-1,2,4-oxadiazol-5-yl)hexanoic acid

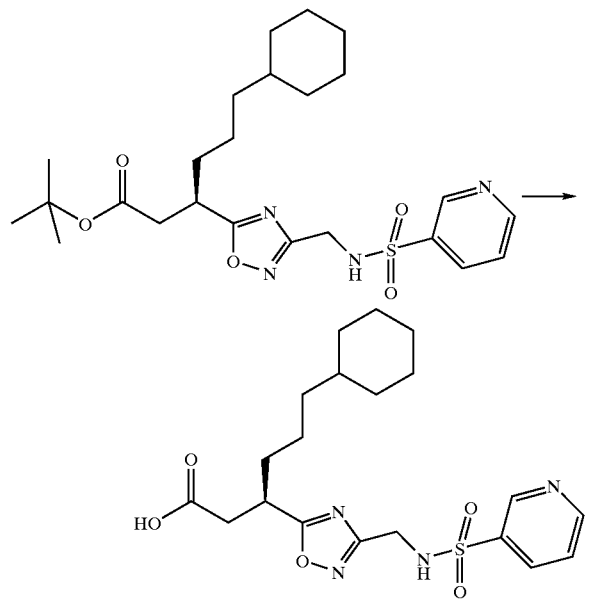

Method same as for preparation 11 using tert-butyl (3R)-6-cyclohexyl-3-(3-{[(3-pyridinylsulfonyl)amino]methyl}-1,2,4-oxadiazol-5-yl)hexanoate (preparation 16) (181 mg, 0.37 mmol) as starting material to afford the title compound as a white foam (177 mg, 94%).

$^{1}$H nmr: (CDCl$_3$) 0.82 (2H, m), 1.05–1.30 (8H, m+EtOAc), 1.55–1.75 (7H, m), 2.63–2.84 (2H, m), 3.37 (1H, m), 4.43 (2H, d), 7.58 (1H, m), 8.28 (1H, d), 8.78 (1H, brs), 9.00 (1H, brs).

MS: 435 (M–H)

CHN: Found: C50.67%; H5.92%; N10.76%; C$_{20}$H$_{28}$N$_4$O$_5$S.0.1 H$_2$O.0.5 TFA. 0.15 EtOAc requires C51.01%; H5.93%; N11.02%.

Preparation 18:

tert-butyl (3R)-3-[3-(aminomethyl)-1,2,4-oxadiazol-5-yl]-6-cyclohexylhexanoate

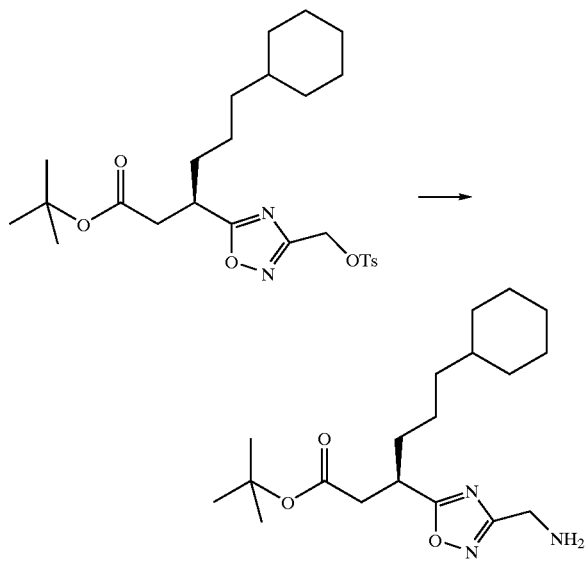

A solution of tert-butyl (3R)-6-cyclohexyl-3-[3-({[(4-methylphenyl)sulfonyl]oxy}methyl)-1,2,4-oxadiazol-5-yl]hexanoate (preparation 177) (1.2 g, 2.37 mmol) in THF (40 ml) was treated with concentrated ammonia solution and heated in a bomb at 40° C. for 18 hours. The reaction mixture was diluted with EtOAc and washed with sat. NaHCO$_3$ solution followed by brine. The organic extract was dried over anhydrous MgSO$_4$, filtered and the solvent removed under reduced pressure. The colourless oil was purified on a silica column eluting with a solvent gradient of pentane:EtOAc (4:1) gradually changing to (1:1) and then changing to DCM:MeOH:NH$_3$ (95:5:0.5) to afford the title compound as a colourless oil (782 mg, 94%).

$^{1}$H nmr: (CDCl$_3$) 0.84 (2H, m), 1.10–1.35 (8H, m), 1.40 (9H, s), 1.60–1.80 (7H, m), 2.61 (1H, dd), 2.79 (1H, dd), 3.42 (1H, m), 3.95 (2H, s).

MS: 374 (MNa$^+$)

Preparation 19:

tert-butyl (3R)-6-cyclohexyl-3-[3-({[(1-methyl-1H-imidazol-4-yl)sulfonyl]amino}methyl)-1,2,4oxadiazol-5-yl]hexanoate

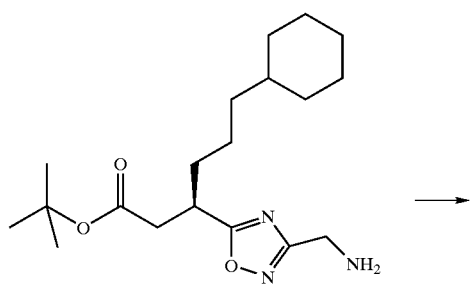

Method same as for preparation 10 using tert-butyl (3R)-3-[3-(aminomethyl)-1,2,4-oxadiazol-5-yl]-6-cyclohexylhexanoate (preparation 18) (145 mg, 0.41 mmol) and 1-methyl-1H-imidazole-4-sulphonyl chloride (75 mg, 0.41 mmol) as starting materials.

Purification: The crude material was purified on a silica column eluting with a solvent gradient of DCM:MeOH (100:0) gradually changing to (90:10) to afford the title compound as a colourless oil.

$^1$H nmr: (CDCl$_3$) 0.83 (2H, m), 1.10–1.30 (8H, m), 1.40 (9H, s), 1.60–1.75 (7H, m), 2.59 (1H, dd), 2.75 (1H, dd), 3.40 (1H, m), 3.73 (3H, s), 4.36 (2H, d), 5.38 (1H, brs), 0.41 (1H), 7.46 (1H, s).

MS: 435 (MNa$^+$)

CHN: Found: C52.40%; H7.07%; N13.12%; C$_{23}$H$_{37}$N$_5$O$_5$S.0.5 DCM requires C52.45%; H7.12%; N13.01%.

Preparation 20:

(3R)-6-cyclohexyl-3-[3-({[(1-methyl-1H-imidazol-4-yl)sulfonyl]amino}methyl)-1,2,4-oxadiazol 5-yl] hexanoic acid Method as for preparation 7 using tert-butyl (3R)-6-cyclohexyl-3-[3-({[(1-methyl-1H-imidazol-4-yl)sulfonyl]amino}methyl)-1,2,4-oxadiazol-5-yl]hexanoate (preparation 19) (490 mg, 1.00 mmol) as starting material.

Purification: Triturated with Et$_2$O to afford the title compound as a white solid 320 mg (320 mg, 74%)

$^1$H nmr: (CD$_3$OD) 0.83 (2H, m), 1.10–1.30 (8H, m), 1.60–1.75 (7H, m), 2.78 (2H, m), 3.40 (1H, m), 3.91 (3H, s), 4.40 (2H, d), 7.98 (1H, s), 8.78 (1H, s).

MS: 438 (M–H)

CHN: Found: C47.18%; H6.25%; N14.33%; C$_{19}$H$_{29}$N$_5$O$_5$S.1HCl.0.1 DCM requires C47.35%; H6.28%; N14.46%.

Preparation 21:

1H-pyrazole-4-sulfonyl chloride

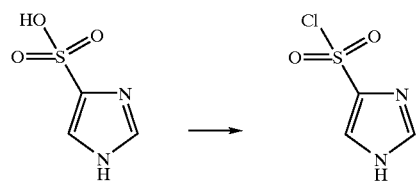

A mixture of 1H-pyrazole-4-sulfonic acid (J. Am. Chem. Soc.; 1955, 77, 6532) (1.0 g, 4.0 mmol) and phosphorous pentachloride (1.6 g, 7.7 mmol) were heated up to 180° C. over the period of an hour. The mixture began to reflux but not fully molten. The reaction mixture was cooled to 130° C. and toluene (5 ml) was added and allowed to cool to room temperature with stirring. The white solid was filtered off. The filtrate solvent was removed under reduced pressure and azeotroped with toluene and DCM to afford the title compound as a colourless oil and impure.

Preparation 22:

tert-butyl (3R)-6-cyclohexyl-3-(3-{[(1H-pyrazol-4-ylsulfonyl)amino]methyl}-1,2,4-oxadiazo-5-yl)hexanoate

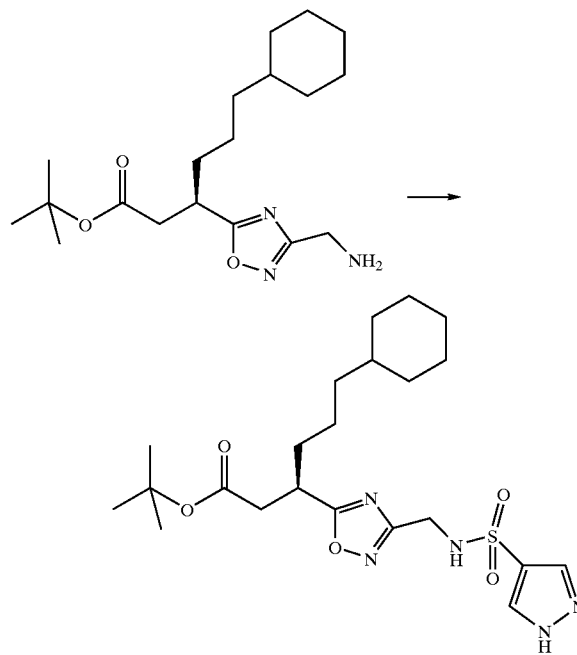

Method as for Preparation 10 using tert-butyl (3R)-3-[3-(aminomethyl)-1,2,4-oxadiazol-5-yl]-6-cyclohexylhexanoate (preparation 18) (310 mg, 0.88 mmol) and 1H-pyrazole-4-sulfonyl chloride (preparation 21) (220 mg, 1.32 mmol) as starting materials.

Purification: The crude material was purified on a silica column eluting with a solvent gradient of DCM:MeOH (98:2) gradually changing to (90:10) to afford the title compound.

$^1$H nmr: (CDCl$_3$) does not integrate for the pyrrole protons

MS: 503 (MNa$^+$)

Preparation 23:

(3R)-6-cyclohexyl-3-(3-{[(1H-pyrazol-4-ylsulfonyl)amino]methyl}-1,2,4-oxadiazol-5-yl)hexanoic acid

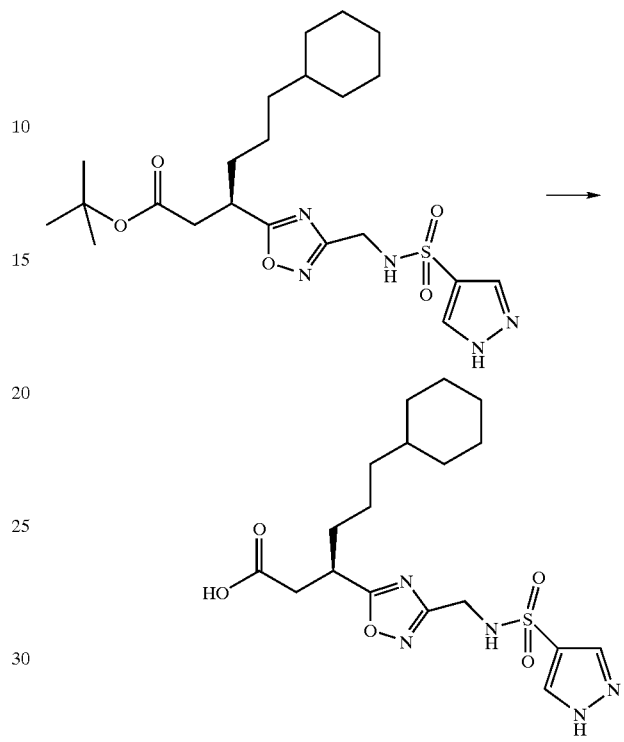

Method as for preparation 7 using tert-butyl (3R)-6-cyclohexyl-3-(3-{[(1H-pyrazol-4-ylsulfonyl)amino]methyl}-1,2,4-oxadiazol-5-yl)hexanoate (preparation 22) (420 mg, 0.87 mmol) as starting material.

Purification: Crude material taken up in Et$_2$O and DIPE and left in the fridge for 2 days. Solid was filtered off and dried under reduced pressure to afford the title compound as a white solid (140 mg, 38%).

$^1$H nmr: (CD$_3$OD) 0.83 (2H, m), 1.05–1.30 (8H, m), 1.55–1.75 (7H, m), 2.69 (1H, dd), 2.81 (1H, dd), 3.41 (1H, m), 4.22 (2H, s), 7.91 (2H, brs).

MS: 424 (M−H)

CHN: Found: C50.23%; H6.33%; N16.46%; C$_{18}$H$_{27}$N$_5$O$_5$S.0.2 H$_2$O requires C50.38%; H6.44%; N16.32%.

Preparation 24:

4H-1,2,4-triazole-3-sulfonyl chloride

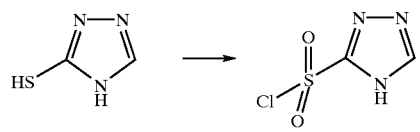

Chlorine gas was bubbled through a suspension of 4H-1,2,4-triazole-3-thiol (2.7 g, 26.7 mmol) in 2M HCl (5 ml) for 1 hour, at 0° C. The reaction mixture became homogenous. Aqueous Na$_2$S$_2$O$_5$ was added to the reaction mixture and nitrogen gas was bubbled through for 10 minutes. The white solid was filtered and washed with cold H$_2$O to afford the title compound (460 mg, 10%).

¹H nmr: (CD₃OD) 8.69 (1H, s).

MS: 166 (M−H)

Preparation 25:

tert-butyl (3R)-6-cyclohexyl-3-(3-{[(4H-1,2,4-triazol-3-ylsulfonyl)amino]methyl}-1,2,4,-oxadiazol-5-yl)hexanoate

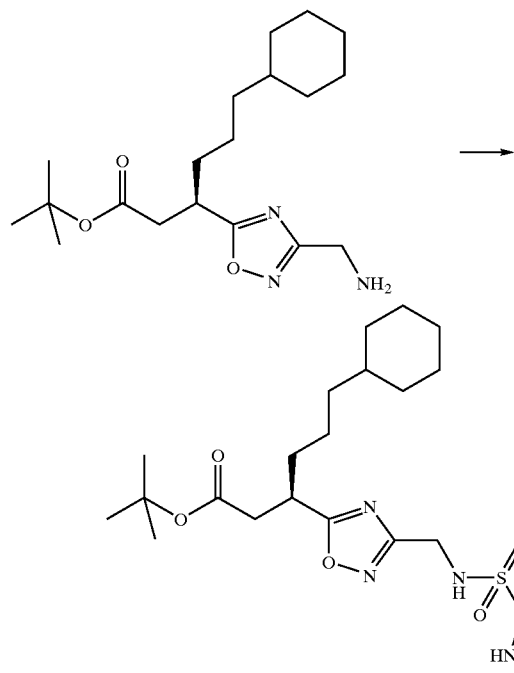

Method as for preparation 10 using tert-butyl (3R)-3-[3-(aminomethyl)-1,2,4-oxadiazol-5-yl]-6-cyclohexylhexanoate (preparation 18) (292 mg, 0.83 mmol) and 4H-1,2,4-triazole-3-sulfonyl chloride (preparation 24) (208 mg, 1.24 mmol) as starting materials.

Purification: The crude material was purified on a silica column eluting with a solvent gradient of DCM:MeOH (98:2) gradually changing to (90:10) to afford the title compound as a colourless oil (412 mg, 102%, contains DCM).

¹H nmr: (CD₃OD) 0.83 (2H, m), 1.05–1.30 (8H, m), 1.38 (9H, s), 1.55–1.75 (7H, m), 2.60–2.80 (2H, m), 3.40 (1H, m), 4.41 (2H, s), 8.50 (1H, s).

MS: 505 (MNa⁺)

Preparation 26:

(3R)-6-cyclohexyl-3-(3-{[(4H-1,2,4-triazol-3-ylsulfonyl)amino]methyl}-1,2,4-oxadiazol-5-yl) hexanoic acid

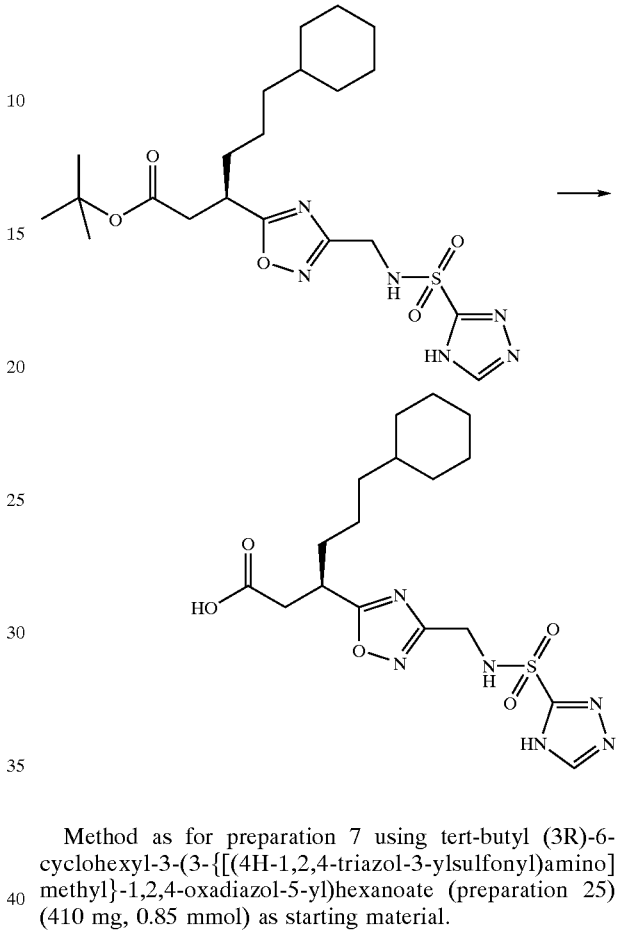

Method as for preparation 7 using tert-butyl (3R)-6-cyclohexyl-3-(3-{[(4H-1,2,4-triazol-3-ylsulfonyl)amino]methyl}-1,2,4-oxadiazol-5-yl)hexanoate (preparation 25) (410 mg, 0.85 mmol) as starting material.

Purification: Material was azeotroped with toluene followed by DCM to afford the title compound as a white solid (320 mg, 88%).

M.pt. 151–153° C.

¹H nmr: (CD₃OD) 0.83 (2H, m), 1.10–1.30 (8H, m), 1.55–1.75 (7H, m), 2.69 (1H, dd), 2.81 (1H, dd), 3.42 (1H, m), 4.40 (2H, s), 8.48 (1H, s).

MS: 425 (M−H)

Preparation 27:

tert-butyl (3R)-6-cyclohexyl-3-[3-({[(3,5-dimethyl-4-isoxazolyl)sulfonyl]amino}methyl)-1,2,4-oxadiazol-5-yl]hexanoate

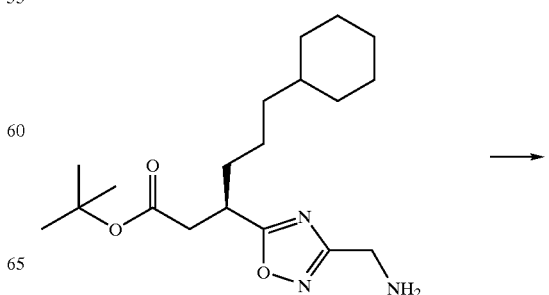

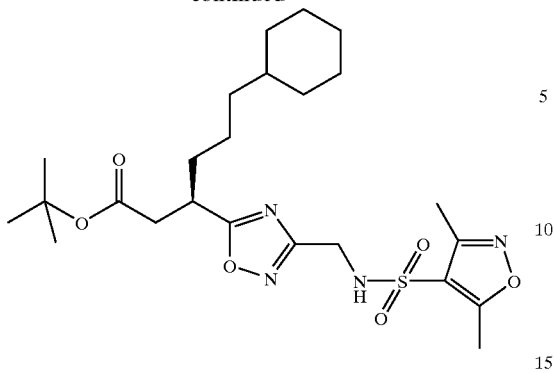

Method as for preparation 6 using tert-butyl (3R)-3-[3-(aminomethyl)-1,2,4-oxadiazol-5-yl]-6-cyclohexylhexanoate (preparation 18) (200 mg, 0.57 mmol) and 3,5-dimethylisoxazolesulphonyl chloride (112 mg, 0.57 mmol) as starting materials.

Purification: The crude material was purified on a silica column eluting with a solvent gradient of pentane:EtOAc (100:0) gradually changing to (70:30) to afford the title compound as a colourless oil (252 mg, 87%).

$^1$H nmr: (CDCl$_3$) 0.82 (2H, m), 1.10–1.30 (8H, m), 1.39 (9H, s), 1.60–1.75 (7H, m), 2.39 (3H, s), 2.58 (2H, dd), 2.61 (3H, s), 2.71 (1H, dd), 3.38 (1H, m), 4.37 (2H, d), 5.26 (1H, brs).

MS: 533 (MNa$^+$)

CHN: Found: C56.17%; H7.48%; N10.65%; C$_{24}$H$_{38}$N$_4$O$_6$S requires C56.45%; H7.50%; N10.97%.

Preparation 28:

(3R)-6-cyclohexyl-3-[3-({[(3,5-dimethyl-4-isoxazolyl)sulfonyl]amino}methyl)-1,2,4-oxadiazol-5-yl]hexanoic acid

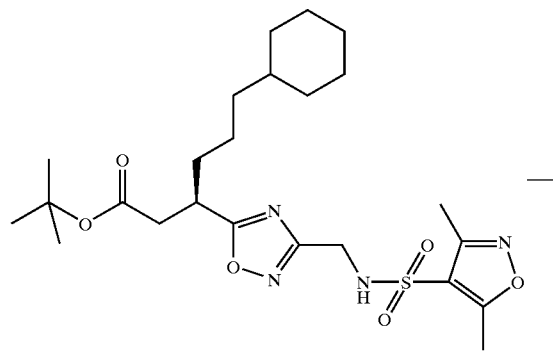

Method same as for Preparation 11 using tert-butyl (3R)-6-cyclohexyl-3-[3-({[(3,5-dimethyl-4-isoxazolyl)sulfonyl]amino}methyl)-1,2,4-oxadiazol-5-yl]hexanoate (preparation 27) (246 mg, 0.48 mmol) as starting material to afford the title compound as a yellow gum (238 mg, 109%, contains EtOAc).

$^1$H nmr: (CDCl$_3$) 0.82 (2H, m), 1.10–1.25 (8H, m), 1.55–1.75 (7H, m), 2.35 (3H, s), 2.74 (1H, dd), 2.83 (1H, dd), 3.41 (1H, m), 4.38 (2H, d), 5.69 (1H, brs).

MS: 453 (M–H)

Preparation 29:

N-(2-cyanoethyl)methanesulfonamide

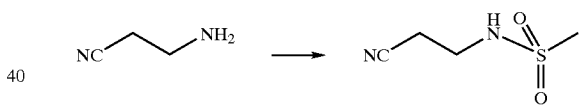

A solution of aminopropionitrile fumarate salt (6.0 g, 47 mmol) in 2M NaOH solution (40 ml) was stirred at room temperaute for 15 minutes. The reaction mixture extracted with DCM (50 ml). The organic extract was dried over anhydrous Na$_2$SO$_4$ and filtered. The filtrate was treated pyridine (11 ml, 136 mmol) and methanesulphonyl chloride (3.9 ml, 50 mmol) and stirred under at nitrogen atmosphere for 18 hours. The solvent was removed under reduced pressure. The oil was dissolved in DCM and washed with 2M HCl (2×100 ml) and saturated NaHCO$_3$ solution. All the product had been extracted into the aqueous washings. NaHCO$_3$ solution was acidified with conc. HCl and combined with the other acidic washes. The aqueous washes were reduced to ~50 ml in volume and extracted with EtOAc. The organic extract was evaporated under reduced pressure to afford the title compound as a pink oil (2.1 g, 30%).

$^1$H nmr: (CDCl$_3$) 2.64 (2H, t), 3.00 (3H, s), 3.42 (2H, m), 4.83 (1H, brs).

MS:171 (MNa$^+$)

Preparation 30:

(1Z)-N'-hydroxy-3-[(methylsulfonyl)amino]
propanimidamide

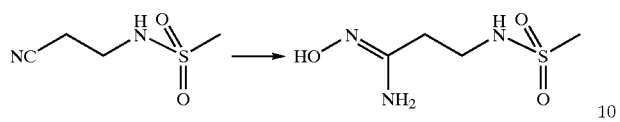

Method as for preparation 1 using N-(2-cyanoethyl)
methanesulfonamide (preparation 29) (1.0 g, 6.75 mmol) as
starting material.

Purification: Crude material was dissolved in hot EtOH
and filtered. The solvent in the filtrate was removed under
reduced pressure to afford the title compound as a colourless
oil (1.13 g).

$^1$H nmr: (CD$_3$OD) contains starting material in ratio
product:SM (3:2)

MS: 204 (MNa$^+$)

Preparation 31:

tert-butyl (6Z,10R)-6-amino-10-(3-
cyclohexylpropyl)-9-oxo-8-oxa-2-thia-3,7-
diazadodec-6-en-12-oate 2,2-dioxide

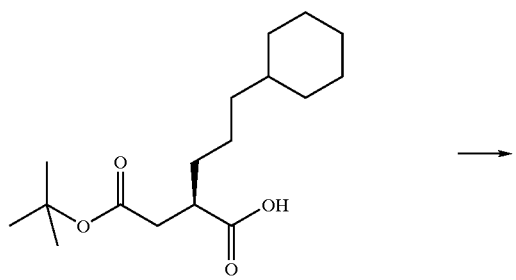

Method as for preparation 2 using (2R)-2-(2-tert-butoxy-
2-oxoethyl)-5-cyclohexylpentanoic acid (preparation 168)
(670 mg, 2.25 mmol) and (1Z)-N'-hydroxy-3-
[(methylsulfonyl)amino]propanimidamide (preparation 30)
(700 mg, 2.50 mmol) as starting materials to afford the title
compound as a yellow oil.

Compound only 90% pure.

Preparation 32:

tert-butyl (3R)-6-cyclohexyl-3-(3-{2-
[(methylsulfonyl)amino]ethyl}-1,2,4-oxadiazol-5-yl)
hexanoate

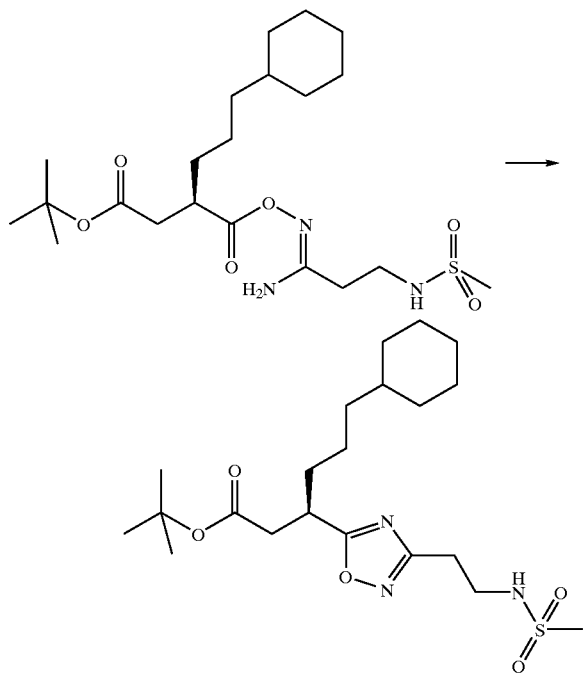

Method as for preparation 3 using tert-butyl (6Z, 10R)-
6-amino-10-(3-cyclohexylpropyl)-9-oxo-8-oxa-2-thia-3,7-
diazadodec-6-en-12-oate 2,2-dioxide (preparation 31) (1.14
g, 2.48 mmol) as starting material.

Purification: The crude material was purified on a silica
column eluting with a solvent gradient of pentane:EtOAc
(90:10) gradually changing to (50:50) to afford the title
compound as a colourless oil (910 mg, 83%).

$^1$H nmr: (CD$_3$OD) 0.85 (2H, m), 1.10–1.35 (8H, m), 1.39
(9H, s), 1.60–1.75 (7H, m), 2.66 (1H, dd), 2.77 (1H, dd),
2.91 (3H, s), 2.98 (2H, t), 3.42 (3H, m).

MS: 466 (MNa$^+$)

CHN: Found: C56.77%; H8.39%; N9.36%;
C$_{21}$H$_{37}$N$_3$O$_5$S requires C56.86%; H8.41%; N9.47%.

Preparation 33:

(3R)-6-cyclohexyl-3-(3-{2-[(methylsulfonyl)amino]
ethyl}-1,2,4-oxadiazol-5-yl)hexanoic acid

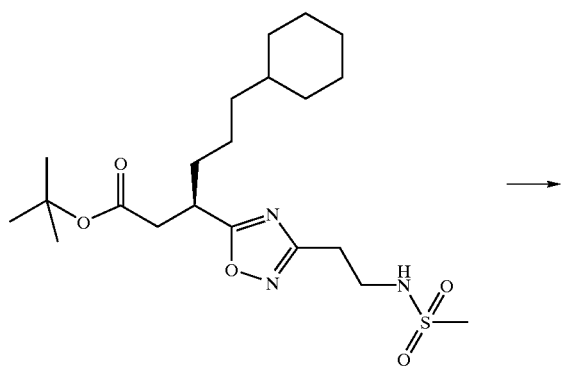

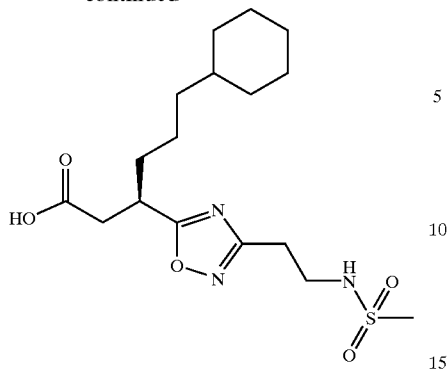

Method as for preparation 11 using tert-butyl (3R)-6-cyclohexyl-3-(3-{2-[(methylsulfonyl)amino]ethyl}-1,2,4-oxadiazol-5-yl)hexanoate (preparation 32) (400 mg, 0.9 mmol) as starting material.

Purification: Crude material was purified on a silica column eluting with a solvent gradient of DCM:MeOH:AcOH (100:0:0) gradually changing to (90:10:1) to afford the title compound as a colourless oil (370 mg)

$^1$H nmr: (CD$_3$OD) 0.85 (2H, m), 1.05–1.35 (8H, m), 1.55–1.75 (7H, m), 2.73 (1H, dd), 2.84 (1H, dd), 2.90 (3H, s), 2.95 (2H, t), 3.43 (3H, t).

MS: 386 (M–H)

CHN: Found: C52.54%; H7.62%; N10.58%; C$_{17}$H$_{29}$N$_3$O$_5$S requires C52.69%; H7.54%; N10.84%.

Preparation 34:

1-benzhydryl-N'-hydroxy-3-azetidinecarboximidamide

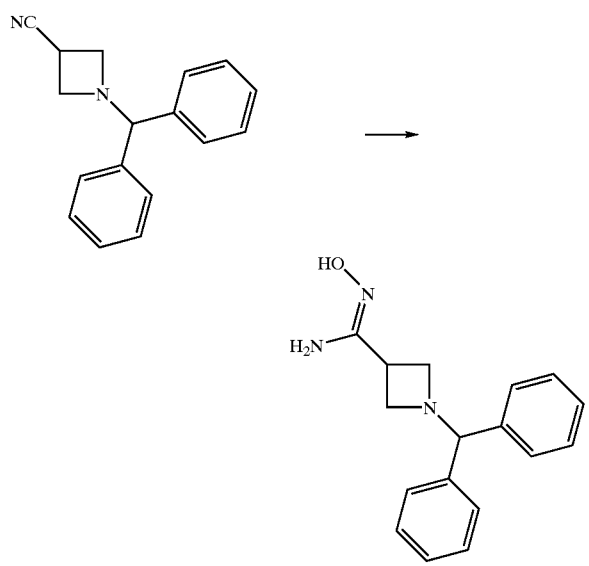

Method as for preparation 1 using 1-benzhydryl-3-azetidinecarbonitrile (2.0 g, 8.0 mmol) was used as starting material.

The title material isolated 90% pure and used as such in the following step.

Preparation 35:

tert-butyl (3R)-3-[({[(Z)-amino(1-benzhydryl-3-azetidinyl)methylidene]amino}oxy)carbonyl]-6-cyclohexylhexanoate

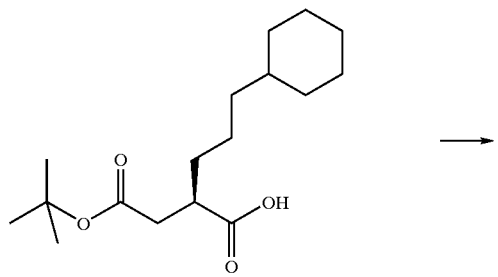

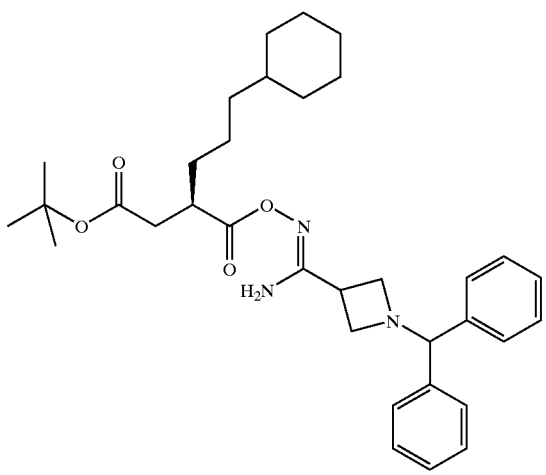

Method as for preparation 2 using (2R)-2-(2-tert-butoxy-2-oxoethyl)-5-cyclohexylpentanoic acid (1.65 g, 5.51 mmol) and 1-benzhydryl-N'-hydroxy-3-azetidinecarboximidamide (preparation 34) (1.74 g, 6.17 mmol) as starting materials.

Purification: The crude material was dissolved in EtOAc and washed with H$_2$O (3×50 ml) and brine. The organic extract was dried over Na$_2$SO$_4$, filtered and the solvent removed under reduced pressure to afford the title compound as a brown oil (3.25 g).

$^1$H nmr: (CDCl$_3$) 0.83 (2H, m), 1.05–1.30 (8H, m), 1.41 (9H, s), 1.60–1.75 (7H, m), 2.41 (1H, brd), 2.65 (1H, m), 2.87 (1H, brs), 3.09 (1H, brs), 3.30 (4H, brs), 4.36 (1H, s), 5.87 (2H, brs), 7.15–7.40 (10H, m+CHCl$_3$)

MS: 584 (MNa$^+$)

Preparation 36:

tert-butyl (3R)-3-[3-(1-benzhydryl-3-azetidinyl)-1,2,4-oxadiazol-5-yl]-6-cyclohexylhexanoate

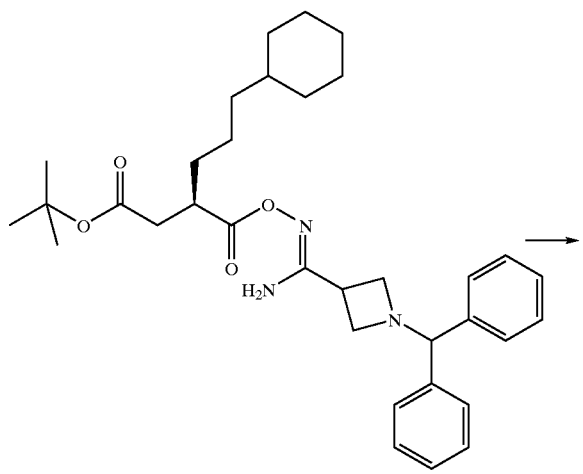

A solution of tert-butyl (3R)-3-[({[(Z)-amino(1-benzhydryl-3-azetidinyl)methylidene]amino}oxy)carbonyl]-6-cyclohexylhexanoate (preparation 35) (2.85 g, 5.07 mmol) in toluene (90 ml) was heated at 140° C. under Dean and Stark conditions for 18 hours. The reaction mixture was allowed to cool to room temperature. The solvent was removed under reduced pressure. The residue was purified on a silica column eluting with a solvent gradient of cyclohexane:Et$_2$O (90:10) gradually changing to (60:40) to afford the title compound as a colourless oil (2.0 g, 73%).

$^1$H nmr: (CDCl$_3$) 0.83 (2H, m), 1.05–1.35 (8H, m), 1.39 (9H, s), 1.60–1.80 (7H, m), 2.60 (1H, dd), 2.79 (1H, dd), 3.34 (2H, t), 3.43 (1H, m), 3.60 (2H, t), 3.80 (1H, m), 4.43 (1H, s), 7.18 (2H, m), 7.26 (4H, t+CHCl$_3$), 7.40 (4H, m).

MS: 544 (MH$^+$)

CHN: Found: C73.58%; H8.15%; N7.66%; C$_{34}$H$_{45}$N$_3$O$_3$.0.2 DCM requires C73.26%; H8.16%; N7.49%.

Preparation 37:

methyl (3R)-3-[3-(3-azetidinyl)-1,2,4-oxadiazol-5-yl]-6-cyclohexylhexanoate

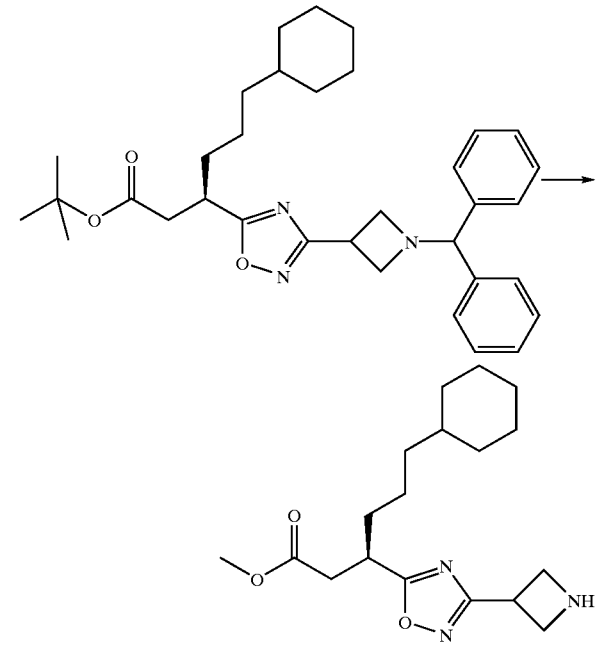

A solution of tert-butyl (3R)-3-[3-(1-benzhydryl-3-azetidinyl)-1,2,4-oxadiazol-5-yl]-6-cyclohexylhexanoate (preparation 36) (1.99 g, 3.66 mmol) in DCM (15 ml) was treated with ACE-Cl (530 μl, 4.90 mmol) and heated at reflux for 4 hours. The solvent was removed under reduced pressure. The residue was dissolved in MeOH (15 ml) and heated at reflux for 1.5 hours. The solvent was removed under reduced pressure. The oil was dissolved in EtOAc (150 ml) and washed with sat. NaHCO$_3$ solution (50 ml) and brine (40 ml). The aqueous extracts were combined and extracted with EtOAc. All of the organic extracts were combined, dried over anhydrous Na$_2$SO$_4$ and filtered. The solvent was removed under reduced pressure to afford the title compound as a colourless oil (900 mg).

$^1$H nmr: (CD$_3$OD) 0.85 (2H, m), 1.10–1.35 (8H, m), 1.60–1.80 (7H, m), 2.78 (1H, dd), 2.86 (1H, dd), 3.49 (1H, m), 3.61 (3H, s), 3.95 (4H, m), 4.06 (1H, m).

MS: 336 (MH$^+$)

Preparation 38:

methyl (3R)-6-cyclohexyl-3-{3-[1-(methylsulfonyl)-3-azetidinyl]-1,2,4-oxadiazol-5-yl}hexanoate

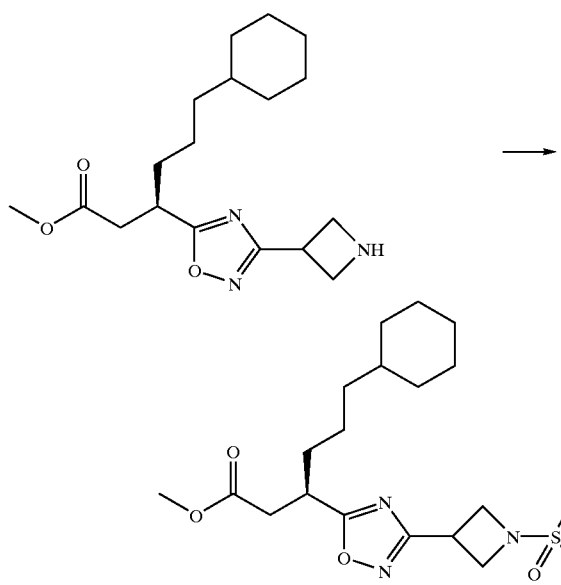

Method as for preparation 10 using methyl (3R)-3-[3-(3-azetidinyl)-1,2,4-oxadiazol-5-yl]-6-cyclohexylhexanoate (preparation 37) (880 mg, 2.64 mmol) and methanesulphonyl chloride (1.53 ml, 19.77 mmol) as starting materials.

Purification: After aqueous work-up MeOH was added to quench the excess methanesulphonyl chloride. The solvent was removed under reduced pressure. The crude material was purified on a silica column eluting with a solvent gradient of cyclohexane:EtOAc (90:10) gradually changing to (50:50) to afford the title compound as a yellow oil (900 mg, contains 3 equivalents of MeSO$_3$Me).

$^1$H nmr: (CDCl$_3$) 0.82 (2H, m), 1.10–1.35 (8H, m), 1.60–1.80 (7H, m), 2.72 (1H, dd), 2.82–2.94 (4H, dd+s), 3.50 (1H, m), 3.64 (3H, s), 3.96 (1H, m), 4.19 (2H, m), 4.28 (2H, m).

MS: 436 (MNa$^+$)

Preparation 39:

(3R)-6-cyclohexyl-3-{3-[1-(methylsulfonyl)-3-azetidinyl]-1,2,4-oxadiazol-5-yl}hexanoic acid

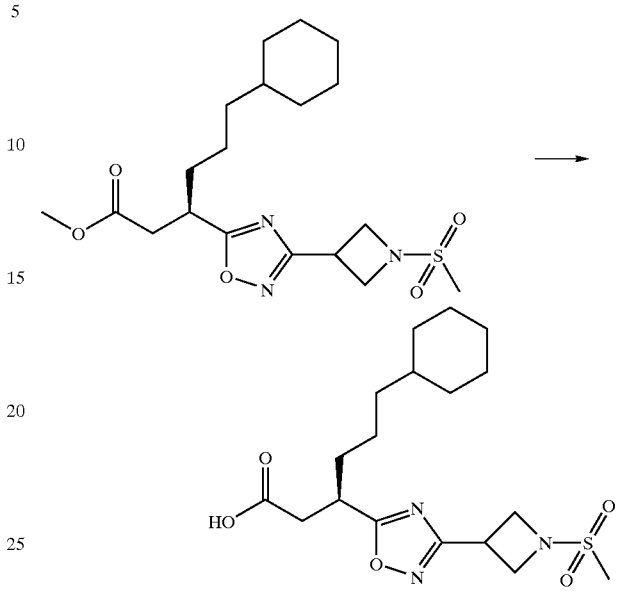

A solution of methyl (3R)-6-cyclohexyl-3-{3-[1-(methylsulfonyl)-3-azetidinyl]-1,2,4-oxadiazol-5-yl}hexanoate (preparation 38) (780 mg, 1.05 mmol) in dioxan (20 ml) and H$_2$O (10 ml) was treated with LiOH.H$_2$O (218 mg, 5.2 mmol) and stirred at room temperature for 2.25 hours. The reaction mixture was acidified with 2M HCl (20 ml) and extracted with EtOAc. The organic extract was washed with H$_2$O and the solvent was removed under reduced pressure. The oil was purified on a silica column eluting with a solvent gradient of DCM:MeOH:AcOH (100:0:0) gradually changing to (90:10:1) to afford a colourless oil which solidified on standing. The solid was triturated with pentane, filtered off and dried under reduced pressure to afford the title compound as a white solid (372 mg, 78%).

$^1$H nmr: (CD$_3$OD) 0.83 (2H, m), 1.05–1.35 (8H, m), 1.55–1.80 (7H, m), 2.75 (1H, dd), 2.84 (1H, dd), 2.98 (3H, s), 3.47 (1H, m), 4.01 (1H, m), 4.12 (2H, m), 4.26 (2H, m).

MS: 398 (M–H)

CHN: Found: C54.08%; H7.34%; N10.37%; C$_{18}$H$_{29}$N$_3$O$_5$S requires C54.12%; H7.32%; N10.52%.

Preparation 40:

1-(methylsulfonyl)-4-piperidinecarbonitrile

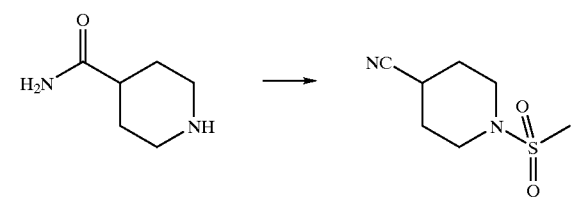

Method as for preparation 6 using 4-piperidinecarboxamide (4.0 g, 31.2 mmol) as starting material and DMF (2 ml) was added.

Purification: The crude material was triturated with Et$_2$O, filtered off and dried under reduced pressure to afford the title compound as a white solid (2.48 g, 42%).

¹H nmr: (CD₃OD) 1.85 (2H, m), 2.01 (2H, m), 2.81 (3H, s), 2.95 (1H, m), 3.18 (2H, m), 3.41 (2H, m).

MS: 211 (MNa⁺)

CHN: Found: C44.52%; H6.46%; N14.77%; $C_7H_{12}N_2O_2S$ requires C44.66%; H6.43%; N14.88%.

Preparation 41:

N'-hydroxy-1-(methylsulfonyl)-4-piperidinecarboximidamide

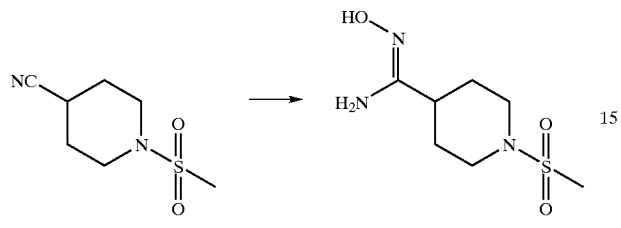

Method as for preparation 1 using 1-(methylsulfonyl)-4-piperidinecarbonitrile (preparation 40) (1.47 g, 7.81 mmol) as starting material.

Purification: The crude material was dissolved in EtOH, filtered and the solvent removed under reduced pressure to afford the title compound as a white solid.

¹H nmr: shows 2:1 mixture starting material:product. Taken on crude to next step.

Preparation 42:

tert-butyl (3R)-3-{[({(Z)-amino[1-(methylsulfonyl)-4-piperidinyl]methylidene}amino)oxy]carbonyl}-6-cyclohexylhexanoate

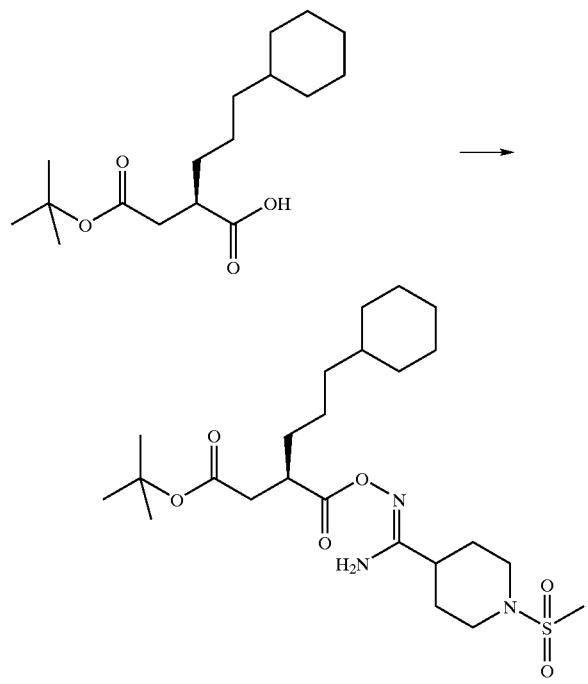

Method as for preparation 2 using (2R)-2-(2-tert-butoxy-2-oxoethyl)-5-cyclohexylpentanoic acid (54 mg, 1.83 mmol) and N'-hydroxy-1-(methylsulfonyl)-4-piperidinecarboximidamide (preparation 41) (1.20 g, 2.0 mmol) as starting materials.

Title compound isolated with 1-(methylsulfonyl)-4-piperidinecarbonitrile (preparation 40) as a major impurity in the ratio product:nitrile 1:1.5. Taken on crude to following stage.

Preparation 43:

tert-butyl (3R)-6-cyclohexyl-3-{3-[1-(methylsulfonyl)-4-piperidinyl]-1,2,4-oxadiazol-5-yl}hexanoate

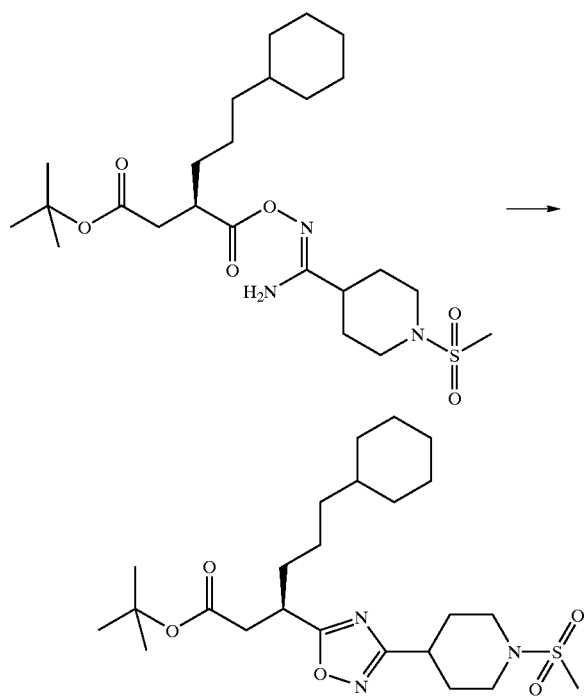

A solution of tert-butyl (3R)-3-{[({(Z)-amino[1-(methylsulfonyl)-4-piperidinyl]methylidene}amino)oxy]carbonyl}-6-cyclohexylhexanoate (preparation 42) (1.50 g, 1.83 mmol) in toluene (100 ml) was treated with pyridine (90 µl, 1.83 mmol) and anhydrous ZnCl₂ (150 mg, 1.83 mmol) and heated at reflux for 20 hours. The reaction mixture was diluted with EtOAc and washed with H₂O, brine and H₂O, dried over anhydrous Na₂SO₄ and filtered. The solvent was removed under reduced pressure. The residue was purified on a silica column eluting with a solvent gradient of cyclohexane:EtOAc (90:10) gradually changing to (50:50). The oil was recrystallised from pentane to afford the title compound as a white solid (320 mg, 36%).

H nmr: (CDCl₃) 0.83 (2H, m), 1.10–1.35 (8H, m), 1.40 (9H, s), 1.60–1.80 (7H, m), 1.99 (2H, m), 2.14 (2H, brd), 2.60 (1H, dd), 2.71–2.80 (4H, dd+s), 2.95 (3H, m), 3.41 (1H, m), 3.74 (2H, m).

MS: 506 (MNa⁺)

CHN: Found: C59.55%; H8.58%; N8.68%; $C_{24}H_{41}N_3O_5S$ requires C59.60%; H8.54%; N8.69%.

Preparation 44:

(3R)-6-cyclohexyl-3-{3-[1-(methylsulfonyl)-4-piperidinyl]-1,2,4-oxadiazol-5-yl}hexanoic acid

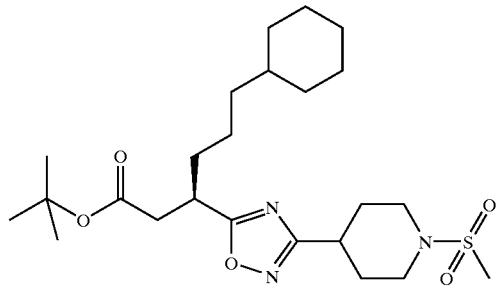

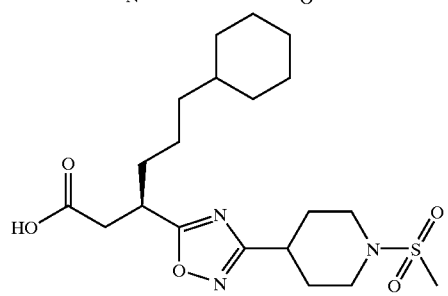

Method as for preparation 11 using tert-butyl (3R)-6-cyclohexyl-3-{3-[1-(methylsulfonyl)-4-piperidinyl]-1,2,4-oxadiazol-5-yl}hexanoate (preparation 43) (310 mg, 0.64 mmol) as starting material.

Purification: The crude material was triturated with pentane and filtered off to afford the title compound as a white solid (245 mg, 89%).

$^1$H nmr: (CDCl$_3$) 0.81 (2H, m), 1.05–1.35 (8H, m), 1.55–1.85 (7H, m), 1.97 (2H, m), 2.10 (2H, m), 2.70–2.80 (4H, dd+s), 2.93 (4H, m), 3.45 (1H, m), 3.72 (2H, m).

MS:426 (M–H)

CHN: Found: C56.15%; H7.77%; N9.64%; C$_{20}$H$_{33}$N$_3$O$_5$S requires C56.18%; H7.78%; N9.83%.

Preparation 45:

tert-butyl (3R)-3-(3-{[(3-chloropropyl)sulfonyl]amino}-1,2,4-oxadiazol-5-yl)-6-cyclohexylhexanoate

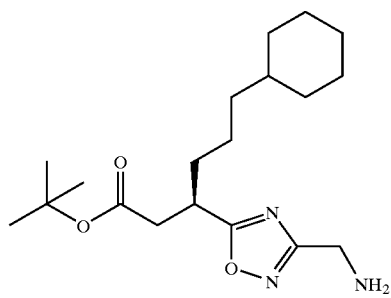

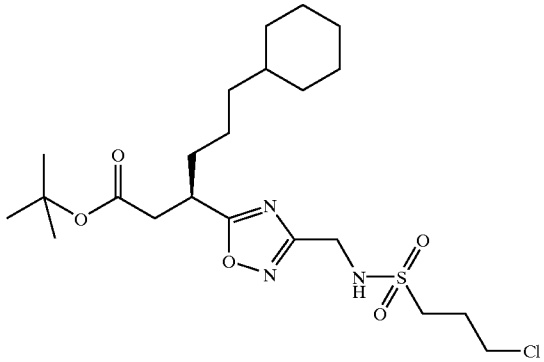

Method as for preparation 10 using tert-butyl (3R)-3-[3-(aminomethyl)-1,2,4-oxadiazol-5-yl]-6-cyclohexylhexanoate (preparation 18) (200 mg, 0.57 mmol) and 3-chloropropanesulphonyl chloride (83 μl, 0.68 mmol) as starting materials and pyridine as the base.

Purification: The crude material was purified on a silica column eluting with pentane Et2O (1:1) to afford the title compound as a colourless oil (225 mg, 93%).

$^1$H nmr: (CDCl$_3$) 0.83 (2H, m), 1.10–1.35 (8H, m), 1.40 (9H, s), 1.60–1.80 (7H, m), 2.28 (2H, m), 2.61 (1H, dd), 2.78 (1H, dd), 3.23 (2H, m), 3.42 (1H, m), 3.62 (2H, t), 4.45 (2H, d), 5.79 (1H, brs).

MS: 514 (MNa$^+$)

CHN: Found: C53.01%; H7.70%; N8.17%; C$_{22}$H$_{38}$ClN$_3$O$_5$S.0.2 H$_2$O requires C53.31%; H7.81%; N8.48%.

Preparation 46:

(3R)-6-cyclohexyl-3-[3-(1,1-dioxido-2-isothiazolidinyl)-1,2,4-oxadiazol-5-yl]hexanoic acid

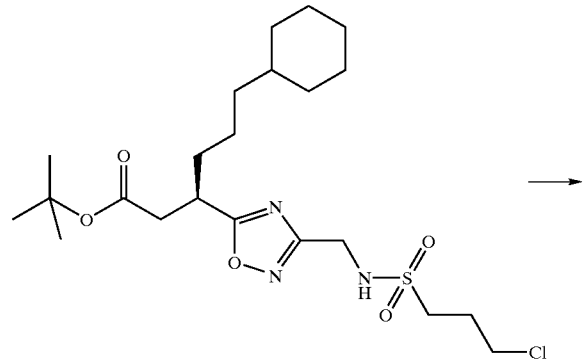

123

-continued

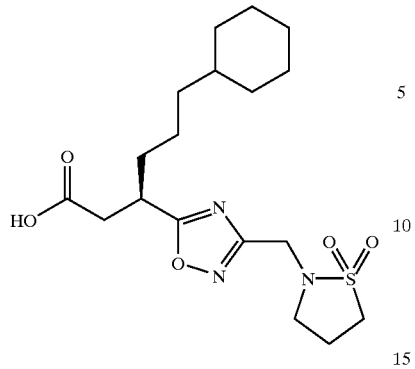

Sodium metal (114 mg, 5.00 mmol) was added in portions to MeOH (10 ml) at 0° C. and stirred until all of the sodium had dissloved (~10 minutes). A solution of tert-butyl (3R)-3-(3-{[(3-chloropropyl)sulfonyl]amino}-1,2,4-oxadiazol-5-yl)-6-cyclohexylhexanoate (preparation 45) (245 mg, 0.50 mmol) in MeOH (3 ml) was added to the reaction mixture and was stirred under a nitrogen atmosphere for 3 days warming to room temperature over this time. The reaction was quenched with $H_2O$ and the solvent removed under reduced pressure. The residue was diluted with water and acidified with 2M HCl (pH~3) and extracted with $Et_2O$ followed by EtOAc. The organic extracts were combined, dried over anhydrous $MgSO_4$ and filtered. The solvent was removed under reduced pressure to afford the title compound as a colourless oil (203 mg, 98%).

$^1$H nmr: ($d_6$-DMSO) 0.81 (2H, m), 1.00–1.25 (8H, m), 1.50–1.70 (7H, m), 2.21 (2H, m), 2.74 (2H, t), 3.26 (2H, t), 3.40 (1H, m), 4.21 (2H, s).

MS: 422 (MNa$^+$)

CHN: Found: C54.33%; H7.49%; N10.10%; $C_{18}H_{29}N_3O_5S.0.05$ $H_2O$ requires C53.99%; H7.33%; N10.49%.

Preparation 47:

tert-butyl (3R)-3-[3-({[(tert-butylamino)sulfonyl]amino}methyl)-1,2,4-oxadiazol-5-yl]-6-cyclohexylhexanoate

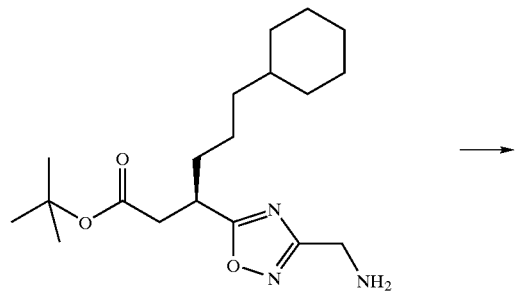

124

-continued

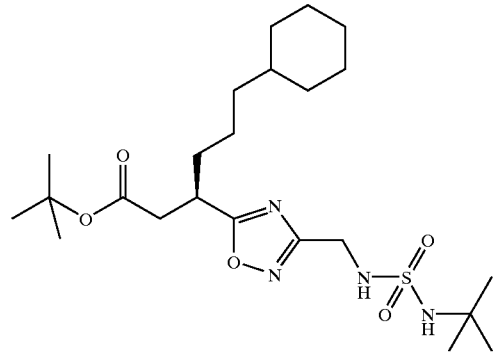

Method as for preparation 10 using tert-butyl (3R)-3-[3-(aminomethyl)-1,2,4-oxadiazol-5-yl]-6-cyclohexylhexanoate (preparation 18) (200 mg, 0.57 mmol) and N-tert-butylsulfamoyl chloride (J. Org. Chem.; 1976, 41, 4028) (108 mg, 0.63 mmol) as starting materials and pyridine as base.

Purification: The crude product was purified on a silica column eluting with a solvent gradient of DCM:MeOH (100:0) gradually changing to (93:7) to afford the title compound as a colourless oil (186 mg, 67%).

$^1$H nmr: (CDCl$_3$) 0.83 (2H, m), 1.10–1.30 (8H, m), 1.38 (9H, s), 1.40 (9H, s), 1.60–1.80 (7H, m), 2.61 (1H, dd), 2.79 (1H, dd), 3.43 (1H, m), 4.22 (1H, brs), 4.38 (2H, d), 4.70 (1H, brs).

MS: 509 (MNa$^+$)

CHN: Found: C56.20%; H8.67%; N11.32%; $C_{23}H_{42}N_4O_5S.0.15$ $H_2O$ requires C56.45%; H8.71%; N11.45%.

Preparations 48 and 49:

(3R)-3-[3-({[(tert-butylamino)sulfonyl]amino}methyl)-1,2,4-oxadiazol-5-yl]-6-cyclohexylhexanoic acid and (3R)-3-(3-{[(aminosulfonyl)amino]methyl}-1,2,4-oxadiazol-5-yl)-6-cyclohexylhexanoic acid

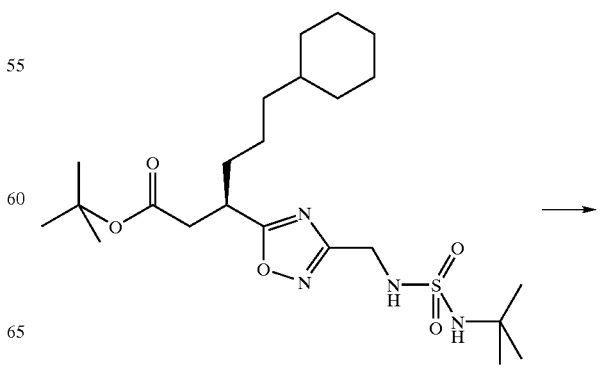

125
-continued

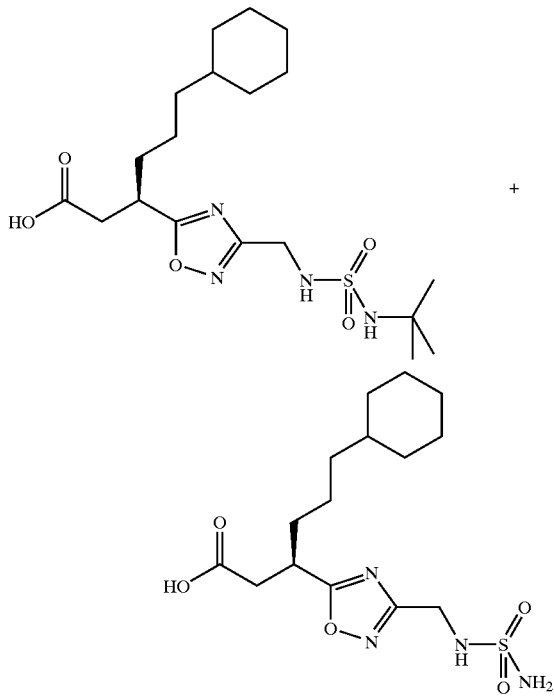

Method as for preparation 11 using tert-butyl (3R)-3-[3-({[(tert-butylamino)sulfonyl]amino}methyl)-1,2,4-oxadiazol-5-yl]-6-cyclohexylhexanoate (preparation 47) (171 mg, 0.35 mmol) as starting material.

Purification: The crude product was dissolved in EtOAc and washed with H$_2$O and brine. The orgainc extract was dried over anhydrous MgSO$_4$ and filtered. The solvent was removed under reduced pressure to afford a mixture of (3R)-3-[3-({[(tert-butylamino)sulfonyl]amino}methyl)-1,2,4-oxadiazol-5-yl]-6-cyclohexylhexanoic acid and (3R)-3-(3-{[(aminosulfonyl)amino]methyl}-1,2,4-oxadiazol-5-yl)-6-cyclohexylhexanoic acid (130 mg).

Taken on as a mixture to the following step (see Examples 16, 17).

Preparation 50:

tert-butyl (3R)-3-{3-[(acetylamino)methyl]-1,2,4-oxadiazol-5-yl}-6-cyclohexylhexanoate

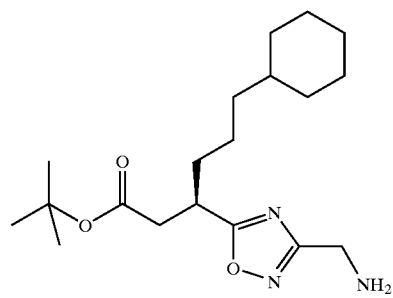

126
-continued

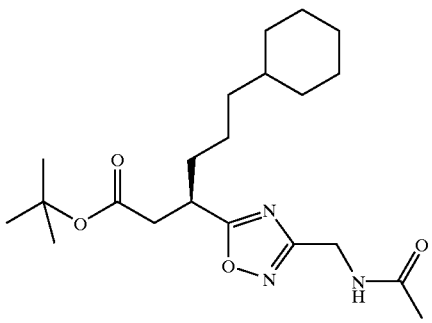

A solution of tert-butyl (3R)-3-[3-(aminomethyl)-1,2,4-oxadiazol-5-yl]-6-cyclohexylhexanoate (preparation 18) (219 mg, 0.62 mmol) in THF (10 ml) was treated with AcCl (53 μl, 0.75 mmol) and stirred at room temperature for 1 hour. More AcCl (200 μl) was added and stirred for a further hour. Sat. NaHCO$_3$ solution was added and the layers separated. The organic extract was washed with brine, dried over anhydrous Na$_2$SO$_4$ and filtered. The solvent was removed under reduced pressure to afford the title compound as a colourless oil (247 mg, 100%).

$^1$H nmr: (CDCl$_3$) 0.83 (2H, m), 1.10–1.35 (8H, m), 1.40 (9H, s), 1.60–1.80 (7H, m), 2.03 (3H, s), 2.60 (1H, dd), 2.79 (1H, dd), 3.42 (1H, m), 4.58 (2H, d), 5.94 (1H, brs).

MS: 416 (MNa$^+$)

Preparation 51:

(3R)-3-{3-[(acetylamino)methyl]-1,2,4-oxadiazol-5-yl}-6-cyclohexylhexanoic acid

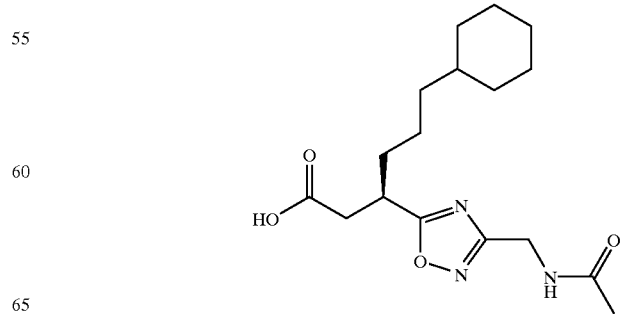

Method as for preparation 7 using tert-butyl (3R)-3-{3-[(acetylamino)methyl]-1,2,4-oxadiazol-5-yl}-6-cyclohexylhexanoate (preparation 50) (229 mg, 0.58 mmol) as starting material to afford the title compound as a pale yellow oil (235 mg).

¹H nmr: (d₆-DMSO) 0.81 (2H, m), 1.05–1.25 (8H, m), 1.50–1.70 (7H, m), 1.83 (3H, s), 2.70 (2H, m), 3.39 (1H, m), 4.32 (2H, d), 8.34 (1H, brs).

MS: 360 (MNa⁺)

CHN: Found: C57.98%; H8.24%; N10.18%; C₁₇H₂₇N₃O₄.0.8 H₂O.0.6 dioxan requires C57.58%; H8.32%; N10.38%.

Preparation 52:

tert-butyl (3R)-3-(3-{[acetyl(methyl)amino]methyl}-1,2,4-oxadiazol-5-yl)-6-cyclohexylhexanoate

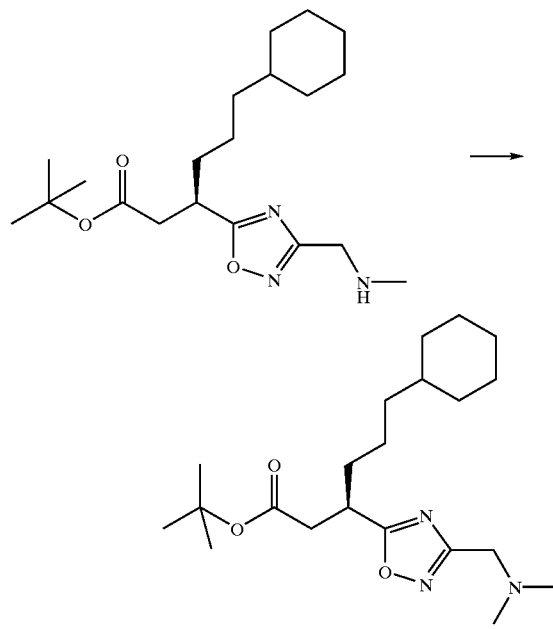

Method as for preparation 50 using tert-butyl (3R)-6-cyclohexyl-3-{3-[(methylamino)methyl]-1,2,4-oxadiazol-5-yl}hexanoate (preparation 5) as starting material.

Purification: Crude material purified on a silica column eluting with DCM:MeOH (19:1) to afford the title compound as a colourless oil (255 mg, 94%).

¹H nmr: (CDCl₃) contains rotamers: 0.86 (2H, m), 1.10–1.35 (8H, m), 1.40 (9H, s) 1.60–1.80 (7H, m), 2.10–2.20 (3H, s+s), 2.60 (1H, m), 2.78 (1H, m), 2.98–3.15 (3H, s+s), 3.42 (1H, m), 4.50–4.70 (2H, s+s).

MS: 430 (MNa⁺)

Preparation 53:

(3R)-3-(3-{[acetyl(methyl)amino]methyl}-1,2,4-oxadiazol-5-yl)-6-cyclohexylhexanoic acid

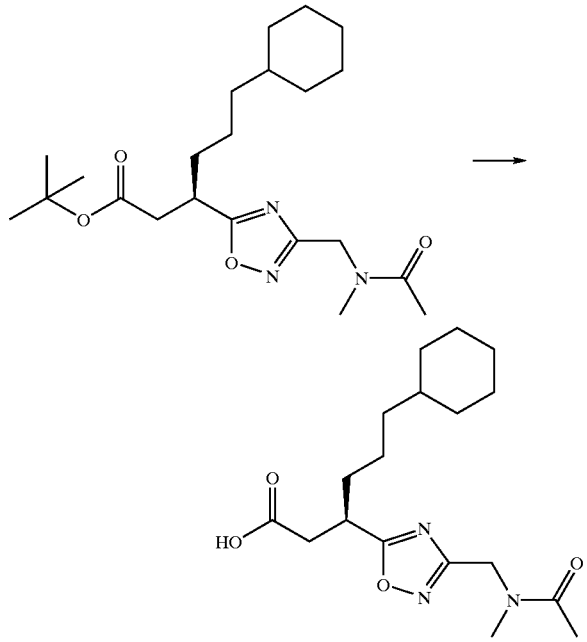

Method as for preparation 7 using tert-butyl (3R)-3-(3-{[acetyl(methyl)amino]methyl}-1,2,4-oxadiazol-5-yl)-6-cyclohexylhexanoate (preparation 52) (241 mg, 0.59 mmol) as starting material to afford the title compound as a colourless oil (146 mg, 46%).

¹H nmr: (CDCl₃) contains rotamers: 0.83 (2H,br), 1.05–1.50 (8H, br), 1.60–1.90 (7H, br), 2.10–2.20 (3H, s+s), 2.62–3.10 (5H, m), 3.47 (1H, m), 4.50–4.70 (2H, s+s).

MS:374 (MNa⁺)

CHN: Found: C59.73%; H8.21%; N11.07%; C₁₈H₂₉N₃O₄.0.45 H₂O.0.1 dioxan requires C60.00%; H8.40%; N11.41%.

Preparation 54:

tert-butyl (3R)-6-cyclohexyl-3-(3-{[(cyclopropylcarbonyl)amino]methyl}-1,2,4-oxadiazol-5-yl)hexanoate

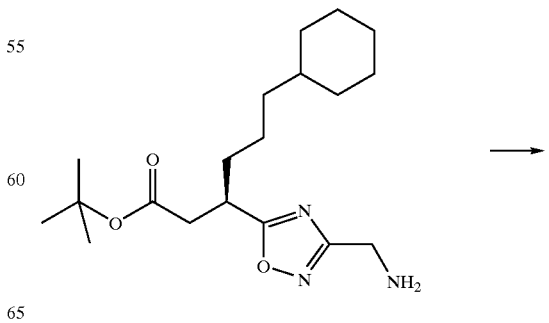

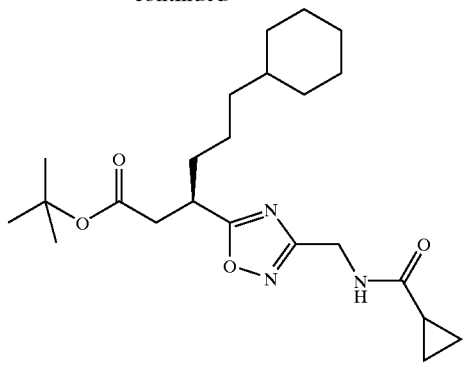

Method as for preparation 50 using tert-butyl (3R)-3-[3-(aminomethyl)-1,2,4-oxadiazol-5-yl]-6-cyclohexylhexanoate (preparation 18) (204 mg, 0.57 mmol) and cyclopropane carboxylic acid chloride (62 μl, 0.68 mmol) as starting materials to afford the title compound as a colourless oil (257 mg).

$^1$H nmr: (CDCl$_3$) 0.75–1.80 (31H, m), 2.61 (1H, dd), 2.78 (1H, dd), 3.42 (1H, m), 4.59 (2H, d), 6.20 (1H, brs).

MS: 442 (MNa$^+$)

CHN: Found: C64.74%; H8.80%; N9.12%; C$_{23}$H$_{37}$N$_3$O$_4$.0.5 H$_2$O requires C64.53%; H9.01%; N9.49%.

Preparation 55:

(3R)-6-cyclohexyl-3-(3-{[(cyclopropylcarbonyl)amino]methyl}-1,2,4-oxadiazol-5-yl)hexanoic acid Method as for preparation 7 using tert-butyl (3R)-6-cyclohexyl-3-(3-{[(cyclopropylcarbonyl)amino]methyl}-1,2,4-oxadiazol-5-yl)hexanoate (preparation 54) (236 mg, 0.56 mmol) as starting material to afford the title compound as a yellow oil (224 mg).

$^1$H nmr: (d$_6$DMSO) 0.68 (4H, m), 0.80 (2H, m), 1.05–1.25 (8H, m), 1.55–1.70 (8H, m), 2.69 (2H, m), 3.38 (1H m), 4.36 (2H, d), 8.51 (1H, brs).

MS: 386 (MNa$^+$)

CHN: Found: C60.81%; H8.09%; N9.47%; C$_{19}$H$_{29}$N$_3$O$_4$.0.2 H$_2$O.0.7 dioxan requires C61.07%; H8.23%; N9.80%.

Preparation 56:

tert-butyl (3R)-6-cyclohexyl-3-(3-{[(methoxyacetyl)amino]methyl}-1,2,4-oxadiazol-5-yl)hexanoate

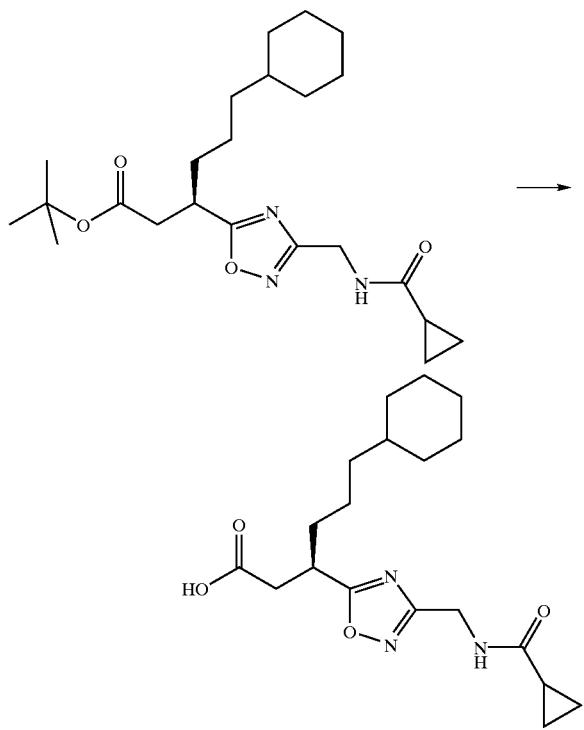

A solution of tert-butyl (3R)-3-[3-(aminomethyl)-1,2,4-oxadiazol-5-yl]-6-cyclohexylhexanoate (preparation 18) (206 mg, 0.57 mmol) and methoxyacetic acid (48 μl, 0.63 mmol) in DCM (5 ml) was treated with a solution of WSCDI (120 mg, 0.63 mmol), HOBt (85 mg, 0.63 mmol) and NMM (69 μl, 0.63 mmol) in DCM (10 ml) and stirred at room temperature for 18 hours. The reaction mixture was washed with sat. NaHCO$_3$ solution followed by brine, dried over MgSO$_4$ and filtered. The solvent was removed under reduced pressure. The residue was purified on a silica column eluting with Et$_2$O to afford the title compound as a colourless oil (230 mg, 93%).

$^1$H nmr: (CDCl$_3$) 0.82 (2H, m), 1.10–1.30 (8H, m), 1.40 (9H, s), 1.60–1.80 (7H, m), 2.60 (1H, dd), 2.79 (1H, dd), 3.40–3.50 (4H, s+m), 3.97 (2H, s), 4.60 (2H, d), 7.00 (1H, brs).

MS: 446 (MNa$^+$)

CHN: Found: C62.28%; H8.84%; N9.62%; C$_{22}$H$_{37}$N$_3$O$_5$ requires C62.39%; H8.81%; N9.92%.

Preparation 57:

(3R)-6-cyclohexyl-3-(3-{[(methoxyacetyl)amino]
methyl}-1,2,4-oxadiazol-5-yl)hexanoic acid

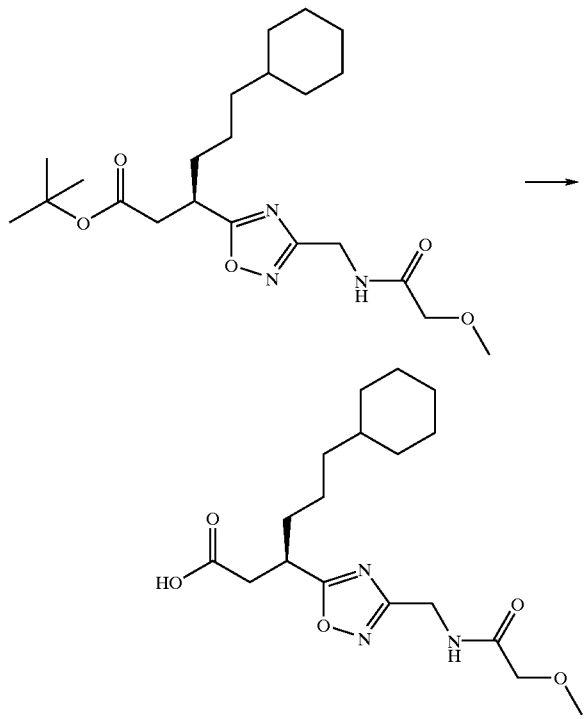

Method as for preparation 7 using tert-butyl (3R)-6-cyclohexyl-3-(3-{[(methoxyacetyl)amino]methyl}-1,2,4-oxadiazol-5-yl)hexanoate (preparation 56) (216 mg, 0.51 mmol) as starting material to afford the title compound as a yellow oil (196 mg).

¹H nmr: (d₆DMSO) 0.80 (2H, m), 1.05–1.25 (8H, m), 1.50–1.70 (7H, m), 2.68 (2H, m), 3.32 (3H, s), 3.39 (1H, m), 3.81 (2H, s), 4.39 (2H, d), 8.21 (1H, brs).

MS: 368 (MH⁺)

CHN: Found: C58.39%; H8.18%; N10.05%; C₁₈H₂₉N₃O₅.0.4 dioxan requires C58.46%; H8.06%; N10.43%.

Preparation 58:

tert-butyl (3R)-6-cyclohexyl-3-[3-({
[(dimethylamino)acetyl]amino}methyl)-1,2,4-
oxadiazol-5-yl]hexanoate

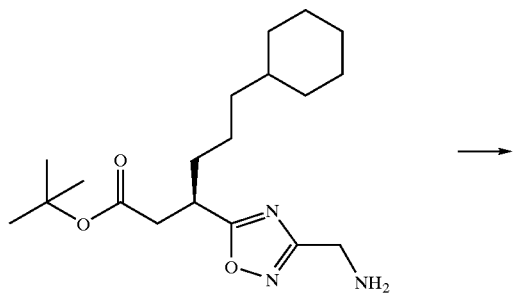

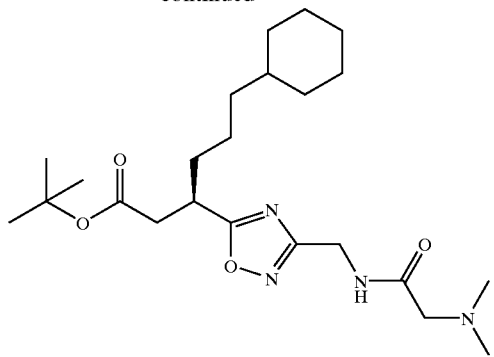

Method as for preparation 56 using tert-butyl (3R)-3-[3-(aminomethyl)-1,2,4-oxadiazol-5-yl]-6-cyclohexylhexanoate (preparation 18) (206 mg, 0.57 mmol) and N,N-dimethylglycine (65 mg, 0.63 mmol) as starting materials.

Purification: The crude material was purified on a silica column eluting with Et₂O:MeOH (9:1) to afford the title compound as a colourless oil (227 mg, 89%).

¹H nmr: (CDCl₃) 0.83 (2H, m), 1.10–1.35 (8H, m), 1.40 (9H, s), 1.60–1.75 (7H, m), 2.32 (6H, s), 2.61 (1H, dd), 2.79 (1H, dd), 3.00 (2H, s), 2.44 (1H, m), 4.60 (2H, d), 7.60 (1H, brs).

MS: 459 (MNa⁺)

CHN: Found: C63.04%; H9.30%; N12.67%; C₂₃H₄₀N₄O₄ requires C63.27%; H9.23%; N12.83%.

Preparation 59:

(3R)-6-cyclohexyl-3-[3-({[(dimethylamino)acetyl]
amino}methyl)-1,2,4-oxadiazol-5-yl]hexanoic acid

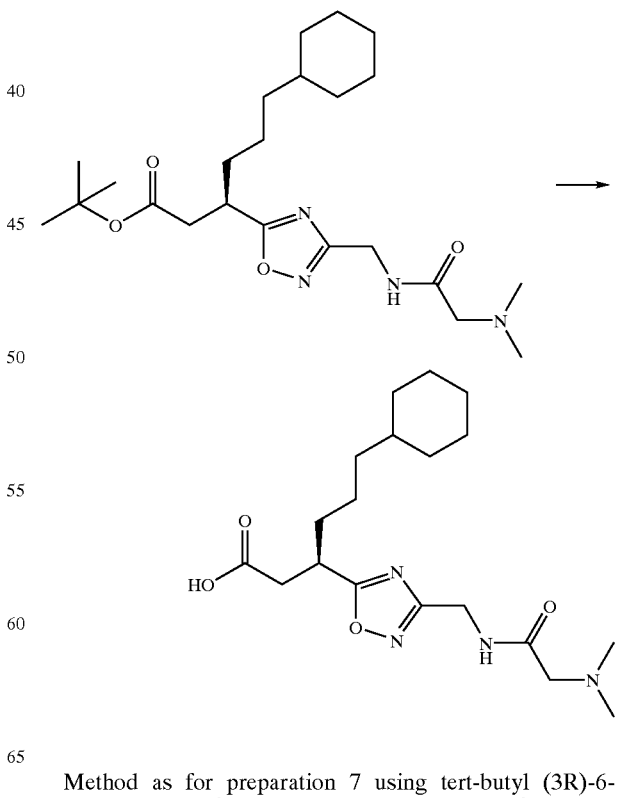

Method as for preparation 7 using tert-butyl (3R)-6-cyclohexyl-3-[3-({[(dimethylamino)acetyl]amino}methyl)-

1,2,4-oxadiazol-5-yl]hexanoate (preparation 58) (216 mg, 0.49 mmol) as starting material to afford the title compound as a white solid (225 mg).

¹H nmr: (d₆DMSO) 0.81 (2H, m), 1.05–1.25 (8H, m), 1.50–1.70 (8H, m), 2.70 (2H, m), 2.79 (6H, s), 3.39 (1H, m), 3.93 (2H, s), 4.44 (2H, d), 9.15 (1H, brs).

MS: 381 (MH⁺)

CHN: Found: C54.46%; H7.96%; N13.17%; $C_{19}H_{32}N_4O_4$·HCl requires C54.73%; H7.98%; N13.44%.

Preparation 60:

tert-butyl (3R)-3-{3-[(benzoylamino)methyl]-1,2,4-oxadiazol-5-yl}-6-cyclohexylhexanoate

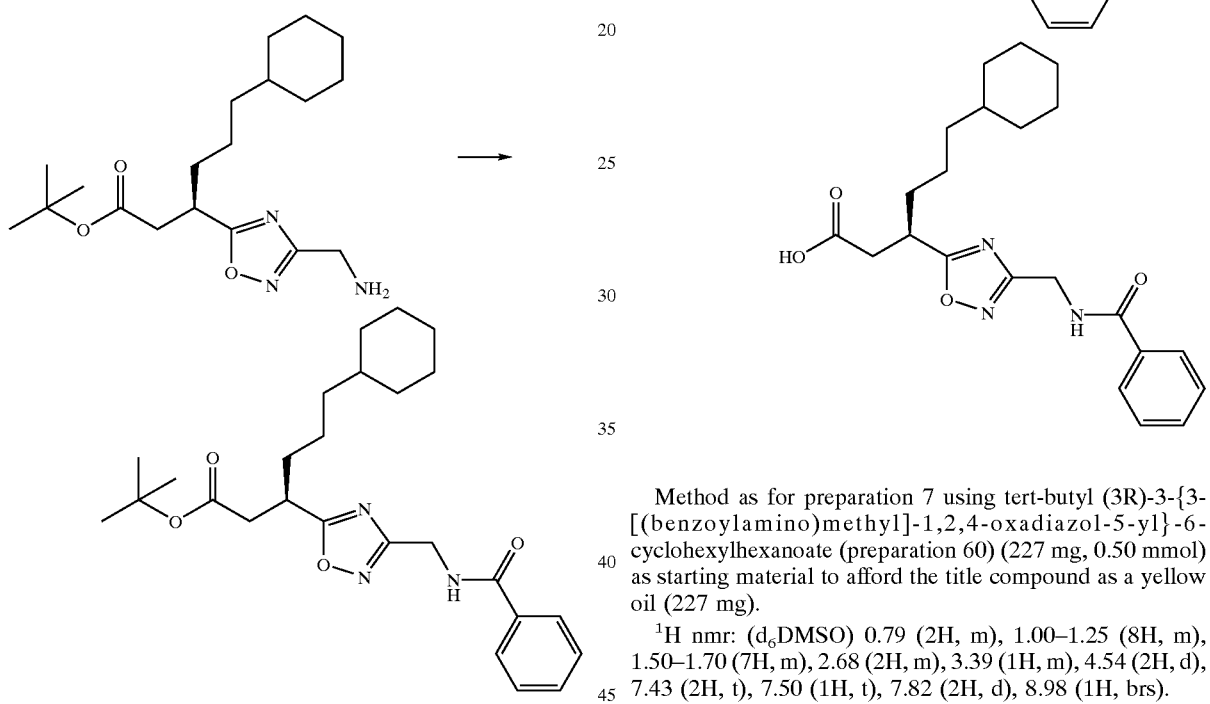

Method as for preparation 50 using tert-butyl (3R)-3-[3-(aminomethyl)-1,2,4-oxadiazol-5-yl]-6-cyclohexylhexanoate (preparation 18) (200 mg, 0.57 mmol) and benzoylchloride (79 μl, 0.68 mmol) as starting materials.

Purification: The crude material was purified on a silica column eluting with Et₂O:pentane (1:1) to afford the title compound as a colourless oil (243 mg, 94%).

¹H nmr: (CDCl₃) 0.82 (2H, m), 1.10–1.80 (24H, m), 2.61 (1H, dd), 2.79 (1H, dd), 3.43 (1H, m), 4.79 (2H, d), 6.60 (1H, brs), 7.42 (2H, t), 7.51 (2H, d), 7.80 (2H, d).

MS: 478 (MNa⁺)

CHN: Found: C68.40%; H8.26%; N9.04%; $C_{26}H_{37}N_3O_4$·0.1 H₂O·0.1 Et₂O requires C68.22%; H8.28%; N9.04%.

Preparation 61:

(3R)-3-{3-[(benzoylamino)methyl]-1,2,4-oxadiazol-5-yl}-6-cyclohexylhexanoic acid

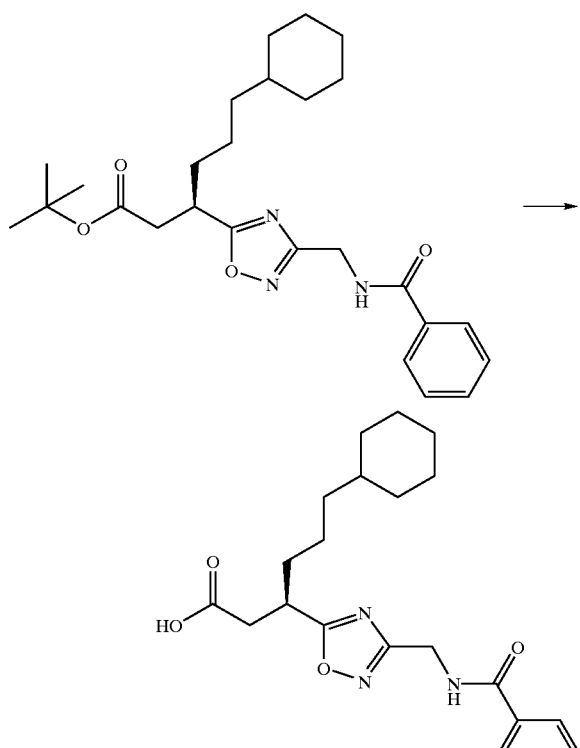

Method as for preparation 7 using tert-butyl (3R)-3-{3-[(benzoylamino)methyl]-1,2,4-oxadiazol-5-yl}-6-cyclohexylhexanoate (preparation 60) (227 mg, 0.50 mmol) as starting material to afford the title compound as a yellow oil (227 mg).

¹H nmr: (d₆DMSO) 0.79 (2H, m), 1.00–1.25 (8H, m), 1.50–1.70 (7H, m), 2.68 (2H, m), 3.39 (1H, m), 4.54 (2H, d), 7.43 (2H, t), 7.50 (1H, t), 7.82 (2H, d), 8.98 (1H, brs).

MS: 422 (MNa⁺)

CHN: Found: C64.32%; H7.64%; N8.73%; $C_{22}H_{29}N_3O_4$·0.7 dioxan requires C64.59%; H7.56%; N9.11%.

Preparation 62:

tert-butyl (3R)-6-cyclohexyl-3-(3-{[(2-pyridinylcarbonyl)amino]methyl}-1,2,4-oxadiazol-5-yl)hexanoate

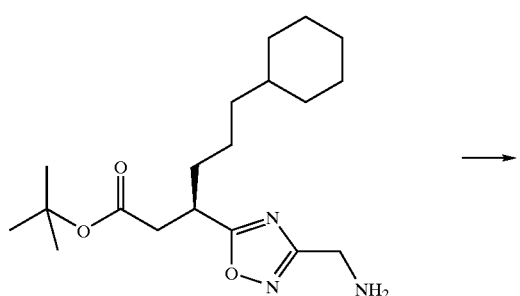

135

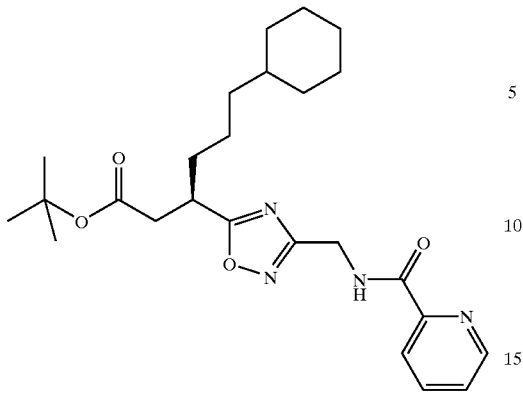

Method as for preparation 56 using tert-butyl (3R)-3-[3-(aminomethyl)-1,2,4-oxadiazol-5-yl]-6-cyclohexylhexanoate (preparation 18) (202 mg, 0.57 mmol) and picolininc acid (77 mg, 0.63 mmol) as starting materials.

Purification: The crude material was purified on a silica column eluting with pentane:Et$_2$O (1:1) to afford the title compound as a colourless oil.

$^1$H nmr: (CDCl$_3$) 0.81 (2H, m), 1.05–1.35 (8H, m), 1.39 (9H, s), 1.55–1.80 (7H, m), 2.60 (1H, dd), 2.80 (1H, dd), 3.43 (1H, m), 4.79 (2H, d), 7.41 (1H, m), 7.82 (1H, t), 8.20 (1H, d), 8.50 (1H, brs), 8.59 (1H, d).

MS: 479 (MNa$^+$)

CHN: Found: C65.39%; H7.98%; N12.00%; C$_{25}$H$_{36}$N$_4$O$_4$ requires C65.77%; H7.95%; N12.27%.

Preparation 63:

(3R)-6-cyclohexyl-3-(3-{[(2-pyridinylcarbonyl)amino]methyl}-1,2,4-oxadiazol-5-yl)hexanoic acid

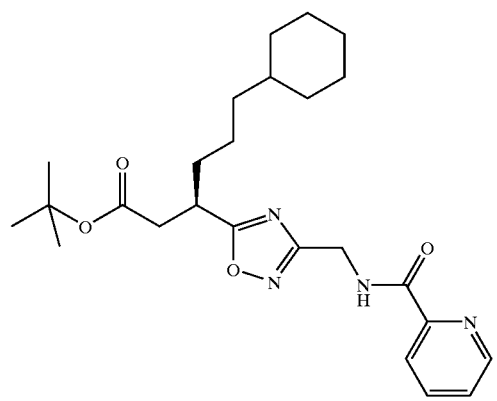

136

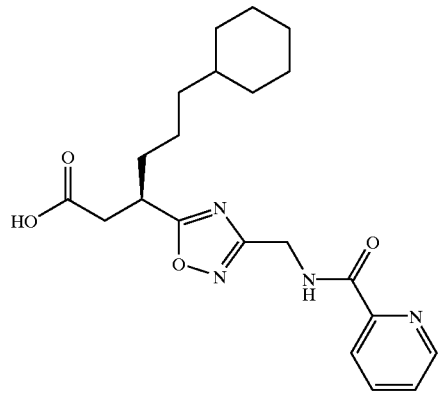

Method as for preparation 7 using tert-butyl (3R)-6-cyclohexyl-3-(3-{[(2-pyridinylcarbonyl)amino]methyl}-1,2,4-oxadiazol-5-yl)hexanoate (preparation 62) (216 mg, 0.47 mmol) as starting material to afford the title compound as a yellow oil (213 mg).

$^1$H nmr: (d$_6$DMSO) 0.77 (2H, m), 1.00–1.20 (8H, m), 1.50–1.65 (7H, m), 2.79 (2H, m), 3.40 (1H, m), 4.58 (2H, d), 7.60 (1H, t), 8.00 (2H, m), 8.62 (1H, d), 9.30 (1H, t).

MS:399 (M–H)

CHN: Found: C61.20%; H7.16%; N12.65%; C$_{21}$H$_{28}$N$_4$O$_4$.0.4 H$_2$O.0.3 dioxan requires C61.42%; H7.24%; N12.91%.

Preparation 64:

tert-butyl (3R)-3-(3-{[(aminocarbonyl)amino]methyl}-1,2,4-oxadiazol-5-yl)-6-cyclohexylhexanoate

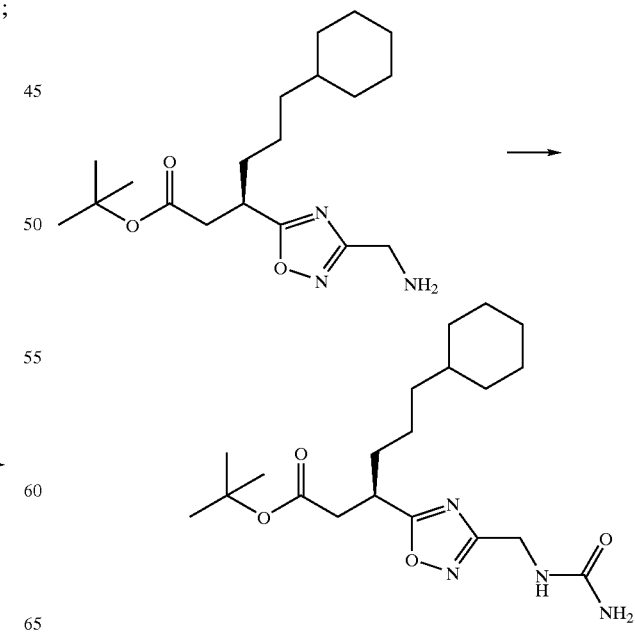

A solution of tert-butyl (3R)-3-[3-(aminomethyl)-1,2,4-oxadiazol-5-yl]-6-cyclohexylhexanoate (preparation 18) (310 mg, 0.88 mmol) in MeCN (10 ml) was treated with N,N-disuccinimidyl carbonate (271 mg, 1.06 mmol) and stirred at room temperature, under a nitrogen atmosphere for 4.5 hours. NH₃ (0.5M in dioxan) was added forming a white precipitate. The reaction mixture was stirred at room temperature for 18 hours. The reaction mixture was filtered and the solvent removed under reduced pressure. The residue was purified on a silica column eluting with a solvent gradient of DCM:MeOH (100:0) gradually changing to (95:5) to afford the title compound as a colourless oil (253 mg, 73%).

¹H nmr: (CDCl₃) 0.83 (2H, m), 1.10–1.35 (8H, m), 1.40 (9H, s), 1.55–1.80 (7H, m), 2.60 (1H, dd), 2.78 (1H, dd), 3.42 (1H, m), 4.54 (2H, d), 5.08 (1H, brs).

Preparation 65:

(3R)-3-(3-{[(aminocarbonyl)amino]methyl}-1,2,4-oxadiazol-5-yl)-6-cyclohexylhexanoic acid

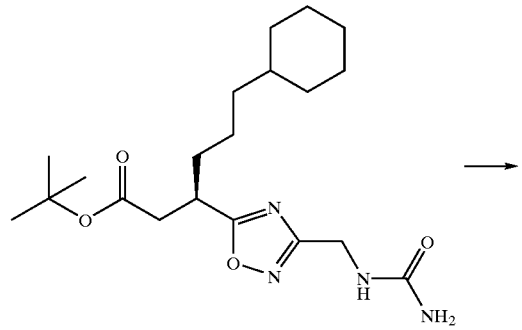

Method as for preparation 11 using tert-butyl (3R)-3-(3-{[(aminocarbonyl)amino]methyl}-1,2,4-oxadiazol-5-yl)-6-cyclohexylhexanoate (preparation 64) (261 mg, 0.66 mmol) as starting material to afford the title compound as a yellow oil (191 mg, 86%).

¹H nmr: (CDCl₃) 0.85 (2H, m), 1.10–1.40 (8H, m), 1.60–1.85 (7H, m), 2.80 (2H, m), 3.44 (1H, m), 4.45 (2H, d).

Preparation 66:

tert-butyl (3R)-6-cyclohexyl-3-[3-({[(methylamino)carbonyl]amino}methyl)-1,2,4-oxadiazol-5-yl] hexanoate

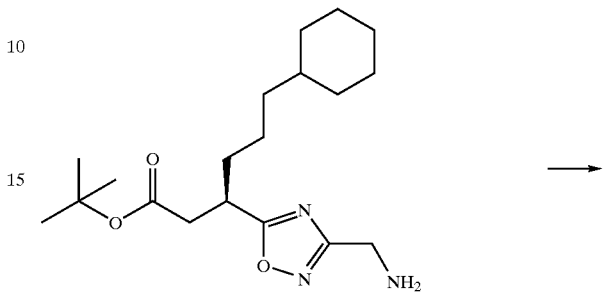

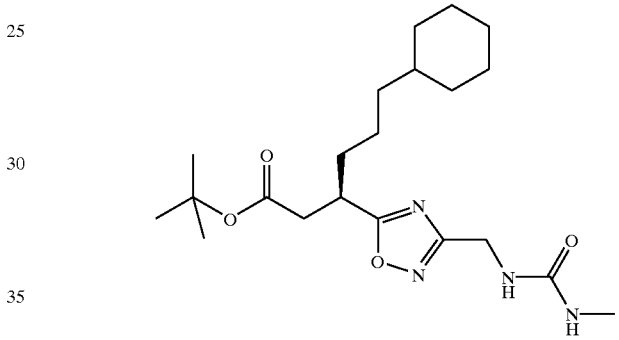

A solution of tert-butyl (3R)-3-[3-(aminomethyl)-1,2,4-oxadiazol-5-yl]-6-cyclohexylhexanoate (preparation 18) (148 mg, 0.42 mmol) in MeCN (10 ml) was treated with N,N-disuccinimidyl carbonate (130 mg, 0.51 mmol) and stirred at room temperature, under a nitrogen atmosphere for 4 hours. The solvent was removed under reduced pressure. The oil was dissolved in THF (5 ml) and treated with MeNH₂ (2.0 M in THF) (1.0 ml) forming a white precipitate. The reaction mixture was stirred at room temperature for 2 days and filtered. The solvent was removed under reduced pressure. The oil was purified on a silica column eluting with a solvent gradient of DCM:MeOH (95:5) gradually changing to (90:10) to afford the title compound as a colourless oil (134 mg, 78%).

hu 1H nmr: (CDCl₃) 0.82 (2H, m), 1.10–1.30 (8H, m), 1.39 (9H, s), 1.60–1.80 (7H, m) 2.60 (1H, dd), 2.78 (1H, dd), 2.80 (3H, d), 3.42 (1H, m), 4.50 (2H, d), 4.83 (1H, brs).

MS: 431 (MNa⁺)

Preparation 67:

(3R)-6-cyclohexyl-3-[3-({[(methylamino)carbonyl]amino}methyl)-1,2,4-oxadiazol-5-yl]hexanoic acid

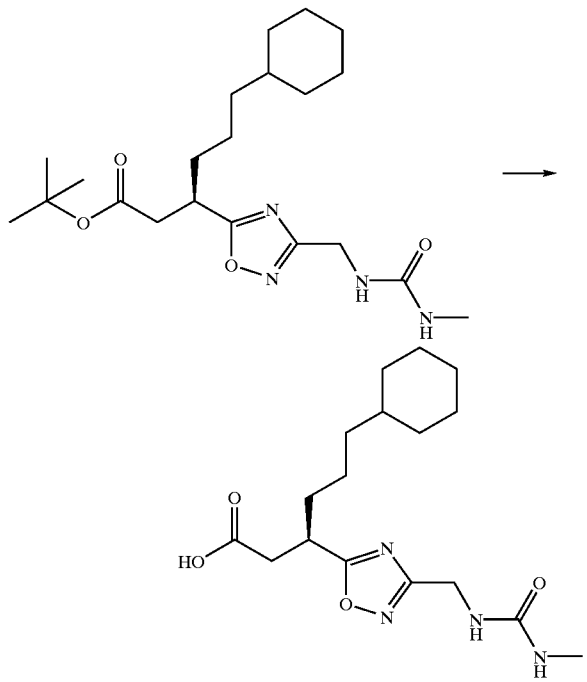

Method as for preparation 11 using tert-butyl (3R)-6-cyclohexyl-3-[3-({[(methylamino)carbonyl]amino}methyl)-1,2,4-oxadiazol-5-yl]hexanoate (preparation 66) (140 mg, 0.34 mmol) as starting material to afford the title compound as a colourless oil (141 mg).

$^1$H nmr: (d$_6$DMSO) 0.81 (2H, m), 1.05–1.30 (8H, m), 1.50–1.70 (7H, m), 2.56 (3H, d), 2.67 (2H, m), 3.38 (1H, m), 4.25 (2H, s).

MS: 375 (MNa$^+$)

Preparation 68:

tert-butyl (3R)-6-cyclohexyl-3-[3-({[(dimethylamino)carbonyl]amino}methyl)-1,2,4-oxadiazol-5-yl]hexanoate

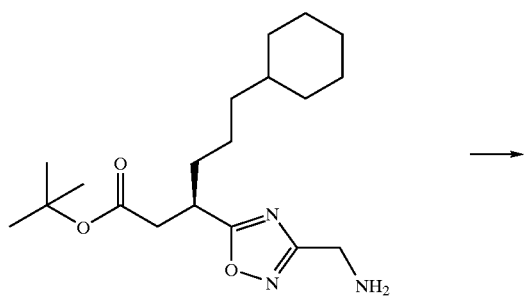

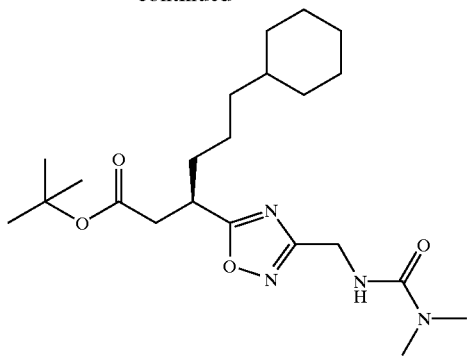

Method as for preparation 66 using tert-butyl (3R)-3-[3-(aminomethyl)-1,2,4-oxadiazol-5-yl]-6-cyclohexylhexanoate (preparation 18) (310 mg, 0.88 mmol) and Me$_2$NH (2.0M in THF) (1.80 ml, 3.52 mmol) as starting materials.

Purification: The crude material was purified on a silica column eluting with a solvent gradient of DCM:MeOH (98:2) gradually changing to (95:5) to afford the title compound (309 mg, 83%).

$^1$H nmr: (CDCl$_3$) 0.81 (2H, m), 1.10–1.30 (8H, m), 1.39 (9H, s), 1.60–1.80 (7H, m), 2.61 (1H, dd), 2.78 (1H, m), 2.94 (6H, s), 3.42 (1H, m), 4.57 (2H, m), 5.01 (1H, brs).

MS: 423 (MH$^+$)

Preparation 69:

(3R)-6-cyclohexyl-3-[3-({[(dimethylamino)carbonyl]amino}methyl)-1,2,4-oxadiazol-5-yl]hexanoic acid

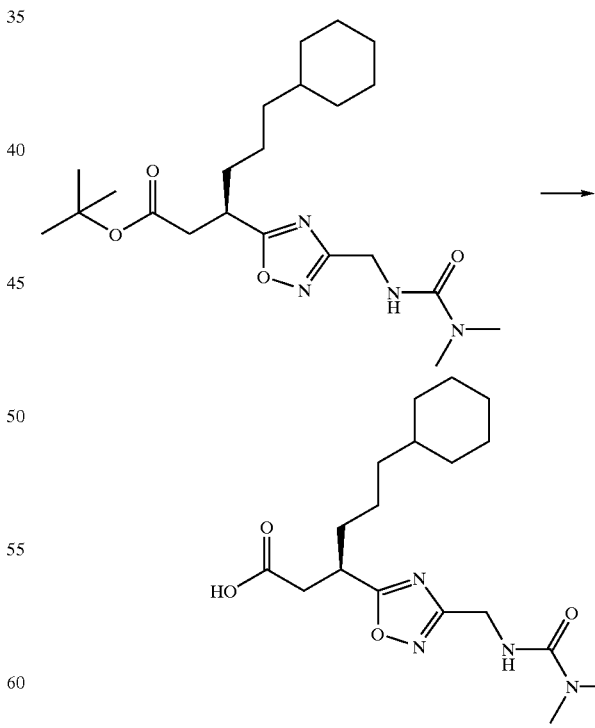

Method as for preparation 11 using tert-butyl (3R)-6-cyclohexyl-3-[3-({[(dimethylamino)carbonyl]amino}methyl)-1,2,4-oxadiazol-5-yl]hexanoate (preparation 68) 9298 mg, 0.71 mmol) as starting material.

Purification: The crude material was purified on a silica column eluting with a solvent gardient of DCM:MeOH (98:2) gradually changing to (90:10) to afford the title compound (214 mg, 83%).

¹H nmr: (CDCl₃) 0.80 (2H, m), 1.05–1.30 (8H, m), 1.60–1.80 (7H, m), 2.73 (1H, dd), 2.92 (7H, m), 3.49 (1H, m), 4.51 (2H, m), 5.37 (1H, brs).

MS: 365 (M−H)

Preparation 70:

(3R)-3-(3-{[(tert-butoxycarbonyl)amino]methyl}-1,2,4-oxadiazol-5-yl)-6-cyclohexylhexanoic acid

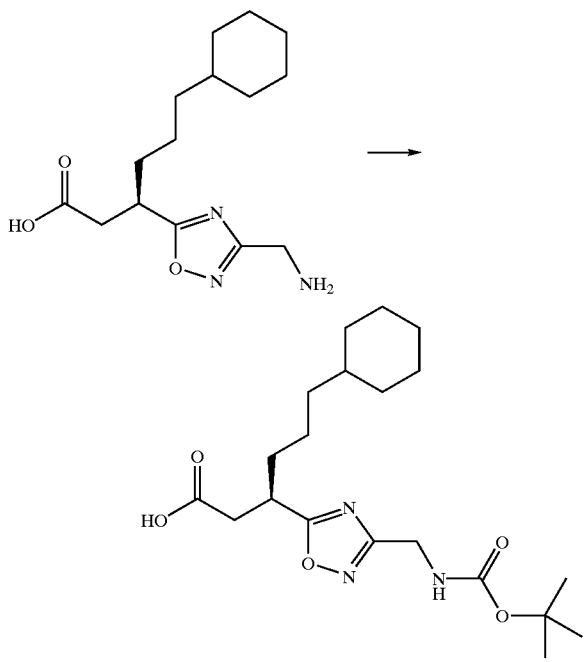

A solution of (3R)-3-[3-(aminomethyl)-1,2,4-oxadiazol-5-yl]-6-cyclohexylhexanoic acid (preparation 163) (177 mg, 0.53 mmol) and Et₃N (186 µl, 1.33 mmol) in dioxan (500 µl) and H₂O (500 µl) was treated with Boc-ON (145 mg, 0.58 mmol) and stirred at room temperature for 18 hours. The reaction mixture was diluted with H₂O and extracted with EtOAc (×2). The organic extracts were combined and the solvent removed under reduced pressure. The crude material was purified on a silica column eluting with DCM:MeOH (100:0) gradually changing to (90:10) to afford the title compound as a colourless gum (15 mg, 55%).

¹H nmr: (CDCl₃) 0.84 (2H, m), 1.10–1.35 (8H, m), 1.42 (9H, s), 1.60–1.80 (7H, m), 2.74 (1H, dd), 2.94 (1H, dd), 3.48 (1H, m), 4.40 (2H, d).

MS: 394 (M−H)

Accurate mass: Found 396.2500 (MH⁺), Calculated C₂₀H₃₄N₃O₅, 396.2493.

Preparation 71:

tert-butyl (3R)-6-cyclohexyl-3-[3-(hydrazinocarbonyl)-1,2,4-oxadiazol-5-yl]hexanoate

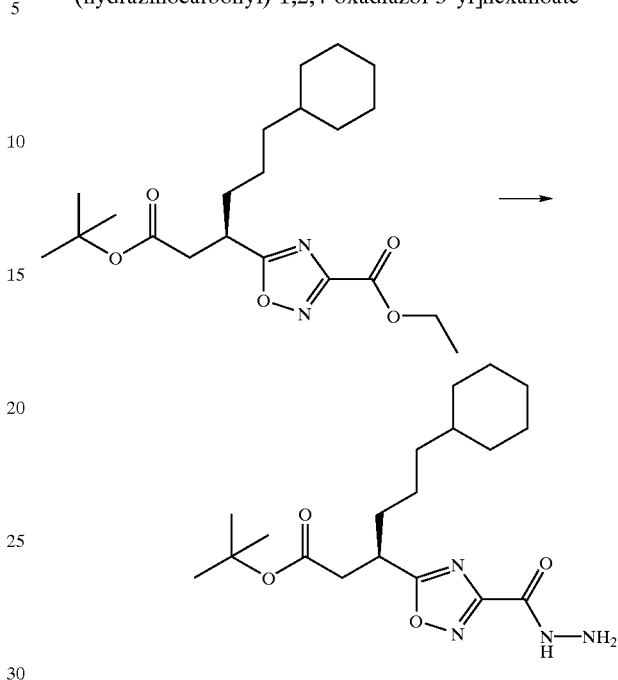

A solution of ethyl 5-[(1R)-1-(2-tert-butoxy-2-oxoethyl)-4-cyclohexylbutyl]-1,2,4-oxadiazole-3-carboxylate (preparation 170) (1.14 g, 2.89 mmol) in EtOH (20 ml) was treated with NH₂NH₂.H₂O (280 µl, 5.78 mmol) and stirred at room temperature for 45 minutes. The solvent was removed under reduced pressure. The residue was partitioned between EtOAc and H₂O/brine. The organic solvent was removed under reduced pressure to afford the title compound (1.06 g, 90%).

¹H nmr: (d₆DMSO) 0.80 (2H, m), 1.00–1.25 (8H, m), 1.38 (9H, s), 1.50–1.70 (7H, m,), 2.74 (2H, d), 3.42 (1H, m), 4.66 (2H, brs), 10.20 (1H, brs).

MS: 403 (MNa⁺)

Preparation 72:

(3R)-3-(3-amino-1,2,4-oxadiazol-5-yl)-6-cyclohexylhexanoic acid

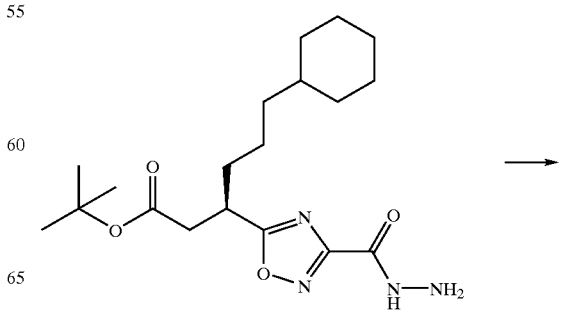

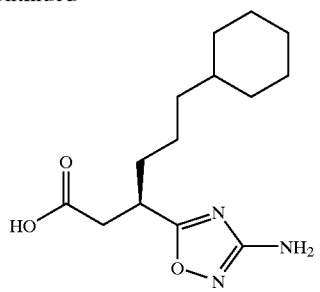

A solution of tert-butyl (3R)-6-cyclohexyl-3-[3-(hydrazinocarbonyl)-1,2,4-oxadiazol-5-yl]hexanoate (preparation 71) (1.06 g, 2.76 mmol) in glacial AcOH (10 ml) was treated with 2M HCl (10 ml) and stirred at room temperature for 30 minutes. The reaction mixture was cooled to 0° C. before being treated with a solution of NaNO$_2$ (278 mg, in 5 ml H$_2$O) making sure the temperature never rose above 5° C. The reaction mixture was stirred at 0° C. for 30 minutes and then allowed to warm to room temperature before being heated at 85° C. until the evolution of gas a finished. The reaction mixture was neutralised with sat. Na$_2$CO$_3$ solution and extracted with EtOAc. The organic extract was washed with brine and the solvent removed under reduced pressure. The residue was treated with TFA (4 ml) and stirred at room temperature for 1 hour. The solvent was removed under reduced pressure and the residue azeotroped from toluene (×3) and DCM (×3) to afford the title compound as a foam (390 mg, 50%).

$^1$H nmr: (CDCl$_3$) 0.82 (2H, m), 1.05–1.40 (8H, m), 1.55–1.85 (7H, m), 2.70 (1H, dd), 2.86 (1H, dd), 3.38 (1H, m), 4.58 (2H, brs).

MS: 304 (MNa$^+$)

Preparation 73:

(3R)-6-cyclohexyl-3-{3-[(methylamino)methyl]-1,2,4-oxadiazol-5-yl}hexanoic acid

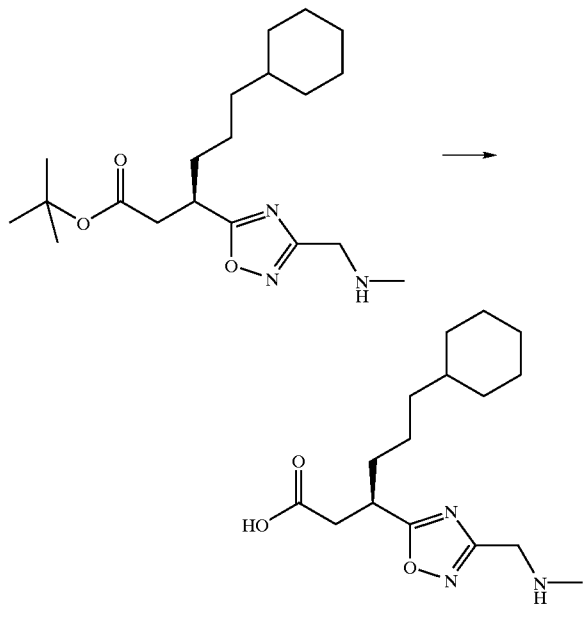

Method as for preparation 7 using tert-butyl (3R)-6-cyclohexyl-3-{3-[(methylamino)methyl]-1,2,4-oxadiazol-5-yl}hexanoate (preparation 5) (400 mg, 1.09 mmol) as starting material to afford the title compound as a yellow oil (389 mg).

$^1$H nmr: (CD$_3$OD) 0.85 (2H, m), 1.10–1.40 (9H, m), 1.60–1.80 (6H, m), 2.75–2.95 (5H, s+m), 3.54 (1H, m), 4.40 (2H, s).

MS: 310 (MH$^+$)

CHN: Found: C55.44%; H8.34%; N10.13%; C$_{16}$H$_{27}$N$_3$O$_3$.0.1 H$_2$O.0.6 dioxan. HCl requires C55.18%; H8.30%; N10.49%.

Preparation 74:

tert-butyl (3R)-6-cyclohexyl-3-{3-[(ethylamino)methyl]-1,2,4-oxadiazol-5-yl}hexanoate

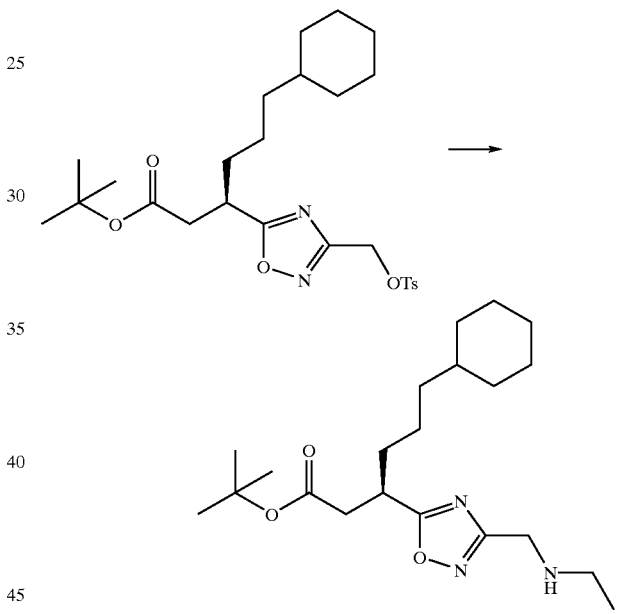

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (750 mg, 1.48 mmol) and ethylamine (2M in THF, 2.22 ml, 4.4 mmol) as starting materials.

Purification: The crude material was purified on a silica column eluting with a solvent gradient of DCM:Et$_2$O (90:10) followed by (0:100) to afford the title compound as a runny oil (275 mg, 49%).

$^1$H nmr: (CDCl$_3$) 0.82 (2H, m), 1.10–1.30 (11H, m), 1.39 (9H, s), 1.60–1.80 (7H, m), 2.55–2.70 (3H, m), 2.79 (1H, dd), 3.43 (1H, m), 3.91 (2H, s).

MS: 380 (MH$^+$)

Preparation 75:

(3R)-6-cyclohexyl-3-{3-[(ethylamino)methyl]-1,2,4-oxadiazol-5-yl}hexanoic acid

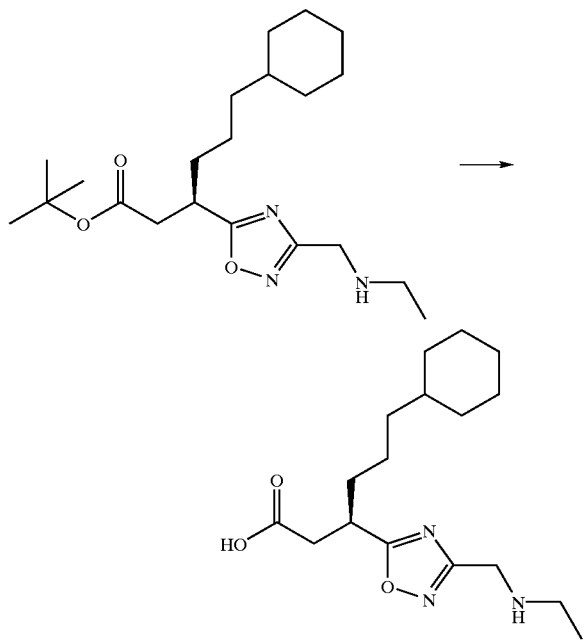

tert-butyl (3R)-6-cyclohexyl-3-{3-[(ethylamino)methyl]-1,2,4-oxadiazol-5-yl}hexanoate (preparation 74) (288 mg, 0.76 mmol) was treated with TFA (5 ml) and stirred at room temperature for 1 hour. The reaction mixture was diluted with DCM and the solvents removed under reduced pressure. The residue was azeotroped from toluene (×3) and DCM (×3) to afford the title compound (373 mg).

$^1$H nmr: (CDCl$_3$) 0.81 (2H, m), 1.10–1.30 (8H, m), 1.36 (3H, t), 1.60–1.80 (7H, m), 2.78 (1H, dd), 2.93 (1H, dd), 3.18 (2H, q), 3.43 (1H, m), 4.24 (2H, s).

MS: 324 (MH$^+$)

CHN: Found: C49.84%; H6.55%; N8.65%; C$_{17}$H$_{29}$N$_3$O$_3$.1.3 TFA requires C49.91%; H6.48%; N8.91%.

Preparation 76:

tert-butyl (3R)-6-cyclohexyl-3-{3-[(propylamino)methyl]-1,2,4-oxadiazol-5-yl}hexanoate

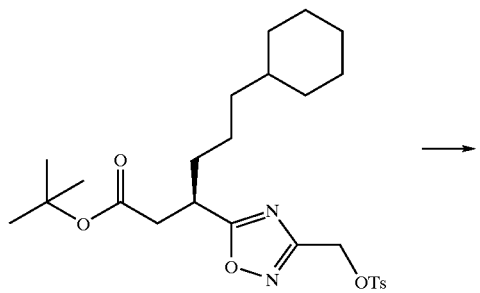

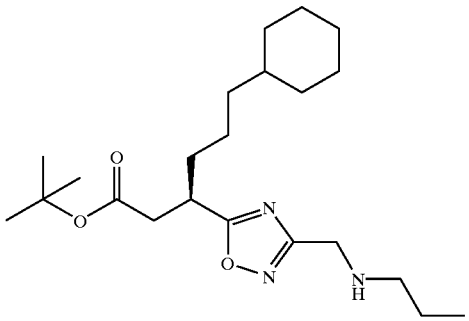

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 1.00 mmol) and propylamine (175 mg, 3.00 mmol) as starting materials.

Purification: The crude material was purified on a silica column eluting with a solvent gradient of DCM:Et$_2$O (90:10) followed by (0:100) to afford the title compound as a colourless oil (257 mg, 66%).

$^1$H nmr: (CDCl$_3$) 0.80 (2H, m), 0.91 (3H, t), 1.10–1.30 (8H, m), 1.39 (9H, s), 1.151 (2H, m), 160–1,80 (7H, m), 2.55–2.6 (3H, t+dd), 2.79 (1H, dd), 3.43 (1H, m), 3.91 (2H, s).

MS: 394 (MH$^+$)

CHN: Found: C67.05%; H10.15%; N10.63%; C$_{22}$H$_{39}$N$_3$O$_3$ requires C67.14; H9.99%; N10.68%.

Preparation 77:

(3R)-6-cyclohexyl-3-{3-[(propylamino)methyl]-1,2,4-oxadiazol-5-yl}hexanoic acid

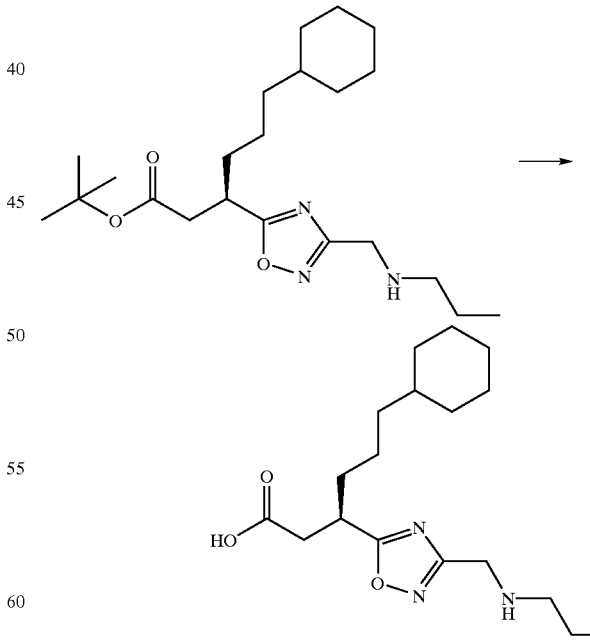

Method as for preparation 75 using tert-butyl (3R)-6-cyclohexyl-3-{3-[(propylamino)methyl]-1,2,4-oxadiazol-5-yl}hexanoate (preparation 76) (257 mg, 0.65 mmol) as starting material.

Purification: Crude material purified on a silica column eluting with DCM:MeOH (90:10) to afford the title compound (272 mg).

¹H nmr: (CDCl₃) 0.81 (2H, m), 0.99 (3H, t), 1.05–1.30 (8H, m), 1.60–1.70 (7H, m), 1.77 (2H, m), 2.77 (1H, dd), 2.91 (1H, dd), 3.03 (2H, t), 3.41 (1H, m), 4.20 (2H, s).

MS: 338 (MH⁺)

CHN: Found: C50.22%; H6.75%; N8.50%; C₁₈H₃₁N₃O₃.1.4 TFA requires C50.26; H6.57%; N8.45%.

Preparation 78:

tert-butyl (3R)-6-cyclohexyl-3-{3-[(isopropylamino)methyl]-1,2,4-oxadiazol-5-yl}hexanoate

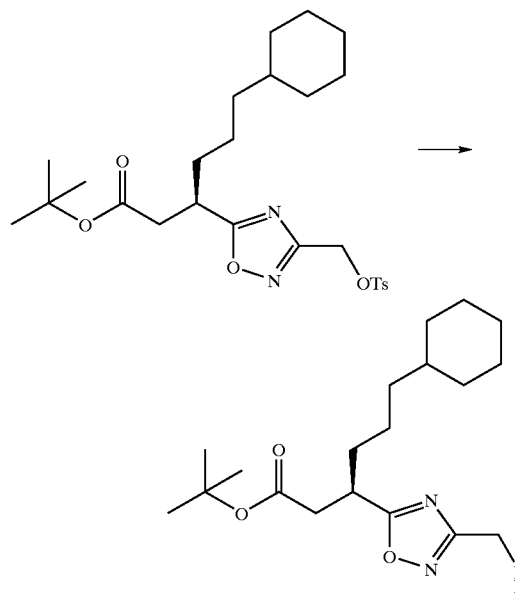

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (490 mg, 0.97 mmol) and isopropylamine (175 mg, 3.00 mmol) as starting materials.

Purification: Crude material was purified on a silica column eluting with DCM:MeOH (97:3) to afford the title compound as a yellow oil (323 mg, 85%).

¹H nmr: (CDCl₃) 0.81 (2H, m), 1.06 (6H, d), 1.10–1.30 (8H, m), 1.39 (9H, s), 1.60–1.80 (7H, m), 2.61 (1H, dd), 2.80 (2H, m), 3.44 (1H, m), 3.91 (2H, s).

MS: 394 (MH⁺)

Preparation 79:

(3R)-6-cyclohexyl-3-{3-[(isopropylamino)methyl]-1,2,4-oxadiazol-5-yl}hexanoic acid

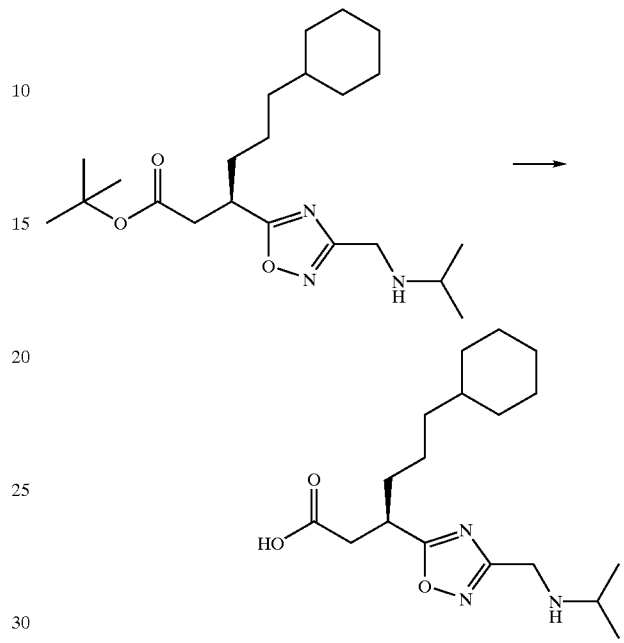

Method as for preparation 75 using tert-butyl (3R)-6-cyclohexyl-3-{3-[(isopropylamino)methyl]-1,2,4-oxadiazol-5-yl}hexanoate (preparation 78) (323 mg, 0.82 mmol) as starting material to afford the title compound as a yellow gum (390 mg, 100%).

¹H nmr: (CDCl₃) 0.81 (2H, m), 1.10–1.30 (8H, m), 1.40 (6H, d), 1.60–1.80 (7H, m), 2.79 (1H, dd), 2.97 (2H, m), 3.42 (1H, m), 4.18 (2H, m).

MS: 338 (MH⁺)

Preparation 80:

tert-butyl (3R)-6-cyclohexyl-3-{3-[(isobutylamino)methyl]-1,2,4-oxadiazol-5-yl}hexanoate

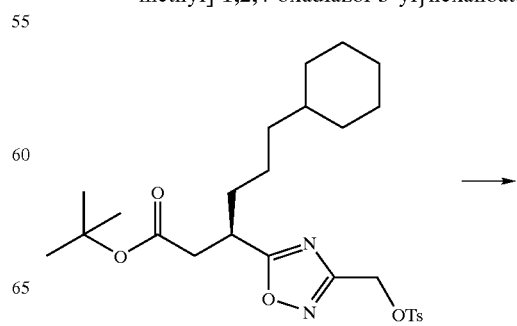

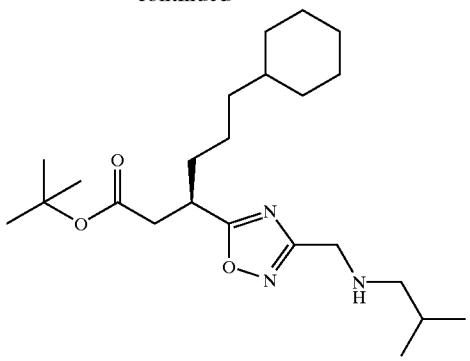

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (750 mg, 1.48 mmol) and isobutylamine (325 mg, 4.44 mmol) as starting materials.

Purification: The crude material was purified on a silica column eluting with a solvent gradient of DCM:Et$_2$O (90:10) followed by (0:100) to afford the title compound as a colourless oil (437 mg, 72%).

$^1$H nmr: (CDCl$_3$) 0.81 (2H, m), 1.92 (6H, d), 1.10–1.30 (8H, m), 1.40 (9H, s), 1.48 (1H, brs), 1.60–1.80 (7H, m), 2.41 (2H, d), 2.61 (1H, dd), 2.80 (1H, dd), 3.43 (1H, m), 3.88 (2H, s).

MS: 408 (MH$^+$)

Preparation 81:

(3R)-6-cyclohexyl-3-{3-[(isobutylamino)methyl]-1,2,4-oxadiazol-5-yl}hexanoic acid

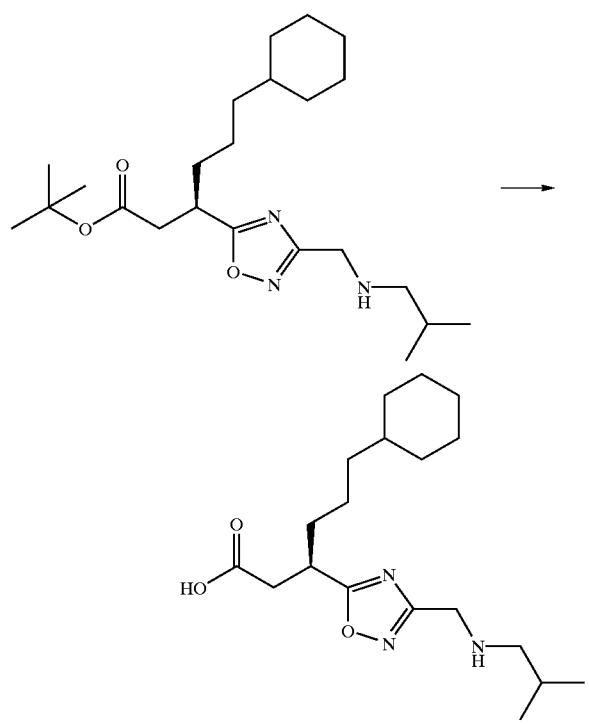

Method as for preparation 75 using tert-butyl (3R)-6-cyclohexyl-3-{3-[(isobutylamino)methyl]-1,2,4-oxadiazol-5-yl}hexanoate (preparation 80) (437 mg, 1.1 mmol) as starting material to afford the title compound (506 mg).

$^1$H nmr: (CDCl$_3$) 0.82 (2H, m), 1.00 (6H, d), 1.10–1.35 (8H, m), 1.60–1.80 (7H, m), 2.09 (1H, m), 2.78 (1H, dd), 2.93 (3H, dd+d), 3.43 (1H, m), 4.22 (2H, s).

MS: 352 (MH$^+$)

CHN: Found: C51.15%; H6.98%; N8.20%; C$_{19}$H$_{33}$N$_3$O$_3$.1.4 TFA requires C51.23; H6.78%; N8.22%.

Preparation 82:

tert-butyl (3R)-3-{3-[(tert-butylamino)methyl]-1,2,4-oxadiazol-5-yl}-6-cyclohexylhexanoate

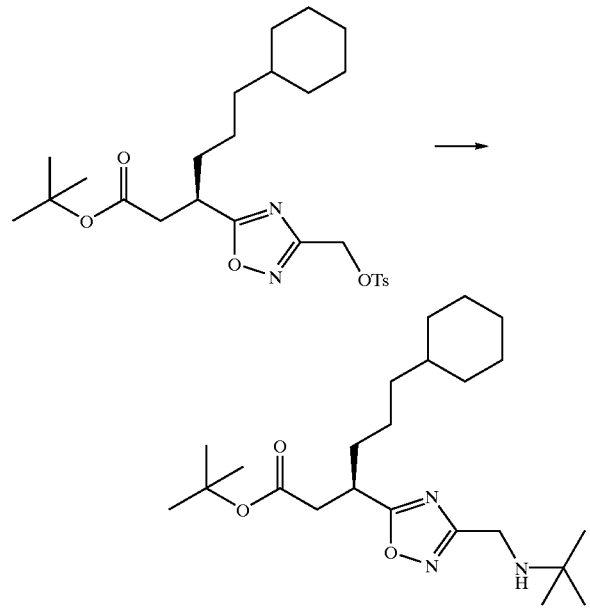

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and tert-butylamine (216 mg, 2.96 mmol) as starting materials.

Purification: The crude material was purified on a silica column eluting with a solvent gradient of DCM:Et$_2$O (90:10) followed by (0:100) to afford the title compound as a colourless oil (253 mg, 63%).

$^1$H nmr: (CDCl$_3$) 0.82 (2H, m), 1.10–1.30 (17H, s+m), 1.39 (9H, s), 1.60–1.80 (7H, m), 2.60 (1H, dd), 2.78 (1H, dd), 3.43 (1H, m), 3.88 (2H, s).

MS: 408 (MH$^+$)

CHN: Found: C67.48%; H10.20%; N10.29%; C$_{23}$H$_{41}$N$_3$O$_3$ requires C67.78; H10.14%; N10.3%.

Preparation 83:

(3R)-3-{3-[(tert-butylamino)methyl]-1,2,4-oxadiazol-5-yl}-6-cyclohexylhexanoic acid

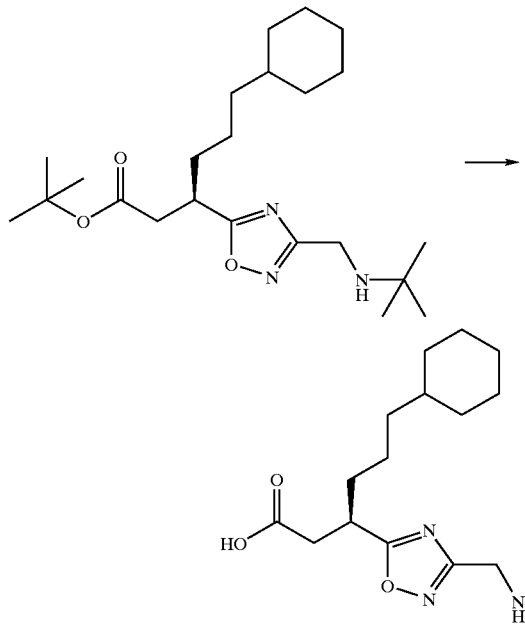

Method as for preparation 75 using tert-butyl (3R)-3-{3-[(tert-butylamino)methyl]-1,2,4-oxadiazol-5-yl}-6-cyclohexylhexanoate (preparation 82) (240 mg, 0.59 mmol) as starting material to afford the title compound (300 mg)

hu 1H nmr: (CDCl$_3$) 0.82 (2H, m), 1.10–1.30 (8H, s+m), 1.40 (9H, s), 1.50–1.70 (7H, m), 2.80 (1H, d), 3.05 (1H, dd), 3.40 (1H, m), 3.79 (1H, d), 4.12 (1H, d).

MS: 352 (MH$^+$)

CHN: Found: C51.29%; H6.93%; N8.17%; C$_{19}$H$_{33}$N$_3$O$_3$.1.4 TFA requires C51.23; H6.78; N8.22%.

Preparation 84:

tert-butyl (3R)-6-cyclohexyl-3-(3-{[(1-ethylpropyl)amino]methyl}-1,2,4-oxadiazol-5-yl)hexanoate

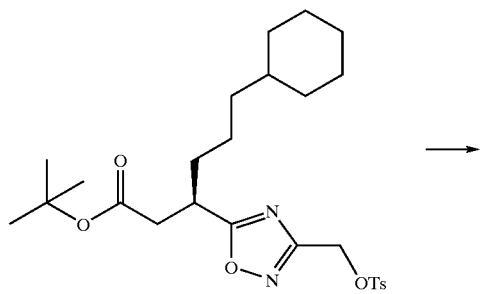

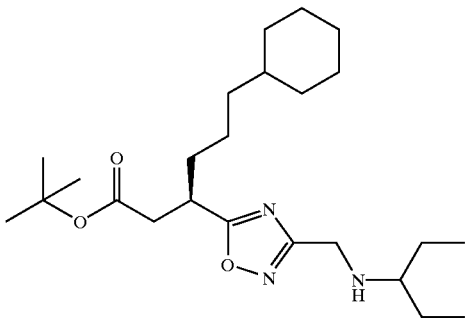

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (750 mg, 1.48 mmol) and 3-aminopentane (520 µl, 4.44 mmol) as starting materials.

Purification: The crude material was purified on a silica column eluting with a solvent gradient of DCM:Et$_2$O (95:5) followed by (0:100) to afford the title compound as a colourless oil (132 mg, 21%).

$^1$H nmr: (CDCl$_3$) 0.84 (8H, m+t), 1.10–1.30 (8H, m), 1.39 (9H, s), 1.42 (4H, m), 1.60–1.80 (7H, m), 2.40 (1H, t), 2.60 (1H, dd), 2.79 (1H, dd), 3.42 (1H, m), 3.88 (2H, s).

CHN: Found: C68.21%; H10.57%; N9.86%; C$_{24}$H$_{43}$N$_3$O$_3$ requires C68.37; H10.28%; N9.97%.

Preparation 85:

(3R)-6-cyclohexyl-3-(3-{[(1-ethylpropyl)amino]methyl}-1,2,4-oxadiazol-5-yl)hexanoic acid

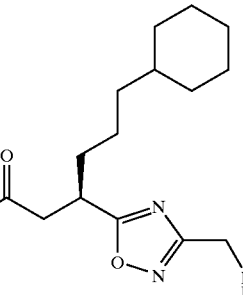

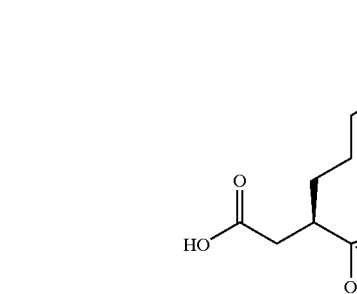

Method as for preparation 75 using tert-butyl (3R)-6-cyclohexyl-3-(3-{[(1-ethylpropyl)amino]methyl}-1,2,4-oxadiazol-5-yl)hexanoate (preparation 84) (682 mg) as starting material.

Purification: The crude material was purified on a silica column eluting with DCM:MeOH (90:10) to afford the title compound (795 mg)

¹H nmr: (CDCl₃) 0.82 (2H, m), 1.00 (6H, t), 1.10–1.35 (8H, m), 1.60–1.85 (11H, m), 2.75 (11H, m), 2.75 (1H, dd), 2.93 (1H, dd), 3.08 (1H, t), 3.42 (1H, m), 4.21 (2H, q).

MS: 366 (MH⁺)

CHN: Found: C52.11%; H7.33%; N8.00%; $C_{20}H_{35}N_3O_3 \cdot 1.4$ TFA requires C52.15; H6.99%; N8.00%.

Preparation 86:

tert-butyl (3R)-6-cyclohexyl-3-{3-[(cyclopropylamino)methyl]-1,2,4-oxadiazol-5-yl}hexanoate

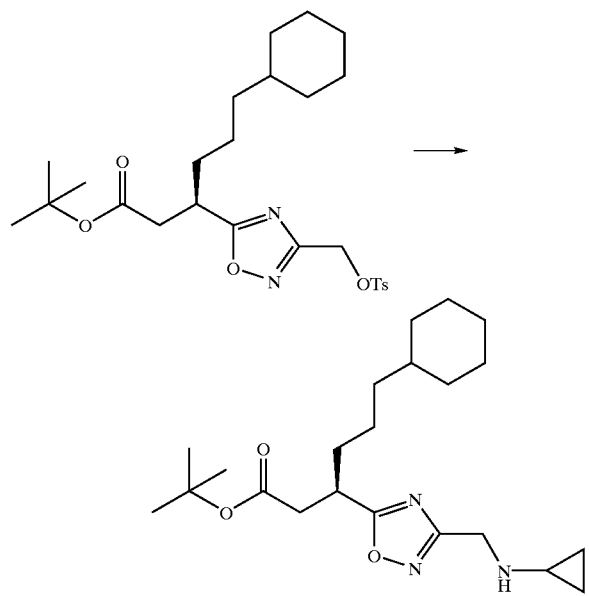

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and cyclopropylamine (210 μl, 2.96 mmol) as starting materials.

Purification: The crude material was purified on a silica column eluting with a solvent gradient of DCM:Et₂O (90:10) followed by (0:100) to afford the title compound (287 mg, 74%).

¹H nmr: (CDCl₃) 0.40 (4H, m), 0.82 (2H, m), 1.10–1.30 (8H, m), 1.39 (9H, s), 1.60–1.80 (7H, m), 2.19 (1H, m), 2.60 (1H, dd), 2.79 (1H, dd), 3.43 (1H, m), 3.94 (2H, s).

MS: 392 (MH⁺)

CHN: Found: C67.31%; H9.62%; N10.72%; $C_{22}H_{37}N_3O_3$ requires C67.49; H9.52%; N10.73%.

Preparation 87:

(3R)-6-cyclohexyl-3-{3-[(cyclopropylamino)methyl]-1,2,4-oxadiazol-5-yl}hexanoic acid

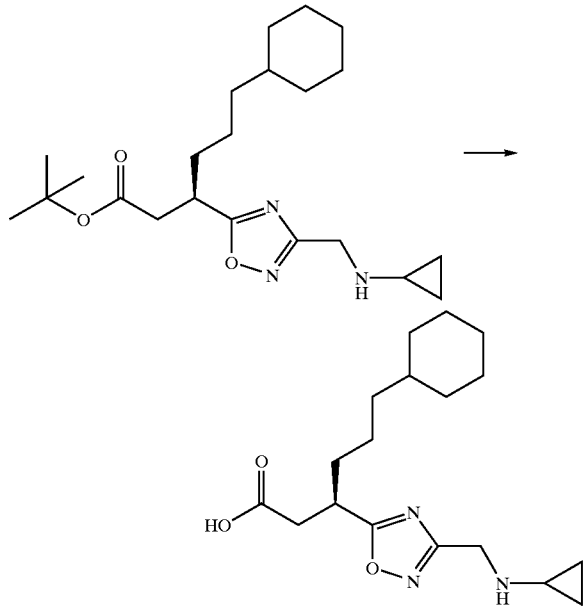

Method as for preparation 75 using tert-butyl (3R)-6-cyclohexyl-3-{3-[(cyclopropylamino)methyl]-1,2,4-oxadiazol-5-yl}hexanoate (preparation 86) (280 mg, 0.72 mmol) as starting material.

Purification: Crude material purified on a silica column eluting with DCM:MeOH (90:10) to afford the title compound (300 mg).

¹H nmr: (CDCl₃) 0.78 (2HM d), 0.82 (2H, m), 0.95 (2H, brs), 1.10–1.35 (8H, m), 1.60–1.80 (7H, m), 2.61 (1H, m), 2.75 (1H, dd), 2.89 (1H, dd), 3.40 (IH, m), 4.20 (2H, s).

MS: 336 (MH⁺)

CHN: Found: C51.59%; H6.73%; N8.74%; $C_{18}H_{29}N_3O_3 \cdot 1.2$ TFA requires C51.88; H6.45%; N8.90%.

Preparation 88:

tert-butyl (3R)-3-{3-[(cyclobutylamino)methyl]-1,2,4-oxadiazol-5-yl}-6-cyclohexylhexanoate

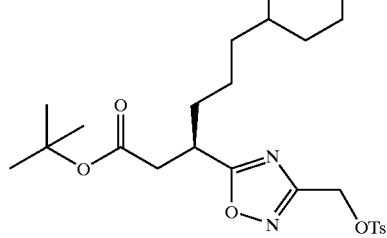

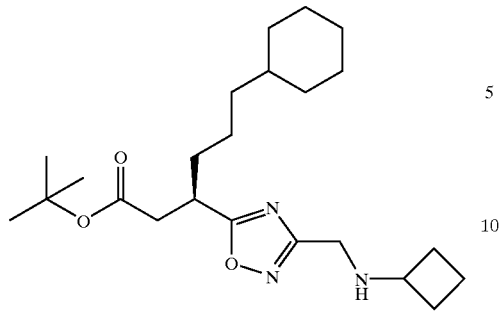

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and cyclobutylamine (250 µl, 2.96 mmol) as starting materials.

Purification: The crude material was purified on a silica column eluting with a solvent gradient of DCM:Et$_2$O (90:10) gradually changing to (50:50) to afford the title compound (180 mg, 45%).

$^1$H nmr: (CDCl$_3$) 0.81 (2H, m), 1.10–1.35 (8H, m), 1.39 (9H, s), 1.55–1.80 (11H, m), 2.17 (2H, M), 2.60 (1H, dd), 2.79 (1H, dd), 3.30 (1H, m), 3.43 (1H, m), 3.81 (2H, s).

MS: 406 (MH$^+$)

CHN: Found: C67.98%; H9.82%; N10.36%; C$_{23}$H$_{39}$N$_3$O$_3$ requires C68.11; H9.69%; N10.36%.

Preparation 89:

(3R)-3-{3-[(cyclobutylamino)methyl]-1,2,4-oxadiazol-5-yl}-6-cyclohexylhexanoic acid

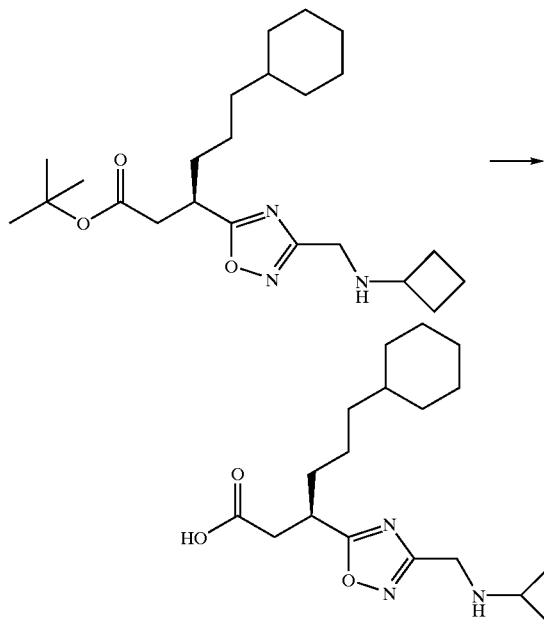

Method as for preparation 75 using tert-butyl (3R)-3-{3-[(cyclobutylamino)methyl]-1,2,4-oxadiazol-5-yl}-6-cyclohexylhexanoate (preparation 88) (180 mg, 0.44 mmol) as starting material to afford the title compound (197 mg).

$^1$H nmr: (CDCl$_3$) 0.81 (2H, m), 1.10–1.35 (8H, m), 1.60–2.00 (9H, m), 2.30 (4H, m), 2.79 (1H, dd), 2.95 (1H, dd), 3.42 (1H, m), 3.74 (1H, m), 4.11 (2H, s).

MS: 350 (MH$^+$)

CHN: Found: C51.68%; H6.78%; N8.40%; C$_{19}$H$_{31}$N$_3$O$_3$.1.35 TFA requires C51.78; H6.48%; N8.35%.

Preparation 90:

tert-butyl (3R)-6-cyclohexyl-3-{3-[(cyclopentylamino)methyl]-1,2,4-oxadiazol-5-yl}hexanoate

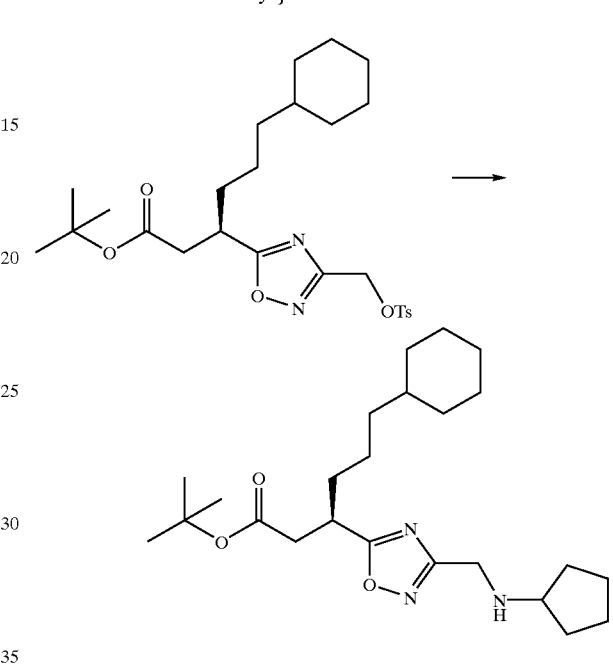

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and cyclopentylamine (170 mg, 1.98 mmol) as starting materials to afford the title compound as a colourless oil (220 mg).

$^1$H nmr: (CDCl$_3$) 0.81 (2H, m), 1.05–1.30 (10H, m), 1.38 (11H, s+m), 1.51 (2H, m), 1.55–1.75 (7H, m), 1.81 (2H, m), 2.60 (1H, dd), 2.79 (1H, dd), 3.06 (1H, m), 3.42 (1H, m), 3.87 (2H, s).

Preparation 91:

(3R)-6-cyclohexyl-3-{3-[(cyclopentylamino)methyl]-1,2,4-oxadiazol-5-yl}hexanoic acid

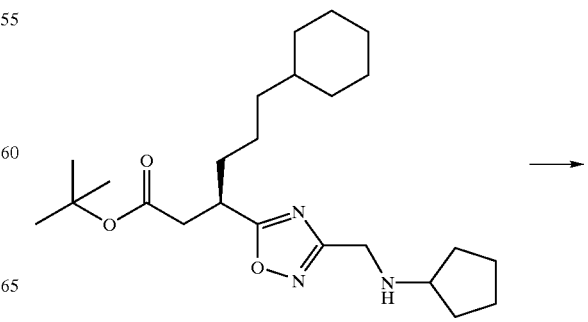

-continued

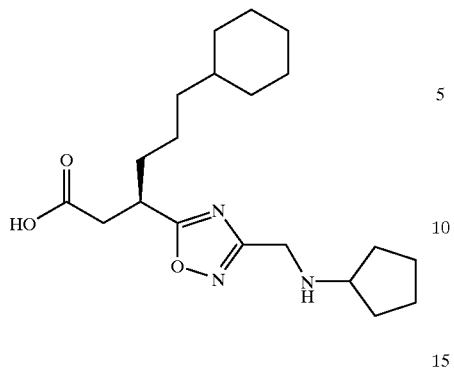

Method as for preparation 75 using tert-butyl (3R)-6-cyclohexyl-3-{3-[(cyclopentylamino)methyl]-1,2,4-oxadiazol-5-yl}hexanoate (preparation 90) (220 mg, 0.53 mmol) as starting material to afford the title compound as a white foam (240 mg).

$^1$H nmr: (CDCl$_3$) 0.81 (2H, m), 1.10–1.35 (10H, m), 1.55–1.75 (7H, m), 1.81 (4H, m), 2.07 (2H, m), 2.78 (1H, dd), 2.95 (1, dd), 3.40–3.60 (3H, m), 4.10–4,25 (2H, q).

MS: 364 (MH$^+$)

Preparation 92:

tert-butyl (3R)-6-cyclohexyl-3-{3-[(cyclohexylamino)methyl]-1,2,4-oxadiazol-5-yl}hexanoate

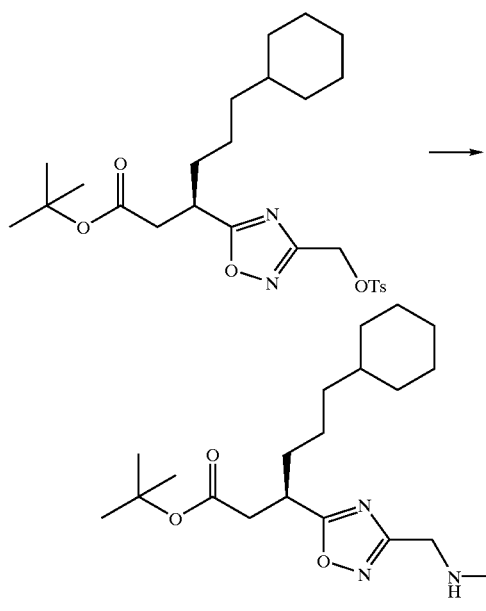

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and cyclohexylamine (198 mg, 1.98 mmol) as starting materials to afford the title compound as a colourless oil (250 mg).

$^1$H nmr: (CDCl$_3$) 0.80 (2H, m), 1.00–1.30 (12H, m), 1.38 (9H, s), 1.55–1.75 (11H, m), 1.82 (2H, m), 2.39 (1H, m), 2.60 (1H, dd), 2.79 (1H, dd), 3.41 (1H, m), 3.89 (2H, s).

Preparation 93:

(3R)-6-cyclohexyl-3-{3-[(cyclohexylamino)methyl]-1,2,4-oxadiazol-5-yl}hexanoic acid

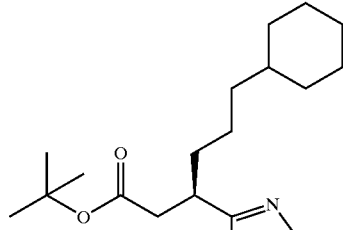

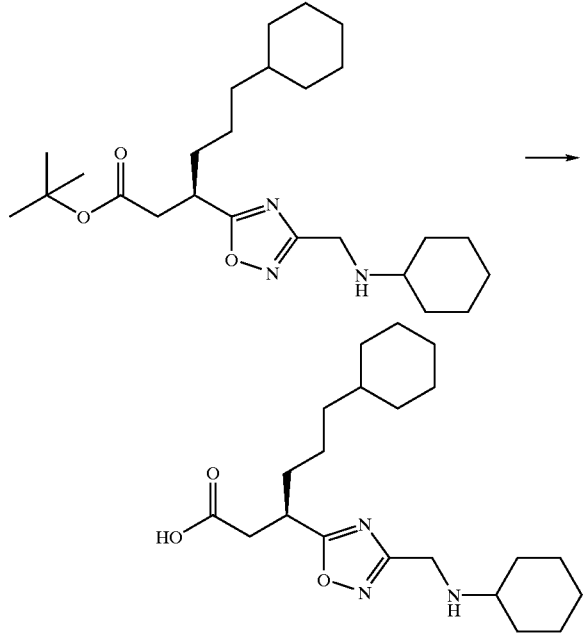

Method as for preparation 75 using tert-butyl (3R)-6-cyclohexyl-3-{3-[(cyclohexylamino)methyl]-1,2,4-oxadiazol-5-yl}hexanoate (preparation 92) (250 mg, 0.58 mmol) as starting material to afford the title compound as a white foam (262 mg).

$^1$H nmr: (CDCl$_3$) 0.81 (2H, m), 1.10–1.35 (12H, m+Et$_2$O), 1.44 (2H, m),1.6–1.80 (7H, m), 1.85 (2H, m), 2.07 (2H, m), 2.78 (1H, dd), 2.96 (1H, dd), 3.05 (1H, m), 3.41 (1H, m), 4.08–4.25 (2H, q).

MS: 378 (MH$^+$)

Preparation 94:

tert-butyl (3R)-6-cyclohexyl-3-(3-{[(2-hydroxyethyl)amino]methyl}-1,2,4-oxadiazol-5-yl)hexanoate

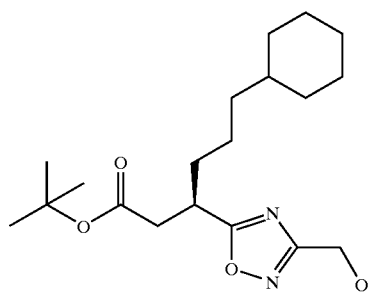

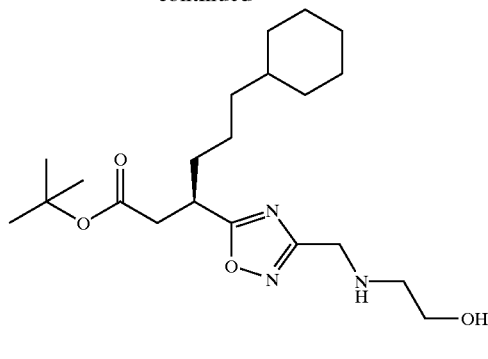

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (489 mg, 0.97 mmol) and ethanolamine (250 μl, 3.87 mmol) as starting materials.

Purification: The crude material was purified on a silica column eluting with DCM:MeOH (95:5) to afford the title compound as a colourless oil (322 mg, 83%).

$^1$H nmr: (CDCl$_3$) 0.81 (2H, m), 1.10–1.35 (8H, m), 1.39 (9H, s), 1.50–1.80 (7H, m), 2.41 (1H, brs), 2.62 (1H, dd), 2.80 (3H, m), 3.43 (1H, m), 3.62 (2H, t), 3.94 (2H, s).

MS: 396 (MH$^+$)

Preparation 95:

(3R)-6-cyclohexyl-3-(3-{[(2-hydroxyethyl)amino]methyl}-1,2,4-oxadiazol-5-yl)hexanoic acid

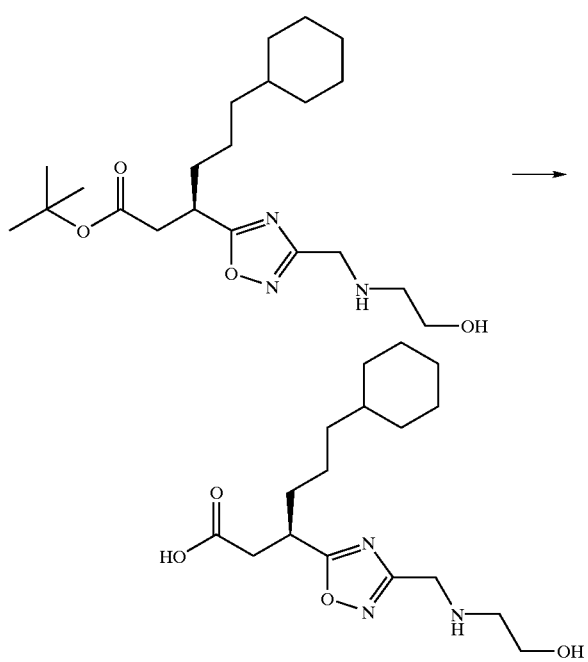

Method as for preparation 75 using tert-butyl (3R)-6-cyclohexyl-3-(3-{[(2-hydroxyethyl)amino]methyl}-1,2,4-oxadiazol-5-yl)hexanoate (preparation 94) (322 mg, 0.82 mmol) as starting material to afford the title compound as a sticky gum (398 mg, 100%).

$^1$H nmr: (CDCl$_3$) 0.81 (2H, m), 1.10–1.35 (8H, m+Et$_2$O), 1.60–1.80 (7H, m), 2.79 (1H, dd), 2.89 (1H, dd), 3.20 (2H, m), 3.43 (1H, m+Et$_2$O), 3.87 (2H, t), 4.36 (2H, m).

MS: 340 (MH$^+$)

Preparation 96:

tert-butyl (3R)-6-cyclohexyl-3-(3-{[(2-hydroxy-1,1-dimethylethyl)amino]methyl}-1,2,4-oxadiazol-5-yl)hexanoate

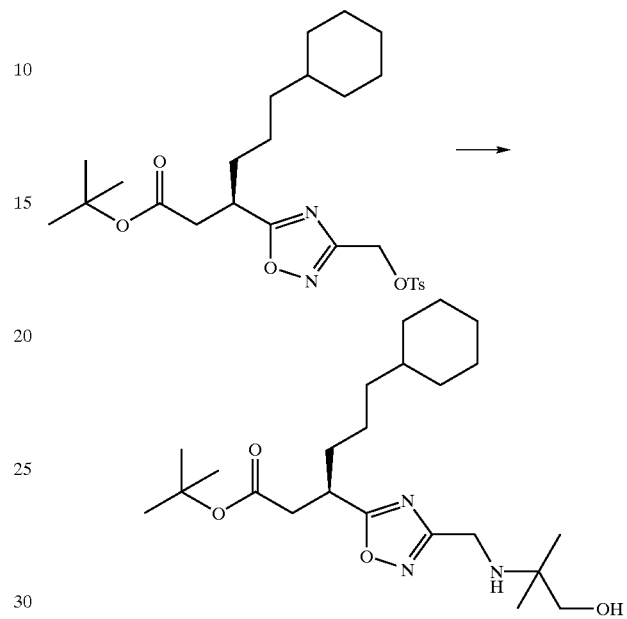

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (3.71 g, 7.32 mmol) and 2-amino-2-methyl-1-propanol (2.10 ml, 22.0 mmol) as starting materials.

Purification: The crude material was purified on a silica column eluting with a solvent gradient of pentane:EtOAc (80:20) gradually changing to (0:100) to afford the title compound as a colourless oil (2.52 g, 81%).

$^1$H nmr: (CDCl$_3$) 0.84 (2H, m), 1.10 (6H, s), 1.15–1.35 (9H, m), 1.40 (9H, s), 1.60–1.80 (6H, m), 2.60 (1H, dd), 2.70 (1H, brs), 2.79 (1H, dd), 3.29 (2H, s), 3.42 (1H, m), 3.83 (2H, s).

MS: 424 (MH$^+$)

Preparation 97:

(3R)-6-cyclohexyl-3-(3-{[(2-hydroxy-1,1-dimethylethyl)amino]methyl}-1,2,4-oxadiazol-5-yl)hexanoic acid

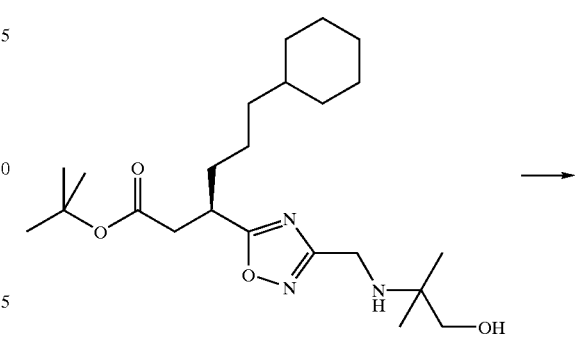

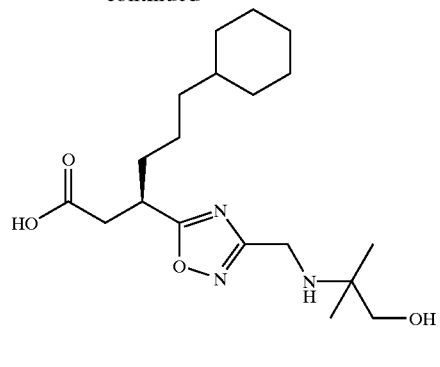

Method as for preparation 75 using tert-butyl (3R)-6-cyclohexyl-3-(3-{[[(2-hydroxy-1,1-dimethylethyl)amino]methyl}-1,2,4-oxadiazol-5-yl)hexanoate (preparation 96) (2.5 g, 5.90 mmol) as starting material.

Purification: The crude material was purified on a silica column eluting with a solvent gradient of DCM:MeOH (100:0) gradually changing to (90:10) to afford the title compound as a colourless oil (2.95 g)

$^1$H nmr: (CDCl$_3$) 0.82 (2H, m), 1.10–1.30 (8H, m), 1.39 (6H, d), 1.60–1.80 (7H, m), 2.78 (1H, dd), 2.92 (1H, dd), 3.42 (1H, m), 3.63 (2H, s), 4.24 (2H, m).
MS: 368 (MH$^+$)

Preparation 98:

tert-butyl (3R)-6-cyclohexyl-3-(3-{[(2-methoxyethyl)amino]methyl}-1,2,4-oxadiazol-5-yl)hexanoate

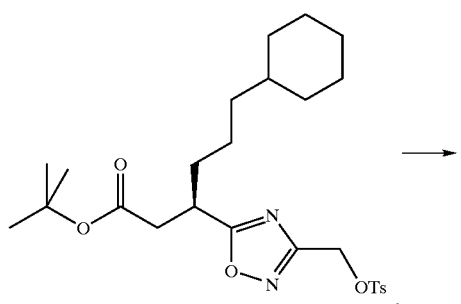

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and 2-methoxyethylamine (225 mg, 2.97 mmol) as starting materials to afford the title compound as a colourless oil (372 mg).

$^1$H nmr: (CDCl$_3$) 0.80 (2H, m), 1.05–1.30 (8H, m+EtOAc), 1.38 (9H, s), 1.55–1.75 (7H, m), 1.95 (1H, brs), 2.60 (1H, dd), 2.79 (1H, dd+t), 3.33 (3H, s), 3.42 (3H, m+t), 3.92 (2H, s).

Preparation 99:

(3R)-6-cyclohexyl-3-(3-{[(2-methoxyethyl)amino]methyl}-1,2,4-oxadiazol-5-yl)hexanoic acid

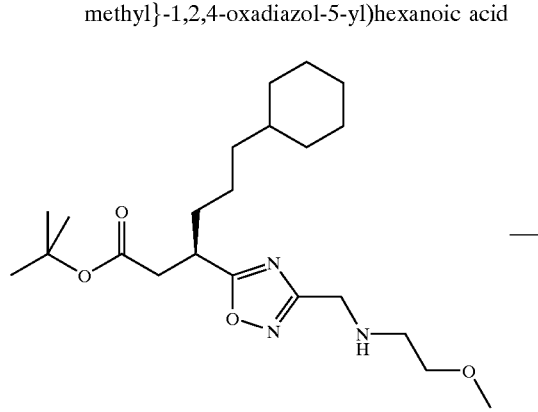

Method as for preparation 75 using tert-butyl (3R)-6-cyclohexyl-3-(3-{[(2-methoxyethyl)amino]methyl}-1,2,4-oxadiazol-5-yl)hexanoate (preparation 98) (372 mg, 0.91 mmol) as starting material to afford the title compound as a pale brown oil.

$^1$H nmr: (d$_6$DMSO) 0.80 (2H, m), 1.00–1.25 (8H, m), 1.55–1.70 (7H, m), 2.78 (2H, d), 3.21 (2H, t), 3.28 (3H, s), 3.44 (1H, m), 3.60 (2H, t), 4.42 (2H, s).

Preparation 100:

tert-butyl (3R)-6-cyclohexyl-3-(3-{[(3-methoxypropyl)amino]methyl}-1,2,4-oxadiazol-5-yl)hexanoate

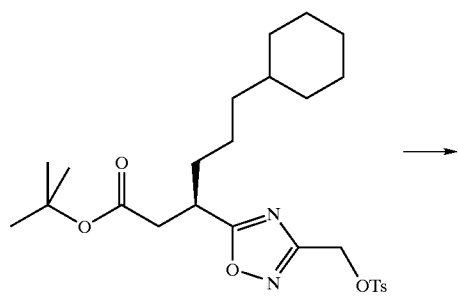

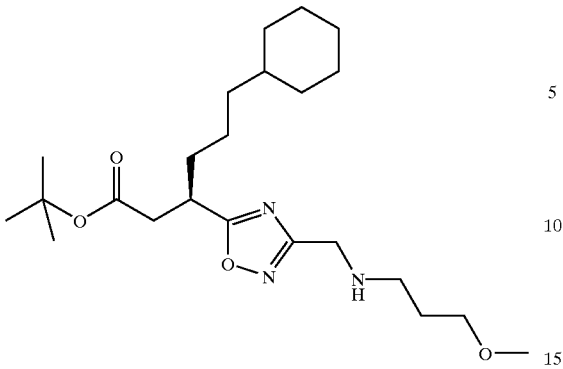

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (488 mg, 0.96 mmol) and 3-methoxypropylamine (325 mg, 3.84 mmol) as starting materials.

Purification: The crude material was purified on a silica column eluting with DCM:MeOH (95:5) to afford the title compound as a colourless oil (397 mg, 97%).

$^1$H nmr: (CDCl$_3$) 0.81 (2H, m), 1.10–1.30 (8H, m), 1.39 (9H, s), 1.55–1.70 (7H, m), 1.79 (2H, quin), 2.61 (1H, dd), 2.72 (2H, t), 2.80 (1H, dd), 3.32 (3H, s), 3.42 (3H, t+m), 3.91 (2H, s).

MS: 425 (MH$^+$)

Preparation 101:

(3R)-6-cyclohexyl-3-(3-{[(3-methoxypropyl)amino]methyl}-1,2,4-oxadiazol-5-yl)hexanoic acid

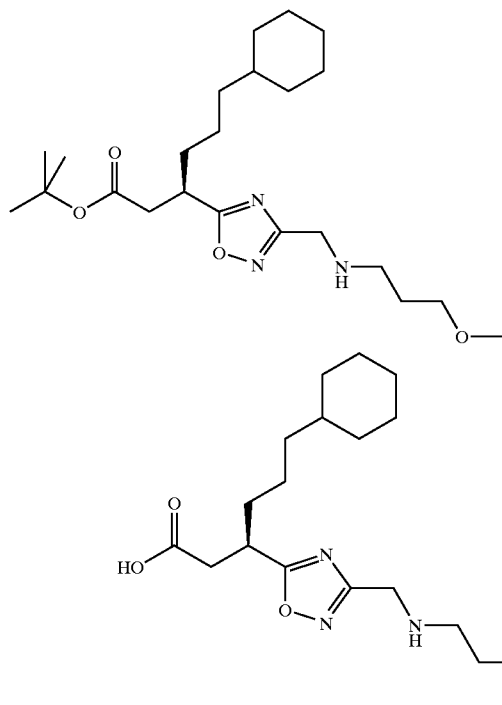

Method as for preparation 75 using tert-butyl (3R)-6-cyclohexyl-3-(3-{[(3-methoxypropyl)amino]methyl}-1,2,4-oxadiazol-5-yl)hexanoate (preparation 100) (390 mg, 0.92 mmol) as starting material to afford the title compound as a pale yellow oil (477 mg).

$^1$H nmr: (CDCl$_3$) 0.81 (2H, m), 1.10–1.25 (8H, m), 1.60–1.70 (7H, m), 2.00 (2H, quin), 2.79 (1H, dd), 2.92 (1H, dd), 3.25 (2H, t), 3.38 (3H, s), 3.44 (1H, m), 3.58 (2H, t), 4.29 (2H, s).

MS: 369 (MH$^+$)

Preparation 102:

tert-butyl (3R)-6-cyclohexyl-3-(3-{[(4-hydroxycyclohexyl)amino]methyl}-1,2,4-oxadiazol-5-yl)hexanoate

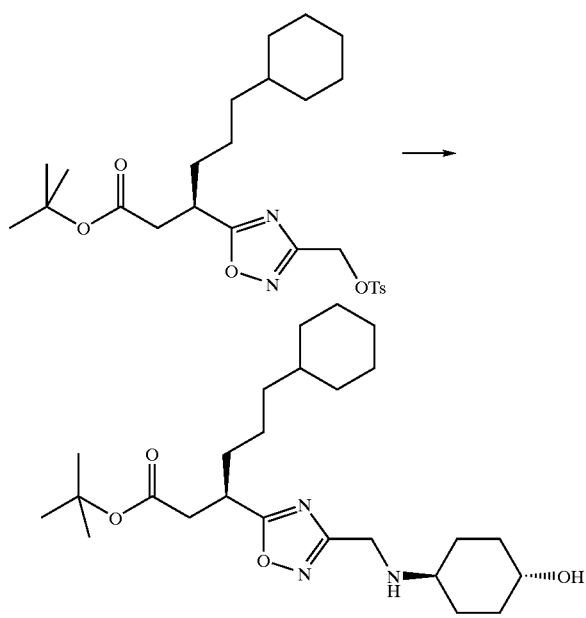

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (282 mg, 0.96 mmol) and trans-4-aminocyclohexanol.HCl (325 mg, 3.84 mmol) as starting materials. Dissolving the solid in 2M NaOH solution with Dowex 50Wx4-200R resin isolated the free base of trans-4-aminocyclohexanol.

Purification: The crude material was purified on a silica column eluting with a solvent gradient of DCM:MeOH (97.5:2.5) gradually changing to (95:5) to afford the title compound (180 mg).

$^1$H nmr: (CDCl$_3$) 0.83 (2H, m), 1.10–1.35 (12H, m), 1.40 (9H, s), 1.60–1.80 (7H, m), 1.96 (4H, m), 2.48 (1H, m), 2.60 (1H, dd), 2.79 (1H, dd), 3.43 (1H, m), 3.60 (1H, m), 3.92 (2H, s).

MS: 450 (MH$^+$)

CHN: Found: C65.65%; H9.60%; N9.07%; $C_{25}H_{43}N_3O_4 \cdot 0.5\ H_2O$ requires C65.47; H9.67%; N9.16%.

Preparation 103:

(3R)-6-cyclohexyl-3-(3-{[(4-hydroxycyclohexyl)amino]methyl}-1,2,4-oxadiazol-5-yl)hexanoic acid

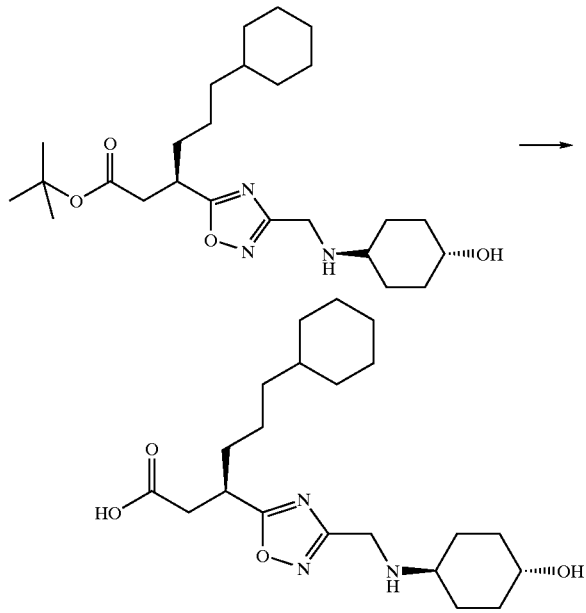

Method as for preparation 75 using tert-butyl (3R)-6-cyclohexyl-3-(3-{[(4-hydroxycyclohexyl)amino]methyl}-1,2,4-oxadiazol-5-yl)hexanoate (preparation 102) (250 mg, 0.56 mmol) as starting material.

Purification: The crude material was purified on a silica column eluting with a solvent gradient of DCM:MeOH (95:5) gradually changing to (85:15) to afford the title compound (190 mg).

$^1$H nmr: (CD$_3$OD) 0.83 (2H, m), 1.10–1.40 (10H, m), 1.43 (2H, q), 1.60–1.80 (7H, m), 2.02 (2H, brd), 2.17 (2H, brd), 2.79 (1H, dd), 2.86 (1H, dd), 3.11 (1H, m), 3.54 (2H, m), 4.40 (2H, s).

MS: 394 (MH$^+$)

Preparation 104:

tert-butyl (3R)-6-cyclohexyl-3-(3-{[(4-methoxycyclohexyl)amino]methyl}-1,2,4-oxadiazol-5-yl)hexanoate

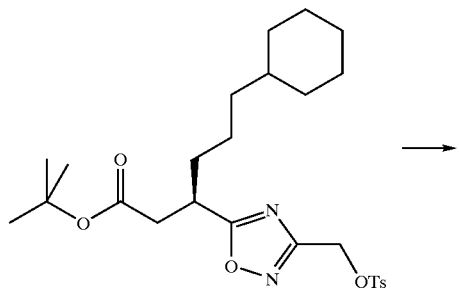

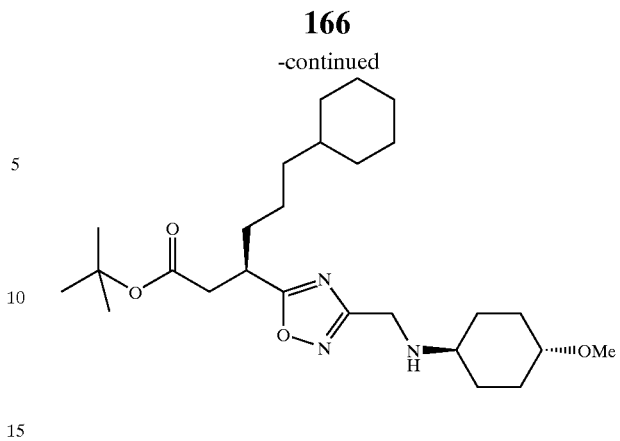

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and trans-4-methoxycyclohexanamine.HCl (490 mg, 2.96 mmol) as starting materials.

Purification: A total of 3 silica columns were required to afford the title compound reasonably pure. First column eluted with DCM:MeOH (97:3), the second column eluted with DCM:MeOH (99:1) and the third column eluted with DCM:MeOH (98:2) to afford the title compound (160 mg).

$^1$H nmr: (CDCl$_3$) 0.82 (2H, m), 1.10–1.30 (10H, m), 1.39 (9H, s), 1.40–1.80 (11H, m+H$_2$O), 1.85 (2H, m), 2.57 (1H, dd), 2.61 (2H, t), 2.79 (1H, dd), 3.23 (3H, s), 3.33 (1H, m), 3.42 (1H, m), 3.90 (2H, s). Evidence of the presence of the cis-isomer of the cyclohexanamine.

MS: 464 (MH$^+$)

Preparation 105:

(3R)-6-cyclohexyl-3-(3-{[(4-methoxycyclohexyl)amino]methyl}-1,2,4-oxadiazol-5-yl)hexanoic acid

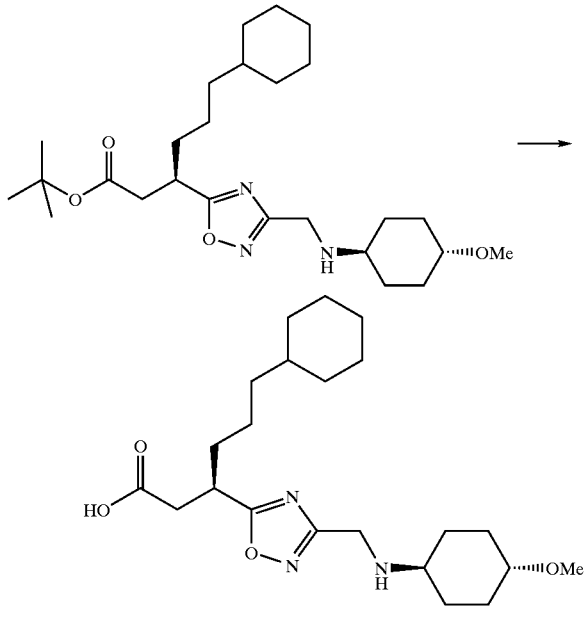

Method as for preparation 75 using tert-butyl (3R)-6-cyclohexyl-3-(3-{[(4-methoxycyclohexyl)amino]methyl}-1,2,4-oxadiazol-5-yl)hexanoate (preparation 104) (160 mg) as starting material to afford the title compound (175 mg).

$^1$H nmr: (CDCl$_3$) 0.82 (2H, m), 1.10–1.35 (8H, m), 1.40 (2H, m), 1.55–1.95 (11H, m) 2.06 (2H, m), 2.78 (1H, dd), 2.95 (1H, dd), 3.19 (1H, m), 3.31 (3H, s), 3.42 (2H, m), 4.21 (2H, d). Evidence of the presence of the cis-isomer of the cyclohexanamine.

MS: 408 (MH⁺)

Preparation 106:

tert-butyl (3R)-6-cyclohexyl-3-(3-{[(2-methoxy-2-oxoethyl)amino]methyl}-1,2,4-oxadiazol-5-yl) hexanoate

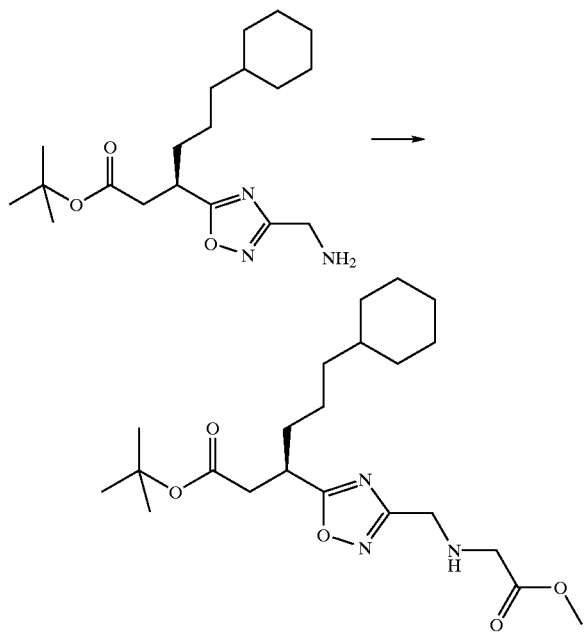

A solution of tert-butyl (3R)-3-[3-(aminomethyl)-1,2,4-oxadiazol-5-yl-]-6-cyclohexyhexanoate (preparation 18) (200 mg, 0.57 mmol) in THF (2 ml) was treated with methyl bromoacetate (55 µl, 0.57 mmol) and NMM (63 µl, 0.57 mmol) and stirred at room temperature, under a nitrogen atmosphere for 3 days. The reaction mixture was diluted with EtOAc and washed with H₂O followed by brine, dried over anhydrous MgSO₄ and filtered. The solvent was removed under reduced pressure. The crude material was purified on a silica column eluting with a solvent gradient of EtOAc:pentane (5:95) gradually changing to (50:50) to afford the title compound as a colourless oil (170 mg, 70%).

¹H nmr: (CDCl₃) 0.83 (2H, m), 1.10–1.35 (9H, m), 1.39 (9H, s), 1.60–1.80 (6H, s), 2.61 (1H, dd), 2.79 (1H, dd), 3.40–3.50 (3H, m+s), 3.73 (3H, s), 3.95 (2H, s).

MS: 421 (M−H)

Preparation 107:

(³R)-⁶-cyclohexyl-3-(3-{[(2-methoxy-2-oxoethyl) amino]methyl}-1,2,4-oxadiazol-5-yl)hexanioc acid

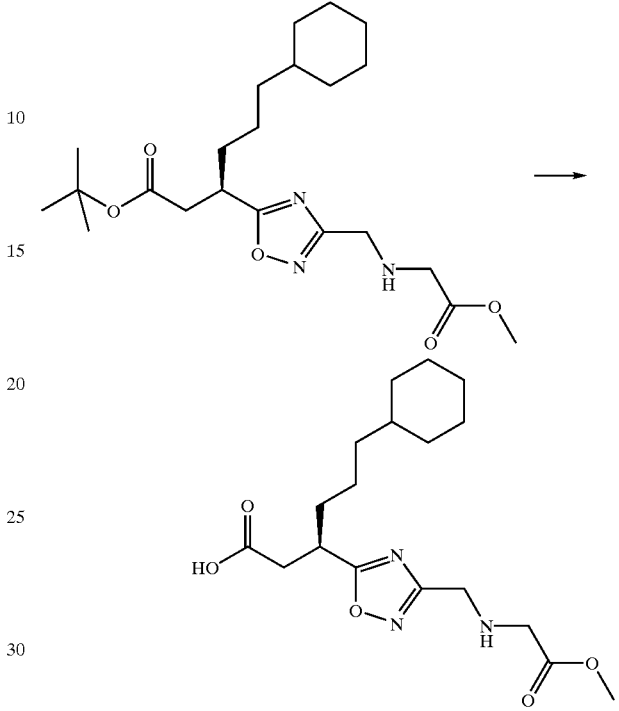

Method as for preparation 11 using tert-butyl (3R)-6-cyclohexyl-3-(3-{[(2-methoxy-2-oxoethyl)amino]methyl}-1,2,4-oxadiazol-5-yl)hexanoate (preparation 106) (198 mg, 0.47 mmol) as starting material.

Purification: The crude material was purified on a silica column eluting with a solvent gradient of DCM:MeOH:A-cOH (100:0:0) gradually changing to (93:7:0.7) to afford the title compound as a pale yellow oil (137 mg, 79%).

¹H nmr: (CDCl₃) 0.81 (2H, m), 1.10–1.35 (8H, m), 1.60–1.80 (7H, m), 2.79 (1H, brd), 2.90 (1H, m), 3.46 (1H, brs), 3.79 (3H, s), 3.86 (2H, brs), 4.26 (2H, brs).

MS: 368 (MH⁺)

Accurate mass: Found 368.2187 (MH⁺), Calculated C₁₈H₂₉N₃O₅, 368.2180

Preparation 108:

tert-butyl (3R)-3-(3-{[(2-amino-2-oxoethyl)amino] methyl}-1,2,4-oxadiazol-5-yl)-6-cyclohexylhexanoate

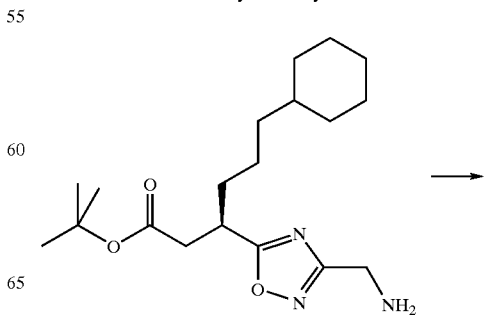

-continued

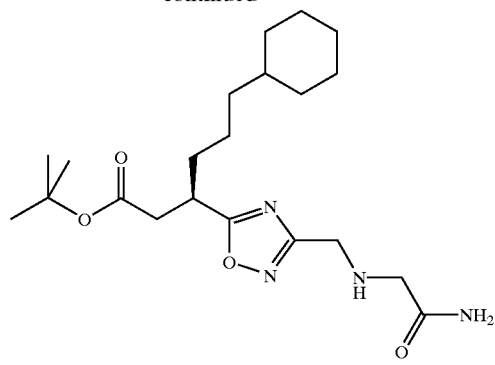

Method as for preparation 106 using tert-butyl (3R)-3-[3-(aminomethyl)-1,2,4-oxadiazol-5-yl]-6-cyclohexylhexanoate (preparation 18) (250 mg, 0.71 mmol) and 2-bromoacetamide (98 mg, 0.71 mmol) as starting materials and Et$_3$N as the base.

Purification: The crude material was purified on a silica column eluting with DCM:MeOH:NH$_3$ (95:6:0.5) to afford the title compound as a colourless oil (150 mg).

$^1$H nmr: (CDCl$_3$) 0.83 (2H, m), 1.10–1.35 (8H, m), 1.39 (9H, s), 1.50–1.80 (7H, m+H$_2$O), 2.60 (1H, dd), 2.79 (1H, dd), 3.35 (2H, s), 3.42 (1H, m), 3.92 (2H, s), 5.40 (1H, brs), 6.92 (1H, brs).

MS: 409 (MH$^+$)

Preparation 109:

(3R)-3-(3-{[(2-amino-2-oxoethyl)amino]methyl}-1,2,4-oxadiazol-5-yl)-6-cyclohexylhexanoic acid

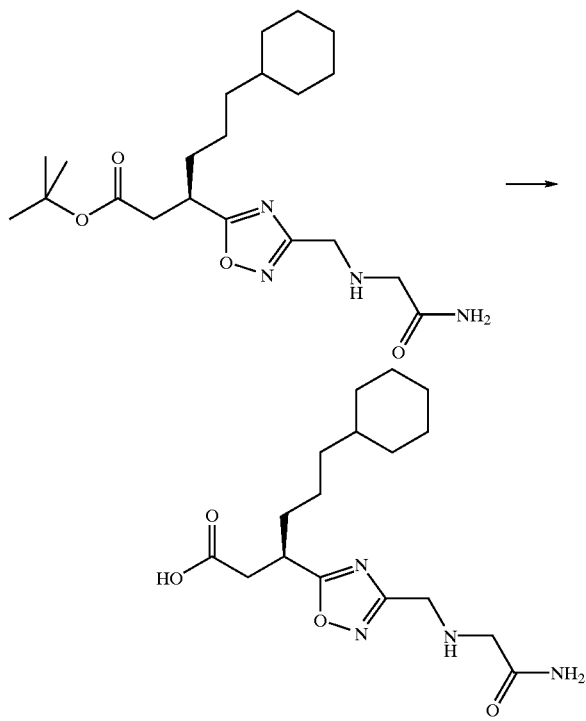

Method as for preparation 7 using tert-butyl (3R)-3-(3-{[(2-amino-2-oxoethyl)amino]methyl}-1,2,4-oxadiazol-5-yl)-6-cyclohexylhexanoate (preparation 108) (138 mg, 0.34 mmol) as starting material to afford the title compound as a yellow oil (147 mg).

$^1$H nmr: (d$_6$DMSO) 0.81 (2H, m), 1.10–1.30 (8H, m), 1.55–1.70 (7H, m), 2.78 (2H, d), 3.43 (1H, m), 3.79 (2H, s), 4.40 (2H, s), 7.42 (1H, brs), 7.80 (1H, brs).

MS: 353 (MH$^+$)

Preparation 110:

tert-butyl (3R)-6-cyclohexyl-3-{3-[(tetrahydro-2H-pyran-4-ylamino)methyl]-1,2,4-oxadiazol-5-yl}hexanoate

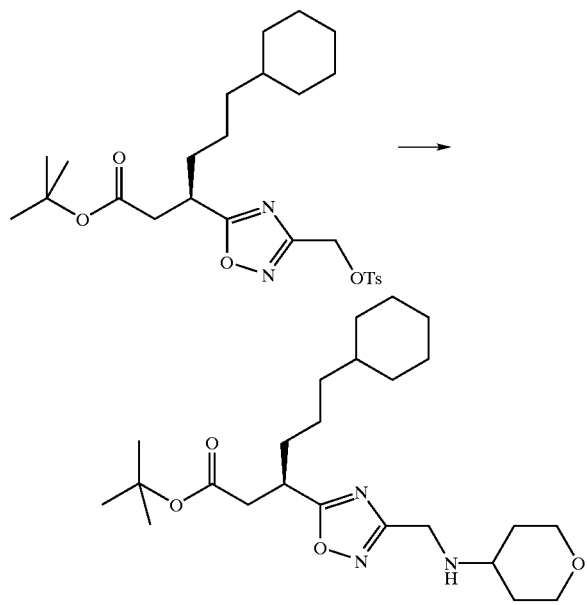

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and 4-aminotetrahydro-4H-pyran.HCl (J. Med. Chem.; 1971, 14, 600–14) (400 mg, 2.90 mmol) as starting materials. Dissolving the solid in 2M NaOH solution with Dowex 50Wx4-200R resin isolated the free base of 4-aminotetrahydro-4H-pyran.

Purification: The crude material was purified on a silica column eluting with a solvent gradient of Et$_2$O:MeOH (100:0) gradually changing to (98:2) to afford the title compound (308 mg)

$^1$H nmr: (CDCl$_3$) 0.83 (2H, m), 1.10–1.30 (8H, m), 1.35–1.55 (13H, s+m), 1.60–1.85 (7H, m), 2.60 (1H, dd), 2.72 (1H, m), 2.79 (1H, dd), 3.39 (2H, t), 3.42 (1H, m), 3.92 (4H, s+m).

MS: 436 (MH$^+$)

Preparation 111:

(3R)-6-cyclohexyl-3-{3-[(tetrahydro-2H-pyran-4-ylamino)methyl]-1,2,4-oxadiazol-5-yl}hexanoic acid

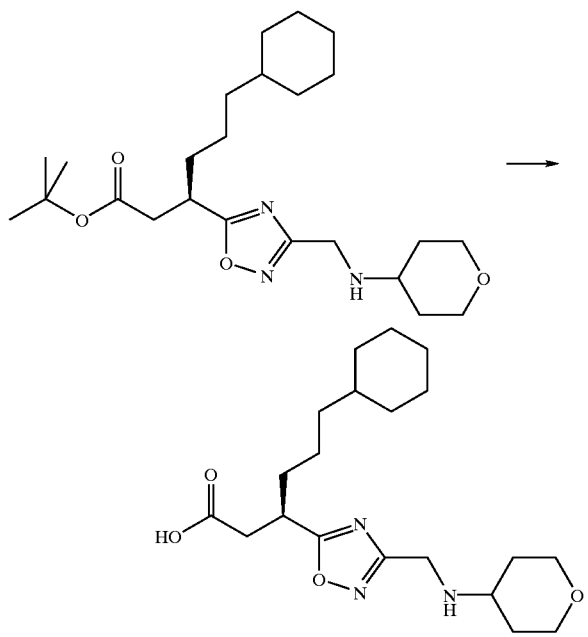

Method as for preparation 11 using tert-butyl (3R)-6-cyclohexyl-3-{3-[(tetrahydro-2H-pyran-4-ylamino)methyl]-1,2,4-oxadiazol-5-yl}hexanoate (preparation 110) (313 mg) as starting material.

Purified on a silica column eluting with a solvent gradient of DCM:MeOH (95:5) gradually changing to (93:7) to afford the title compound (231 mg).

$^1$H nmr: (CDCl$_3$) 0.84 (2H, m), 1.10–1.35 (8H, m), 1.60–1.75 (7H, m), 1.81 2H, m), 2.00 (2H, m), 2.73 (1H, brd), 2.84 (1H, m), 3.28 (1H, m), 3.40 (3H, m), 4.05 (2H, d), 4.20 (2H, m).

MS: 380 (MH$^+$)

Preparation 112:

tert-butyl (3R)-6-cyclohexyl-3-{3-[(1H-pyrazol-3-ylamino)methyl]-1,2,4-oxadiazol-5-yl}hexanoate

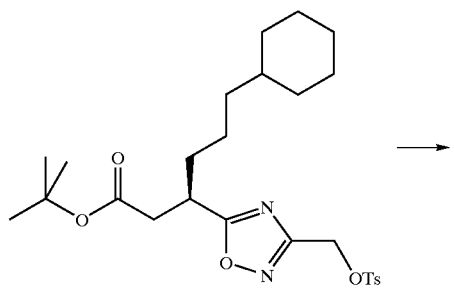

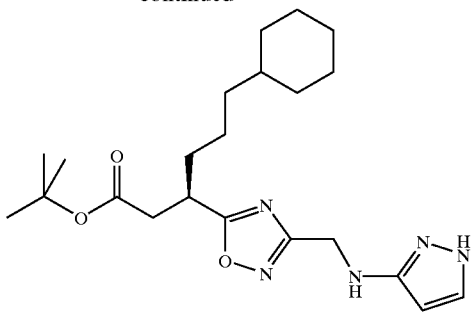

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and 3-aminopyrazole (249 mg, 2.97 mmol) as starting materials.

Purification: The crude material was purified on a silica column eluting with DCM:MeOH (95:5) to afford the title compound (132 mg).

$^1$H nmr: (d$_6$DMSO) 0.79 (2H, m), 1.05–1.25 (8H, m), 1.28 (9H, s), 1.55–1.65 (7H, m) 2.66 (2H, d), 3.36 (1H, m), 5.19 (2H, s), 5.25 (3H, s), 7.01 (1H, s).

MS: 419 (MH$^+$)

Preparation 113:

(3R)-6-cyclohexyl-3-{3-[(1 H-pyrazol-3-ylamino)methyl]-1,2,4-oxadiazol-5-yl}hexanoic acid Method as for preparation 75 using tert-butyl (3R)-6-cyclohexyl-3-{3-[(1H-pyrazol-3-ylamino)methyl]-1,2,4-oxadiazol-5-yl}hexanoate (preparation 112) (139 mg, 0.33 mmol) as starting material to afford the title compound as a colourless oil (132 mg)

$^1$H nmr: (CDCl$_3$) 0.81 (2H, m), 1.05–1.35 (8H, m), 1.55–1.80 (7H, m), 2.73 (1H, dd), 2.81 (1H, dd), 3.42 (1H, m), 5.50 (2H, m), 5.74 (1H, s), 7.18 (1H, d), 7.56 (1H, s).

MS: 362 (MH$^+$)

Preparation 114:

tert-butyl (3R)-6-cyclohexyl-3-(3-{[(1-ethyl-1H-pyrazol-5-yl)amino]methyl}-1,2,4-oxadiazol-5-yl)hexanoate

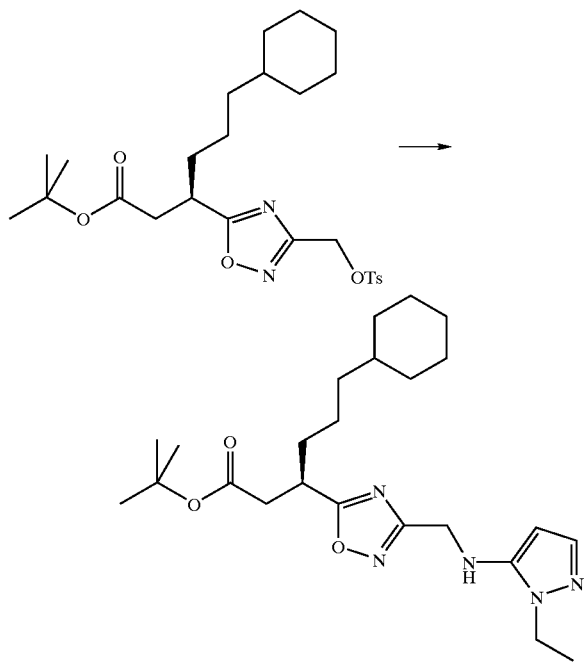

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (493 mg, 0.97 mmol) and 5-amino-3-ethylpyrazole (321 mg, 2.97 mmol) as starting materials.

Purification: The crude material was purified on a silica column eluting with pentane:EtOAc (1:1) to afford the title compound as an oil (47 mg).

$^1$H nmr: (CDCl$_3$) 0.80 (2H, m), 1.10–1.30 (8H, m), 1.39 (12H, s+t), 1.50–1.80 (7H, m), 2.60 (1H, dd), 2.79 (1H, dd), 3.42 (1H, m), 3.81 (1H, brs), 3.99 (2H, q), 4.38 (2H, d), 5.57 (1H, s), 7.24 (1H, s).

MS: 446 (MH$^+$)

Preparation 115:

(3R)-6-cyclohexyl-3-(3-{[(1-ethyl-1H-pyrazol-5-yl)amino]methyl}-1,2,4-oxadiazol-5-yl)hexanoic acid

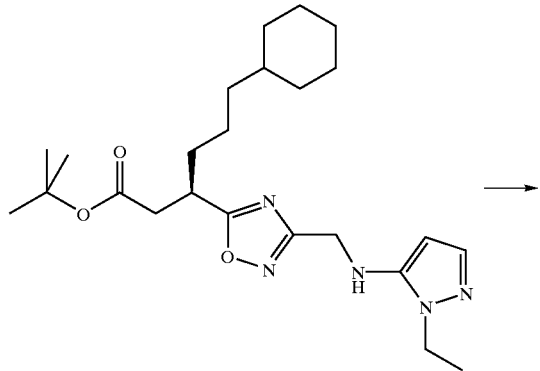

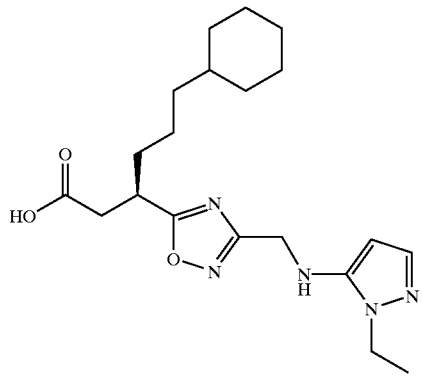

Method as for preparation 7 using tert-butyl (3R)-6-cyclohexyl-3-(3-{[(1-ethyl-1H-pyrazol-5-yl)amino]methyl}-1,2,4-oxadiazol-5-yl)hexanoate (preparation 114) (45 mg, 0.10 mmol) as starting material to afford the title compound as a gum (38 mg).

$^1$H nmr: (CDCl$_3$) very broad.

MS: 390 (MH$^+$)

Preparation 116:

tert-butyl (2S)-2-cyano-1-pyrrolidinecarboxylate

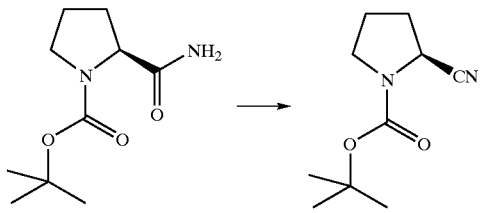

A solution of oxalyl chloride (11.0 ml, 0.126 mol) and DMF (11.4 ml, 0.138 mol) in MeCN (170 ml) was treated dropwise with a solution of N-Boc-L-proline amide (12.3 g, 0.57 mol) and pyridine (20.4 ml, 0.253 mol) in MeCN (30 ml) at 0° C. and stirred at this temperature for 15 minutes. The reaction mixture was diluted with EtOAc and washed with H$_2$O (×3). The organic extract was dried over anhydrous MgSO$_4$ and filtered. The solvent was removed under reduced pressure. The residue was purified on a silica column eluting with a solvent gradient of pentane:EtOAc (80:20) gradually changing to (60:40) to afford the title compound (7.40 g, 66%).

$^1$H nmr: (d$_6$DMSO) 1.40 (9H, s), 1.88 (2H, brs), 2.05–2.30 (2H, m), 3.21 (1H, m), 3.35 (1H, brs), 4.60 (1H, d).

MS: 214 (MNH$_4^+$)

Preparation 117:

tert-butyl (2S)-2-[(Z)-amino(hydroxyimino)methyl]-1-pyrrolidinecarboxylate

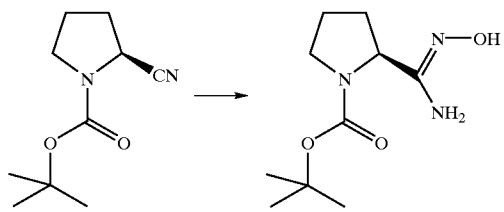

Method as for preparation 1 using tert-butyl (2S)-2-cyano-1-pyrrolidinecarboxylate (preparation 116) (1.96 g, 10.0 mmol) as starting material to afford the title compound as a white solid (1.63 g)

$^1$H nmr: (d$_6$DMSO) 1.34 (9H, d), 1.65–2.00 (4H, m), 3.15–3.35 (2H, m+H$_2$O), 4.05 (0.5H, brs), 4.19 (0.5H, brs), 5.19 (2H, brd), 8.91 (1H, brs).

Preparation 118:

tert-butyl (2S)-2-{5-[(1R)-1-(2-tert-butoxy-2-oxoethyl)-4-cyclohexylbutyl]-1,2,4-oxadiazol-3-yl}-1-pyrrolidinecarboxylate

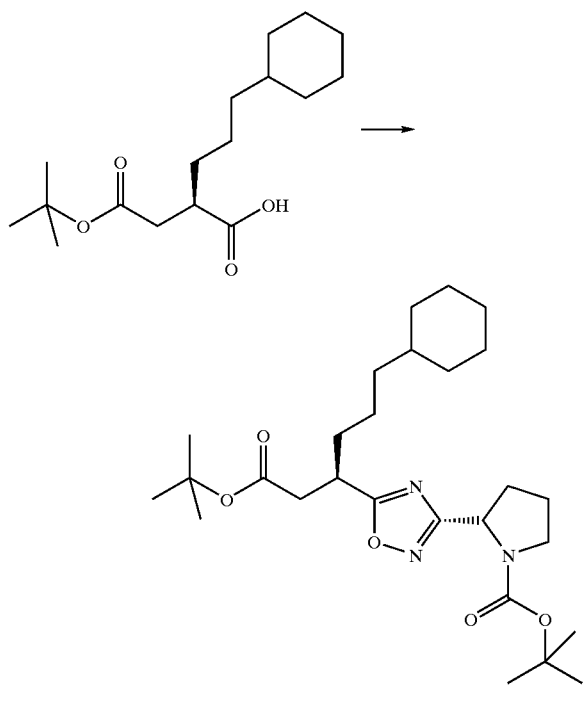

Method as for preparation 2 using tert-butyl (2S)-2-[(Z)-amino(hydroxyimino)methyl]-1-pyrrolidinecarboxylate (preparation 117) (1.60 g, 7.00 mmol) as starting material. The crude material was taken onto the cyclisation using the method as preparation 3.

Purification: The crude material was purified on a silica column eluting with DCM to afford the title compound as a colourless oil (1.42 g).

$^1$H nmr: (CDCl$_3$) 0.81 (2H, m), 1.10–1.50 (26H, m), 1.60–1.80 (6H, m), 1.85–2.10 (4H, m) 2.22 (1H, m), 2.59 (1H, dd), 2.79 (1H, dd), 3.41 (1H, m), 3.50–3.65 (2H, m), 4.91 (0.5H. brs), 5.03 (0.5H, brs).

MS: 492 (MH$^+$)

Preparation 119:

(3R)-6-cyclohexyl-3-{3-[(2 S)-pyrrolidinyl]-1,2,4-oxadiazol-5-yl}hexanoic acid

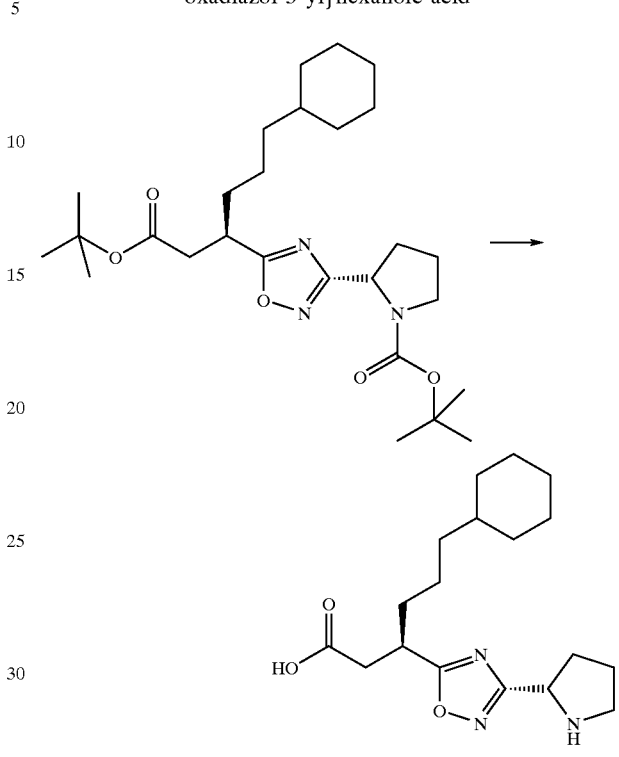

Method as for preparation 75 using tert-butyl (2S)-2-{5-[(1R)-1-(2-tert-butoxy-2-oxoethyl)-4-cyclohexylbutyl]-1,2,4-oxadiazol-3-yl}-1-pyrrolidinecarboxylate (preparation 118) (1.42 g, 2.89 mmol) as starting material to afford the title compound as a colourless oil.

$^1$H nmr: (d$_6$DMSO) 0.79 (2H, m), 1.05–1.30 (8H, m), 1.50–1.70 (7H, m), 2.01 (3H, m) 2.39 (1H, m), 2.78 (2H, d), 3.30 (2H, m), 3.42 (1H, m), 4.86 (1H, m).

MS: 336 (MH$^+$)

Preparation 120:

(3R)-3-{3-[(2S)-1-(tert-butoxycarbonyl)pyrrolidinyl]-1,2,4-oxadiazol-5-yl}-6-cyclohexylhexanoic acid

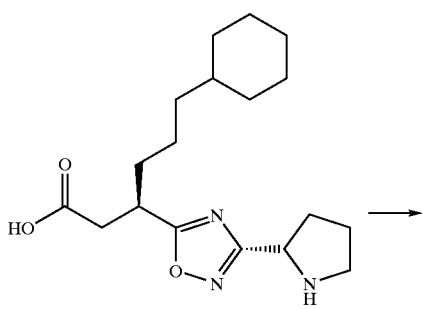

-continued

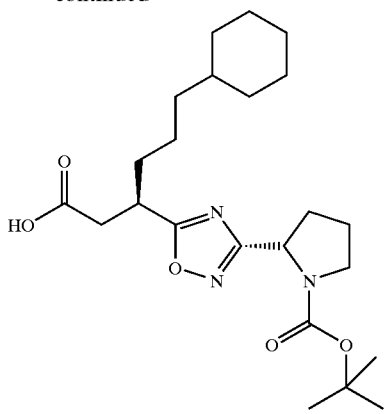

A solution of (3R)-6-cyclohexyl-3-{3-[(2S)-pyrrolidinyl]-1,2,4-oxadiazol-5-yl}hexanoic acid (preparation 119) (1.30 g, 3.88 mmol) in dioxan (10 ml) was treated with sat. NaHCO₃ solution (10 ml) followed by Boc anhydride (1.00 g, 4.59 mmol) and stirred at room temperature for 18 hours. The reaction mixture was partitioned between EtOAc and 5% citric acid solution. The organic extract was dried over anhydrous MgSO₄ and filtered. The solvent was removed under reduced pressure. The residue was purified on a silica column eluting with pentane:EtOAc (70:30) to afford the title compound as a colourless gum (1.18 g)

¹H nmr: (d6DMSO) 0.79 (2H, m), 1.10–1.25 (8H, m+$^t$BuOH+EtOAc), 1.42 (9H, s), 1.50–1.70 (7H, m), 1.70–1.95 (3H, m), 2.22 (1H, m), 2.69 (2H, m), 3.38 (3H, m), 4.81 (1 H. brs).

Preparation 121:

tert-butyl (2S)-2-[(Z)-amino({[(2R)-2-(2-tert-butoxy-2-oxoethyl)-5-cyclohexylpentanoyl]oxy}imino)methyl]-1-piperidinecarboxylate

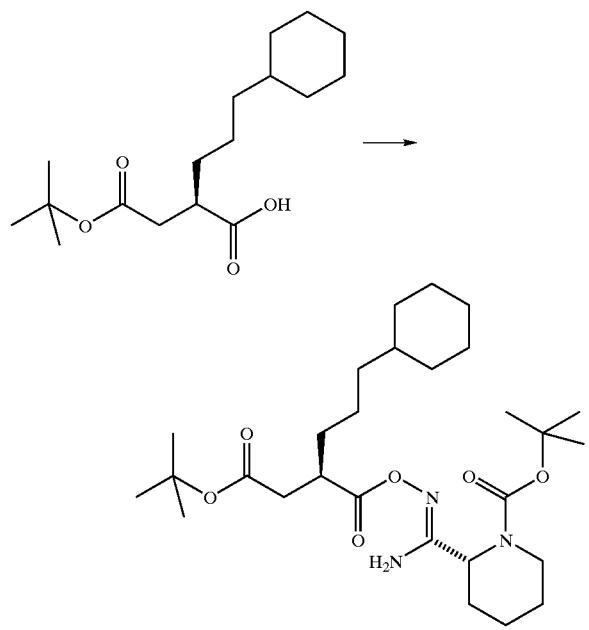

A solution of (2R)-2-(2-tert-butoxy-2-oxoethyl)-5-cyclohexylpentanoic acid (preparation 168) (500 mg, 1.67 mmol) in DCM (20 ml) was treated with HOBt (227 mg, 1.67 mmol), NMM (203 μl, 1.85 mmol) and WSCDI (354 mg, 1.85 mmol) followed by tert-butyl (2S)-2-[(Z)-amino(hydroxyimino)methyl]-1-piperidinecarboxylate (WO 9945006) (406 mg, 1.67 mmol) and stirred at room temperature, under a nitrogen atmosphere for 18 hours. H₂O (10 ml) was added and after 10 minutes the reaction mixture was separated in a 5 micron filter cartridge. The solvent was removed under reduced pressure to afford the title compound as a colourless foam.

¹H nmr: (CDCl₃) 0.86 (2H, m), 1.10–1.30 (6H, m), 1.30–1.50 (20H, m+s+s), 1.50–1.70 (11H, m), 1.90 (1H, m), 2.30 (1H, brd), 2.41 (1H, dd), 2.68 (1H, dd), 2.80 (1H, brd), 2.89 (1H, m) 3.99 (1H, brd), 4.98 (1H, d), 5.17 (2H, brs).

MS: 547 (MNa⁺)

Preparation 122:

tert-butyl (2S)-2-{5-[(1R)-1-(2-tert-butoxy-2-oxoethyl)-4-cyclohexylbutyl]-1,2,4-oxadiazol-3-yl}-1-piperidinecarboxylate

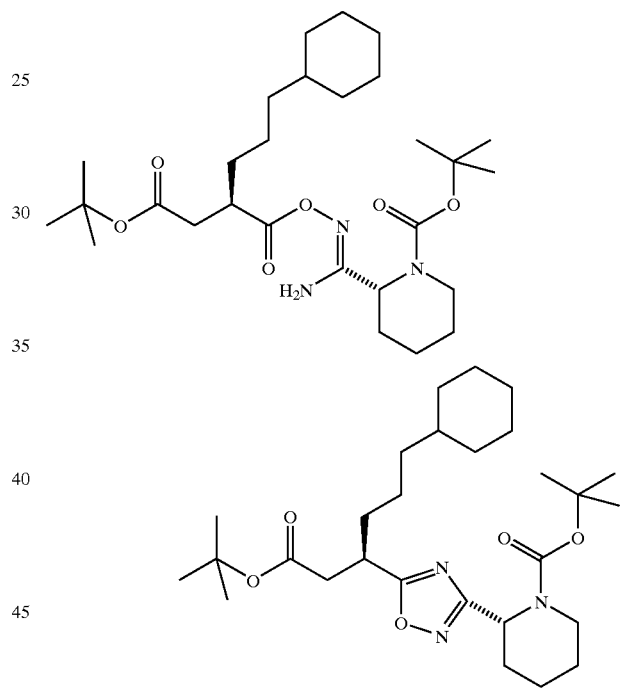

Method as for preparation 3 using tert-butyl (2S)-2-[(Z)-amino({[(2R)-2-(2-tert-butoxy-2-oxoethyl)-5-cyclohexylpentanoyl]oxy}imino)methyl]-1-piperidinecarboxylate (preparation 121) (870 mg, 1.60 mmol) as starting material.

Purification: The crude material was purified on a silica column eluting with DCM:MeOH (100:0) gradually changing to (95:5) to afford the title compound as a pale yellow oil (472 mg, 58%).

¹H nmr: (CDCl₃) 0.83 (2H, m), 1.10–1.30 (8H, m), 1.35–1.50 (21H, s+m+s), 1.60–1.75 (8H, m), 1.82 (1H, m), 2.21 (1H, brd), 2.59 (1H, dd), 2.78 (1H, dd), 1.98 (1H, brt), 3.41 (1H, m), 4.00 (1H, brd), 5.43 (1H, brs).

MS: 529 (MNa⁺)

CHN: Found: C66.36%; H9.37%; N8.22%; C₂₈H₄₇N₃O₅ requires C66.50; H9.37%; N8.31%.

Preparation 123:

(3R)-6-cyclohexyl-3-{3-[(2S)-piperidinyl]-1,2,4-oxadiazol-5-yl}hexanoic acid

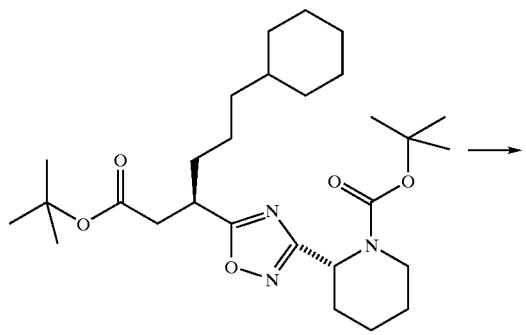

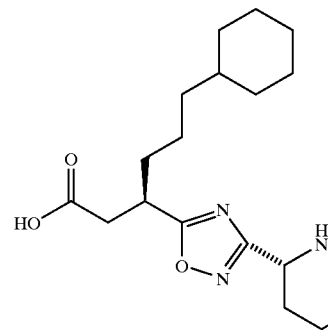

Method as for preparation 7 using tert-butyl (2S)-2-{5-[(1R)-1-(2-tert-butoxy-2-oxoethyl)-4-cyclohexylbutyl]-1,2,4-oxadiazol-3-yl}-1-piperidinecarboxylate (preparation 122) (437 mg, 0.86 mmol) as starting material.

$^1$H nmr: (d$_6$DMSO) 0.81 (2H, m), 1.05–1.30 (8H, m), 1.55–1.85 (12H, m), 2.12 (1H, d) 2.48 (2H, obs), 3.04 (1H, t), 3.23 (1H, t), 3.42 (1H, m), 4.61 (1H, d).

MS: 348 (M−H)

CHN: Found: C57.81%; H8.42%; N10.13%; C$_{19}$H$_{31}$N$_3$O$_3$.HCl.0.4H$_2$O.0.1 dioxan requires C57.97; H8.43%; N10.45%.

Preparation 124:

tert-butyl (3R)-6-cyclohexyl-3-{3-[(dimethylamino)methyl]-1,2,4-oxadiazol-5-yl)hexanoate

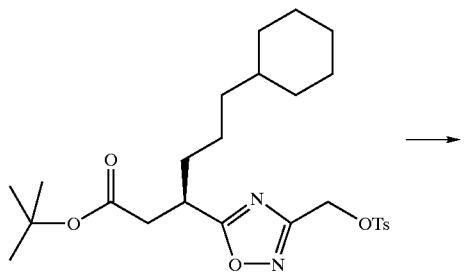

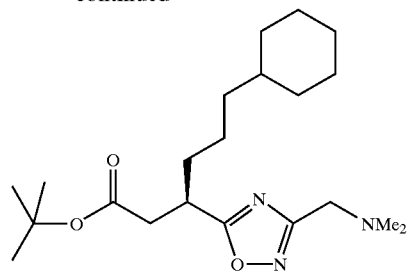

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (730 mg, 1.44 mmol) and N,N-dimethylamine (2M in THF) (800 μl, 1.60 mmol) as starting materials.

Purification: The residue was purified on a silica column eluting with DCM:MeOH (95:5) to afford the title compound as a pale orange oil (430 mg).

$^1$Hnmr (CDCl$_3$): 0.82 (2H, m), 1.05–1.35 (8H, m), 1.39 (9H, s), 1.60–1.85 (7H, m), 2.35 (6H, s), 2.63 (1H, dd), 2.85 (1H, dd), 3.46 (1H, m), 3.60 (2H, s).

MS: 402 (MNa$^+$)

Preparation 125:

(3R)-6-cyclohexyl-3-{3-[(dimethylamino)methyl]-1,2,4-oxadiazol-5-yl}hexanoic acid

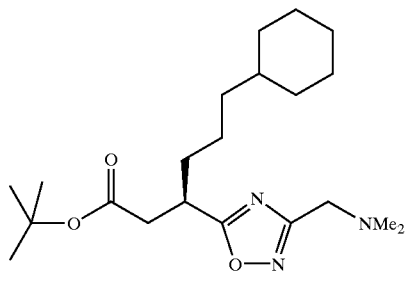

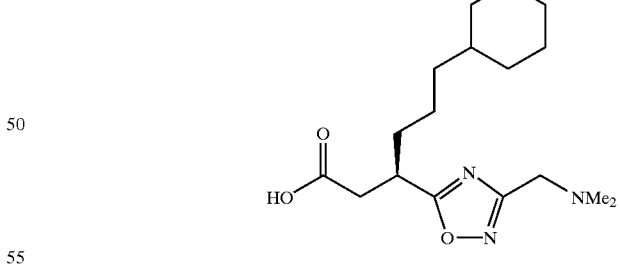

Method as for preparation 75 using tert-butyl (3R)-6-cyclohexyl-3-{3-[(dimethylamino)methyl]-1,2,4-oxadiazol-5-yl}hexanoate (preparation 124) (430 mg, 1.14 mmol) as starting material to afford the title compound as a yellow oil (495/550 mg).

$^1$Hnmr (CDCl$_3$): 0.83 (2H, m), 1.05–1.40 (8H, m), 1.55–1.85 (7H, m), 2.74–2.99 (8H, m), 3.50 (1H, m), 4.32 (2H, s).

MS: 324 (MH$^+$)

Preparation 126:

tert-butyl (3R)-6-cyclohexyl-3-(3-{[(2-methoxyethyl)(methyl)amino]methyl}-1,2,4-oxadiazol-5-yl)hexanoate

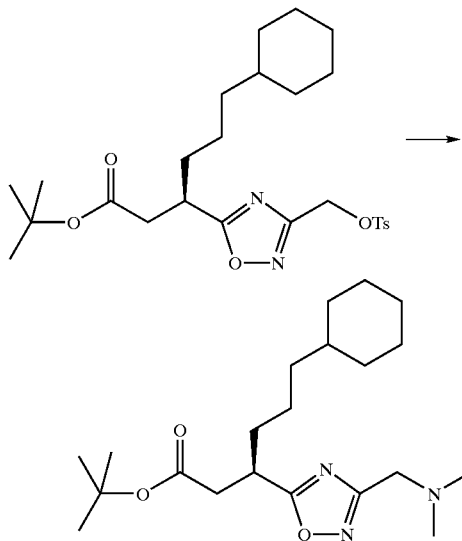

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (367 mg, 0.72 mmol) and 2-methoxyethylmethyl amine (130 mg, 1.45 mmol) as starting materials.

Purification: The residue was purified on a silica column eluting with DCM:MeOH (96:4) to afford the title compound as a pale yellow oil (240 mg).

$^1$Hnmr (CDCl$_3$): 0.81 (2H, m), 1.10–1.30 (8H, m), 1.39 (9H, s), 1.55–1.80 (7H, m), 2.39 (3H, s), 2.61 (1H, dd), 2.74 (2H, t), 2.82 (1H, dd), 3.37 (3H, s), 3.45 (1H, m), 3.55 (2H, t), 3.82 (2H, s).

MS: 425 (MH$^+$)

Preparation 127:

(3R)-6-cyclohexyl-3-(3-{[(2-methoxyethyl)(methyl)amino]methyl}-1,2,4-oxadiazol-5-yl)hexanoic acid

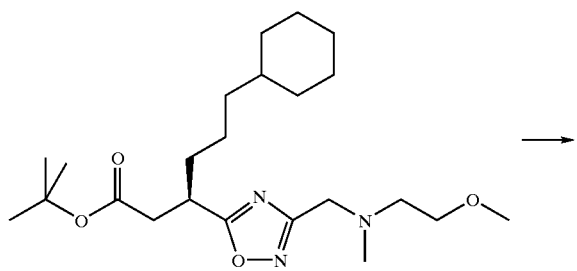

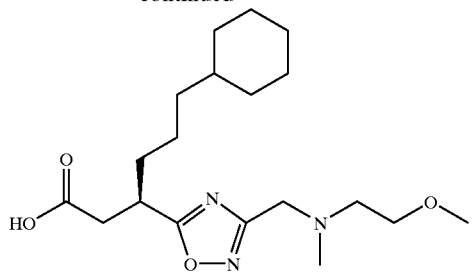

Method as for preparation 75 using tert-butyl (3R)-6-cyclohexyl-3-(3-{[(2-methoxyethyl)(methyl)amino]methyl}-1,2,4-oxadiazol-5-yl)hexanoate (preparation 126) (240 mg, 0.57 mmol) as starting material to afford the title compound as a pale orange oil (294 mg).

$^1$Hnmr (CDCl$_3$): 0.82 (2H, m), 1.10–1.35 (8H, m), 1.60–1.85 (7H, m), 2.80 (1H, dd), 2.90 (4H, s+dd), 3.38 (5H, s), 3.51 (1H, m), 3.79 (2H, t), 4.42 (2H, s).

MS: 368 (MH$^+$)

Preparation 128:

tert-butyl (3R)-6-cyclohexyl-3-(3-{[[2-(dimethylamino)ethyl](methyl)amino]methyl}-1,2,4-oxediazol-5-yl)hexanoate

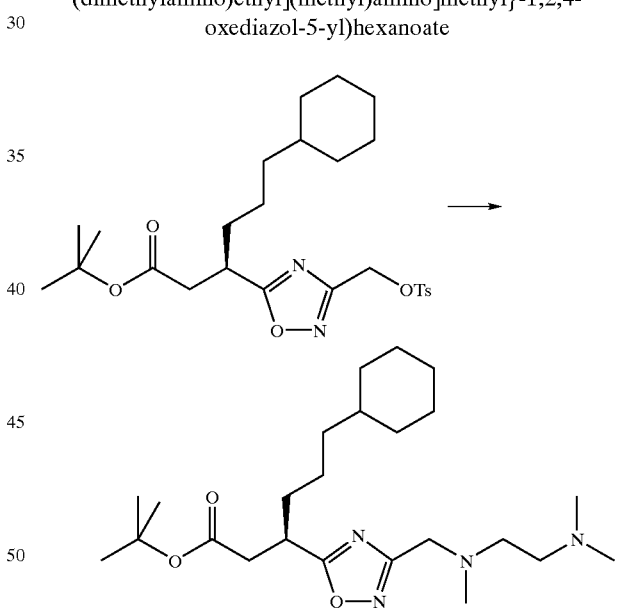

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and N,N,N'-trimethylethylenediamine (200 mg, 1.98 mmol) as starting materials to afford the title compound as a colourless oil (241 mg).

$^1$Hnmr (CDCl$_3$): 0.80 (2H, m), 1.05–1.25 (8H, m), 1.38 (9H, s), 1.55–1.75 (7H, m), 2.22 (6H, s), 2.35 (3H, s), 2.45 (2H, t), 2.60 (3H, m), 2.79 (1H, dd), 3.41 (1H, m), 3.77 (2H, s).

MS: 437 (MH$^+$)

Preparation 129:

(3R)-6-cyclohexyl-3-(3-{[[2-(dimethylamino)ethyl](methyl)amino]methyl}-1,2,4-oxadiazol-5-yl)hexanoic acid

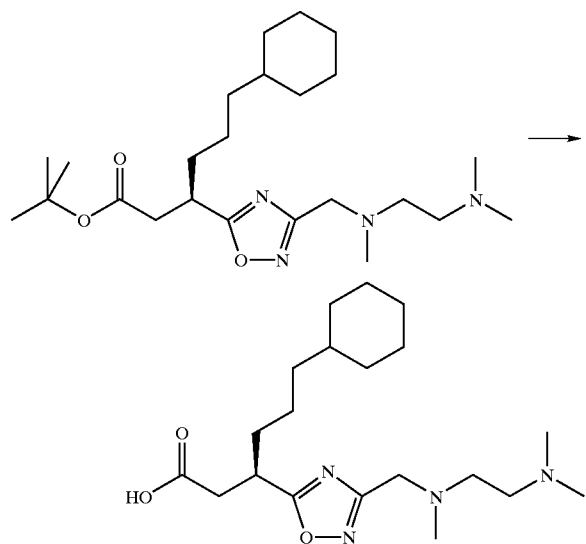

Method as for preparation 75 using tert-butyl (3R)-6-cyclohexyl-3-(3-{[[2-(dimethylamino)ethyl](methyl)amino]methyl}-1,2,4-oxadiazol-5-yl)hexanoate (preparation 128) (241 mg, 0.55 mmol) as starting material to afford the title compound as a pale brown oil.

¹Hnmr (d₆DMSO): 0.79 (2H, m), 1.00–1.25 (8H, m), 1.50–1.70 (7H, m), 2.28 (3H, s), 2.75 (8H, m), 3.21 (3H, m), 3.39 (1H, m), 3.82 (2H, s).

Preparation 130:

tert-butyl (3R)-3-(3-{[[(2-amino-2-oxoethyl)(methyl)amino]methyl}-1,2,4-oxadiazol-5-yl)-6-cyclohexylhexanoate

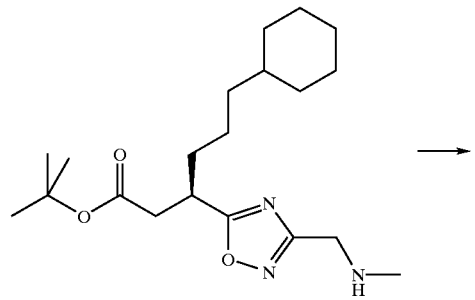

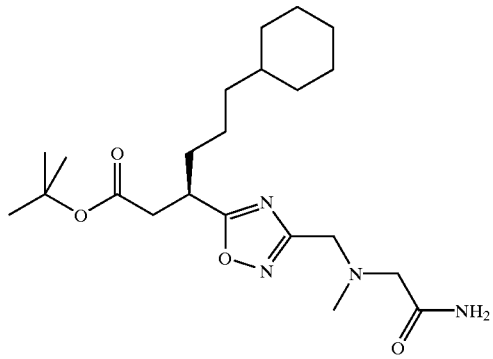

Method as for preparation 106 using tert-butyl (3R)-6-cyclohexyl-3-{3-[(methylamino)methyl]-1,2,4-oxadiazol-5-yl}hexanoate (preparation 5) (244 mg, 0.67 mmol) and 2-bromoacetamide (95 mg, 0.69 mmol) as starting materials and Et₃N as the base to afford the title compound as a colourless oil (296 mg).

¹H nmr: (CDCl₃) 0.85 (2H, m), 1.10–1.35 (8H, m), 1.40 (9H, s), 1.55–1.80 (7H, m), 2.40 (3H, s), 2.61 (1H, dd), 2.79 (1H, dd), 3.19 (2H, s), 3.42 (1H, m), 3.75 (2H, s), 5.35 (1H, brs), 7.20 (1H, brs).
MS: 445 (MNa⁺)

Preparation 131:

(3R)-3-(3-{[[(2-amino-2-oxoethyl)(methyl)amino]methyl}-1,2,4-oxadiazol-5-yl)-6-cyclohexylhexanoic acid

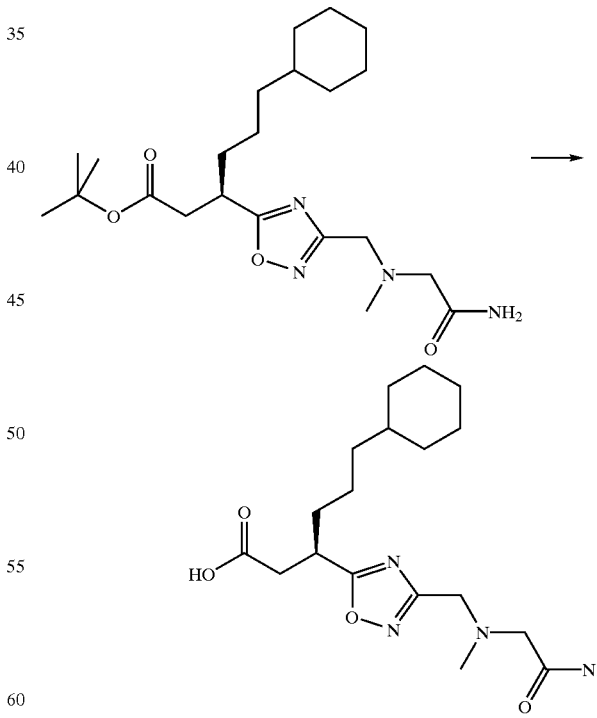

Method as for preparation 7 using tert-butyl (3R)-3-(3-{[(2-amino-2-oxoethyl)(methyl)amino]methyl}-1,2,4-oxadiazol-5-yl)-6-cyclohexylhexanoate (preparation 130) as starting material to afford the title compound as a yellow oil (250 mg).

¹H nmr: (CD₃OD) 0.85 (2H, m), 1.10–1.40 (8H, m), 1.60–1.80 (7H, m), 2.81 (1H, dd), 2.90 (1H, dd), 3.02 (3H, s), 3.54 (1H, m), 4.08 (2H, s), 4.62 (2H, s).

MS: 389 (MNa⁺)

CHN: Found: C53.94%; H8.17%; N11.71%; $C_{18}H_{30}N_4O_4 \cdot HCl \cdot 0.7$ dioxan requires C53.77; H7.94%; N12.06%.

Preparation 132:

tert-butyl (3R)-6-cyclohexyl-3-(3-{[(2-ethoxy-2-oxoethyl)(methyl)amino]methyl}-1,2,4-oxadiazol-5-yl)hexanoate

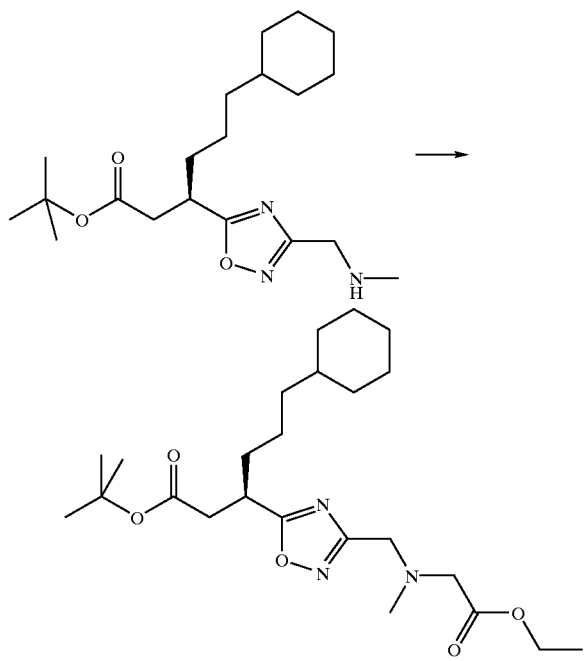

Method as for preparation 106 using tert-butyl (3R)-6-cyclohexyl-3-{3-[(methylamino)methyl]-1,2,4-oxadiazol-5-yl}hexanoate (preparation 5) (1.50 g, 4.10 mmol) and ethyl bromoacetate (460 μl, 4.10 mmol) as starting materials.

Purification: The crude material was purified on a silica column eluting with hexane:Et₂O (1:1) to afford the title compound as a colourless oil (1.04 g, 55%).

¹H nmr: (CDCl₃) 0.84 (2H, m), 1.10–1.35 (11H, m), 1.40 (9H, s), 1.60–1.80 (7H, m), 2.48 (3H, s), 2.60 (1H, dd), 2.80 (1H, dd), 3.41 (3H, s+m), 3.97 (2H, s), 4.19 (2H, q).

MS: 474 (MNa⁺)

CHN: Found: C63.65%; H9.17%; N9.04%; $C_{24}H_{41}N_3O_5$, requires C63.83; H9.15%; N9.30%.

Preparation 133:

[({5-[(1R)-1-(2-tert-butoxy-2-oxoethyl)-4-cyclohexylbutyl]-1,2,4-oxadiazol-3-yl}methyl)(methyl)amino]acetic acid

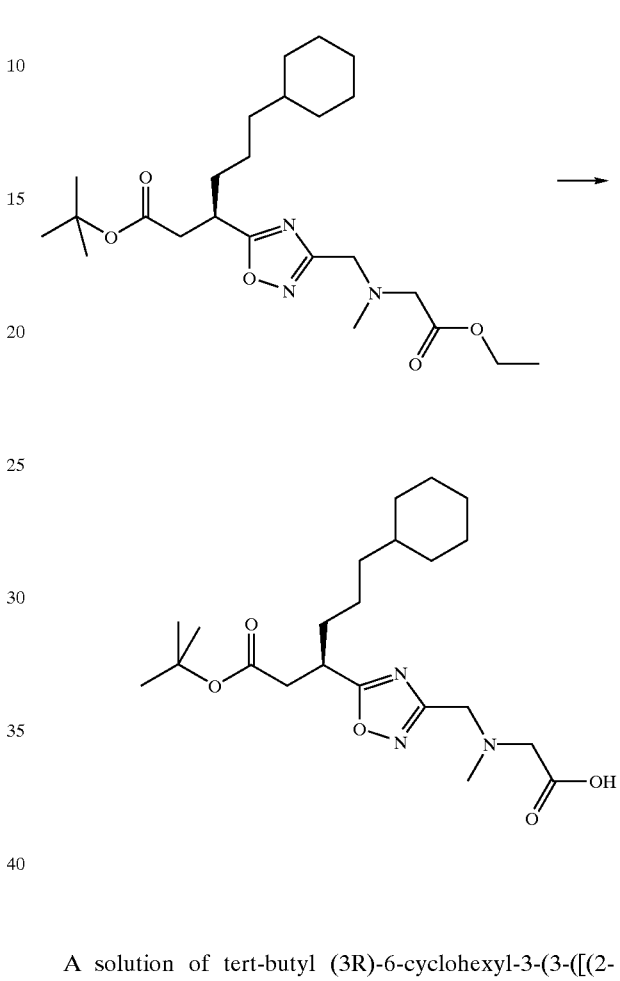

A solution of tert-butyl (3R)-6-cyclohexyl-3-(3-([(2-ethoxy-2-oxoethyl)(methyl)amino]methyl}-1,2,4-oxadiazol-5-yl)hexanoate (preparation 132) (1.00 g, 2.21 mmol) in dioxan (20 ml) and H₂O (20 ml) was treated with LiOH.H₂O (193 mg, 2.21 mmol) and the reaction mixture stirred at room temperature for 19 hours. The solvent was removed under reduced pressure. The residue was dissolved in EtOAc and washed with brine. The aqueous was extracted with EtOAc (×3). The combined organic extracts were dried over anhydrous Na₂SO₄ and filtered. The solvent was removed under reduced pressure to afford the title compound as a white foam (1.13 g).

¹H nmr: (CDCl₃) 0.82 (2H, m), 1.05–1.30 (8H, m), 1.39 (9H, s), 1.55–1.80 (7H, m), 3.75 (2H, s), 2.61 (1H, dd), 2.82 (1H, dd), 3.04 (2H, s), 3.41 (1H, m), 3.75 (2H, s).

MS: 446 (MNa⁺)

Preparation 134:

tert-butyl (3R)-6-cyclohexyl-3-[3-({methyl[2-(methylamino)-2-oxoethyl]amino}methyl)-1,2,4-oxadiazol-5-yl]hexanoate

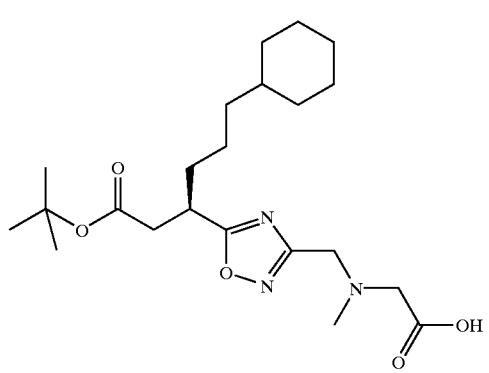

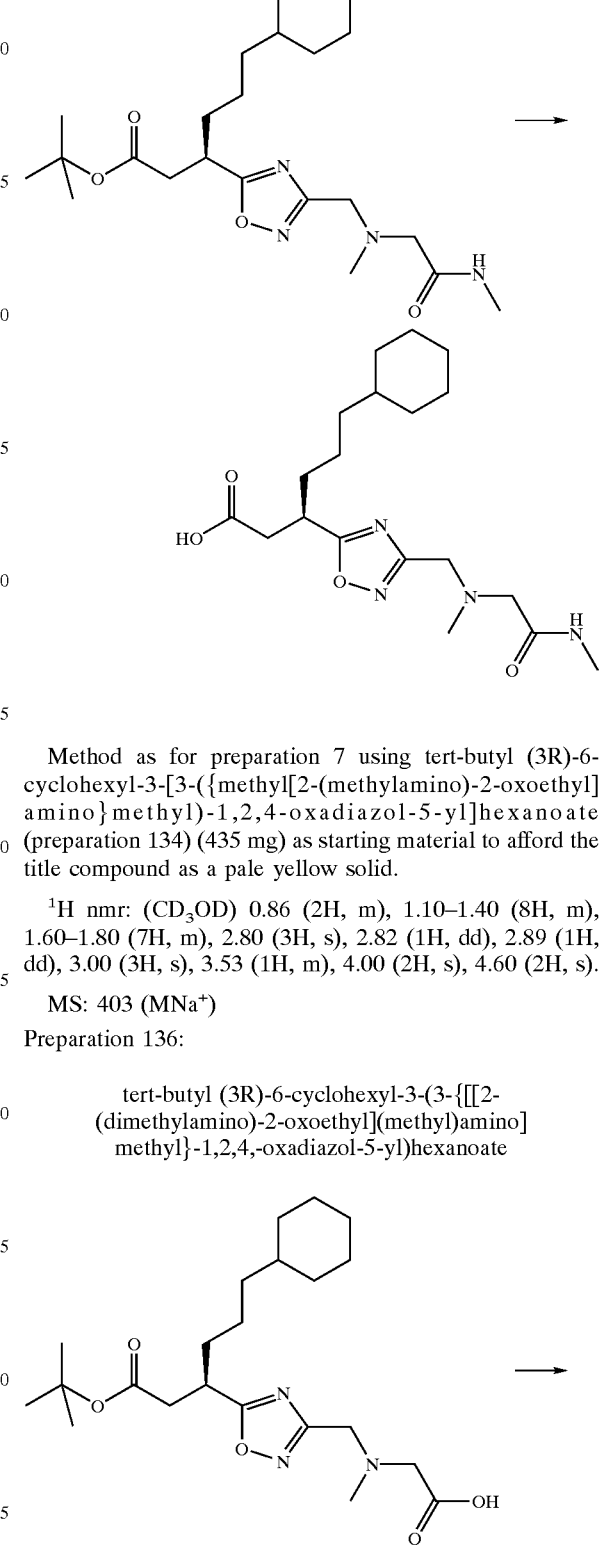

Method as for preparation 56 using [({5-[(1R)-1-(2-tert-butoxy-2-oxoethyl)-4-cyclohexylbutyl]-1,2,4-oxadiazol-3-yl}methyl)(methyl)amino]acetic acid (preparation 133) (618 mg, 1.46 mmol) and methylamine (2M in THF) (1.4 ml, 2.80 mmol) as starting materials.

Purification: The crude material was purified on a silica column eluting with a solvent gradient of DCM:MeOH (95:5) gradually changing to (90:10) to afford the title compound as a colourless oil (455 mg).

$^1$H nmr: (CDCl$_3$) 0.82 (2H, m), 1.05–1.30 (8H, m), 1.39 (9H, s), 1.55–1.80 (7H, m), 2.39 (3H, s), 2.61 (1H, dd), 2.79 (1H, dd), 2.81 (3H, s), 3.18 (2H, s), 3.42 (1H, m), 3.71 (2H, s).

MS: 459 (MNa$^+$)

Preparation 135:

(3R)-6-cyclohexyl-3-[3-({methyl[2-(methylamino)-2-oxoethyl]amino}methyl)-1,2,4-oxadiazol-5-yl]hexanoic acid

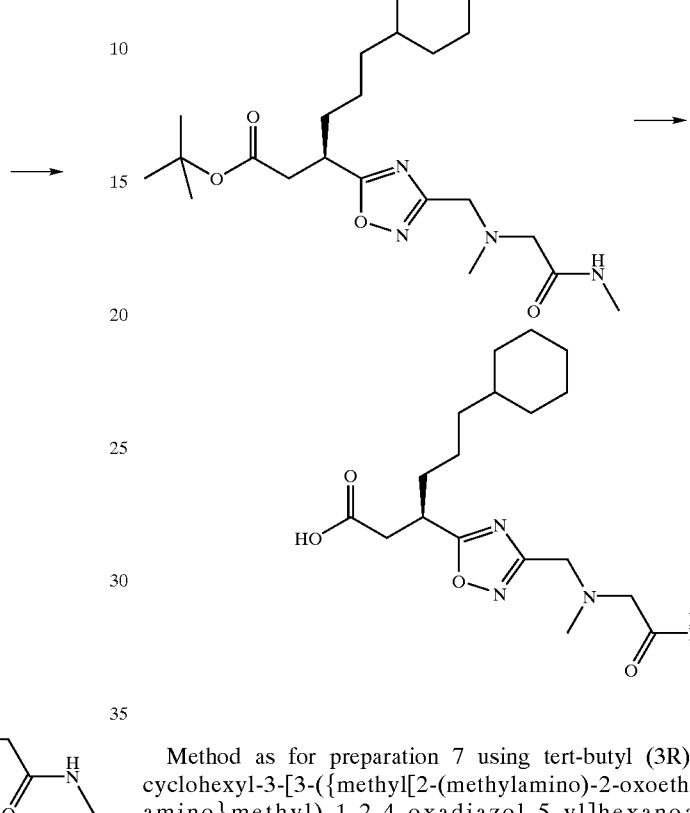

Method as for preparation 7 using tert-butyl (3R)-6-cyclohexyl-3-[3-({methyl[2-(methylamino)-2-oxoethyl]amino}methyl)-1,2,4-oxadiazol-5-yl]hexanoate (preparation 134) (435 mg) as starting material to afford the title compound as a pale yellow solid.

$^1$H nmr: (CD$_3$OD) 0.86 (2H, m), 1.10–1.40 (8H, m), 1.60–1.80 (7H, m), 2.80 (3H, s), 2.82 (1H, dd), 2.89 (1H, dd), 3.00 (3H, s), 3.53 (1H, m), 4.00 (2H, s), 4.60 (2H, s).

MS: 403 (MNa$^+$)

Preparation 136:

tert-butyl (3R)-6-cyclohexyl-3-(3-{[[2-(dimethylamino)-2-oxoethyl](methyl)amino]methyl}-1,2,4,-oxadiazol-5-yl)hexanoate

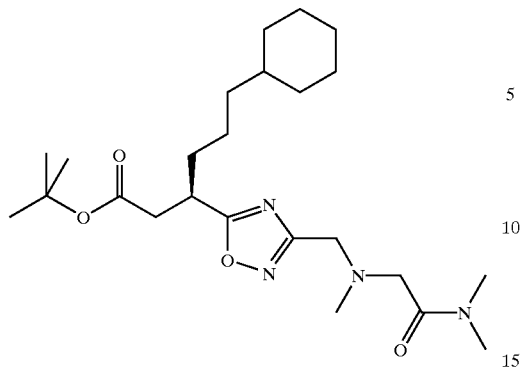

Method as for preparation 56 using [({5-[(1R)-1-(2-tert-butoxy-2-oxoethyl)-4-cyclohexylbutyl]-1,2,4-oxadiazol-3-yl}methyl)(methyl)amino]acetic acid (preparation 133) (725 mg, 1.71 mmol) and Me$_2$NH.HCl (106 mg, 1.30 mmol) as starting materials.

Purification: The crude material was purified on a silica column eluting with DCM:MeOH (19:1) to afford the title compound as a colourless oil (504 mg).

$^1$H nmr: (CDCl$_3$) 0.82 (2H, m), 1.05–1.30 (8H, m), 1.39 (9H, s), 1.60–1.80 (7H, m), 2.41 (3H, s), 2.60 (1H, dd), 2.79 (1H, dd), 2.94 (3H, s), 3.00 (3H, s), 3.39 (2H, s), 3.42 (1H, m), 3.81 (2H, s).

MS: 473 (MNa$^+$)

Preparation 137:

(3R)-6-cyclohexyl-3-(3-{[[2-(dimethylamino)-2-oxoethyl](methyl)amino]methyl}-1,2,4-oxadiazol-5-yl)hexanoic acid

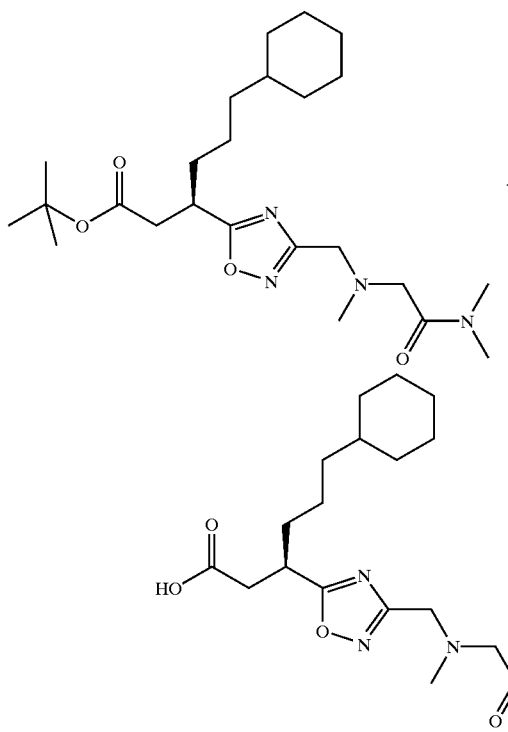

Method as for preparation 7 using tert-butyl (3R)-6-cyclohexyl-3-(3-{[[2-(dimethylamino)-2-oxoethyl](methyl) amino]methyl}-1,2,4-oxadiazol-5-yl)hexanoate (preparation 136) (489 mg) as starting material to afford the title compound as pale yellow gum (439 mg).

$^1$H nmr: (CD$_3$OD) 0.85 (2H, m), 1.10–1.40 (8H, m), 1.60–1.80 (7H, m), 2.82 (2H, m), 2.99 (6H, d), 3.01 (3H, s), 3.55 (1H, m), 4.31 (2H, s), 4.61 (2H, s).

MS: 395 (MH$^+$)

Preparation 138:

tert-butyl (3R)-3-(3-{[bis(2-methoxyethyl)amino] methyl}-1,2,4-oxadiazol-5-yl)-6-cyclohexylhexanoate

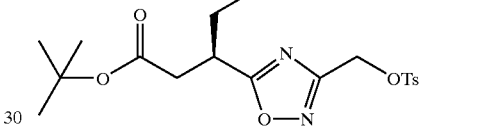

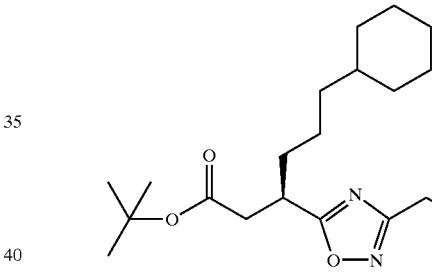

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and bis-(2-methoxyethyl)amine (280 µl, 1.98 mmol) as starting materials.

Purification: The residue was purified on a silica column eluting with a solvent gradient of DCM:MeOH (99:1) gradually changing to (97:3) to afford the title compound as a colourless oil (220 mg).

$^1$Hnmr (CDCl$_3$) δ: 0.81 (2H, m), 1.10–1.30 (8H, m), 1.39 (9H, s), 1.60–1.85 (7H, m+H$_2$O), 2.61 (1H, dd), 2.79 (1H, dd), 2.82 (4H, t), 3.35 (6H, s), 3.43 (1H, m), 3.50 (4H, t), 3.98 (2H, s).

MS: 468 (MH$^+$)

Preparation 139:

(3R)-3-(3-{[bis(2-methoxyethyl)amino]methyl}-1,2,4-oxadiazol-5-yl)-6-cyclohexylhexanoic acid

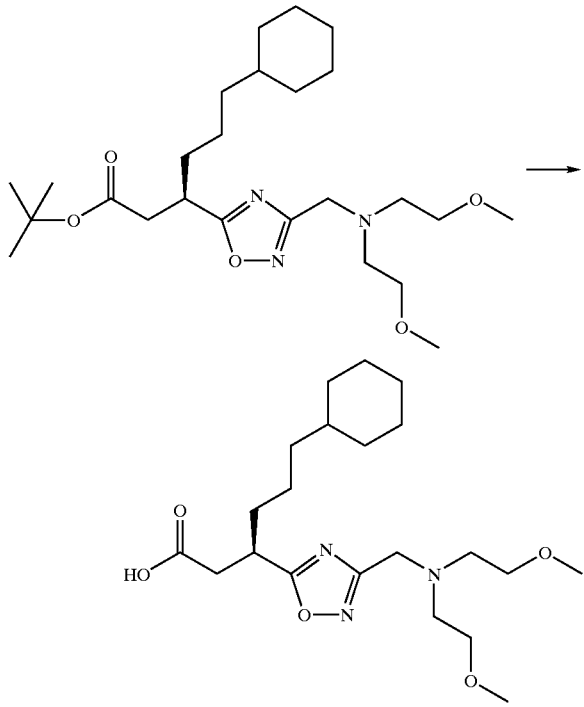

Method as for preparation 75 using tert-butyl (3R)-3-(3-{[bis(2-methoxyethyl)amino]methyl}-1,2,4-oxadiazol-5-yl)-6-cyclohexylhexanoate (preparation 138) (220 mg, 0.46 mmol) as staring material to afford the title compound as a yellow oil (176 mg).

¹Hnmr (CDCl₃) δ: 0.80 (2H, m), 1.05–1.35 (8H, m), 1.55–1.85 (7H, m), 2.79 (1H, dd), 2.92 (1H, dd), 3.34 (6H, s), 3.42 (4H, t), 3.51 (1H, m), 3.79 (4H, t), 4.60 (2H, s).

Preparation 140:

tert-butyl (3R)-6-cyclohexyl-3-[3-(1-pyrrolidinylmethyl)-1,2,4-oxadiazol-5-yl]hexanoate

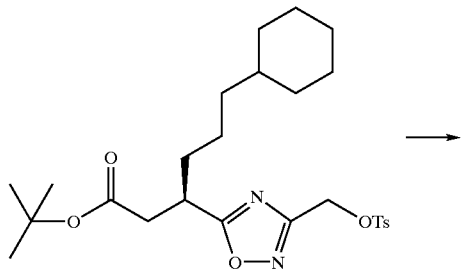

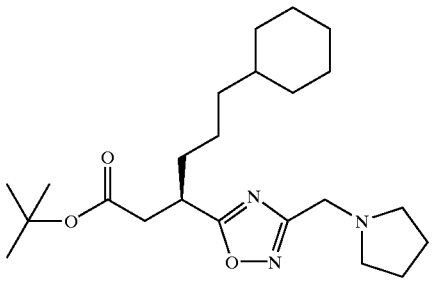

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (126 mg, 0.25 mmol) and pyrrolidine (100 μl, 1.20 mmol) as starting materials.

Purification: The crude material was purified on a silica column eluting with DCM:MeOH (98:2) to afford the title compound as a colourless oil (99 mg).

¹Hnmr (CDCl₃): 0.82 (2H, m), 1.05–1.35 (8H, m), 1.39 (9H, s), 1.50–1.85 (11H, m), 2.62 (5H, m), 2.83 (1H, dd), 3.46 (1H, m), 3.77 (2H, s).

MS: 428 (MNa⁺)

Preparation 141:

(3R)-6-cyclohexyl-3-[3-(1-pyrrolidinylmethyl)-1,2,4-oxadiazol-5-yl]hexanoic acid

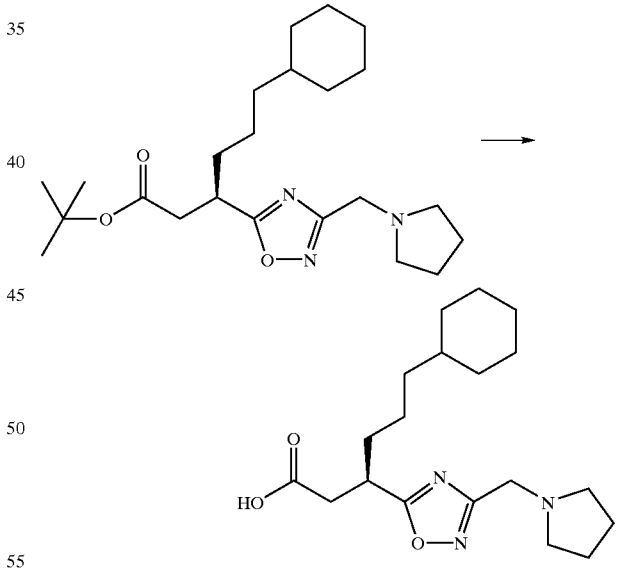

Method as for preparation 75 using tert-butyl (3R)-6-cyclohexyl-3-[3-(1-pyrrolidinylmethyl)-1,2,4-oxadiazol-5-yl]hexanoate (preparation 140) (99 mg, 0.24 mmol) as starting material to afford the title compound as a colourless oil (85 mg).

¹Hmnr (CDCl₃): 0.82 (2H, m), 1.00–1.35 (10H, m), 1.55–1.85 (7H, m), 2.00–2.20 (4H, m), 2.97–2.71 (2H, m), 3.51 (1H, m), 4.38 (2H, s).

MS: 349 (M⁺)

Preparation 142:

tert-butyl (3R)-6-cyclohexyl-3-{3-[(4-hydroxy-1-piperidinyl)methyl]-1,2,4-oxadiazol-5-yl}hexanoate

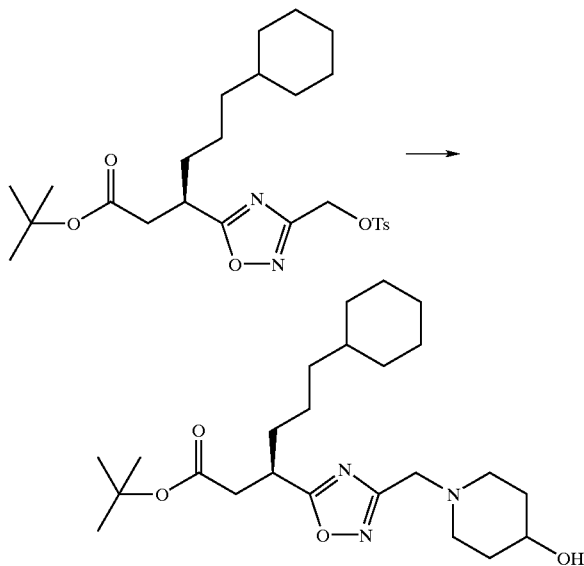

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 177) (500 mg, 0.99 mmol) and N-hydroxypiperidine (150 mg, 1.48 mmol) as starting materials.

Purification: The crude material was purified on a silica column eluting with DCM:MeOH (95:5) to afford the title compound as a pale yellow oil (366 mg).

$^1$Hnmr (CDCl$_3$): 0.83 (2H, m), 1.05–1.35 (8H, m), 1.39 (9H, s), 1.60–1.80 (9H, m), 1.90 (2H, m), 2.31 (2H, m), 2.63 (1H, dd), 2.83 (3H, m), 3.45 (1H, m), 3.67 (3H, m),

MS: 436 (MH$^+$)

Preparation 143:

(3R)-6-cyclohexyl-3-{3-[(4-hydroxy-1-piperidinyl)methyl]-1,2,4-oxadiazol-5-yl}hexanoic acid trifluoroacetate

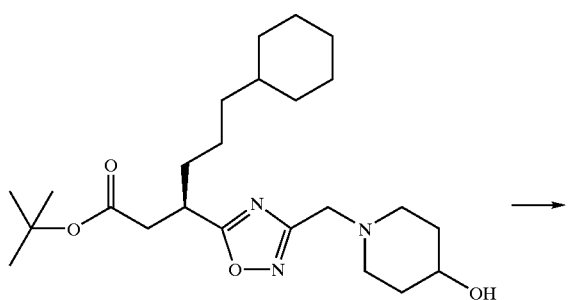

Method as for preparation 75 using tert-butyl (3R)-6-cyclohexyl-3-{3-[(4-hydroxy-1-piperidinyl)methyl]-1,2,4-oxadiazol-5-yl}hexanoate (Preparation 142) (366 mg, 0.84 mmol) as starting material to afford the title compound as a pale yellow oil (460 mg).

$^1$Hnmr (CDCl$_3$): 0.85 (2H, m), 1.05–1.40 (8H, m), 1.60–1.85 (7H, m), 1.92 (2H, m), 2.20 (2H, m), 2.79 (1H, dd), 2.90 (1H, dd), 3.59–3.12 (5H, m), 4.16 (1H, m), 4.34 (2H, m),

MS: 380 (MH$^+$)

Preparation 144:

tert-butyl (3R)-6-cyclohexyl-3-[3-(4-morpholinylmethyl)-1,2,4-oxadiazol-5-yl]hexanoate

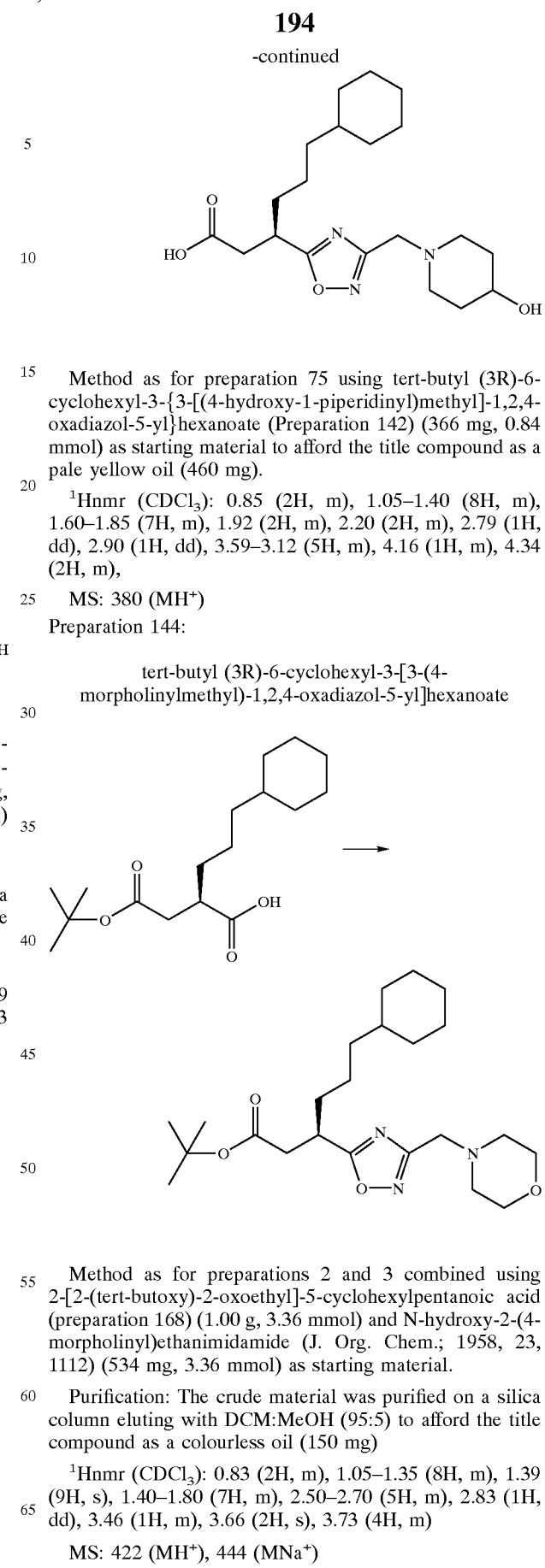

Method as for preparations 2 and 3 combined using 2-[2-(tert-butoxy)-2-oxoethyl]-5-cyclohexylpentanoic acid (preparation 168) (1.00 g, 3.36 mmol) and N-hydroxy-2-(4-morpholinyl)ethanimidamide (J. Org. Chem.; 1958, 23, 1112) (534 mg, 3.36 mmol) as starting material.

Purification: The crude material was purified on a silica column eluting with DCM:MeOH (95:5) to afford the title compound as a colourless oil (150 mg)

$^1$Hnmr (CDCl$_3$): 0.83 (2H, m), 1.05–1.35 (8H, m), 1.39 (9H, s), 1.40–1.80 (7H, m), 2.50–2.70 (5H, m), 2.83 (1H, dd), 3.46 (1H, m), 3.66 (2H, s), 3.73 (4H, m)

MS: 422 (MH$^+$), 444 (MNa$^+$)

Preparation 145:

(3R)-6-cyclohexyl-3-[3-(4-morpholinylmethyl)-1,2,4-oxadiazol-5-yl]hexanoic acid

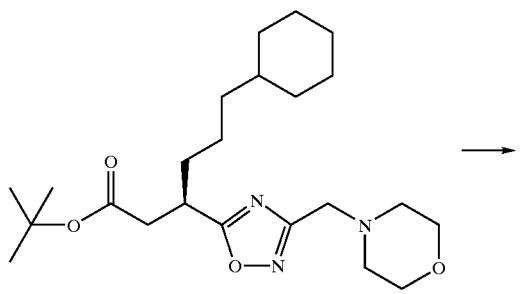

Method as for preparation 75 using tert-butyl (3R)-6-cyclohexyl-3-[3-(4-morpholinylmethyl)-1,2,4-oxadiazol-5-yl]hexanoate (Preparation 144) (150 mg, 0.36 mmol) as starting material to afford the title compound as a pale brown oil (120 mg).

¹Hnmr (CDCl₃) δ: 0.84 (2H, m), 1.05–1.40 (8H, m), 1.55–1.85 (7H, m), 2.76 (1H, dd), 2.90 (1H, dd), 3.22 (4H, m), 3.47 (1H, m), 3.92 (4H, m), 4.28 (2H, m), 9.80 (1H, br s)

MS: 366 (MH⁺)

Preparation 146:

tert-butyl (3R)-6-cyclohexyl-3-{3-[(4-methyl-1-piperazinyl)methyl]-1,2,4-oxadiazol-5-yl}hexanoate

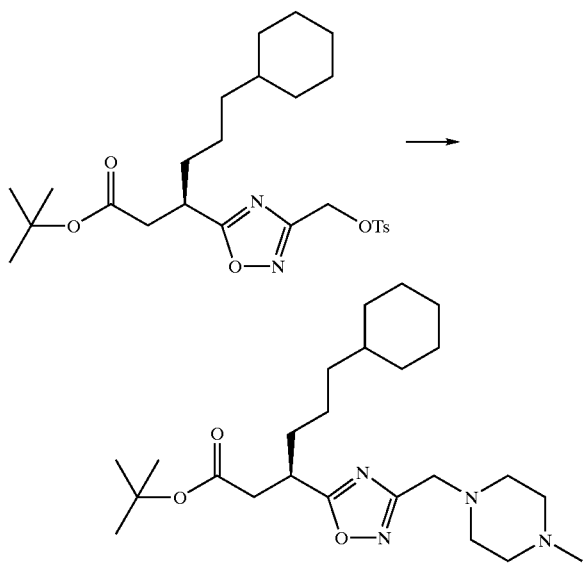

Method as for preparation 5 using tert-butyl (3R)-6-cyclohexyl-3-[3-({[(4-methylphenyl)sulfonyl]oxy}methyl)-1,2,4-oxadiazol-5-yl]hexanoate (preparation 168) (598 mg, 1.18 mmol) and N-methylpiperazine (120 mg, 1.18 mmol) as starting materials.

Purification: The crude material was purified on a silica column eluting with DCM:MeOH:NH₃ (95:5:0.5) to afford the title compound as a pale orange oil (395 mg).

¹Hnmr (CDCl₃): 0.83 (2H, m), 1.05–1.35 (8H, m), 1.40 (9H, s), 1.60–1.80 (7H, m), 2.29 (3H, s), 2.35–2.75 (9H, m), 2.83 (1H, dd), 3.45 (1H, m), 3.68 (2H, s)

MS: 436 (M2H⁺)

Preparation 147:

(3R)-6-cyclohexyl-3-{3-[(4-methyl-1-piperazinyl)methyl]-1,2,4-oxadiazol-5-yl}hexanoic acid trifluoroacetate

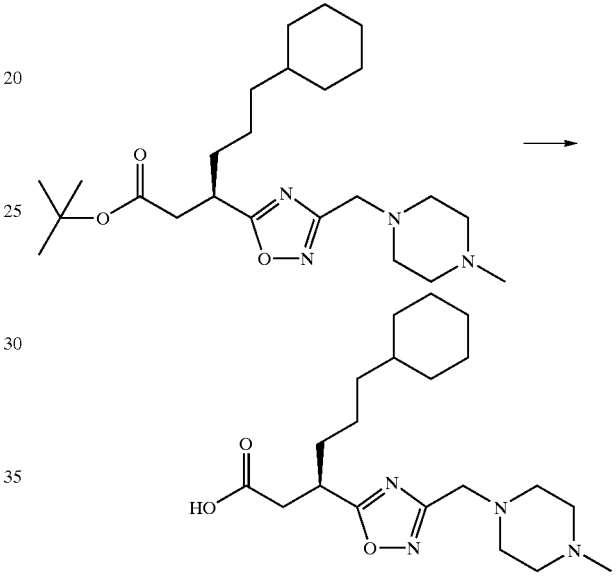

Method as for preparation 75 using tert-butyl (3R)-6-cyclohexyl-3-{3-[(4-methyl-1-piperazinyl)methyl]-1,2,4-oxadiazol-5-yl}hexanoate (Preparation 146) (395 mg, 0.91 mmol) as starting material to afford the title compound as a foam (585 mg).

¹Hnmr (CDCl₃): 0.84 (2H, m), 1.10–1.40 (8H, m), 1.60–1.85 (7H, m), 2.75–2.95 (5H, m), 3.00–3.25 (4H, m), 3.45–3.70 (3H, m), 4.05 (2H, m)

MS: 379 (MH⁺)

Preparation 148:

N-hydroxy-2-(1H-1,2,4-triazol-1-yl)ethanimidamide

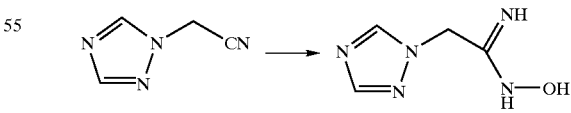

Method as for preparation 1 using 2-(1H-1,2,4-triazol-1-yl)acetonitrile (J.Org.Chem. USSR, 18; 2; 1982; 407) (2.16 g, 20 mmol) as starting material. The crystalline precipitate was filtered off and washed with cold MeOH and Et₂O to afford the title compound (2.37 g)

¹Hnmr (d₆DMSO): 4.72 (2H, s), 5.54 (2H, br s), 7.93 (1H, s), 8.46 (1H, s), 9.29 (1H, s),

Preparation 149:

tert-butyl (3R)-6-cyclohexyl-3-[3-(1H-1,2,4-triazol-1-ylmethyl)-1,2,4-oxadiazol-5-yl]hexanoate

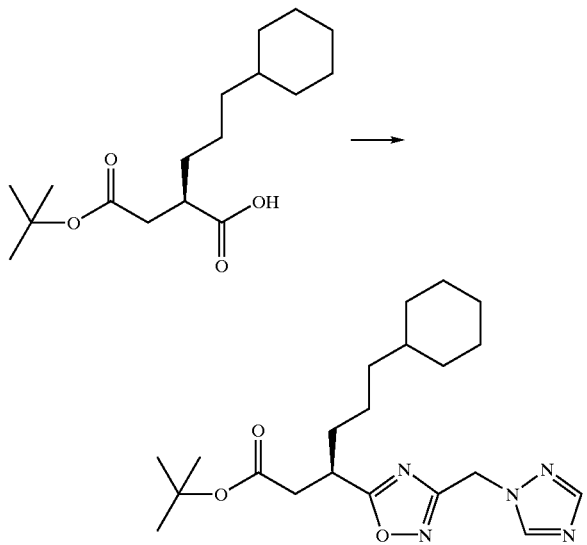

Method as for preparation 2 and 3 combined using 2-[2-(tert-butoxy)-2-oxoethyl]-5-cyclohexylpentanoic acid (preparation 168) (2.98 g, 10 mmol) and N-hydroxy-2-(1H-1,2,4-triazol-1-yl)ethanimidamide (preparation 148) (1.01 g, 10 mmol) as starting materials.

Purification: The crude material was purified on a silica column eluting with a solvent gradient EtOAc:pentane (100:0) gradually changing to (50:50) to afford the title compound as a golden oil (1.10 g)

$^1$Hnmr (CDCl$_3$): 0.82 (2H, m), 1.05–1.40 (17H, m), 1.60–1.80 (7H, m), 2.62 (1H, dd), 2.77 (1H, dd), 3.44 (1H, m), 5.46 (2H, s), 7.96 (1H, s), 8.25 (1H, s), MS: 404 (MH$^+$), 426 (MNa$^+$)

Preparation 150:

(3R)-6-cyclohexyl-3-[3-(1H-1,2,4-triazol-1-ylmethyl)-1,2,4-oxadiazol-5-yl]hexanoic acid

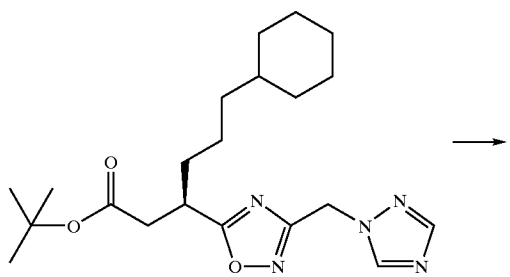

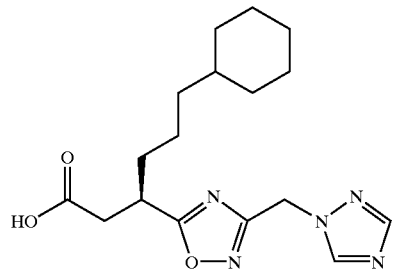

Method as for preparation 75 using tert-butyl (3R)-6-cyclohexyl-3-[3-(1H-1,2,4-triazol-1-ylmethyl)-1,2,4-oxadiazol-5-yl]hexanoate (Preparation 149) (500 mg, 1.24 mmol) as starting material to afford the title compound as an oil which crystallised on standing (420 mg).

$^1$Hnmr (CDCl$_3$): 0.83 (2H, m), 1.05–1.40 (8H, m), 1.55–1.85 (7H, m), 2.78 (1H, dd), 2.92 (1H, dd), 3.51 (1H, m), 5.53 (2H, d), 8.06 (1H, s), 8.52 (1H, s)

MS: 346 (MH$^-$)

Preparation 151:

tert-butyl (3R)-6-cyclohexyl-3-({[(1S)-2-ethoxy-1-(hydroxymethyl)-2-oxoethyl]amino}carbonyl)hexanoate

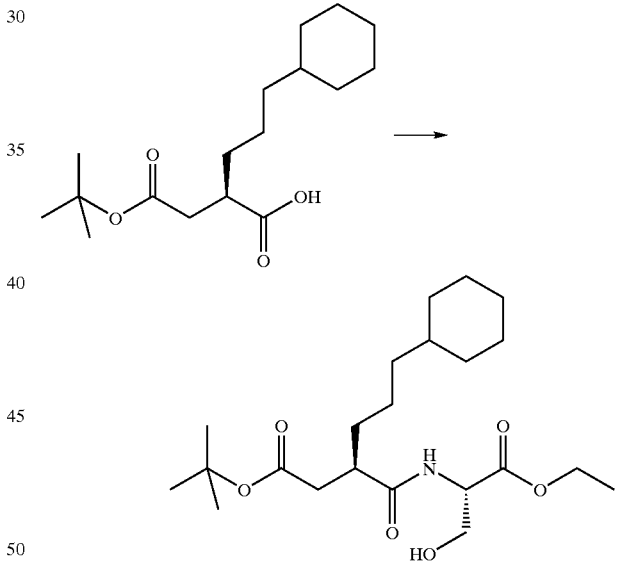

Method as for preparation 56 using 2-[2-(tert-butoxy)-2-oxoethyl]-5-cyclohexylpentanoic acid (preparation 168) (15.0 g, 50.3 mmol) and L-serine (9.38 g, 55.3 mmol) as starting materials.

Purification: The crude material was combined with another batch and purified on a silica column eluting with a solvent gradient of pentane:EtOAc (100:0) gradually changing to (60:40) to afford the title compound as a pale yellow oil (21.6 g, 78%).

$^1$Hnmr (CDCl$_3$): 0.81 (2H, m), 1.10–1.35 (11H, m), 1.40 (9H, s), 1.55–1.70 (7H, m), 2.34 (1H, dd), 2.49 (1H, m), 2.65 (1H, dd), 3.81 (1H, d), 4.01 (1H, d), 4.21 (2H, q), 4.59 (1H, m), 6.56 (1H, d).

MS: 413 (M$^+$)

Preparation 152:

ethyl (4S)-2-[(1R)-1-(2-tert-butoxy-2-oxoethyl)-4-cyclohexylbutyl]-4,5-dihydro-1,3-oxazole-4-carboxylate

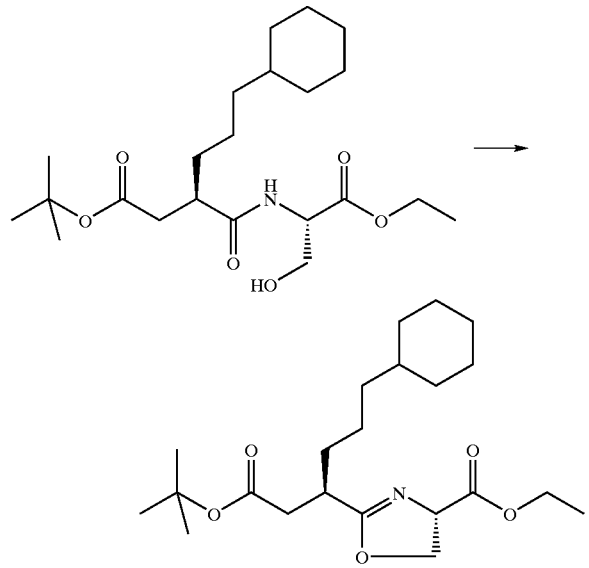

A solution of tert-butyl (3R)-6-cyclohexyl-3-({[(1S)-2-ethoxy-1-(hydroxymethyl)-2-oxoethyl]amino}carbonyl)hexanoate (preparation 151) (10.0 g, 24.2 mmol) in THF (80 ml) was treated with Burgess reagent (6.34 g, 26.6 mmol) and heated at reflux for 1 hour. The reaction mixture was allowed to cool to room temperature and stored in a fridge for 3 days. The solvent was removed under reduced pressure. The crude material was ourifiifed on a silica column eluting with a solvent gradient of pentane:EtOAc (100:0) gradually changing to (80:20) to afford the title compound as a colourless oil (9.26 g, 97%).

¹Hnmr (CDCl₃): 0.81 (2H, m), 1.10–1.35 (11H, m), 1.40 (9H, s), 1.45–1.70 (7H, m), 2.39 (1H, dd), 2.60 (1 H, dd), 2.85 (1H, m), 4.20 (2H, m), 4.30–4.45 (2H, m), 4.66 (1H, dd).

MS: 396 (MH⁺)

Preparation 153:

ethyl 2-[(1R)-1-(2-tert-butoxy-2-oxoethyl)-4-cyclohexylbutyl]-1,3-oxazole-4-carboxylate

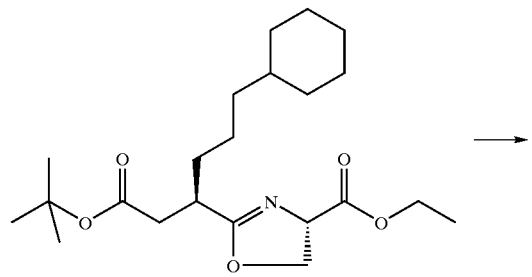

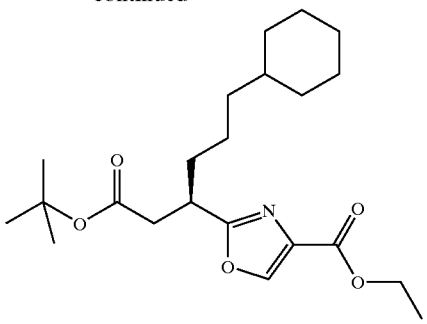

A suspension of CuBr₂ (20.88 g, 93.5 mmol) and HMTA (13.1 g, 93.5 mmol) in degassed DCM (250 ml) was treated with DBU (14.0 ml, 93.5 mmol) and the dark solution formed was stirred in a water bath for 5 minutes. A solution of ethyl (4S)-2-[(1R)-1-(2-tert-butoxy-2-oxoethyl)-4-cyclohexylbutyl]-4,5-dihydro-1,3-oxazole-4-carboxylate (preparation 152) (9.24 g, 23.4 mmol) in degassed DCM (30 ml) was added dropwise to the reaction mixture and stirred at room temperature for a further 3 hours. The solvent was removed under reduced pressure. The resdue was dissolved in EtOAc and washed with a 1:1 solution of NH₃(aq):NH₄Cl. The aqueous extract was washed with EtOAc (2×380 ml). The combined organic extracts were washed with 2M HCl (500 ml), sat. NaHCO₃ (500 mL) and brine (500 ml). The organic extracts were dried over anhydrous MgSO₄ and filtered. The solvent was removed under reduced pressure. The crude material was purified on a silica column eluting with a solvent gradient of EtOAc:pentane (0:100) gradually changing to (25:75) to afford the title compound as colourless oil which formed needles on standing (7.39 g, 80%).

¹Hnmr (CDCl₃): 0.81 (2H, m), 1.10–1.30 (8H, m), 1.39 (12H, t+s), 1.55–1.80 (7H, m), 2.58 (1H, dd), 2.79 (1H, dd), 3.38 (1H, m), 4.39 (2H, q), 8.09 (1H, s).

Preparation 154:

(3R)-6-cyclohexyl-3-[4-(ethoxycarbonyl)-1,3-oxazol-2-yl]hexanoic acid

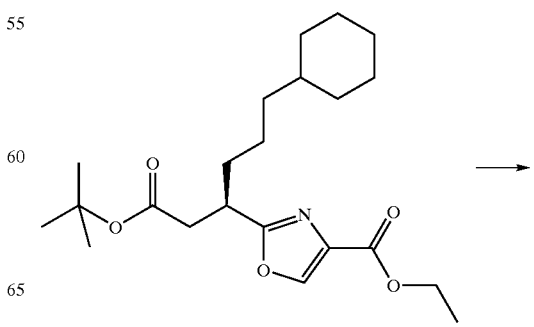

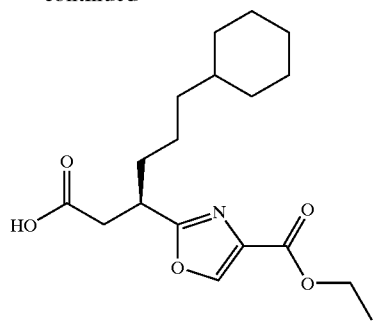

Method as for preparation 11 using ethyl 2-[(1R)-1-(2-tert-butoxy-2-oxoethyl)-4-cyclohexylbutyl]-1,3-oxazole-4-carboxylate (preparation 153) (7.39 g, 18.8 mmol) as starting material to afford the title compound as a pale yellow oil (6.34 g, 99%).

¹Hnmr (CDCl₃): 0.80 (2H, m), 1.05–1.30 (8H, m), 1.38 (3H, t), 1.55–1.80 (7H, dd), 2.97 (1H, dd), 3.44 (1H, m), 4.38 (2H, q), 8.15 (1H, s).

Preparation 155:

ethyl 2-((1R)-1-{2-[(benzyloxy)amino]-2-oxoethyl}-4-cyclohexylbutyl)-1,3-oxazole-4-carboxylate

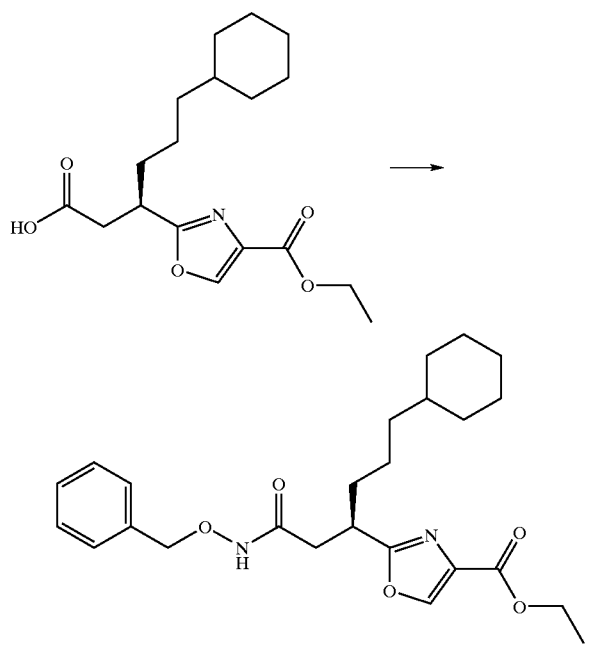

Method as for preparation 56 using (3R)-6-cyclohexyl-3-[4-(ethoxycarbonyl)-1,3-oxazol-2-yl]hexanoic acid (preparation 154) (2.21 g, 6.55 mmol) and o-benzylhydroxylamine (1.05 g, (6.55 mmol) as starting materials.

Purification: The crude material was purified on a silica column eluting with a solvent gradient of pentane:EtOAc (100:0) gradually changing to (50:50) to afford the title compound as a colourless oil which solidified on standing (2.3 g, 80%).

¹H nmr: (CDCl₃) 0.80 (2H, m), 1.10–1.30 (8H, m+EtOAc), 1.38 (3H, t), 1.55–1.75 (7H, m+H₂O), 2.41 (1H, brs), 2.65 (1H, brs), 3.45 (1H, brs), 4.39 (2H, q), 4.84 (2H, s), 7.37 (5H, s), 8.08 (1H, s), 8.50 (1H, brs).

MS: 443 (MH⁺)

CHN: Found: C67.62%; H7.78%; N6.30%; C₂₅H₃₄N₂O requires C67.85; H7.74%; N6.33%.

Preparation 156:

(3R)-N-(benzyloxy)-6-cyclohexyl-3-(4-formyl-1,3-oxazol-2-yl)hexanamide

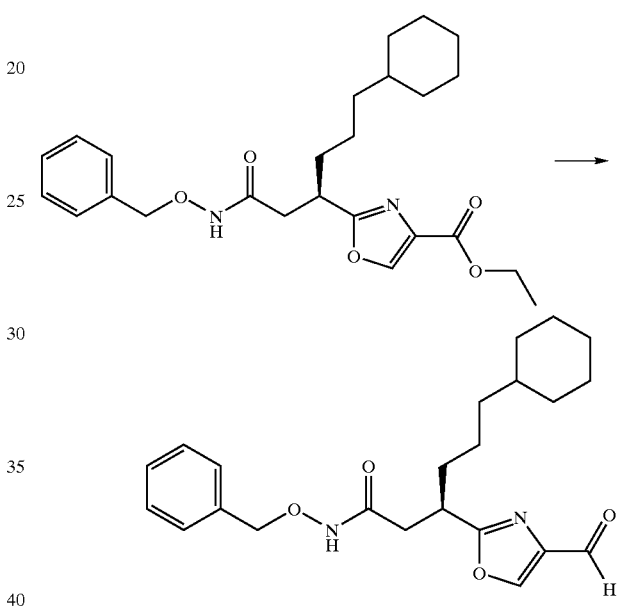

A solution of ethyl 2-((1R)-1-{2-[(benzyloxy)amino]-2-oxoethyl}-4-cyclohexylbutyl)-1,3-oxazole-4-carboxylate (preparation 155) (1.50 g, 3.39 mmol) in toluene (50 ml) at −78° C. was treated dropwise with DIBAL (1M in hexanes) (11.86 ml, 11.86 mmol) and stirred at this temperature for 30 minutes. MeOH (12 ml) was added to quench the reaction and the reaction mixture allowed to warm to room temperature. Alternate portions of NaHCO₃ and MgSO₄ were added to the reaction mixture to form a white paste. EtOAc was added and the solid filtered off. The solvent was removed under reduced pressure. The crude material was purified on a silica column eluting with a solvent gradient of EtOAc-:pentane (1:1) gradually changing to (1:0) to afford the title compound as a colourless oil (605 mg, 45%).

¹H nmr: (CDCl₃) 0.80 (2H, m), 1.10–1.30 (8H, m+EtOAc), 1.55–1.70 (7H, m+H₂O), 2.42 (1H, brs), 2.61 (1H, brs), 3.48 (1H, m+MeOH), 4.83 (2H, s), 7.35 (5H, s), 8.16 (1H, s), 8.43 (1H, brs), 9.81 (1H, brs).

MS: 399 (MH⁺)

Preparation 157:

(3R)-N-(benzyloxy)-6-cyclohexyl-3-{-4-[(isopropylamino)methyl]-1,3-oxazol-2-yl}hexanamide

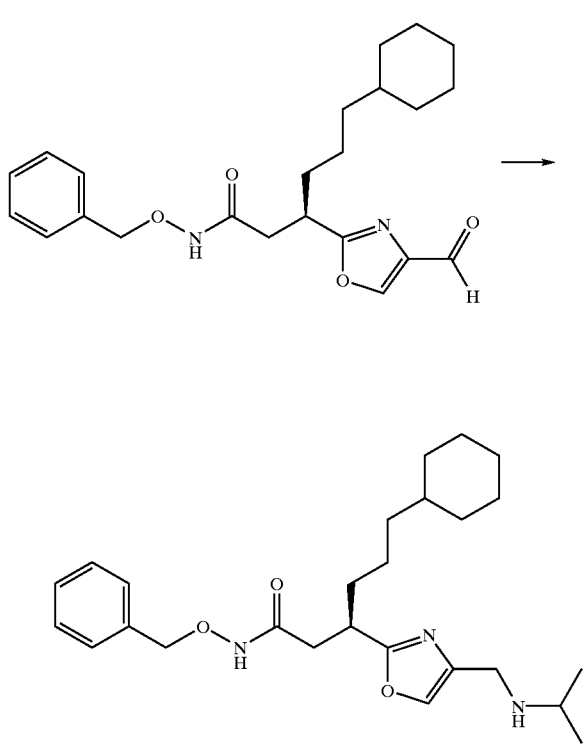

A solution of (3R)-N-(benzyloxy)-6-cyclohexyl-3-(4-formyl-1,3-oxazol-2-yl)hexanamide (preparation 156) (200 mg, 0.50 mmol) in DCM (10 ml) was treated with isopropylamine (43 μl, 0.50 mmol) and stirred at room temperature for 15 minutes. NaHB(OAc)$_3$ (170 mg, 0.80 mmol) and AcOH (29 μl, 0.50 mmol) were added and the reaction mixture stirred at room temperature for 1 hour. The reaction mixture was diluted with DCM and washed with sat. NaHCO$_3$ solution followed by brine. The organic extract was dried over anhydrous MgSO$_4$ and filtered. The solvent was removed under reduced pressure. The crude material was purified on a silica column eluting with a solvent gradient of DCM:MeOH:NH$_3$ (100:0:0) gradually changing to (95:5:0.5) to afford the title compound as a colourless oil (75 mg, 32%).

$^1$H nmr: (CDCl$_3$) 0.80 (2H, m), 1.00–1.30 (14H, d+m), 1.55–1.75 (7H, m), 2.40 (1H, brs), 2.59 (1H, brs), 2.80 (1H, m), 3.35 (1H, brs), 3.59 (2H, s), 4.81 (2H, s), 7.37 (5H, s), 7.39 (1H, s), 8.50 (1H, s).

MS: 442 (MH$^+$)

Preparation 158:

(3R)-N-(benzyloxy)-6-cyclohexyl-3-{4-[(cyclopentylamino)methyl]-1,3-oxazol-2-yl}hexanamide

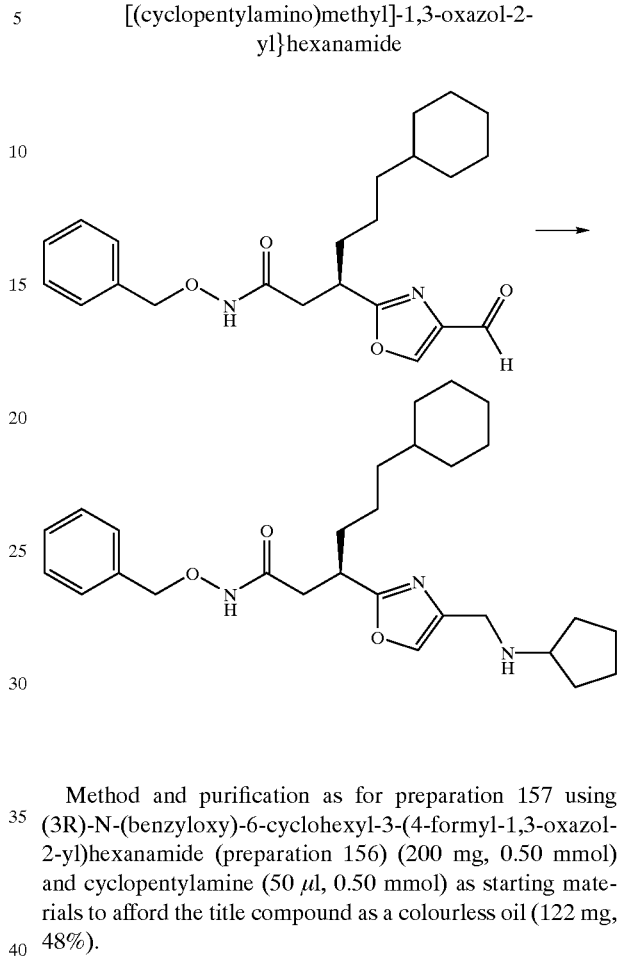

Method and purification as for preparation 157 using (3R)-N-(benzyloxy)-6-cyclohexyl-3-(4-formyl-1,3-oxazol-2-yl)hexanamide (preparation 156) (200 mg, 0.50 mmol) and cyclopentylamine (50 μl, 0.50 mmol) as starting materials to afford the title compound as a colourless oil (122 mg, 48%).

$^1$H nmr: (CDCl$_3$) 0.80 (2H, m), 1.05–1.30 (8H, m), 1.34 (2H, m), 1.50 (2H, m), 1.55–1.75 (9H, m), 1.80 (2H, m), 2.40 (1H, brs), 2.59 (1H, brs), 3.03 (1H, m), 3.35 (1H, brs), 3.58 (2H, s), 4.82 (2H, s), 7.34 (5H, s), 7.38 (1H, s).

MS: 468 (MH$^+$)

Preparation 159:

(3R)-N-(benzyloxy)-6-cyclohexyl-3-[4-(4-morpholinylmethyl)-1,3-oxazol-2-yl]hexanamide

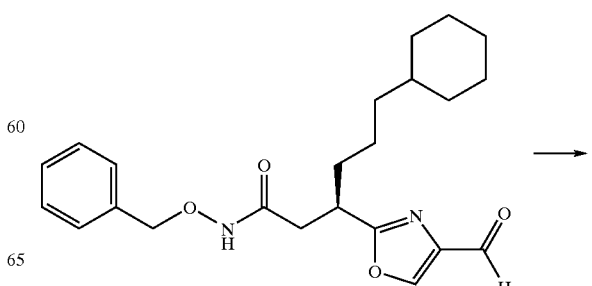

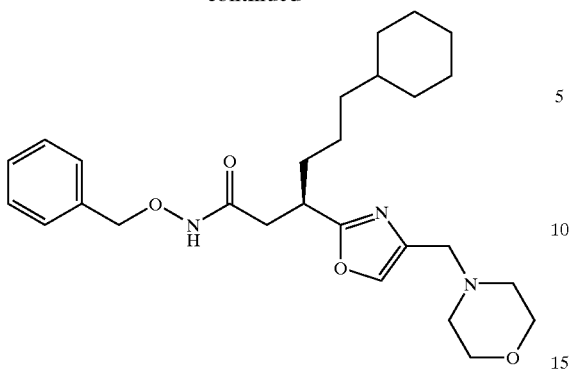

Method and purification as for preparation 157 using (3R)-N-(benzyloxy)-6-cyclohexyl-3-(4-formyl-1,3-oxazol-2-yl)hexanamide (preparation 156) (180 mg, 0.45 mmol) and morpholine (40 μl, 0.45 mmol) as starting materials to afford the title compound as a colourless oil (130 mg, 62%).

$^1$H nmr: (CDCl$_3$) 0.80 (2H, m), 1.05–1.30 (8H, m), 1.55–1.75 (9H, m), 2.37 (1 H, brs), 2.41 (4H, brs), 2.60 (1H, brs), 3.38 (2H, brs), 3.46 (1H, m), 3.35 (1H, brs), 3.66 (4H, brs), 4.82 (2H, s), 7.37 (5H, s), 7.40 (1H, s), 8.77 (1H, brs).

MS: 470 (MH$^+$)

Preparation 160:

(3R)-N-(benzyloxy)-6-cyclohexyl-3-(4-formyl-5-methyl-1,3-oxazol-2-yl)hexanamide

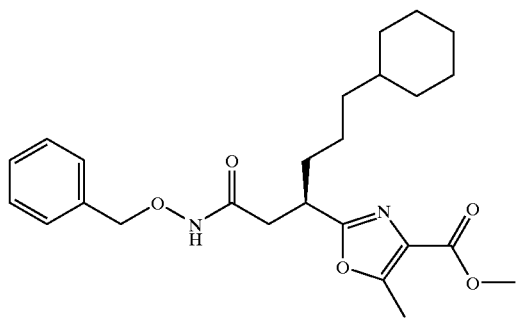

Method as for preparation 156 using methyl 2-((1R)-1-{2-[(benzyloxy)amino]-2-oxoethyl}-4-cyclohexylbutyl)-5-methyl-1,3-oxazole-4-carboxylate (preparation 175) (1.86 g, 4.20 mmol) as starting material.

Purification: The crude material was purified on a silica column eluting with EtOAc:pentane (1:1) to afford the title compound as a colourless oil (1.06 g, 61%).

$^1$H nmr: (CDCl$_3$) 0.81 (2H, m), 1.05–1.30 (8H, m+EtOAc), 1.55–1.75 (7H, m), 2.46 (1H, brs), 2.55 (3H, s), 2.66 (1H, brs), 3.39 (1H, brs), 4.82 (2H, s), 7.33 (5H, brs), 9.81 (1H, brs).

MS: 413 (MH$^+$)

Preparation 161:

(3R)-N-(benzyloxy)-6-cyclohexyl-3-{5-methyl-4-[(tetrahydro-2H-pyran-4-ylamino)methyl]-1,3-oxazol-2-yl}hexanamide

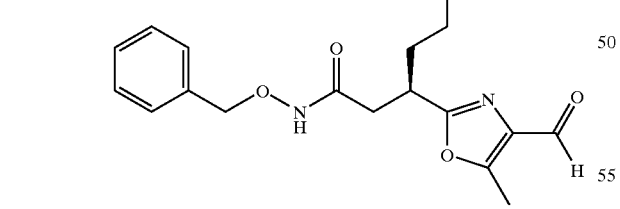

Method as for preparation 157 using (3R)-N-(benzyloxy)-6-cyclohexyl-3-(4-formyl-5-methyl-1,3-oxazol-2-yl)hexanamide (preparation 160) (300 mg, 0.73 mmol) and 4-aminotetrahydro-4H-pyran. HCl (J. Med. Chem.; 1971, 14, 600–14) (110 mg, 0.80 mmol) as starting materials and DIPEA as base.

Purification: The crude material was purified on a silica column eluting with a solvent gradient of DCM:MeOH:NH$_3$ (98:2:0.2) gradually changing to (95:5:0.5) to afford the title compound as a colourless oil (222 mg, 61%).

$^1$H nmr: (CDCl$_3$) 0.82 (2H, m), 1.10–1.30 (8H, m), 1.38–1.70 (9H, m+H$_2$O), 1.79 (2H, brd), 2.21 (3H, s), 2.41 (1H, m), 2.65 (2H, m), 3.27 (1H, brs), 3.38 (2H, t), 3.58 (2H, s), 3.95 (2H, m), 4.83 (2H, s), 7.35 (5H, s).

MS: 499 (M2H$^+$)

Preparation 162:

(3R)-N-(benzyloxy)-6-cyclohexyl-3-[5-methyl-4-(4-morpholinylmethyl)-1,3-oxazol-2-yl]hexanamide

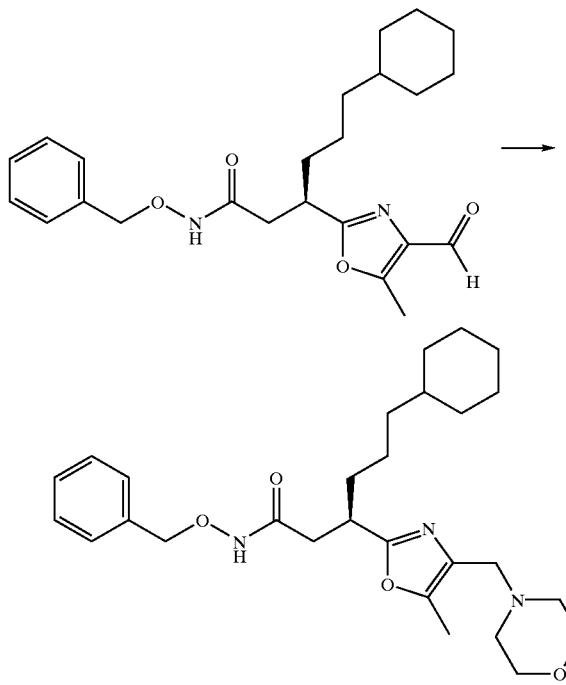

Method as for preparation 157 using (3R)-N-(benzyloxy)-6-cyclohexyl-3-(4-formyl-5-methyl-1,3-oxazol-2-yl) hexanamide (preparation 160) (300 mg, 0.73 mmol) and morpholine (64 µl, 0.73 mmol) as starting materials.

Purification: The crude material was purified on a silica column eluting with a solvent gradient of DCM:MeOH:NH₃ (100:0:0) gradually changing to (95:5:0.5) to afford the title compound as a colourless oil (156 mg, 44%).

¹H nmr: (CDCl₃) 0.82 (2H, m), 1.05–1.35 (8H, m), 1.50–1.75 (7H, m), 2.21 (3H, s), 2.40 (5H, m), 2.62 (1H, brs), 3.23 (3H, m), 3.63 (4H, m), 4.83 (2H, s), 7.34 (5H, s).

MS: 484 (MH⁺)

Acc. Mass.: Found 484.3164 (MH⁺), Calculated C₂₈H₄₁N₃O₄ 484.3175 (MH⁺)

Preparation 163:

(3R)-3-[3-(aminomethyl)-1,2,4-oxadiazol-5-yl]-6-cyclohexylhexanoic acid

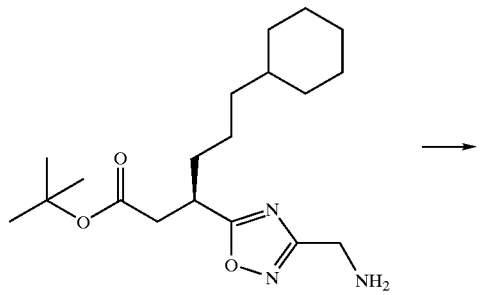

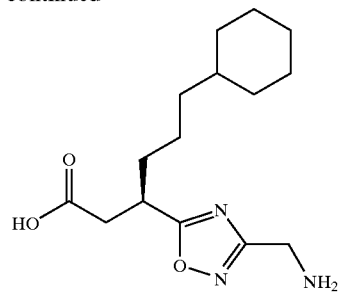

Method as for preparation 7 using (3R)-3-[3-(aminomethyl)-1,2,4-oxadiazol-5-yl]-6-cyclohexylhexanoate (preparation 18) (220 mg, 0.63 mmol) as starting material.

Purification: The crude material was azeotroped from EtOAc, DCM and Et₂O and dried under reduced pressure to afford the title compound (192 mg, 92%).

¹H nmr: (d₆DMSO) 0.80 (2H, m), 1.05–1.30 (8H, m), 1.50–1.70 (7H, m), 2.75 (2H, d), 3.42 (1H, m), 4.20 (2H, s), 8.72 (2H, brs).

MS: 296 (MH⁺) CHN: Found: C54.04%; H7.95%; N12.00%; C₁₅H₂₅N₃O₃. HCl. 0.1 EtOAc requires C54.30; H7.93%; N12.34%

Preparation 164:

3-(diethoxyphosphoryl)succinic acid 1-tert-butyl ester

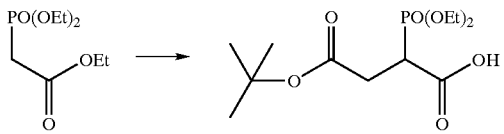

Triethylphosphonoacetate (12.0 Kg, 53.5 mol) was added over 30 minutes to a stirred solution of potassium tert-butoxide (7.20 Kg, 64.2 mol) in THF (118 liters), between 0 and 5° C., under nitrogen. The mixture was warmed to 25–30° C. where it was stirred for 1 hour and then added over 45 minutes to a solution of tert-butyl bromoacetate (11.5 Kg, 59.0 mol) in THF (28 liters), between 0 and 5° C., under nitrogen. The mixture was stirred at 0–5° C. for 1 hour and then demineralised water (6.1 liters) and ethanol (30 liters) were added. A solution of potassium hydroxide (4.2 Kg, 75.0 mol) in demineralised water (84 liters) was then added over 2 hours, between −5 and 0° C. The mixture was stirred at −10° C. for 16 hours and then a solution of citric acid (16.5 Kg, 85.8 mol) in demineralised water (32 liters) was added. The mixture was concentrated in vacuo to a volume of 180 liters and then ethyl acetate (90 liters) was added. The organic phase was separated and the aqueous phase was re-extracted with ethyl acetate (30 liters). The combined organic phases were washed with water (30 liters) and then stripped and replaced with cyclohexane by distillation at atmospheric pressure, at a constant volume of 72 liters. tert-Butylmethyl ether (18 liters) was added and the mixture was stirred at ambient temperature for 12 hours and then filtered. The residue was washed with a mixture of cyclohexane (16 liters) and tert-butylmethyl ether (3.6 liters) then dried in vacuo for 16 hours to give the title compound as a colourless solid (10.0 Kg, 60% yield, 98% pure by HPLC).

¹H-NMR (CDCl₃) δ: 4.20–4.10 (4H, m), 3.49–3.36 (1H, m), 3.00–2.85 (1H, m), 2.72–2.60 (1H, m), 1.20 (9H, s), 1.37–1.27 (6H, m)

Preparation 165:

(E)-2-[2-(tert-butoxy)-2-oxoethyl]-5-phenyl-2-pentenoic acid

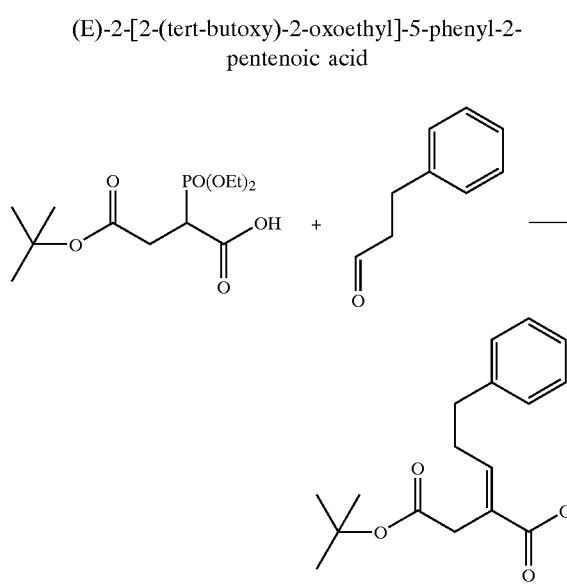

A solution of 3-(diethoxyphosphoryl)succinic acid 1-tert-butyl ester (Preparation 164, 100 g, 0.32 mol) in THF (300 ml) was added dropwise over 15 min to a stirred solution of potassium tert-butoxide (110 g, 0.98 mol) in THF (300 ml), between −10 and −5° C., under nitrogen. The mixture was stirred at −10° C. for 15 min and then a solution of hydrocinnamaldehyde (46.8 g, 0.35 mmol) in THF (100 ml) was added dropwise over 15 min, between −13 and −8° C. The mixture was stirred at −10° C. for 30 min and then a solution of citric acid (111 g, 0.58 mol) in demineralised water (500 ml), and ethyl acetate (500 ml), were added. The pH was adjusted to pH 4 with aqueous sodium hydroxide solution (50%) and the phases were separated. The aqueous fraction was washed with ethyl acetate (500 ml) and the combined organic fractions were washed with saturated sodium bicarbonate solution (500 ml), citric acid solution (10%, 500 ml) and demineralised water (500 ml) and then concentrated in vacuo. The resulting solid was slurried in cyclohexane (470 ml) for 1 hour and then the mixture was filtered. The residue was washed with cyclohexane (2×50 ml) and dried in vacuo to leave the title compound as a colourless solid (76 g, 81% yield, 99% pure by HPLC).

MS: 289 [(M−H)]⁻

¹H-NMR (CDCl₃) δ: 7.33–7.16 (5H, m), 7.05 (1H, br t), 3.20 (2H, s), 2.89 (2H, br t), 2.50 (2H, br dd), 1.41 (9H, s)

Preparation 166:

(R)-2-[2-(tert-butoxy)-2-oxoethyl]-5-phenylpentanoic acid cyclohexylamine salt

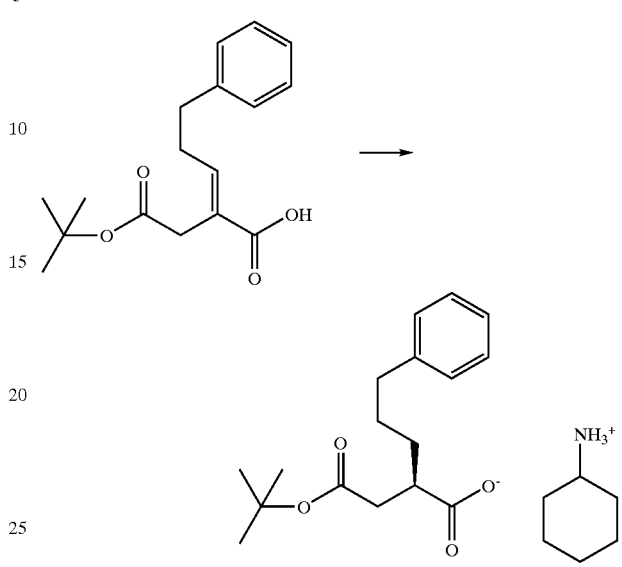

A stirred solution of cyclohexylamine (266 ml, 2.32 mol), (E)-2-[2-(tert-butoxy)-2-oxoethyl]-5-phenyl-2-pentenoic acid (Preparation 165, 688 g, 2.37 mol) and [(S)-2,2'-bis(diphenylphosphino-1,1'-binaphthyl]chloro(p-cymene)ruthenium chloride (4.4 g, 4.7 mmol) in methanol (6.9 liters) was heated to 60° C., under hydrogen (60 p.s.i.), for 47 hours and then allowed to cool to room temperature (enantiomeric excess=88%). The mixture was filtered through celite and then the solvent was stripped and replaced with acetone by distillation at atmospheric pressure, at a constant volume of 4.2 liters. The resulting suspension was cooled to room temperature where it was stirred for 4 hours and then filtered. The residue was washed with acetone (2×1 liter) and then dried in vacuo at 45° C. for 16 hours to leave the title compound as a colourless solid (590 g, 64% yield, enantiomeric excess=98.9%, 97% pure by HPLC).

¹H-NMR (CD₃OD) δ: 7.23–7.09 (5H, m), 3.05–2.98 (1H, m), 2.64–2.56 (3H, m), 2.53 (1H, dd, J 15.2, 7.2 Hz), 2.23 (1H, dd, J 15.2, 7.2 Hz), 2.00–1.97, (2H, m), 1.85–1.81 (2H, m), 1.72–1.20 (10 H, m), 1.40 (9H, s)

Preparation 167:

(R)-2-[2-(tert-butoxy)-2-oxoethyl]-5-cyclohexylpentanoic acid sodium salt

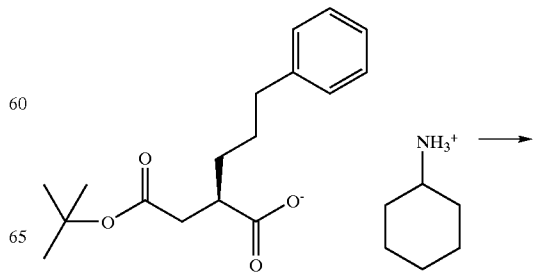

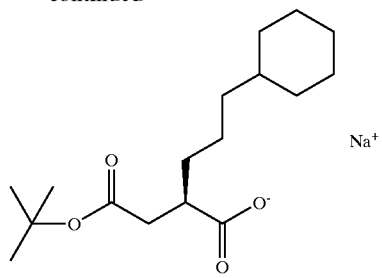

(R)-2-[2-(tert-Butoxy)-2-oxoethyl]-5-phenylpentanoic acid cyclohexylamine salt (Preparation 166, 6.8 g, 17 mmol) and ethyl acetate (100 ml) were added to an aqueous solution of citric acid (10%, 100 ml) and the organic phase was separated and washed with water (100 ml). Iso-propyl alcohol (20 ml) and 5% rhodium on alumina (51.6 g) were added and the mixture was stirred at room temperature, under hydrogen (10 atmospheres, 150 p.s.i.) for 48 hours and then filtered through celite. To the filtrate was added a solution of sodium hydroxide (0.67 g, 17 mmol) in water and the mixture was stripped and replaced with acetonitrile by distillation at atmospheric pressure to a volume of 30 ml. The mixture was allowed to cool to room temperature where it was stirred for 24 hours. The mixture was cooled to 0° C. and then filtered. The residue was washed with acetonitrile (2×10 ml) and then dried in vacuo at 45° C. for 2 hours to leave the title compound as a colourless solid (3.8 g, 69% yield, 95% pure by NMR).

$^1$H-NMR (CD$_3$OD) δ: 2.62–2.57 (1H, m), 2.53 (1H, dd, J 14.8, 7.2 Hz), 2.23 (1H, dd, J 14.8, 7.2 Hz), 1.76–1.18 (15H, m), 1.44 (9H, s), 0.93–0.82 (2H, m)

Preparation 168:

(2R)-2-[2-(tert-Butoxy)-2-oxoethyl]-5-cyclohexylpentanoic acid

Route A:

(2R)-2-[2-(tert-butoxy)-2-oxoethyl]-5-cyclohexylpentanoic acid

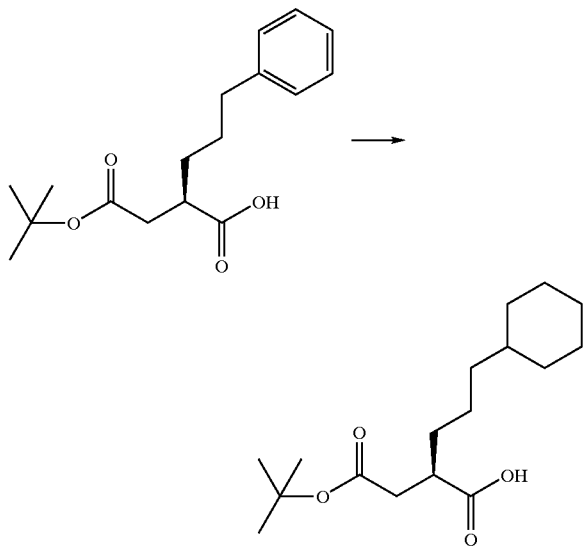

A solution of (2R)-2-[2-(tert-butoxy)-2-oxoethyl]-5-phenylpentanoic acid (Syn. Lett.; 1998; 637–639) (10.00 g, 34.2 mmol) in acetic acid (120 ml) was treated with 5% Rhodium on alumina catalyst, pressurised to 60 psi with hydrogen in a sealed vessel and stirred at room temperature for 17 hours. The mixture was filtered through a pad of Arbocel® and the solvent was removed from the filtrate under reduced pressure. The residue was azeotroped from toluene to afford the title compound (7.53 g).

MS: 299 (MH$^+$)

$^1$H-NMR (CDCl$_3$) δ: 2.80 (1H, m), 2.61 (1H, m), 2.38 (1H, m), 1.75–1.56 (7H, m), 1.55–1.04 (17H, m), 0.84 (2H, m).

Route B:

(4S)-4-Benzyl-3-(5-cyclohexylpentanoyl)-1,3-oxazolidin-2-one

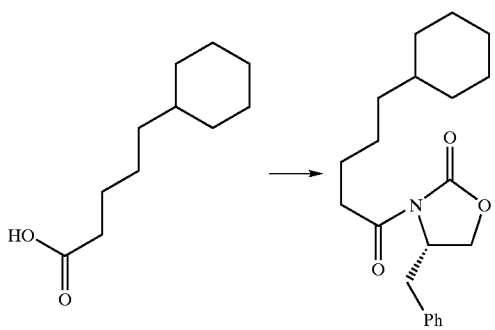

A solution of 5-cyclohexylpentanoic acid (63.50 g, 345 mmol) in N,N-dimethylformamide (0.5 ml) and dichloromethane (350 ml) was cooled to 5° C. and treated dropwise with oxalyl chloride (31.6 ml, 362 mmol) over 30 minutes. The mixture was stirred at 0° C. for 3 hours then the solvent was removed under reduced pressure to afford 5-cyclohexylpentanoyl chloride as a pale yellow solid (70.0 g).

A solution of n-butyllithium (100 ml, 250 mmol, 2.5M in hexanes) was added via a cannula to a solution of (4S)-4-benzyl-1,3-oxazolidin-2-one (44.30 g, 250 mmol) in anhydrous tetrahydrofuran (400 ml) at −78° C. The yellow solution was then stirred for 45 minutes. A solution of 5-cyclohexylpentanoyl chloride (55.5 g, 275 mmol) in tetrahydrofuran (100 ml) was then added over 1 hour. The mixture was stirred at −78° C. for 30 minutes then warmed to room temperature over 1 hour. The mixture was quenched with an aqueous solution of ammonium chloride (20% w/v, 400 ml) and extracted with ethyl acetate. The layers were separated and the organic layer was washed with brine, dried over anhydrous sodium sulphate and the solvent removed under reduced pressure. The solid was recrystallised from hexane (500 ml) to afford the title compound as a white solid (81.0 g).

MS: 344 (MH$^+$)

$^1$H-NMR (CDCl$_3$) δ: 7.41–7.13 (5H, m), 4.68 (1H, m), 4.27–4.02 (2H, m), 3.31 (1H, dd, J=16, 4 Hz), 3.06–2.70 (3H, m), 1.81–1.53 (7H, m), 1.49–1.04 (8H, m), 0.88 (2H, m)

tert-Butyl 3-{[(4S)-4-benzyl-2-oxo-1,3-oxazolidin-3-yl]carbonyl}-6-cyclohexylhexanoate

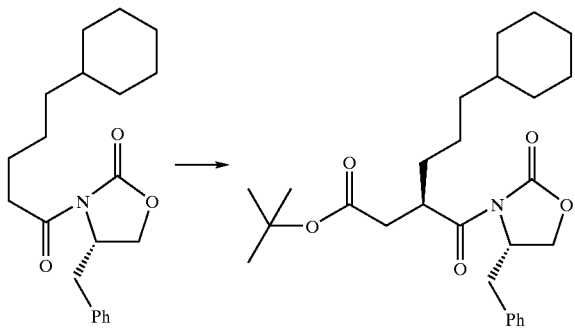

A solution of (4S)-4-benzyl-3-(5-cyclohexylpentanoyl)-1,3-oxazolidin-2-one (70.0 g, 204 mmol) in anhydrous tetrahydrofuran (650 ml) was cooled to −70° C. and treated dropwise with sodium hexamethyldisilazide (1M in tetrahydrofuran, 224 ml, 224 mmol) over 45 minutes. The mixture was stirred for a further 45 minutes before being treated with t-butylbromoacetate (31.6 ml, 214 mmol). This mixture was stirred at −70° C. for 30 minutes then warmed to −30° C. and quenched with an aqueous solution of ammonium chloride (20%w/v, 400 ml) and warmed to room temperature. The mixture was extracted with ethyl acetate and the combined organic extracts were washed with brine, dried over anhydrous sodium sulphate and the solvent removed under reduced pressure. The solid was recrystallised from hexane to afford the title compound as a white solid (71.4 g).

MS: 458(MH$^+$)

$^1$H-NMR (CDCl$_3$) δ: 7.41–7.13 (5H, m), 4.66 (1H, m), 4.23–4.03 (3H, m), 3.35 (1H, dd, J=16, 4 Hz), 2.95–2.68 (3H, m), 2.47 (1H, m), 1.80–1.07 (24H, m), 0.85 (2H, m)

2-[2-(tert-Butoxy)-2-oxoethyl]-5-cyclohexylpentanoic acid

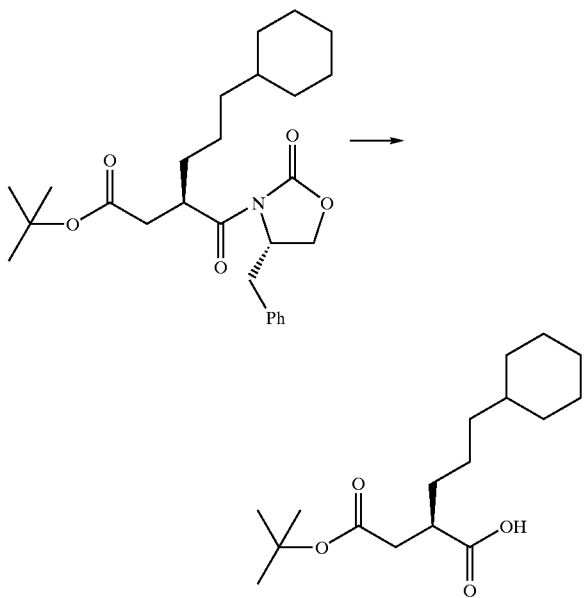

A solution of tert-butyl 3-{[(4S)-4-benzyl-2-oxo-1,3-oxazolidin-3-yl]carbonyl}-6-cyclohexylhexanoate (64.0 g, 139.9 mmol) in tetrahydrofuran:water (3:1, 800 ml) was cooled to 5° C. then treated sequentially with hydrogen peroxide (30%w/v water, 87 ml, 769 mmol) then lithium hydroxide hydrate (10.0 g, 238 mmol). The reaction was stirred for 1 hour then quenched by dropwise addition of an aqueous solution of sodium thiosulphate (500 ml) keeping the temperature below 20° C. The mixture was extracted with ethyl acetate (discarded) and the aqueous phase was acidifed to pH 2 with solid citric acid and extracted with ethyl acetate. The combined organic phases were washed with brine, dried over anhydrous sodium sulphate and the solvent removed under reduced pressure. The residue was purified by column chromatography on silica gel eluting with a gradient system of hexane:ethyl acetate (2:1) gradually changing to hexane:ethyl acetate (1:1) to afford the title compound (40.7 g)

Route C:

3-(Diethoxyphosphoryl)succinic acid 1-tert-butyl ester

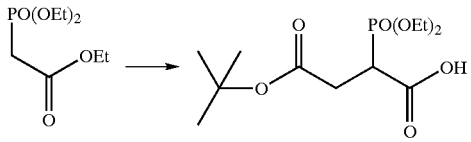

Triethylphosphonoacetate (102 g, 0.45 mol) was added dropwise over 11 min to a stirred solution of potassium tert-butoxide (60 g, 0.54 mol) in THF (500 ml), at 0° C., under nitrogen. The mixture was stirred for 1 hour at 0° C. and then dichloromethane (300 ml) was added and the reaction mixture was warmed to 25–30° C. The mixture was stirred at 25–30° C. for 1 hour and then added dropwise over 33 minutes to a solution of tert-butyl bromoacetate (96 g, 0.49 mol) in THF (500 ml), at 0° C., under nitrogen. The mixture was stirred at 0–5° C. for 2 hours and then a solution of citric acid (174 g, 0.91 mol) in demineralised water (250 ml) was added. The mixture was concentrated in vacuo to remove most of the THF and then toluene (750 ml) was added. The organic phase was separated, washed with brine (2×150 ml) and concentrated in vacuo to leave a colourless oil. The oil was taken up in ethanol and a solution of potassium hydroxide (36. g, 0.64 mol) in demineralised water (150 ml) was added dropwise over 15 mins. The mixture was stirred at 0° C. for 4 hours and then a solution of citric acid (158 g, 0.82 mol) in demineralised water (600 ml), and toluene (600 ml), were added. The organic phase was separated and the aqueous phase was re-extracted with toluene (600 ml). The combined organic phases were washed with demineralised water (2×150 ml) and concentrated in vacuo to leave a white solid. Toluene (150 ml) was added and the slurry was re-concentrated in vacuo to leave a white solid. The product was purified by crystallisation from tert-butylmethyl ether (300 ml) and cyclohexane (600 ml) to give the title compound as a solid (79 g).

$^1$H-NMR (CDCl$_3$) δ: 4.20–4.10 (4H, m), 3.49–3.36 (1H, m), 3.00–2.85 (1H, m), 2.72–2.60 (1H, m), 1.20 (9H, s), 1.37–1.27 (6H, m)

Alternative preparation:

Triethylphosphonoacetate (12.0 Kg, 53.5 mol) was added over 30 minutes to a stirred solution of potassium tert-butoxide (7.20 Kg, 64.2 mol) in THF (118 liters), between 0 and 5° C., under nitrogen. The mixture was warmed to 25–30° C. where it was stirred for 1 hour and then added over 45 minutes to a solution of tert-butyl bromoacetate (11.5 Kg, 59.0 mol) in THF (28 liters), between 0 and 5° C., under nitrogen. The mixture was stirred at 0–5° C. for 1 hour and then demineralised water (6.1 liters) and ethanol (30 liters) were added. A solution of potassium hydroxide (4.2 Kg, 75.0 mol) in demineralised water (84 liters) was then added over 2 hours, between −5 and 0° C. The mixture was stirred at −10° C. for 16 hours and then a solution of citric acid (16.5 Kg, 85.8 mol) in demineralised water (32 liters) was added. The mixture was concentrated in vacuo to a volume of 180 liters and then ethyl acetate (90 liters) was added. The organic phase was separated and the aqueous phase was re-extracted with ethyl acetate (30 liters). The combined organic phases were washed with water (30 liters) and then stripped and replaced with cyclohexane by distillation at atmospheric pressure, at a constant volume of 72 liters. tert-Butylmethyl ether (18 liters) was added and the mixture was stirred at ambient temperature for 12 hours and then filtered. The residue was washed with a mixture of cyclohexane (16 liters) and tert-butylmethyl ether (3.6 liters) then dried in vacuo for 16 hours to give the title compound as a colourless solid (10.0 Kg, 60%).

$^1$H-NMR (CDCl$_3$) δ: 4.20–4.10 (4H, m), 3.49–3.36 (1H, m), 3.00–2.85 (1H, m), 2.72–2.60 (1H, m), 1.20 (9H, s), 1.37–1.27 (6H, m)

(E)-2-[2-(tert-Butoxy)-2-oxoethyl]-5-phenyl-2-pentenoic acid

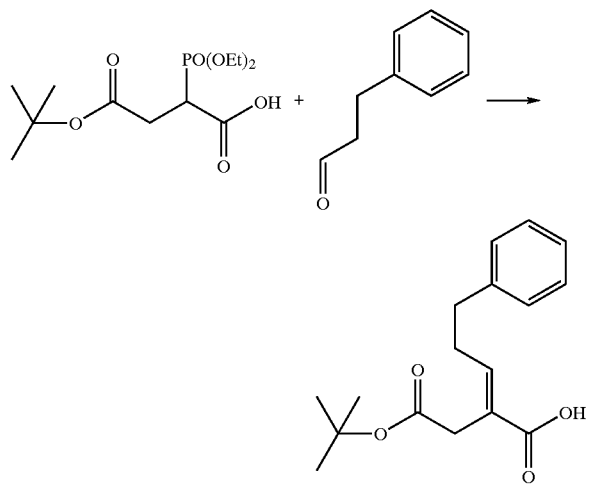

A solution of 3-(diethoxyphosphoryl)succinic acid 1-tert-butyl ester (100 g, 0.32 mol) in THF (300 ml) was added dropwise over 15 min to a stirred solution of potassium tert-butoxide (110 g, 0.98 mol) in THF (300 ml), between −10 and −5° C., under nitrogen. The mixture was stirred at −10° C. for 15 min and then a solution of hydrocinnamaldehyde (46.8 g, 0.35 mmol) in THF (100 ml) was added dropwise over 15 min, between −13 and −8° C. The mixture was stirred at −10° C. for 30 min and then a solution of citric acid (111 g, 0.58 mol) in demineralised water (500 ml), and ethyl acetate (500 ml), were added. The pH was adjusted to pH 4 with aqueous sodium hydroxide solution (50%) and the phases were separated. The aqueous fraction was washed with ethyl acetate (500 ml) and the combined organic fractions were washed with saturated sodium bicarbonate solution (500 ml), citric acid solution (10%, 500 ml) and demineralised water (500 ml) and then concentrated in vacuo. The resulting solid was slurried in cyclohexane (470 ml) for 1 hour and then the mixture was filtered. The residue was washed with cyclohexane (2×50 ml) and dried in vacuo to leave the title compound as a colourless solid (76 g, 81%).

MS: 289 [(M−H)]$^-$ $^1$H-NMR (CDCl$_3$) δ: 7.33–7.16 (5H, m), 7.05 (1H, br t), 3.20 (2H, s), 2.89 (2H, br t), 2.50 (2H, br dd), 1.41 (9H, s)

(R)-2-[2-(tert-Butoxy)-2-oxoethyl]-5-phenylpentanoic acid

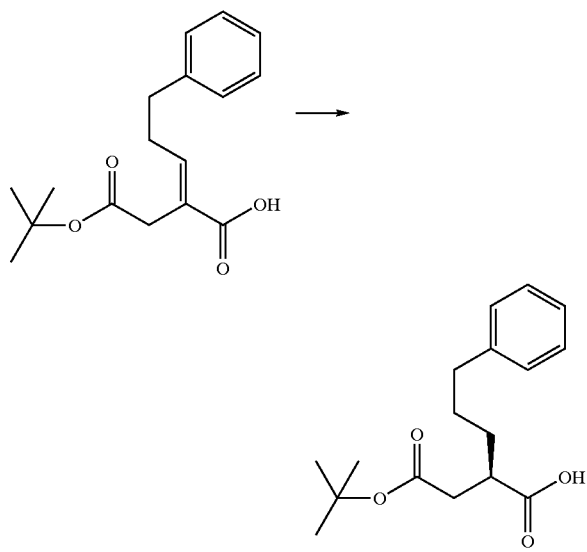

A stirred solution of (E)-2-[2-(tert-butoxy)-2-oxoethyl]-5-phenyl-2-pentenoic acid (100 g, 0.34 mol), cyclohexylamine (39 ml, 0.34 mol) and [(S)-2,2'-bis(diphenylphosphino-1,1'-binaphthyl]chloro(p-cymene) ruthenium chloride (0.64 g, 0.69 mmol) in methanol (1000 ml) was heated to 60° C., under hydrogen (60 p.s.i.), for 42 hours and then allowed to cool to room temperature. The mixture was filtered through celite and then concentrated in vacuo to a yellow solid which was purified by re-crystallisation from acetone (850 ml). The resulting solid was partitioned between ethyl acetate (1200 ml) and citric acid solution (10%, 1200 ml) and the organic phase was separated, washed with demineralised water (1200 ml) and concentrated in vacuo to leave the title compound as an oil (80 g).

$^1$H-NMR (CDCl$_3$) δ: 7.30–7.17 (5H, m), 2.85–2.78 (1H, m), 2.66–2.58 (3H, m), 2.37 (1H, br dd), 1.75–1.51 (4H, m), 1.40 (9H, s)

Preparation of cyclohexylamine salt:

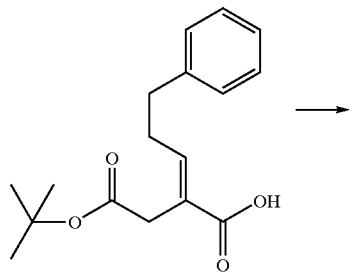

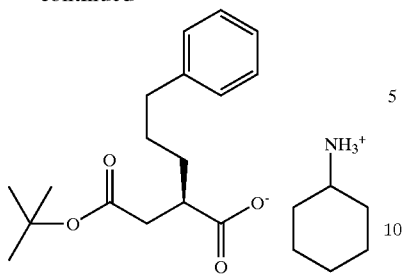

A stirred solution of cyclohexylamine (266 ml, 2.32 mol), (E)-2-[2-(tert-butoxy)-2-oxoethyl]-5-phenyl-2-pentenoic acid (688 g, 2.37 mol) and [(S)-2,2'-bis(diphenylphosphino-1,1'-binaphthyl]chloro(p-cymene)ruthenium chloride (4.4 g, 4.7 mmol) in methanol (6.9 liters) was heated to 60° C., under hydrogen (60 p.s.i.), for 47 hours and then allowed to cool to room temperature (enantiomeric excess=88%). The mixture was filtered through celite and then the solvent was stripped and replaced with acetone by distillation at atmospheric pressure, at a constant volume of 4.2 liters. The resulting suspension was cooled to room temperature where it was stirred for 4 hours and then filtered. The residue was washed with acetone (2×1 liter) and then dried in vacuo at 45° C. for 16 hours to leave the title compound as a colourless solid (590 g, 64%, enantiomeric excess=98.9%).

$^1$H-NMR (CD$_3$OD) δ: 7.23–7.09 (5H, m), 3.05–2.98 (1H, m), 2.64–2.56 (3H, m), 2.53 (1H, dd, J 15.2, 7.2 Hz), 2.23 (1H, dd, J 15.2, 7.2 Hz), 2.00–1.97, (2H, m), 1.85–1.81 (2H, m), 1.72–1.20 (10H, m), 1.40 (9H, s)

(R)-2-[2-(tert-Butoxy)-2-oxoethyl]-5-cyclohexylpentanoic acid cyclohexylamine salt

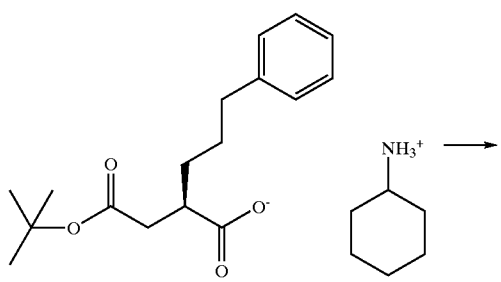

(R)-2-[2-(tert-Butoxy)-2-oxoethyl]-5-phenylpentanoic acid cyclohexylamine salt (691 g, 1.77 mol) and ethyl acetate (7.0 liters) were added to an aqueous solution of citric acid (10%, 6.3 liters) and the organic phase was separated, washed with water (7.0 liters) and concentrated in vacuo to a yellow oil. A solution of the oil and 5% rhodium on carbon (51.6 g) in methanol (7.0 liters) was stirred at ambient temperature, under hydrogen (150 p.s.i.) for 48 hours and then filtered through celite. To the filtrate was added cyclohexylamine (202 ml, 1.77 mol) and the methanol solution was stripped and replaced with methylethyl ketone by distillation at atmospheric pressure, to a volume of 5.5 liters. The mixture was allowed to cool to ambient temperature where it was stirred for 48 hours and then filtered. The residue was washed with methylethyl ketone (2×500 ml) and then dried in vacuo at 45° C. for 4 hours to leave the title compound as a colourless solid (495 g, 71%).

$^1$H-NMR (CD$_3$OD) δ: 3.06–2.99 (1H, m), 2.63–2.56 (1H, m), 2.53 (1H, dd, J 15.2, 7.2 Hz), 2.23 (1H, dd, J 15.2, 7.2 Hz), 2.02–1.97 (2H, m), 1.77–1.15 (21H, m), 1.43 (9H, s), 0.93–0.82 (2H, m)

(R)-2-[2-(tert-Butoxy)-2-oxoethyl]-5-cyclohexylpentanoic acid

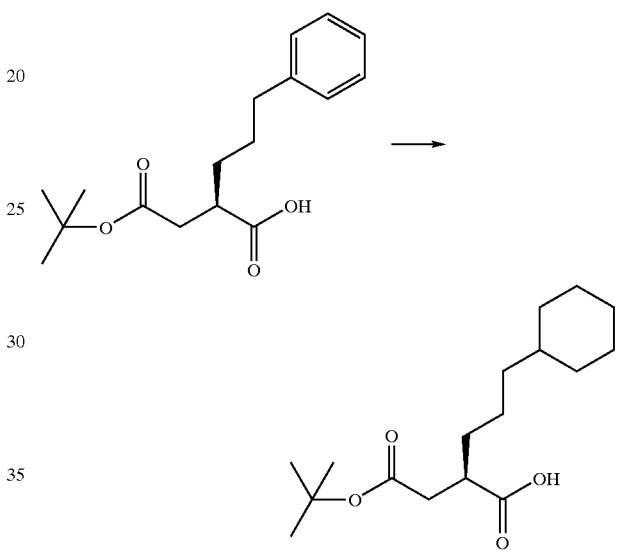

A solution of (R)-2-[2-(tert-butoxy)-2-oxoethyl]-5-phenylpentanoic acid (2.2 g, 7.5 mmol) and 5%Rh/C (0.22 g) in methanol (220 ml) was stirred at room temperature, under hydrogen (150 p.s.i.) for 24 hours and then filtered through celite. The filtrate was concentrated in vacuo to leave the title compound as an oil (2.0 g).

$^1$H-NMR (CDCl$_3$) δ: 2.82–2.76 (1H, m), 2.60 (1H, br dd), 2.37 (1H, br dd), 1.70–1.60 (6H, m), 1.51–1.30 (3H, m), 1.42 (9H, s), 1.23–1.11 (6H, m), 0.96–0.80 (2H, m)

Preparation 169:

tert-Butyl (3R)-3-[({[(Z)-1-amino-2-ethoxy-2-oxoethylidene]amino}oxy)carbonyl]-6-cyclohexylhexanoate

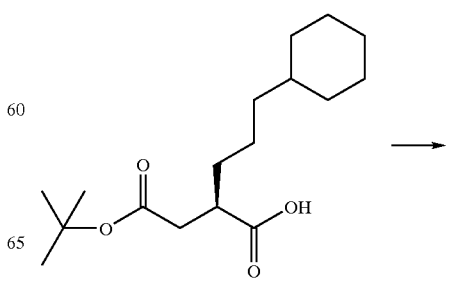

219
-continued

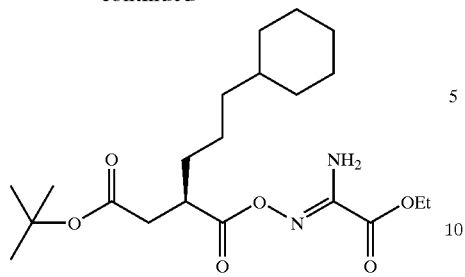

A solution of (2R)-2-[2-(tert-butoxy)-2-oxoethyl]-5-cyclohexylpentanoic acid (Preparation 168) (7.53 g, 25.2 mmol) in 1,4-dioxane (175 ml) was treated with 1-hydroxybenzotriazole hydrate (3.75 g, 27.8 mmol) and the mixture cooled to 0° C. N,N'-Dicyclohexylcarbodiimide (5.47 g, 26.5 mmol) was then added and the mixture was stirred for 3 hours being allowed to warm to room temperature over this time. The mixture was then filtered and washed with 1,4-dioxane (2×50 ml). The filtrate was then treated with sodium carbonate (4.01 g, 37.8 mmol) and ethyl 2-amino-2-(hydroxyimino)acetate (J.Org.Chem.;23; 1958; 1794) (3.33 g, 25.2 mmol). The resulting mixture was stirred at room temperature for 17 hours. The solvent was removed under reduced pressure and the residue was partitioned between ethyl acetate and water. The layers were separated and the aqueous phase was extracted with ethyl acetate (×2). The combined organic layers were dried over anhydrous magnesium sulphate, filtered and the solvent removed under reduced pressure. The residue was purified by column chromatography on silica gel eluting with a gradient system of ethyl acetate:pentane (30:70) gradually changing to ethyl acetate:pentane (50:50) to afford the title compound as a white solid (6.50 g).

MS:413 (MH$^+$)

$^1$H-NMR (CDCl$_3$) δ: 5.71 (2H, br s), 4.39 (2H, q), 2.92 (1H, m), 2.67 (1H, dd), 2.44 (1H, dd), 1.75–1.32 (22H, m), 1.26–1.04 (5H, m), 0.84 (2H, m).

Preparation 170:

Ethyl 5-{(1R)-1-[2-(tert-butoxy)-2-oxoethyl]-4-cyclohexylbutyl}-1,2,4-oxadiazole-3-carboxylate

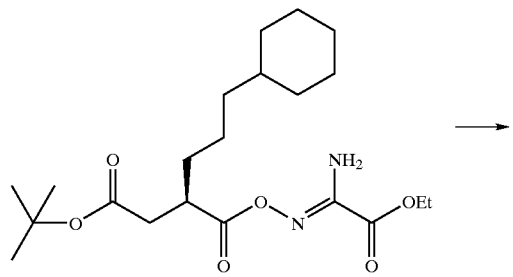

220
-continued

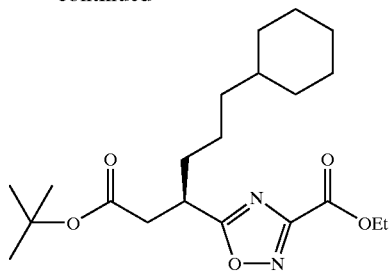

A solution of tert-Butyl (3R)-3-[({[(Z)-1-amino-2-ethoxy-2-oxoethylidene]amino}oxy)carbonyl]-6-cyclohexylhexanoate (Preparation 169) (21.0 g, 50.82 mmol) in xylene (400 ml) was heated at 130° C. for 17 hours, then allowed to cool to room temperature. The residue was purified by column chromatography on silica gel eluting with a gradient system of ethyl acetate:pentane (5:95) gradually changing to ethyl acetate:pentane (20:80) to afford the title compound as a colourless oil (20.0 g).

MS: 395 (MH$^+$), 412 (MNH$_4{^+}$)

$^1$H-NMR (CDCl$_3$) δ: 4.51 (2H, m), 3.54 (1H, m), 2.86 (1H, dd), 2.65 (1H, dd), 1.86–1.57 (7H, m), 1.50–1.33 (12H, m), 1.30–1.03 (8H, m), 0.82 (2H, m).

Preparation 171:

tert-Butyl (3R)-6-cyclohexyl-3-({[2-hydroxy-1-(methoxycarbonyl)propyl]amino}carbonyl)hexanoate

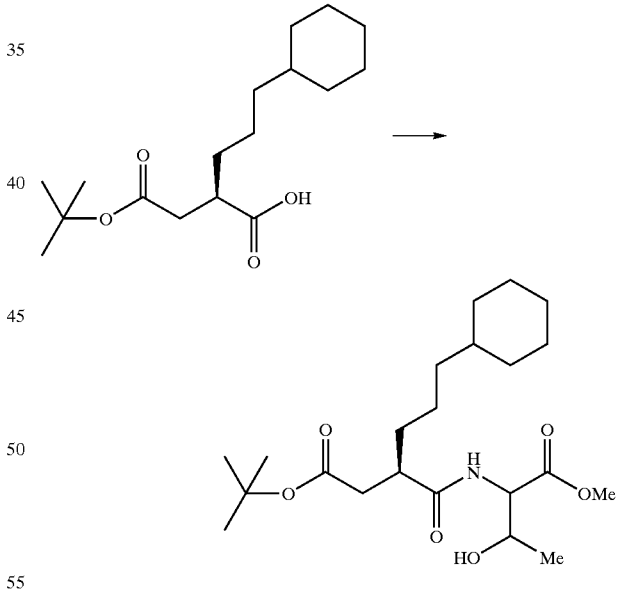

An ice-cooled solution of (2R)-2-[2-(tert-butoxy)-2-oxoethyl]-5-cyclohexylpentanoic acid (Preparation 168) (6.40 g, 21.45 mmol) in dichloromethane (75 ml) was treated sequentially with 1-hydroxybenzotriazole hydrate (3.19 g, 23.60 mmol), threonine methyl ester hydrochloride (4.00 g, 23.60 mmol), N,N-diisopropylethylamine (7.85 ml, 45.10 mmol) and 1-[3-(dimethylamino)propyl]-3-ethylcarbodiimide hydrochloride (4.52 g, 23.58 mmol) and the mixture was stirred for 17 hours being allowed to warm to room temperature over this time. The solvent was removed under reduced pressure and the residue was dissolved in ethyl acetate then washed sequentially with water, aqueous citric acid solution (10% w/v), a saturated aqueous sodium hydrogen carbonate solution and brine, dried over anhydrous magnesium sulphate, filtered and the solvent removed under reduced pressure. The residue was dissolved in diethyl ether (100 ml) and treated with pentane (150 ml) to produce a white precipitate. This was filtered off and washed with pentane to afford the title compound as a white powder (6.48 g).

MS: 436 (MNa$^+$)

$^1$H-NMR (CDCl$_3$) δ: 6.35 (1H, br d), 4.63 (1H, m), 4.26 (1H, m), 3.76 (3H, s), 2.73–3.53 (3H, m), 2.34 (1H, m), 1.73–1.56 (7H, m), 1.45–1.09 (20H, m), 0.84 (2H, m)

Preparation 172:

tert-Butyl (3R)-6-cyclohexyl-3-({[1-(methoxycarbonyl)-2-oxopropyl]amino}carbonyl)hexanoate

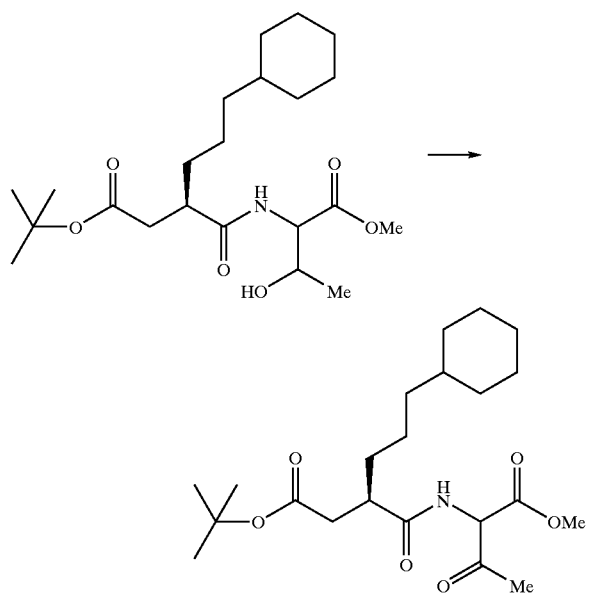

A solution of tert-butyl (3R)-6-cyclohexyl-3-({[2-hydroxy-1-(methoxycarbonyl)propyl]amino}carbonyl)hexanoate (Preparation 171) (6.48 g, 15.69 mmol) in dichloromethane (60 ml) was treated with Dess-Martin periodinane [1,1,1-triacetoxy-1,1-dihydro-1,2-benziodoxol-3(1H)-one] (7.32 g, 17.26 mmol) and the resulting mixture was stirred at room temperature under a nitrogen atmosphere for 1 hour. A solution of sodium thiosulphate (6 g in 50 ml water) and a saturated aqueous sodium hydrogen carbonate solution (50 ml) were then added to the mixture which was stirred for a further 10 minutes. The layers were separated and the aqueous layer was extracted with dichloromethane. The combined organic layers were sequentially washed with water and brine, dried over anhydrous magnesium sulphate, filtered and the solvent removed under reduced pressure. The residue was purified by column chromatography on silica gel eluting with a gradient system of pentane: ethyl acetate (100:0 to 90:10) to afford the title compound as a colourless oil (4.86 g)

MS: 412 (MH$^+$), 434 (MNa$^+$)

$^1$H-NMR (CDCl$_3$) δ: 6.82 (1H, br d), 5.21 (1H, m), 3.78 (3H, s), 2.72–2.52 (2H, m), 2.40–2.25 (4H, m), 1.72–1.53 (7H, m), 1.45–1.04 (17H, m), 0.83 (2H, m)

Preparation 173:

Methyl 2-{(1R)-1-[2-(tert-butoxy)-2-oxoethyl]-4-cyclohexylbutyl}-5-methyl-1,3-oxazole-4-carboxylate

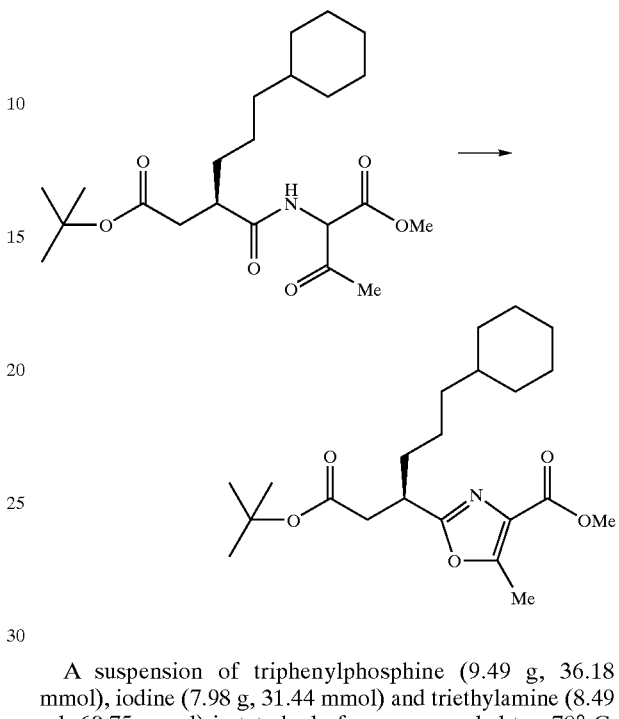

A suspension of triphenylphosphine (9.49 g, 36.18 mmol), iodine (7.98 g, 31.44 mmol) and triethylamine (8.49 ml, 60.75 mmol) in tetrahydrofuran was cooled to −78° C. then treated with tert-butyl (3R)-6-cyclohexyl-3-({[1-(methoxycarbonyl)-2-oxopropyl]amino}carbonyl)hexanoate (Preparation 172) (4.86 g, 11.80 mmol) over 15 minutes. The mixture was stirred at −78° C. for 30 minutes then at 0–5° C. for 2 hours. The mixture was diluted with water and extracted with dichloromethane. The combined organic layers were dried over anhydrous magnesium sulphate, filtered and the solvent removed under reduced pressure. The residue was purified by column chromatography on silica gel eluting with a gradient system of ethyl acetate:pentane (0:100 to 10:90) to afford the title compound as a colourless oil (2.92 g).

MS: 394 (MH$^+$), 416 (MNa$^+$)

$^1$H-NMR (CDCl$_3$) δ: 3.89 (3H, s), 3.29 (1H, m), 2.74 (1H, dd, J=14, 6 Hz), 2.60–2.49 (4H, m), 1.79–1.54 (7H, m), 1.38 (9H, s), 1.31–1.05 (8H, m), 0.82 (2H, m)

Preparation 174:

(3R)-6-Cyclohexyl-3-[4-(methoxycarbonyl)-5-methyl-1,3-oxazol-2-yl]hexanoic acid

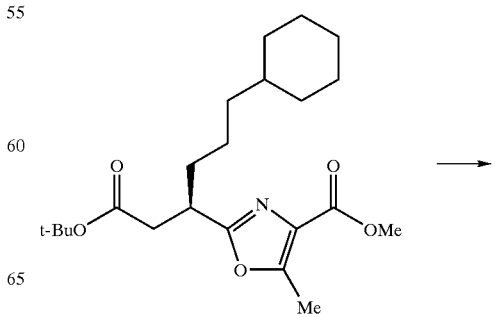

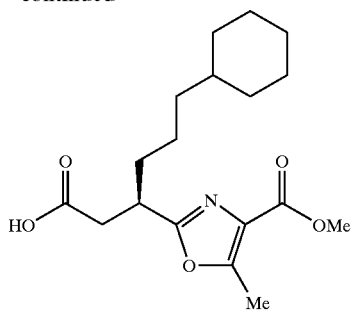

A solution of methyl 2-{(1R)-1-[2-(tert-butoxy)-2-oxoethyl]-4-cyclohexylbutyl}-5-methyl-1,3-oxazole-4-carboxylate (Preparation 173) (2.92 g, 7.43 mmol) in anhydrous dichloromethane (15 ml) was treated with trifluoroacetic acid (7.5 ml) and the resulting mixture was stirred at room temperature under a nitrogen atmosphere for 24 hours. The solvent was removed under reduced pressure and the residue was azeotroped with dichloromethane (×3). The residue was purified by column chromatography on silica gel eluting with a gradient system of ethyl acetate-:pentane (0:100 to 40:60) to afford the title compound as a colourless oil (2.50 g).

MS: 338 (MH$^+$), 360 (MNa$^+$)

Analysis: Found C, 62.90; H, 8.18; N, 3.93%; $C_{18}H_{27}NO_5$. 0.3 EtOAc requires C, 63.38; H, 8.14; N, 3.85%

$^1$H-NMR (CDCl$_3$) δ: 3.86 (3H, s), 3.33 (1H, m), 2.92 (1H, dd, J=17, 8 Hz), 2.67 (1H, dd, J=17, 5 Hz), 2.58 (3H, s), 1.81–1.56 (7H, m), 1.34–1.03 (8H, m), 0.81 (2H, m)

Preparation 175:

Methyl 2-((1R)-1-{2-[(benzyloxy)amino]-2-oxoethyl}-4-cyclohexylbutyl)-5-methyl-1,3-oxazole-4-carboxylate

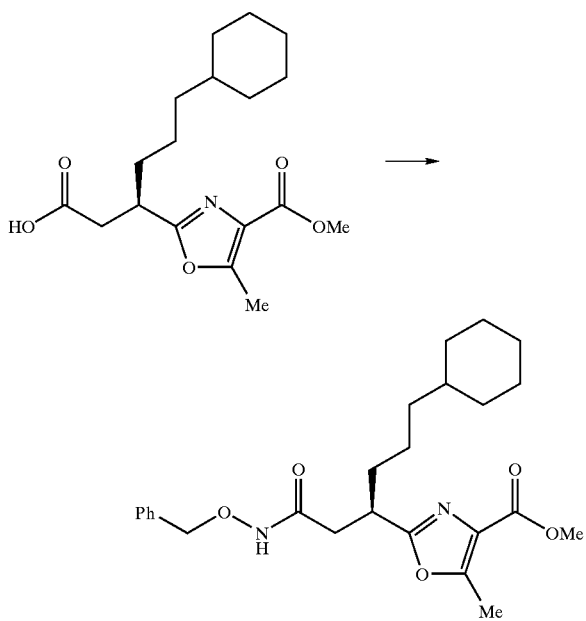

A solution of (3R)-6-cyclohexyl-3-[4-(methoxycarbonyl)-5-methyl-1,3-oxazol-2-yl]hexanoic acid (Preparation 174) (2.48 g, 7.36 mmol) was cooled to 0° and treated with 1-hydroxybenzotriazole hydrate (994 mg, 7.36 mmol), 1-[3-(dimethylamino)propyl]-3-ethylcarbodiimide hydrochloride (2.12 g, 11.06 mmol) and N-methylmorpholine (1.21 ml, 11.04 mmol). The mixture was stirred for 15 minutes then treated with O-benzylhydroxyamine (1.17 g, 7.36 mmol) and further N-methylmorpholine (0.81 ml, 7.36 mmol). The mixture was stirred for 1 hour being allowed to warm to room temperature over this time. The solvent was removed under reduced pressure and the residue was dissolved in ethyl acetate, washed sequentially with water, a saturated solution of sodium hydrogen carbonate and brine, dried over anhydrous magnesium sulphate, filtered and the solvent removed under reduced pressure to afford the title compound as a colourless oil (3.22 g).

MS: 443 (MH$^+$), 465 (MNa$^+$)

Analysis : Found C, 66.78; H, 7.77; N, 6.19%; $C_{25}H_{34}N_2O_5$. 0.3 EtOAc requires C, 67.10; H, 7.82; N, 5.97%

$^1$H-NMR (CDCl$_3$) δ: 8.62 (1H, br S), 7.33 (5H, m), 4.84 (2H, s), 3.84 (3H, s), 3.36 (1H, m), 2.70–2.33 (5H, m), 1.78–1.54 (7H, m), 1.30–1.03 (8H, m), 0.82 (2H, m)

Preparation 176:

tert-Butyl (3R)-6-cyclohexyl-3-[3-(hydroxymethyl)-1,2,4-oxadiazol-5-yl]hexanoate

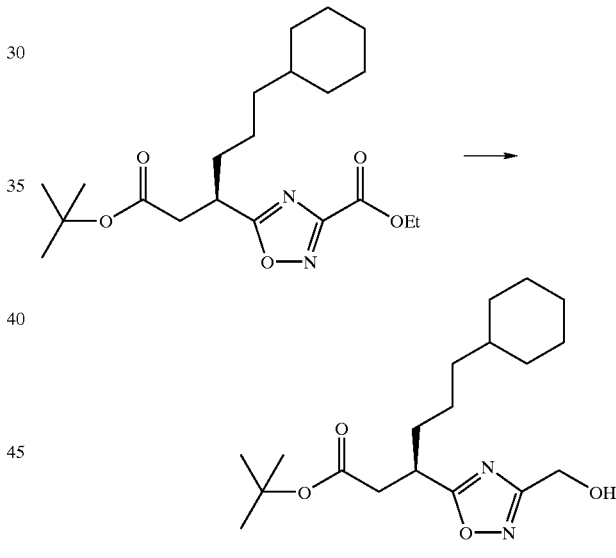

A solution of ethyl 5-{(1R)-1-[2-(tert-butoxy)-2-oxoethyl]-4-cyclohexylbutyl}-1,2,4-oxadiazole-3-carboxylate (Preparation 170) (15.2 g, 38.50 mmol) in ethanol (120 ml) was treated with portions of sodium borohydrideb (1.46 g, 38.50 mmol) and the resulting mixture was was stirred at room temperature under a nitrogen atmosphere for 5 hours. Aqueous citric acid (5%w/v, solution) was added slowly and the mixture was stirred at room temperature for a further 30 minutes. The organic solvent was removed under reduced pressure. The aqueous layer was diluted with water and extracted with ethyl acetate giving an emulsion. Anhydrous sodium chloride was added to break up the emulsion. The combined organic layers were washed with saturated sodium hydrogen carbonate solution and brine, dried over anhydrous sodium sulphate, filtered and the solvent removed under reduced pressure to afford the title compound as a colourless oil (13.4 g).

MS: 375 (MH+)

¹H-NMR (CDCl₃) δ: 4.77 (2H, s), 3.46 (1H, m), 2.80 (1H, dd), 2.62 (1H, dd), 1.58–1.80 (7H, m), 1.39 (9H, s), 1.07–1.33 (8H, m), 0.82 (2H, m).

Preparation 177:

tert-Butyl (3R)-6-cyclohexyl-3-[3-({[(4-methylphenyl)sulfonyl]oxy}methyl)-1,2,4-oxadiazol-5-yl]hexanoate

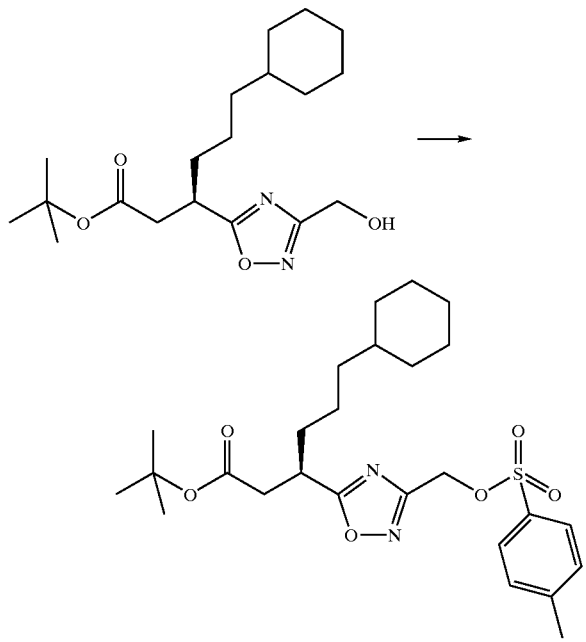

A suspension of sodium hydride 60% suspension in mineral oil (1.52 g, 38.00 mmol) in anhydrous tetrahydrofuran (30 ml) was cooled to 0° C. and treated with a solution of tert-butyl (3R)-6-cyclohexyl-3-[3-(hydroxymethyl)-1,2,4-oxadiazol-5-yl]hexanoate (Preparation 176) (13.40 g, 38.00 mmol) in anhydrous tetrahydrofuran (120 ml) and stirred under a nitrogen atmosphere for 30 minutes. p-Toluene sulphonyl chloride (7.25 g, 38.00 mmol) was added portionwise and the mixture was allowed to warm to room temperature over 18 hours. The solvent was removed under reduced pressure. The residue was dissolved in ethyl acetate and washed with water, saturated sodium hydrogen carbonate solution and brine, dried over anhydrous sodium sulphate, filtered and the solvent removed under reduced pressure. The oil was purified by column chromatography on silica gel eluting with dichloromethane to afford the title compound (10.75 g).

MS: 529 (MNa+)

¹H-NMR (CDCl₃) δ: 7.80 (2H, d), 7.33 (2H, d), 5.12 (2H, s), 3.40 (1H, m), 2.72 (1H, dd), 2.58 (1H, dd), 2.43 (3H, s), 1.56–1.78 (7H, m), 1.35 (9H, s), 1.05–1.30 (8H, m), 0.82 (2H, m).

What is claimed is:

1. A compound of formula (I):

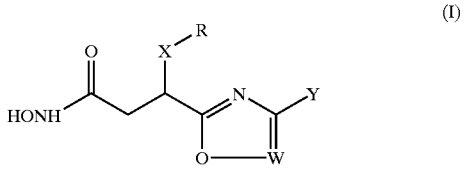

wherein:

X is $C_{1-6}$ alkylene or $C_{2-6}$ alkenylene, each of which is optionally substituted by one or more fluorine atoms;

R is $C_{3-8}$ cycloalkyl, optionally substituted by one or more fluorine atoms;

W is N;

Y is represented $C_{1-4}$ alkyl, substituted by $NR^1R^2$;

$R^1$ is represented by H or $C_{1-4}$ alkyl which may optionally be substituted by OH, $NR^4R^5$ or $C_{1-4}$ alkoxy;

$R^2$ is represented by $SO_2(C_{1-4}$ alkyl);

$R^4$ is represented by H or $C_{1-4}$ alkyl;

$R^5$ is represented by H or $C_{1-4}$ alkyl, and;

the pharmaceutically acceptable salts, solvates (including hydrates) and prodrugs thereof.

2. A compound, salt, solvate or prodrug according to claim 1 wherein the compound of formula (I) has the following stereochemistry (IA):

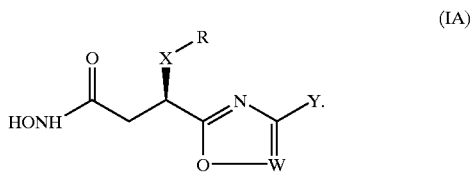

3. A compound, salt, solvate or prodrug according to claim 1 wherein X is a linear $C_{1-6}$ alkylene moiety optionally substituted by one or more fluorine atoms.

4. A compound, salt, solvate or prodrug according to claim 1 wherein X is propylene.

5. A compound, salt, solvate or prodrug according to claim 1 wherein R is cyclobutyl, cyclopentyl or cyclohexyl optionally substituted by one or more fluorine atoms.

6. A compound, salt solvate or prodrug according to claim 1 wherein Y is $CH_2$ substituted by $NR^1R^2$.

7. A compound, salt, solvate or prodrug according to claim 1 wherein R is cyclohexyl.

8. A compound, salt, solvate or prodrug according to claim 1 wherein Y is $CH_2N(H$ or $CH_3)(SO_2(C_{1-4}$ alkyl).

9. A compound, salt, solvate or prodrug according to claim 1 wherein Y is $CH_2NHSO_2(C_{1-4}$ alkyl).

10. A compound, salt, solvate or prodrug according to claim 1 wherein Y is $CH_2NHSO_2CH_3$.

11. A pharmaceutical composition comprising a compound, salt, solvate or prodrug according to claim 1 and a pharmaceutically acceptable adjuvant, diluent or carrier.

12. A method of alleviating a condition mediated by PCP which comprises administration of an effective amount of a compound, salt, solvate or prodrug according to claim 1 to a patient in need thereof.

13. The compound (3R)-6-cyclohexyl-N-hydroxy-3-(3-{[(methylsulfonyl)amino]methyl}-1,2,4-oxadiazol-5-yl)hexanamide, and; the pharmaceutically acceptable salts, solvates (including hydrates) and prodrugs thereof.

14. The compound (3R)-6-cyclohexyl-N-hydroxy-3-(3-{[methyl(methylsulfonyl)amino]mettyl}-1,2,4-oxadiazol-5-yl)hexanamide, and; the pharmaceutically acceptable salts, solvates (including hydrates) and prodrugs thereof.

15. The compound (3R)-6-cyclohexyl-3-(3-{[(ethylsulfonyl)amino]methyl}-1,2,4-oxadiazol-5-yl)-N-hydroxyhexanamide and;

the pharmaceutically acceptable salts, solvates (including hydrates) and prodrugs thereof.

16. The compound (3R)-6-cyclohexyl-N-hydroxy-3-(3-{[(isopropylsulfonyl)amino]methyl}-1,2,4-oxadiazol-5-yl)hexanamide and; the pharmaceutically acceptable salts. solvates (including hydrates) and prodrugs thereof.

17. The compound (3R)-6-cyclohexyl-N-hydroxy-3-(3-{2-[(methylsulfonyl)amino]ethyl}-1,2,4-oxadiazol-5-yl)hexanamide, and; the pharmaceutically acceptable salts, solvates (including hydrates) and prodrugs thereof.

* * * * *